United States Patent
Metz et al.

(10) Patent No.: US 7,923,253 B2
(45) Date of Patent: Apr. 12, 2011

(54) METHOD FOR IDENTIFYING TYPE I DIABETES MELLITUS IN HUMANS

(75) Inventors: Thomas O Metz, Kennewick, WA (US); Weijun Qian, Richland, WA (US); Jon M. Jacobs, Pasco, WA (US); David G. Camp, II, Richland, WA (US); Richard D. Smith, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 202 days.

(21) Appl. No.: 12/291,173

(22) Filed: Nov. 5, 2008

(65) Prior Publication Data
US 2009/0117578 A1 May 7, 2009

Related U.S. Application Data

(60) Provisional application No. 60/985,333, filed on Nov. 5, 2007.

(51) Int. Cl.
*G01N 33/48* (2006.01)
*G01N 33/68* (2006.01)

(52) U.S. Cl. ............... 436/63; 436/86; 436/87

(58) Field of Classification Search ............. 436/63, 436/86, 87; 435/6
See application file for complete search history.

(56) References Cited

U.S. PATENT DOCUMENTS

| | | | |
|---|---|---|---|
| 2007/0218519 A1* | 9/2007 | Urdea et al. | 435/7.92 |
| 2008/0280811 A1* | 11/2008 | Feener et al. | 514/2 |
| 2008/0317771 A1* | 12/2008 | Spagnoli et al. | 424/185.1 |
| 2009/0286324 A1* | 11/2009 | Metz et al. | 436/86 |
| 2010/0068729 A1* | 3/2010 | Labrie et al. | 435/7.1 |

FOREIGN PATENT DOCUMENTS

WO 2007146385 * 12/2007

OTHER PUBLICATIONS

Angeli et al. (abstract) "Increased Plasma Corticosteroid-binding Globulin in Insulin-dependent Pubertal Diabetics: relationships with other Glycoproteins, Growth Hormone and Prolactin", Acta Diabetologica Latina, vol. 16, No. 4, Oct.-Dec. 1979, pp. 295-304.*
Hirtz et al. "Salivary Protein Profiling in Type I Diabetes Using Two-Dimensional Electrophoresis and Mass Spectrometry", Clinical Proteomics, vol. 2, 2006, pp. 117-127.*

* cited by examiner

*Primary Examiner* — Maureen M Wallenhorst
(74) *Attorney, Agent, or Firm* — Derek H. Maughan

(57) ABSTRACT

A method and system for classifying subject populations utilizing predictive and diagnostic biomarkers for type I diabetes mellitus. The method including determining the levels of a variety of markers within the serum or plasma of a target organism and correlating this level to general populations as a screen for predisposition or progressive monitoring of disease presence or predisposition.

6 Claims, 1 Drawing Sheet

SEQUENCE LISTING

<160> NUMBER OF SEQ ID NOS: 1661

<210> SEQ ID NO 1
<211> LENGTH: 18
<212> TYPE: PRT
<213> ORGANISM: Homo sapiens

<400> SEQUENCE: 1

Cys Leu Leu Phe Ser Phe Leu Pro Ala Ser Ser Ile Asn Asp Met Glu
1               5                   10                  15

Lys Arg

<210> SEQ ID NO 2
<211> LENGTH: 12
<212> TYPE: PRT
<213> ORGANISM: Homo sapiens

<400> SEQUENCE: 2

Ala Ala Val Ser Asn Phe Gly Tyr Asp Leu Tyr Arg
1               5                   10

<210> SEQ ID NO 3
<211> LENGTH: 14
<212> TYPE: PRT
<213> ORGANISM: Homo sapiens

<400> SEQUENCE: 3

Leu Ala Ala Ala Val Ser Asn Phe Gly Tyr Asp Leu Tyr Arg
1               5                   10

<210> SEQ ID NO 4
<211> LENGTH: 32
<212> TYPE: PRT
<213> ORGANISM: Homo sapiens

<400> SEQUENCE: 4

Pro Ala Ser Pro Pro Glu Glu Gly Ser Pro Asp Pro Asp Ser Thr Gly
1               5                   10                  15

Ala Leu Val Glu Glu Glu Asp Pro Phe Phe Lys Val Pro Val Asn Lys
                20                  25                  30

<210> SEQ ID NO 5
<211> LENGTH: 30
<212> TYPE: PRT
<213> ORGANISM: Homo sapiens

<400> SEQUENCE: 5

Ser Pro Pro Glu Glu Gly Ser Pro Asp Pro Asp Ser Thr Gly Ala Leu
1               5                   10                  15

Val Glu Glu Glu Asp Pro Phe Phe Lys Val Pro Val Asn Lys
                20                  25                  30

<210> SEQ ID NO 6
<211> LENGTH: 6
<212> TYPE: PRT
<213> ORGANISM: Homo sapiens

<400> SEQUENCE: 6

Cys Thr Phe His Pro Arg
1               5

<210> SEQ ID NO 7

```
<211> LENGTH: 9
<212> TYPE: PRT
<213> ORGANISM: Homo sapiens

<400> SEQUENCE: 7

Asp Ser Val Thr Gly Thr Leu Pro Lys
1               5

<210> SEQ ID NO 8
<211> LENGTH: 15
<212> TYPE: PRT
<213> ORGANISM: Homo sapiens

<400> SEQUENCE: 8

Phe Gly Cys Phe Leu Lys Asp Ser Val Thr Gly Thr Leu Pro Lys
1               5                   10                  15

<210> SEQ ID NO 9
<211> LENGTH: 10
<212> TYPE: PRT
<213> ORGANISM: Homo sapiens

<400> SEQUENCE: 9

Thr Gly Ala Val Ser Gly His Ser Leu Lys
1               5                   10

<210> SEQ ID NO 10
<211> LENGTH: 10
<212> TYPE: PRT
<213> ORGANISM: Homo sapiens

<400> SEQUENCE: 10

Val Ser Ser Val Glu Glu Cys Gln Lys Arg
1               5                   10

<210> SEQ ID NO 11
<211> LENGTH: 15
<212> TYPE: PRT
<213> ORGANISM: Homo sapiens

<400> SEQUENCE: 11

Glu Trp Val Ala Ile Glu Ser Asp Ser Val Gln Pro Val Pro Arg
1               5                   10                  15

<210> SEQ ID NO 12
<211> LENGTH: 11
<212> TYPE: PRT
<213> ORGANISM: Homo sapiens

<400> SEQUENCE: 12

Met Met Ala Val Ala Ala Asp Thr Leu Gln Arg
1               5                   10

<210> SEQ ID NO 13
<211> LENGTH: 17
<212> TYPE: PRT
<213> ORGANISM: Homo sapiens

<400> SEQUENCE: 13

Val Phe Gln Tyr Ile Asp Leu His Gln Asp Glu Phe Val Gln Thr Leu
1               5                   10                  15

Lys

<210> SEQ ID NO 14
<211> LENGTH: 22
```

<212> TYPE: PRT
<213> ORGANISM: Homo sapiens

<400> SEQUENCE: 14

Cys Pro Ile Asn Cys Leu Leu Gly Asp Phe Gly Pro Trp Ser Asp Cys
1               5                   10                  15

Asp Pro Cys Ile Glu Lys
            20

<210> SEQ ID NO 15
<211> LENGTH: 19
<212> TYPE: PRT
<213> ORGANISM: Homo sapiens

<400> SEQUENCE: 15

Gln Ile Val Val Asp Lys Tyr Tyr Gln Glu Asn Phe Cys Glu Gln Ile
1               5                   10                  15

Cys Ser Lys

<210> SEQ ID NO 16
<211> LENGTH: 27
<212> TYPE: PRT
<213> ORGANISM: Homo sapiens

<400> SEQUENCE: 16

Ser Val Leu Arg Pro Ser Gln Phe Gly Gly Gln Pro Cys Thr Ala Pro
1               5                   10                  15

Leu Val Ala Phe Gln Pro Cys Ile Pro Ser Lys
            20                  25

<210> SEQ ID NO 17
<211> LENGTH: 13
<212> TYPE: PRT
<213> ORGANISM: Homo sapiens

<400> SEQUENCE: 17

Tyr Tyr Gln Glu Asn Phe Cys Glu Gln Ile Cys Ser Lys
1               5                   10

<210> SEQ ID NO 18
<211> LENGTH: 18
<212> TYPE: PRT
<213> ORGANISM: Homo sapiens

<400> SEQUENCE: 18

Cys Leu Leu Phe Ser Phe Leu Pro Ala Ser Ser Ile Asn Asp Met Glu
1               5                   10                  15

Lys Arg

<210> SEQ ID NO 19
<211> LENGTH: 13
<212> TYPE: PRT
<213> ORGANISM: Homo sapiens

<400> SEQUENCE: 19

Cys Gln Phe Phe Ser Tyr Ala Thr Gln Thr Phe His Lys
1               5                   10

<210> SEQ ID NO 20
<211> LENGTH: 6
<212> TYPE: PRT
<213> ORGANISM: Homo sapiens

<400> SEQUENCE: 20

```
Cys Thr Phe His Pro Arg
1               5

<210> SEQ ID NO 21
<211> LENGTH: 9
<212> TYPE: PRT
<213> ORGANISM: Homo sapiens

<400> SEQUENCE: 21

Asp Ser Val Thr Gly Thr Leu Pro Lys
1               5

<210> SEQ ID NO 22
<211> LENGTH: 15
<212> TYPE: PRT
<213> ORGANISM: Homo sapiens

<400> SEQUENCE: 22

Phe Gly Cys Phe Leu Lys Asp Ser Val Thr Gly Thr Leu Pro Lys
1               5                   10                  15

<210> SEQ ID NO 23
<211> LENGTH: 10
<212> TYPE: PRT
<213> ORGANISM: Homo sapiens

<400> SEQUENCE: 23

Thr Gly Ala Val Ser Gly His Ser Leu Lys
1               5                   10

<210> SEQ ID NO 24
<211> LENGTH: 10
<212> TYPE: PRT
<213> ORGANISM: Homo sapiens

<400> SEQUENCE: 24

Val Ser Ser Val Glu Glu Cys Gln Lys Arg
1               5                   10

<210> SEQ ID NO 25
<211> LENGTH: 18
<212> TYPE: PRT
<213> ORGANISM: Homo sapiens

<400> SEQUENCE: 25

Cys Leu Leu Phe Ser Phe Leu Pro Ala Ser Ser Ile Asn Asp Met Glu
1               5                   10                  15

Lys Arg

<210> SEQ ID NO 26
<211> LENGTH: 6
<212> TYPE: PRT
<213> ORGANISM: Homo sapiens

<400> SEQUENCE: 26

Cys Thr Phe His Pro Arg
1               5

<210> SEQ ID NO 27
<211> LENGTH: 9
<212> TYPE: PRT
<213> ORGANISM: Homo sapiens

<400> SEQUENCE: 27
```

```
Asp Ser Val Thr Gly Thr Leu Pro Lys
1               5

<210> SEQ ID NO 28
<211> LENGTH: 15
<212> TYPE: PRT
<213> ORGANISM: Homo sapiens

<400> SEQUENCE: 28

Phe Gly Cys Phe Leu Lys Asp Ser Val Thr Gly Thr Leu Pro Lys
1               5                   10                  15

<210> SEQ ID NO 29
<211> LENGTH: 13
<212> TYPE: PRT
<213> ORGANISM: Homo sapiens

<400> SEQUENCE: 29

Gly Cys Leu Thr Gln Leu Tyr Glu Asn Ala Phe Phe Arg
1               5                   10

<210> SEQ ID NO 30
<211> LENGTH: 18
<212> TYPE: PRT
<213> ORGANISM: Homo sapiens

<400> SEQUENCE: 30

Gly Gly Asp Val Ala Ser Met Tyr Thr Pro Asn Ala Gln Tyr Cys Gln
1               5                   10                  15

Met Arg

<210> SEQ ID NO 31
<211> LENGTH: 10
<212> TYPE: PRT
<213> ORGANISM: Homo sapiens

<400> SEQUENCE: 31

Thr Gly Ala Val Ser Gly His Ser Leu Lys
1               5                   10

<210> SEQ ID NO 32
<211> LENGTH: 10
<212> TYPE: PRT
<213> ORGANISM: Homo sapiens

<400> SEQUENCE: 32

Val Ser Ser Val Glu Glu Cys Gln Lys Arg
1               5                   10

<210> SEQ ID NO 33
<211> LENGTH: 9
<212> TYPE: PRT
<213> ORGANISM: Homo sapiens

<400> SEQUENCE: 33

Leu Tyr His Ala Phe Ser Ala Met Lys
1               5

<210> SEQ ID NO 34
<211> LENGTH: 10
<212> TYPE: PRT
<213> ORGANISM: Homo sapiens

<400> SEQUENCE: 34

Leu Tyr His Ala Phe Ser Ala Met Lys Lys
```

-continued

```
1               5                   10
```

<210> SEQ ID NO 35
<211> LENGTH: 8
<212> TYPE: PRT
<213> ORGANISM: Homo sapiens

<400> SEQUENCE: 35

```
Val Ala Thr Thr Val Ile Ser Lys
1               5
```

<210> SEQ ID NO 36
<211> LENGTH: 11
<212> TYPE: PRT
<213> ORGANISM: Homo sapiens

<400> SEQUENCE: 36

```
Leu Cys Gln Asp Leu Gly Pro Gly Ala Phe Arg
1               5                   10
```

<210> SEQ ID NO 37
<211> LENGTH: 19
<212> TYPE: PRT
<213> ORGANISM: Homo sapiens

<400> SEQUENCE: 37

```
Leu Gln Gln Val Leu His Ala Gly Ser Gly Pro Cys Leu Pro His Leu
1               5                   10                  15

Leu Ser Arg
```

<210> SEQ ID NO 38
<211> LENGTH: 21
<212> TYPE: PRT
<213> ORGANISM: Homo sapiens

<400> SEQUENCE: 38

```
Met Phe Thr Thr Ala Pro Asp Gln Val Asp Lys Glu Asp Glu Asp Phe
1               5                   10                  15

Gln Glu Ser Asn Lys
            20
```

<210> SEQ ID NO 39
<211> LENGTH: 26
<212> TYPE: PRT
<213> ORGANISM: Homo sapiens

<400> SEQUENCE: 39

```
Asp Val Asp Lys Glu Phe Tyr Leu Phe Pro Thr Val Phe Asp Glu Asn
1               5                   10                  15

Glu Ser Leu Leu Leu Glu Asp Asn Ile Arg
            20                  25
```

<210> SEQ ID NO 40
<211> LENGTH: 28
<212> TYPE: PRT
<213> ORGANISM: Homo sapiens

<400> SEQUENCE: 40

```
Gln Lys Asp Val Asp Lys Glu Phe Tyr Leu Phe Pro Thr Val Phe Asp
1               5                   10                  15

Glu Asn Glu Ser Leu Leu Leu Glu Asp Asn Ile Arg
            20                  25
```

```
<210> SEQ ID NO 41
<211> LENGTH: 7
<212> TYPE: PRT
<213> ORGANISM: Homo sapiens

<400> SEQUENCE: 41

Tyr Thr Val Asn Gln Cys Arg
1               5

<210> SEQ ID NO 42
<211> LENGTH: 40
<212> TYPE: PRT
<213> ORGANISM: Homo sapiens

<400> SEQUENCE: 42

Ala Gly Phe Glu Trp Asn Glu Asp Gly Ala Gly Thr Thr Pro Ser Pro
1               5                   10                  15

Gly Leu Gln Pro Ala His Leu Thr Phe Pro Leu Asp Tyr His Leu Asn
            20                  25                  30

Gln Pro Phe Ile Phe Val Leu Arg
        35                  40

<210> SEQ ID NO 43
<211> LENGTH: 12
<212> TYPE: PRT
<213> ORGANISM: Homo sapiens

<400> SEQUENCE: 43

Asp Thr Asp Thr Gly Ala Leu Leu Phe Ile Gly Lys
1               5                   10

<210> SEQ ID NO 44
<211> LENGTH: 19
<212> TYPE: PRT
<213> ORGANISM: Homo sapiens

<400> SEQUENCE: 44

Ile Ala Gln Leu Pro Leu Thr Gly Ser Met Ser Ile Ile Phe Phe Leu
1               5                   10                  15

Pro Leu Lys

<210> SEQ ID NO 45
<211> LENGTH: 7
<212> TYPE: PRT
<213> ORGANISM: Homo sapiens

<400> SEQUENCE: 45

Ile Thr Gly Lys Pro Ile Lys
1               5

<210> SEQ ID NO 46
<211> LENGTH: 14
<212> TYPE: PRT
<213> ORGANISM: Homo sapiens

<400> SEQUENCE: 46

Ile Thr Gly Lys Pro Ile Lys Leu Thr Gln Val Glu His Arg
1               5                   10

<210> SEQ ID NO 47
<211> LENGTH: 13
<212> TYPE: PRT
<213> ORGANISM: Homo sapiens

<400> SEQUENCE: 47
```

Lys Thr Ser Leu Glu Asp Phe Tyr Leu Asp Glu Arg
1               5                  10

<210> SEQ ID NO 48
<211> LENGTH: 11
<212> TYPE: PRT
<213> ORGANISM: Homo sapiens

<400> SEQUENCE: 48

Leu Lys Leu Ser Tyr Glu Gly Glu Val Thr Lys
1               5                  10

<210> SEQ ID NO 49
<211> LENGTH: 12
<212> TYPE: PRT
<213> ORGANISM: Homo sapiens

<400> SEQUENCE: 49

Leu Gln Ser Leu Phe Asp Ser Pro Asp Phe Ser Lys
1               5                  10

<210> SEQ ID NO 50
<211> LENGTH: 9
<212> TYPE: PRT
<213> ORGANISM: Homo sapiens

<400> SEQUENCE: 50

Leu Ser Tyr Glu Gly Glu Val Thr Lys
1               5

<210> SEQ ID NO 51
<211> LENGTH: 10
<212> TYPE: PRT
<213> ORGANISM: Homo sapiens

<400> SEQUENCE: 51

Thr Val Gln Ala Val Leu Thr Val Pro Lys
1               5                  10

<210> SEQ ID NO 52
<211> LENGTH: 11
<212> TYPE: PRT
<213> ORGANISM: Homo sapiens

<400> SEQUENCE: 52

Thr Val Arg Val Pro Met Met Ser Asp Pro Lys
1               5                  10

<210> SEQ ID NO 53
<211> LENGTH: 10
<212> TYPE: PRT
<213> ORGANISM: Homo sapiens

<400> SEQUENCE: 53

Tyr Gly Leu Asp Ser Asp Leu Ser Cys Lys
1               5                  10

<210> SEQ ID NO 54
<211> LENGTH: 7
<212> TYPE: PRT
<213> ORGANISM: Homo sapiens

<400> SEQUENCE: 54

Gly Tyr Gly Phe Tyr Thr Lys
1               5

```
<210> SEQ ID NO 55
<211> LENGTH: 14
<212> TYPE: PRT
<213> ORGANISM: Homo sapiens

<400> SEQUENCE: 55

Leu Pro Val Ala Asn Pro Gln Ala Cys Glu Asn Trp Leu Arg
1               5                   10

<210> SEQ ID NO 56
<211> LENGTH: 13
<212> TYPE: PRT
<213> ORGANISM: Homo sapiens

<400> SEQUENCE: 56

Leu Gly Asn Gln Glu Pro Gly Gly Gln Thr Ala Leu Lys
1               5                   10

<210> SEQ ID NO 57
<211> LENGTH: 19
<212> TYPE: PRT
<213> ORGANISM: Homo sapiens

<400> SEQUENCE: 57

Leu Gln Gln Val Leu His Ala Gly Ser Gly Pro Cys Leu Pro His Leu
1               5                   10                  15

Leu Ser Arg

<210> SEQ ID NO 58
<211> LENGTH: 10
<212> TYPE: PRT
<213> ORGANISM: Homo sapiens

<400> SEQUENCE: 58

Asn Lys Phe Asp Pro Ser Leu Thr Gln Arg
1               5                   10

<210> SEQ ID NO 59
<211> LENGTH: 27
<212> TYPE: PRT
<213> ORGANISM: Homo sapiens

<400> SEQUENCE: 59

Ile Gln Glu Phe Leu Ser Gly Leu Pro Glu Asp Thr Val Leu Leu Leu
1               5                   10                  15

Leu Asn Ala Ile His Phe Gln Gly Phe Trp Arg
                20                  25

<210> SEQ ID NO 60
<211> LENGTH: 11
<212> TYPE: PRT
<213> ORGANISM: Homo sapiens

<400> SEQUENCE: 60

Leu Cys Gln Asp Leu Gly Pro Gly Ala Phe Arg
1               5                   10

<210> SEQ ID NO 61
<211> LENGTH: 21
<212> TYPE: PRT
<213> ORGANISM: Homo sapiens

<400> SEQUENCE: 61
```

```
Leu Gly Asn Gln Glu Pro Gly Gly Gln Thr Ala Leu Lys Ser Pro Pro
1               5                   10                  15

Gly Val Cys Ser Arg
            20

<210> SEQ ID NO 62
<211> LENGTH: 17
<212> TYPE: PRT
<213> ORGANISM: Homo sapiens

<400> SEQUENCE: 62

Ser Pro Pro Gly Val Cys Ser Arg Asp Pro Thr Pro Glu Gln Thr His
1               5                   10                  15

Arg

<210> SEQ ID NO 63
<211> LENGTH: 39
<212> TYPE: PRT
<213> ORGANISM: Homo sapiens

<400> SEQUENCE: 63

Ala Pro His Gly Pro Gly Leu Ile Tyr Arg Gln Pro Asn Cys Asp Asp
1               5                   10                  15

Pro Glu Thr Glu Glu Ala Ala Leu Val Ala Ile Asp Tyr Ile Asn Gln
                20                  25                  30

Asn Leu Pro Trp Gly Tyr Lys
            35

<210> SEQ ID NO 64
<211> LENGTH: 24
<212> TYPE: PRT
<213> ORGANISM: Homo sapiens

<400> SEQUENCE: 64

Ala Gln Leu Val Pro Leu Pro Pro Ser Thr Tyr Val Glu Phe Thr Val
1               5                   10                  15

Ser Gly Thr Asp Cys Val Ala Lys
            20

<210> SEQ ID NO 65
<211> LENGTH: 7
<212> TYPE: PRT
<213> ORGANISM: Homo sapiens

<400> SEQUENCE: 65

Cys Asn Leu Leu Ala Glu Lys
1               5

<210> SEQ ID NO 66
<211> LENGTH: 14
<212> TYPE: PRT
<213> ORGANISM: Homo sapiens

<400> SEQUENCE: 66

Glu His Ala Val Glu Gly Asp Cys Asp Phe Gln Leu Leu Lys
1               5                   10

<210> SEQ ID NO 67
<211> LENGTH: 7
<212> TYPE: PRT
<213> ORGANISM: Homo sapiens

<400> SEQUENCE: 67
```

```
Phe Ser Val Val Tyr Ala Lys
1               5

<210> SEQ ID NO 68
<211> LENGTH: 17
<212> TYPE: PRT
<213> ORGANISM: Homo sapiens

<400> SEQUENCE: 68

Gln Leu Lys Glu His Ala Val Glu Gly Asp Cys Asp Phe Gln Leu Leu
1               5                   10                  15

Lys

<210> SEQ ID NO 69
<211> LENGTH: 6
<212> TYPE: PRT
<213> ORGANISM: Homo sapiens

<400> SEQUENCE: 69

Gln Tyr Gly Phe Cys Lys
1               5

<210> SEQ ID NO 70
<211> LENGTH: 21
<212> TYPE: PRT
<213> ORGANISM: Homo sapiens

<400> SEQUENCE: 70

Val Ile Ile Ser Ala Pro Ser Ala Asp Ala Pro Met Phe Val Met Gly
1               5                   10                  15

Val Asn His Glu Lys
            20

<210> SEQ ID NO 71
<211> LENGTH: 27
<212> TYPE: PRT
<213> ORGANISM: Homo sapiens

<400> SEQUENCE: 71

Val Ile Ile Ser Ala Pro Ser Ala Asp Ala Pro Met Phe Val Met Gly
1               5                   10                  15

Val Asn His Glu Lys Tyr Asp Asn Ser Leu Lys
            20                  25

<210> SEQ ID NO 72
<211> LENGTH: 15
<212> TYPE: PRT
<213> ORGANISM: Homo sapiens

<400> SEQUENCE: 72

Phe Leu Phe Asp Thr Lys Glu Glu Ile Leu Met His Leu Trp Arg
1               5                   10                  15

<210> SEQ ID NO 73
<211> LENGTH: 13
<212> TYPE: PRT
<213> ORGANISM: Homo sapiens

<400> SEQUENCE: 73

Leu Phe Ala Ala Phe Phe Leu Glu Met Ala Gln Leu His
1               5                   10

<210> SEQ ID NO 74
<211> LENGTH: 20
```

```
<212> TYPE: PRT
<213> ORGANISM: Homo sapiens

<400> SEQUENCE: 74

Ser Val Val Leu Ile Pro Leu Gly Ala Val Asp Asp Gly Glu His Ser
1               5                   10                  15

Gln Asn Glu Lys
            20

<210> SEQ ID NO 75
<211> LENGTH: 19
<212> TYPE: PRT
<213> ORGANISM: Homo sapiens

<400> SEQUENCE: 75

Tyr Pro Ser Leu Ser Ile His Gly Ile Glu Gly Ala Phe Asp Glu Pro
1               5                   10                  15

Gly Thr Lys

<210> SEQ ID NO 76
<211> LENGTH: 21
<212> TYPE: PRT
<213> ORGANISM: Homo sapiens

<400> SEQUENCE: 76

Val Ile Ile Ser Ala Pro Ser Ala Asp Ala Pro Met Phe Val Met Gly
1               5                   10                  15

Val Asn His Glu Lys
            20

<210> SEQ ID NO 77
<211> LENGTH: 27
<212> TYPE: PRT
<213> ORGANISM: Homo sapiens

<400> SEQUENCE: 77

Val Ile Ile Ser Ala Pro Ser Ala Asp Ala Pro Met Phe Val Met Gly
1               5                   10                  15

Val Asn His Glu Lys Tyr Asp Asn Ser Leu Lys
            20                  25

<210> SEQ ID NO 78
<211> LENGTH: 15
<212> TYPE: PRT
<213> ORGANISM: Homo sapiens

<400> SEQUENCE: 78

Ala Asp Ser Pro Met Asp Asp Phe Phe Gln Cys Val Asn Gly Lys
1               5                   10                  15

<210> SEQ ID NO 79
<211> LENGTH: 12
<212> TYPE: PRT
<213> ORGANISM: Homo sapiens

<400> SEQUENCE: 79

Leu Val Asp Gln Asp Lys Thr Met Phe Ile Cys Lys
1               5                   10

<210> SEQ ID NO 80
<211> LENGTH: 16
<212> TYPE: PRT
<213> ORGANISM: Homo sapiens
```

```
<400> SEQUENCE: 80

Thr Met Gly Tyr Gln Asp Phe Ala Asp Val Val Cys Tyr Thr Gln Lys
1               5                   10                  15

<210> SEQ ID NO 81
<211> LENGTH: 18
<212> TYPE: PRT
<213> ORGANISM: Homo sapiens

<400> SEQUENCE: 81

Ala Cys Asp Gly Ile Asn Asp Cys Gly Asp Gln Ser Asp Glu Leu Cys
1               5                   10                  15

Cys Lys

<210> SEQ ID NO 82
<211> LENGTH: 9
<212> TYPE: PRT
<213> ORGANISM: Homo sapiens

<400> SEQUENCE: 82

Cys Ile Glu Gly Thr Cys Val Cys Lys
1               5

<210> SEQ ID NO 83
<211> LENGTH: 19
<212> TYPE: PRT
<213> ORGANISM: Homo sapiens

<400> SEQUENCE: 83

Glu Ala Asn Val Ala Cys Leu Asp Leu Gly Phe Gln Gln Gly Ala Asp
1               5                   10                  15

Thr Gln Arg

<210> SEQ ID NO 84
<211> LENGTH: 13
<212> TYPE: PRT
<213> ORGANISM: Homo sapiens

<400> SEQUENCE: 84

Gly Leu Glu Thr Ser Leu Ala Glu Cys Thr Phe Thr Lys
1               5                   10

<210> SEQ ID NO 85
<211> LENGTH: 13
<212> TYPE: PRT
<213> ORGANISM: Homo sapiens

<400> SEQUENCE: 85

His Gly Asn Thr Asp Ser Glu Gly Ile Val Glu Val Lys
1               5                   10

<210> SEQ ID NO 86
<211> LENGTH: 14
<212> TYPE: PRT
<213> ORGANISM: Homo sapiens

<400> SEQUENCE: 86

Lys Val Thr Tyr Thr Ser Gln Glu Asp Leu Val Glu Lys Lys
1               5                   10

<210> SEQ ID NO 87
<211> LENGTH: 9
<212> TYPE: PRT
<213> ORGANISM: Homo sapiens
```

```
<400> SEQUENCE: 87

Lys Tyr Thr His Leu Ser Cys Asp Lys
1               5

<210> SEQ ID NO 88
<211> LENGTH: 17
<212> TYPE: PRT
<213> ORGANISM: Homo sapiens

<400> SEQUENCE: 88

Lys Tyr Thr His Leu Ser Cys Asp Lys Val Phe Cys Gln Pro Trp Gln
1               5                   10                  15

Arg

<210> SEQ ID NO 89
<211> LENGTH: 10
<212> TYPE: PRT
<213> ORGANISM: Homo sapiens

<400> SEQUENCE: 89

Arg Ser Phe Pro Thr Tyr Cys Gln Gln Lys
1               5                   10

<210> SEQ ID NO 90
<211> LENGTH: 17
<212> TYPE: PRT
<213> ORGANISM: Homo sapiens

<400> SEQUENCE: 90

Arg Thr Met Gly Tyr Gln Asp Phe Ala Asp Val Val Cys Tyr Thr Gln
1               5                   10                  15

Lys

<210> SEQ ID NO 91
<211> LENGTH: 9
<212> TYPE: PRT
<213> ORGANISM: Homo sapiens

<400> SEQUENCE: 91

Ser Phe Pro Thr Tyr Cys Gln Gln Lys
1               5

<210> SEQ ID NO 92
<211> LENGTH: 10
<212> TYPE: PRT
<213> ORGANISM: Homo sapiens

<400> SEQUENCE: 92

Ser Leu Glu Cys Leu His Pro Gly Thr Lys
1               5                   10

<210> SEQ ID NO 93
<211> LENGTH: 6
<212> TYPE: PRT
<213> ORGANISM: Homo sapiens

<400> SEQUENCE: 93

Thr Met Phe Ile Cys Lys
1               5

<210> SEQ ID NO 94
<211> LENGTH: 8
<212> TYPE: PRT
```

<213> ORGANISM: Homo sapiens

<400> SEQUENCE: 94

Tyr Thr His Leu Ser Cys Asp Lys
1               5

<210> SEQ ID NO 95
<211> LENGTH: 12
<212> TYPE: PRT
<213> ORGANISM: Homo sapiens

<400> SEQUENCE: 95

Ala Ser Ser Ile Ile Asp Glu Leu Phe Gln Asp Arg
1               5                   10

<210> SEQ ID NO 96
<211> LENGTH: 16
<212> TYPE: PRT
<213> ORGANISM: Homo sapiens

<400> SEQUENCE: 96

Ala Ser Ser Ile Ile Asp Glu Leu Phe Gln Asp Arg Phe Phe Thr Arg
1               5                   10                  15

<210> SEQ ID NO 97
<211> LENGTH: 18
<212> TYPE: PRT
<213> ORGANISM: Homo sapiens

<400> SEQUENCE: 97

Cys Arg Glu Ile Leu Ser Val Asp Cys Ser Thr Asn Asn Pro Ser Gln
1               5                   10                  15

Ala Lys

<210> SEQ ID NO 98
<211> LENGTH: 18
<212> TYPE: PRT
<213> ORGANISM: Homo sapiens

<400> SEQUENCE: 98

Asp Gln Thr Val Ser Asp Asn Glu Leu Gln Glu Met Ser Asn Gln Gly
1               5                   10                  15

Ser Lys

<210> SEQ ID NO 99
<211> LENGTH: 16
<212> TYPE: PRT
<213> ORGANISM: Homo sapiens

<400> SEQUENCE: 99

Glu Ile Leu Ser Val Asp Cys Ser Thr Asn Asn Pro Ser Gln Ala Lys
1               5                   10                  15

<210> SEQ ID NO 100
<211> LENGTH: 10
<212> TYPE: PRT
<213> ORGANISM: Homo sapiens

<400> SEQUENCE: 100

Glu Ile Gln Asn Ala Val Asn Gly Val Lys
1               5                   10

<210> SEQ ID NO 101
<211> LENGTH: 11

```
<210> SEQ ID NO 101
<211> LENGTH: 11
<212> TYPE: PRT
<213> ORGANISM: Homo sapiens

<400> SEQUENCE: 101

Glu Leu Asp Glu Ser Leu Gln Val Ala Glu Arg
1               5                   10

<210> SEQ ID NO 102
<211> LENGTH: 16
<212> TYPE: PRT
<213> ORGANISM: Homo sapiens

<400> SEQUENCE: 102

Glu Pro Gln Asp Thr Tyr His Tyr Leu Pro Phe Ser Leu Pro His Arg
1               5                   10                  15

<210> SEQ ID NO 103
<211> LENGTH: 20
<212> TYPE: PRT
<213> ORGANISM: Homo sapiens

<400> SEQUENCE: 103

Phe Phe Thr Arg Glu Pro Gln Asp Thr Tyr His Tyr Leu Pro Phe Ser
1               5                   10                  15

Leu Pro His Arg
            20

<210> SEQ ID NO 104
<211> LENGTH: 15
<212> TYPE: PRT
<213> ORGANISM: Homo sapiens

<400> SEQUENCE: 104

Gln Gln Thr His Met Leu Asp Val Met Gln Asp His Phe Ser Arg
1               5                   10                  15

<210> SEQ ID NO 105
<211> LENGTH: 8
<212> TYPE: PRT
<213> ORGANISM: Homo sapiens

<400> SEQUENCE: 105

Arg Pro His Phe Phe Phe Pro Lys
1               5

<210> SEQ ID NO 106
<211> LENGTH: 10
<212> TYPE: PRT
<213> ORGANISM: Homo sapiens

<400> SEQUENCE: 106

Thr Leu Leu Ser Asn Leu Glu Glu Ala Lys
1               5                   10

<210> SEQ ID NO 107
<211> LENGTH: 11
<212> TYPE: PRT
<213> ORGANISM: Homo sapiens

<400> SEQUENCE: 107

Thr Leu Leu Ser Asn Leu Glu Glu Ala Lys Lys
1               5                   10

<210> SEQ ID NO 108
<211> LENGTH: 6
```

<212> TYPE: PRT
<213> ORGANISM: Homo sapiens

<400> SEQUENCE: 108

Tyr Asn Glu Leu Leu Lys
1               5

<210> SEQ ID NO 109
<211> LENGTH: 14
<212> TYPE: PRT
<213> ORGANISM: Homo sapiens

<400> SEQUENCE: 109

Tyr Val Asn Lys Glu Ile Gln Asn Ala Val Asn Gly Val Lys
1               5                   10

<210> SEQ ID NO 110
<211> LENGTH: 8
<212> TYPE: PRT
<213> ORGANISM: Homo sapiens

<400> SEQUENCE: 110

Asn Val Val Phe Val Ile Asp Lys
1               5

<210> SEQ ID NO 111
<211> LENGTH: 15
<212> TYPE: PRT
<213> ORGANISM: Homo sapiens

<400> SEQUENCE: 111

Asn Val Val Phe Val Ile Asp Lys Ser Gly Ser Met Ser Gly Arg
1               5                   10                  15

<210> SEQ ID NO 112
<211> LENGTH: 16
<212> TYPE: PRT
<213> ORGANISM: Homo sapiens

<400> SEQUENCE: 112

Ala Ala Gly Asn Glu Cys Pro Glu Leu Gln Pro Pro Val His Gly Lys
1               5                   10                  15

<210> SEQ ID NO 113
<211> LENGTH: 15
<212> TYPE: PRT
<213> ORGANISM: Homo sapiens

<400> SEQUENCE: 113

Thr Gly Val Ile Thr Ser Pro Asp Phe Pro Asn Pro Tyr Pro Lys
1               5                   10                  15

<210> SEQ ID NO 114
<211> LENGTH: 16
<212> TYPE: PRT
<213> ORGANISM: Homo sapiens

<400> SEQUENCE: 114

Tyr Phe Phe Lys Asp Gln Val Leu Val Ser Cys Asp Thr Gly Tyr Lys
1               5                   10                  15

<210> SEQ ID NO 115
<211> LENGTH: 13
<212> TYPE: PRT
<213> ORGANISM: Homo sapiens

<400> SEQUENCE: 115

Glu Ser Leu Leu Asn His Phe Leu Tyr Glu Val Ala Arg
1               5                   10

<210> SEQ ID NO 116
<211> LENGTH: 7
<212> TYPE: PRT
<213> ORGANISM: Homo sapiens

<400> SEQUENCE: 116

Phe Leu Val Asn Leu Val Lys
1               5

<210> SEQ ID NO 117
<211> LENGTH: 11
<212> TYPE: PRT
<213> ORGANISM: Homo sapiens

<400> SEQUENCE: 117

Phe Thr Asp Ser Glu Asn Val Cys Gln Glu Arg
1               5                   10

<210> SEQ ID NO 118
<211> LENGTH: 14
<212> TYPE: PRT
<213> ORGANISM: Homo sapiens

<400> SEQUENCE: 118

Gly Gln Cys Ile Ile Asn Ser Asn Lys Asp Asp Arg Pro Lys
1               5                   10

<210> SEQ ID NO 119
<211> LENGTH: 16
<212> TYPE: PRT
<213> ORGANISM: Homo sapiens

<400> SEQUENCE: 119

Ile Ala Pro Gln Leu Ser Thr Glu Glu Leu Val Ser Leu Gly Glu Lys
1               5                   10                  15

<210> SEQ ID NO 120
<211> LENGTH: 23
<212> TYPE: PRT
<213> ORGANISM: Homo sapiens

<400> SEQUENCE: 120

Leu Lys His Glu Leu Thr Asp Glu Glu Leu Gln Ser Leu Phe Thr Asn
1               5                   10                  15

Phe Ala Asn Val Val Asp Lys
                20

<210> SEQ ID NO 121
<211> LENGTH: 12
<212> TYPE: PRT
<213> ORGANISM: Homo sapiens

<400> SEQUENCE: 121

Arg His Pro Asp Leu Ser Ile Pro Glu Leu Leu Arg
1               5                   10

<210> SEQ ID NO 122
<211> LENGTH: 22
<212> TYPE: PRT
<213> ORGANISM: Homo sapiens

```
<400> SEQUENCE: 122

Arg Asn Pro Phe Val Phe Ala Pro Thr Leu Leu Thr Val Ala Val His
1               5                   10                  15

Phe Glu Glu Val Ala Lys
            20

<210> SEQ ID NO 123
<211> LENGTH: 11
<212> TYPE: PRT
<213> ORGANISM: Homo sapiens

<400> SEQUENCE: 123

Arg Pro Cys Phe Glu Ser Leu Lys Ala Asp Lys
1               5                   10

<210> SEQ ID NO 124
<211> LENGTH: 15
<212> TYPE: PRT
<213> ORGANISM: Homo sapiens

<400> SEQUENCE: 124

Ser Cys Cys Glu Glu Gln Asn Lys Val Asn Cys Leu Gln Thr Arg
1               5                   10                  15

<210> SEQ ID NO 125
<211> LENGTH: 17
<212> TYPE: PRT
<213> ORGANISM: Homo sapiens

<400> SEQUENCE: 125

Ser Asp Val Gly Phe Leu Pro Pro Phe Pro Thr Leu Asp Pro Glu Glu
1               5                   10                  15

Lys

<210> SEQ ID NO 126
<211> LENGTH: 11
<212> TYPE: PRT
<213> ORGANISM: Homo sapiens

<400> SEQUENCE: 126

Thr Ile Asn Pro Ala Val Asp His Cys Cys Lys
1               5                   10

<210> SEQ ID NO 127
<211> LENGTH: 6
<212> TYPE: PRT
<213> ORGANISM: Homo sapiens

<400> SEQUENCE: 127

Thr Asn Phe Ala Phe Arg
1               5

<210> SEQ ID NO 128
<211> LENGTH: 22
<212> TYPE: PRT
<213> ORGANISM: Homo sapiens

<400> SEQUENCE: 128

Phe Asn Arg Pro Phe Leu Met Ile Ile Val Pro Thr Asp Thr Gln Asn
1               5                   10                  15

Ile Phe Phe Met Ser Lys
            20
```

<210> SEQ ID NO 129
<211> LENGTH: 16
<212> TYPE: PRT
<213> ORGANISM: Homo sapiens

<400> SEQUENCE: 129

Ala Lys Trp Glu Met Pro Phe Asp Pro Gln Asp Thr His Gln Ser Arg
1               5                   10                  15

<210> SEQ ID NO 130
<211> LENGTH: 10
<212> TYPE: PRT
<213> ORGANISM: Homo sapiens

<400> SEQUENCE: 130

Ala Asp Leu Ser Gly Ile Thr Gly Ala Arg
1               5                   10

<210> SEQ ID NO 131
<211> LENGTH: 19
<212> TYPE: PRT
<213> ORGANISM: Homo sapiens

<400> SEQUENCE: 131

Ala Val Leu Asp Val Phe Glu Glu Gly Thr Glu Ala Ser Ala Ala Thr
1               5                   10                  15

Ala Val Lys

<210> SEQ ID NO 132
<211> LENGTH: 12
<212> TYPE: PRT
<213> ORGANISM: Homo sapiens

<400> SEQUENCE: 132

Asp Glu Glu Leu Ser Cys Thr Val Val Glu Leu Lys
1               5                   10

<210> SEQ ID NO 133
<211> LENGTH: 20
<212> TYPE: PRT
<213> ORGANISM: Homo sapiens

<400> SEQUENCE: 133

Asp Tyr Asn Leu Asn Asp Ile Leu Leu Gln Leu Gly Ile Glu Glu Ala
1               5                   10                  15

Phe Thr Ser Lys
            20

<210> SEQ ID NO 134
<211> LENGTH: 9
<212> TYPE: PRT
<213> ORGANISM: Homo sapiens

<400> SEQUENCE: 134

Glu Ile Gly Glu Leu Tyr Leu Pro Lys
1               5

<210> SEQ ID NO 135
<211> LENGTH: 8
<212> TYPE: PRT
<213> ORGANISM: Homo sapiens

<400> SEQUENCE: 135

Glu Gln Leu Ser Leu Leu Asp Arg
1               5

<210> SEQ ID NO 136
<211> LENGTH: 14
<212> TYPE: PRT
<213> ORGANISM: Homo sapiens

<400> SEQUENCE: 136

Glu Gln Leu Ser Leu Leu Asp Arg Phe Thr Glu Asp Ala Lys
1               5                   10

<210> SEQ ID NO 137
<211> LENGTH: 8
<212> TYPE: PRT
<213> ORGANISM: Homo sapiens

<400> SEQUENCE: 137

Gly Lys Ile Thr Asp Leu Ile Lys
1               5

<210> SEQ ID NO 138
<211> LENGTH: 25
<212> TYPE: PRT
<213> ORGANISM: Homo sapiens

<400> SEQUENCE: 138

Gly Lys Ile Thr Asp Leu Ile Lys Asp Leu Asp Ser Gln Thr Met Met
1               5                   10                  15

Val Leu Val Asn Tyr Ile Phe Phe Lys
            20                  25

<210> SEQ ID NO 139
<211> LENGTH: 18
<212> TYPE: PRT
<213> ORGANISM: Homo sapiens

<400> SEQUENCE: 139

His Pro Asn Ser Pro Leu Asp Glu Glu Asn Leu Thr Gln Glu Asn Gln
1               5                   10                  15

Asp Arg

<210> SEQ ID NO 140
<211> LENGTH: 23
<212> TYPE: PRT
<213> ORGANISM: Homo sapiens

<400> SEQUENCE: 140

Ile Thr Asp Leu Ile Lys Asp Leu Asp Ser Gln Thr Met Met Val Leu
1               5                   10                  15

Val Asn Tyr Ile Phe Phe Lys
            20

<210> SEQ ID NO 141
<211> LENGTH: 11
<212> TYPE: PRT
<213> ORGANISM: Homo sapiens

<400> SEQUENCE: 141

Ile Thr Leu Leu Ser Ala Leu Val Glu Thr Arg
1               5                   10

<210> SEQ ID NO 142
<211> LENGTH: 7
<212> TYPE: PRT
<213> ORGANISM: Homo sapiens

```
<400> SEQUENCE: 142

Leu Ile Asn Asp Tyr Val Lys
1               5

<210> SEQ ID NO 143
<211> LENGTH: 18
<212> TYPE: PRT
<213> ORGANISM: Homo sapiens

<400> SEQUENCE: 143

Leu Tyr Gly Ser Glu Ala Phe Ala Thr Asp Phe Gln Asp Ser Ala Ala
1               5                   10                  15

Ala Lys

<210> SEQ ID NO 144
<211> LENGTH: 19
<212> TYPE: PRT
<213> ORGANISM: Homo sapiens

<400> SEQUENCE: 144

Leu Tyr Gly Ser Glu Ala Phe Ala Thr Asp Phe Gln Asp Ser Ala Ala
1               5                   10                  15

Ala Lys Lys

<210> SEQ ID NO 145
<211> LENGTH: 15
<212> TYPE: PRT
<213> ORGANISM: Homo sapiens

<400> SEQUENCE: 145

Met Glu Glu Val Glu Ala Met Leu Leu Pro Glu Thr Leu Lys Arg
1               5                   10                  15

<210> SEQ ID NO 146
<211> LENGTH: 24
<212> TYPE: PRT
<213> ORGANISM: Homo sapiens

<400> SEQUENCE: 146

Met Ser Leu His His Leu Thr Ile Pro Tyr Phe Arg Asp Glu Glu Leu
1               5                   10                  15

Ser Cys Thr Val Val Glu Leu Lys
            20

<210> SEQ ID NO 147
<211> LENGTH: 16
<212> TYPE: PRT
<213> ORGANISM: Homo sapiens

<400> SEQUENCE: 147

Asn Ser Pro Leu Asp Glu Glu Asn Leu Thr Gln Glu Asn Gln Asp Arg
1               5                   10                  15

<210> SEQ ID NO 148
<211> LENGTH: 19
<212> TYPE: PRT
<213> ORGANISM: Homo sapiens

<400> SEQUENCE: 148

Arg Leu Tyr Gly Ser Glu Ala Phe Ala Thr Asp Phe Gln Asp Ser Ala
1               5                   10                  15

Ala Ala Lys
```

<210> SEQ ID NO 149
<211> LENGTH: 20
<212> TYPE: PRT
<213> ORGANISM: Homo sapiens

<400> SEQUENCE: 149

Arg Leu Tyr Gly Ser Glu Ala Phe Ala Thr Asp Phe Gln Asp Ser Ala
1               5                   10                  15

Ala Ala Lys Lys
            20

<210> SEQ ID NO 150
<211> LENGTH: 26
<212> TYPE: PRT
<213> ORGANISM: Homo sapiens

<400> SEQUENCE: 150

Thr Ile Val Arg Phe Asn Arg Pro Phe Leu Met Ile Ile Val Pro Thr
1               5                   10                  15

Asp Thr Gln Asn Ile Phe Phe Met Ser Lys
            20                  25

<210> SEQ ID NO 151
<211> LENGTH: 14
<212> TYPE: PRT
<213> ORGANISM: Homo sapiens

<400> SEQUENCE: 151

Trp Glu Met Pro Phe Asp Pro Gln Asp Thr His Gln Ser Arg
1               5                   10

<210> SEQ ID NO 152
<211> LENGTH: 8
<212> TYPE: PRT
<213> ORGANISM: Homo sapiens

<400> SEQUENCE: 152

Trp Arg Asp Ser Leu Glu Phe Arg
1               5

<210> SEQ ID NO 153
<211> LENGTH: 19
<212> TYPE: PRT
<213> ORGANISM: Homo sapiens

<400> SEQUENCE: 153

Glu Leu Lys Glu Gln Gln Asp Ser Pro Gly Asn Lys Asp Phe Leu Gln
1               5                   10                  15

Ser Leu Lys

<210> SEQ ID NO 154
<211> LENGTH: 24
<212> TYPE: PRT
<213> ORGANISM: Homo sapiens

<400> SEQUENCE: 154

His Gln Met Asp Leu Val Ala Thr Leu Ser Gln Leu Gly Leu Gln Glu
1               5                   10                  15

Leu Phe Gln Ala Pro Asp Leu Arg
            20

<210> SEQ ID NO 155

```
<211> LENGTH: 13
<212> TYPE: PRT
<213> ORGANISM: Homo sapiens

<400> SEQUENCE: 155

Leu Gly Asn Gln Glu Pro Gly Gly Gln Thr Ala Leu Lys
1               5                   10

<210> SEQ ID NO 156
<211> LENGTH: 19
<212> TYPE: PRT
<213> ORGANISM: Homo sapiens

<400> SEQUENCE: 156

Leu Gln Gln Val Leu His Ala Gly Ser Gly Pro Cys Leu Pro His Leu
1               5                   10                  15

Leu Ser Arg

<210> SEQ ID NO 157
<211> LENGTH: 16
<212> TYPE: PRT
<213> ORGANISM: Homo sapiens

<400> SEQUENCE: 157

Leu Val Pro Pro Met Glu Glu Asp Tyr Pro Gln Phe Gly Ser Pro Lys
1               5                   10                  15

<210> SEQ ID NO 158
<211> LENGTH: 10
<212> TYPE: PRT
<213> ORGANISM: Homo sapiens

<400> SEQUENCE: 158

Asn Lys Phe Asp Pro Ser Leu Thr Gln Arg
1               5                   10

<210> SEQ ID NO 159
<211> LENGTH: 19
<212> TYPE: PRT
<213> ORGANISM: Homo sapiens

<400> SEQUENCE: 159

Asp Ser Phe His Leu Asp Glu Gln Phe Thr Val Pro Val Glu Met Met
1               5                   10                  15

Gln Ala Arg

<210> SEQ ID NO 160
<211> LENGTH: 10
<212> TYPE: PRT
<213> ORGANISM: Homo sapiens

<400> SEQUENCE: 160

Gly Asp Lys Leu Phe Gly Pro Asp Leu Lys
1               5                   10

<210> SEQ ID NO 161
<211> LENGTH: 27
<212> TYPE: PRT
<213> ORGANISM: Homo sapiens

<400> SEQUENCE: 161

Ile Gln Glu Phe Leu Ser Gly Leu Pro Glu Asp Thr Val Leu Leu Leu
1               5                   10                  15

Leu Asn Ala Ile His Phe Gln Gly Phe Trp Arg
```

<210> SEQ ID NO 162
<211> LENGTH: 11
<212> TYPE: PRT
<213> ORGANISM: Homo sapiens

<400> SEQUENCE: 162

Leu Cys Gln Asp Leu Gly Pro Gly Ala Phe Arg
1               5                   10

<210> SEQ ID NO 163
<211> LENGTH: 7
<212> TYPE: PRT
<213> ORGANISM: Homo sapiens

<400> SEQUENCE: 163

Leu Phe Gly Pro Asp Leu Lys
1               5

<210> SEQ ID NO 164
<211> LENGTH: 21
<212> TYPE: PRT
<213> ORGANISM: Homo sapiens

<400> SEQUENCE: 164

Leu Gly Asn Gln Glu Pro Gly Gly Gln Thr Ala Leu Lys Ser Pro Pro
1               5                   10                  15

Gly Val Cys Ser Arg
            20

<210> SEQ ID NO 165
<211> LENGTH: 31
<212> TYPE: PRT
<213> ORGANISM: Homo sapiens

<400> SEQUENCE: 165

Met Ser Leu Ser Ser Phe Ser Val Asn Arg Pro Phe Leu Phe Phe Ile
1               5                   10                  15

Phe Glu Asp Thr Thr Gly Leu Pro Leu Phe Val Gly Ser Val Arg
            20                  25                  30

<210> SEQ ID NO 166
<211> LENGTH: 17
<212> TYPE: PRT
<213> ORGANISM: Homo sapiens

<400> SEQUENCE: 166

Ser Pro Pro Gly Val Cys Ser Arg Asp Pro Thr Pro Glu Gln Thr His
1               5                   10                  15

Arg

<210> SEQ ID NO 167
<211> LENGTH: 17
<212> TYPE: PRT
<213> ORGANISM: Homo sapiens

<400> SEQUENCE: 167

Trp Phe Leu Leu Glu Gln Pro Glu Ile Gln Val Ala His Phe Pro Phe
1               5                   10                  15

Lys

<210> SEQ ID NO 168

```
<211> LENGTH: 10
<212> TYPE: PRT
<213> ORGANISM: Homo sapiens

<400> SEQUENCE: 168

Ala Gly Glu Val Gln Glu Pro Glu Leu Arg
1               5                   10

<210> SEQ ID NO 169
<211> LENGTH: 16
<212> TYPE: PRT
<213> ORGANISM: Homo sapiens

<400> SEQUENCE: 169

Glu Ile Pro Ala Trp Val Pro Phe Asp Pro Ala Ala Gln Ile Thr Lys
1               5                   10                  15

<210> SEQ ID NO 170
<211> LENGTH: 21
<212> TYPE: PRT
<213> ORGANISM: Homo sapiens

<400> SEQUENCE: 170

His Val Glu Asp Val Pro Ala Phe Gln Ala Leu Gly Ser Leu Asn Asp
1               5                   10                  15

Leu Gln Phe Phe Arg
            20

<210> SEQ ID NO 171
<211> LENGTH: 12
<212> TYPE: PRT
<213> ORGANISM: Homo sapiens

<400> SEQUENCE: 171

Ala Tyr Leu Glu Glu Glu Cys Pro Ala Thr Leu Arg
1               5                   10

<210> SEQ ID NO 172
<211> LENGTH: 10
<212> TYPE: PRT
<213> ORGANISM: Homo sapiens

<400> SEQUENCE: 172

Cys Leu Ala Tyr Asp Phe Tyr Pro Gly Lys
1               5                   10

<210> SEQ ID NO 173
<211> LENGTH: 7
<212> TYPE: PRT
<213> ORGANISM: Homo sapiens

<400> SEQUENCE: 173

Ile Asp Val His Trp Thr Arg
1               5

<210> SEQ ID NO 174
<211> LENGTH: 13
<212> TYPE: PRT
<213> ORGANISM: Homo sapiens

<400> SEQUENCE: 174

Lys Ala Tyr Leu Glu Glu Glu Cys Pro Ala Thr Leu Arg
1               5                   10

<210> SEQ ID NO 175
```

```
<211> LENGTH: 22
<212> TYPE: PRT
<213> ORGANISM: Homo sapiens

<400> SEQUENCE: 175

Asn Ile Leu Asp Arg Gln Asp Pro Pro Ser Val Val Val Thr Ser His
1               5                   10                  15

Gln Ala Pro Gly Glu Lys
            20

<210> SEQ ID NO 176
<211> LENGTH: 17
<212> TYPE: PRT
<213> ORGANISM: Homo sapiens

<400> SEQUENCE: 176

Gln Asp Pro Pro Ser Val Val Val Thr Ser His Gln Ala Pro Gly Glu
1               5                   10                  15

Lys

<210> SEQ ID NO 177
<211> LENGTH: 12
<212> TYPE: PRT
<213> ORGANISM: Homo sapiens

<400> SEQUENCE: 177

Gln Lys Trp Glu Ala Glu Pro Val Tyr Val Gln Arg
1               5                   10

<210> SEQ ID NO 178
<211> LENGTH: 16
<212> TYPE: PRT
<213> ORGANISM: Homo sapiens

<400> SEQUENCE: 178

Gln Val Glu Gly Met Glu Asp Trp Lys Gln Asp Ser Gln Leu Gln Lys
1               5                   10                  15

<210> SEQ ID NO 179
<211> LENGTH: 7
<212> TYPE: PRT
<213> ORGANISM: Homo sapiens

<400> SEQUENCE: 179

Ser Ser Gly Ala Phe Trp Lys
1               5

<210> SEQ ID NO 180
<211> LENGTH: 12
<212> TYPE: PRT
<213> ORGANISM: Homo sapiens

<400> SEQUENCE: 180

Tyr Ser Leu Thr Tyr Ile Tyr Thr Gly Leu Ser Lys
1               5                   10

<210> SEQ ID NO 181
<211> LENGTH: 13
<212> TYPE: PRT
<213> ORGANISM: Homo sapiens

<400> SEQUENCE: 181

Tyr Tyr Tyr Asp Gly Lys Asp Tyr Ile Glu Phe Asn Lys
1               5                   10
```

```
<210> SEQ ID NO 182
<211> LENGTH: 39
<212> TYPE: PRT
<213> ORGANISM: Homo sapiens

<400> SEQUENCE: 182

Ala Pro His Gly Pro Gly Leu Ile Tyr Arg Gln Pro Asn Cys Asp Asp
1               5                   10                  15

Pro Glu Thr Glu Ala Ala Leu Val Ala Ile Asp Tyr Ile Asn Gln
            20                  25                  30

Asn Leu Pro Trp Gly Tyr Lys
            35

<210> SEQ ID NO 183
<211> LENGTH: 24
<212> TYPE: PRT
<213> ORGANISM: Homo sapiens

<400> SEQUENCE: 183

Ala Gln Leu Val Pro Leu Pro Pro Ser Thr Tyr Val Glu Phe Thr Val
1               5                   10                  15

Ser Gly Thr Asp Cys Val Ala Lys
            20

<210> SEQ ID NO 184
<211> LENGTH: 7
<212> TYPE: PRT
<213> ORGANISM: Homo sapiens

<400> SEQUENCE: 184

Cys Asn Leu Leu Ala Glu Lys
1               5

<210> SEQ ID NO 185
<211> LENGTH: 14
<212> TYPE: PRT
<213> ORGANISM: Homo sapiens

<400> SEQUENCE: 185

Glu His Ala Val Glu Gly Asp Cys Asp Phe Gln Leu Leu Lys
1               5                   10

<210> SEQ ID NO 186
<211> LENGTH: 7
<212> TYPE: PRT
<213> ORGANISM: Homo sapiens

<400> SEQUENCE: 186

Phe Ser Val Val Tyr Ala Lys
1               5

<210> SEQ ID NO 187
<211> LENGTH: 20
<212> TYPE: PRT
<213> ORGANISM: Homo sapiens

<400> SEQUENCE: 187

His Thr Phe Met Gly Val Val Ser Leu Gly Ser Pro Ser Gly Glu Val
1               5                   10                  15

Ser His Pro Arg
            20

<210> SEQ ID NO 188
```

```
<211> LENGTH: 42
<212> TYPE: PRT
<213> ORGANISM: Homo sapiens

<400> SEQUENCE: 188

His Thr Leu Asn Gln Ile Asp Glu Val Lys Val Trp Pro Gln Gln Pro
1               5                   10                  15

Ser Gly Glu Leu Phe Glu Ile Glu Ile Asp Thr Leu Glu Thr Thr Cys
            20                  25                  30

His Val Leu Asp Pro Thr Pro Val Ala Arg
        35                  40

<210> SEQ ID NO 189
<211> LENGTH: 17
<212> TYPE: PRT
<213> ORGANISM: Homo sapiens

<400> SEQUENCE: 189

Gln Leu Lys Glu His Ala Val Glu Gly Asp Cys Asp Phe Gln Leu Leu
1               5                   10                  15

Lys

<210> SEQ ID NO 190
<211> LENGTH: 6
<212> TYPE: PRT
<213> ORGANISM: Homo sapiens

<400> SEQUENCE: 190

Gln Tyr Gly Phe Cys Lys
1               5

<210> SEQ ID NO 191
<211> LENGTH: 21
<212> TYPE: PRT
<213> ORGANISM: Homo sapiens

<400> SEQUENCE: 191

Thr Val Val Gln Pro Ser Val Gly Ala Ala Gly Pro Val Val Pro
1               5                   10                  15

Pro Cys Pro Gly Arg
            20

<210> SEQ ID NO 192
<211> LENGTH: 32
<212> TYPE: PRT
<213> ORGANISM: Homo sapiens

<400> SEQUENCE: 192

Val Trp Pro Gln Gln Pro Ser Gly Glu Leu Phe Glu Ile Glu Ile Asp
1               5                   10                  15

Thr Leu Glu Thr Thr Cys His Val Leu Asp Pro Thr Pro Val Ala Arg
            20                  25                  30

<210> SEQ ID NO 193
<211> LENGTH: 23
<212> TYPE: PRT
<213> ORGANISM: Homo sapiens

<400> SEQUENCE: 193

Lys Met Thr Ser Asn Phe Pro Val Asp Leu Ser Asp Tyr Pro Lys Ser
1               5                   10                  15

Leu His Met Tyr Ala Asn Arg
            20
```

```
<210> SEQ ID NO 194
<211> LENGTH: 23
<212> TYPE: PRT
<213> ORGANISM: Homo sapiens

<400> SEQUENCE: 194

Asn Phe Val Ala Ser His Ile Ala Asn Ile Leu Asn Ser Glu Glu Leu
1               5                   10                  15

Asp Ile Gln Asp Leu Lys Lys
            20

<210> SEQ ID NO 195
<211> LENGTH: 8
<212> TYPE: PRT
<213> ORGANISM: Homo sapiens

<400> SEQUENCE: 195

Phe Trp Thr Ser Phe Phe Pro Lys
1               5

<210> SEQ ID NO 196
<211> LENGTH: 16
<212> TYPE: PRT
<213> ORGANISM: Homo sapiens

<400> SEQUENCE: 196

Val Leu Glu Met Thr Gly Asn Ile Asp Glu Ala Glu Trp Glu Trp Lys
1               5                   10                  15

<210> SEQ ID NO 197
<211> LENGTH: 11
<212> TYPE: PRT
<213> ORGANISM: Homo sapiens

<400> SEQUENCE: 197

Ala Leu Glu Gln Asp Leu Pro Val Asn Ile Lys
1               5                   10

<210> SEQ ID NO 198
<211> LENGTH: 15
<212> TYPE: PRT
<213> ORGANISM: Homo sapiens

<400> SEQUENCE: 198

Glu Trp Val Ala Ile Glu Ser Asp Ser Val Gln Pro Val Pro Arg
1               5                   10                  15

<210> SEQ ID NO 199
<211> LENGTH: 15
<212> TYPE: PRT
<213> ORGANISM: Homo sapiens

<400> SEQUENCE: 199

Phe Leu Phe Asp Thr Lys Glu Glu Ile Leu Met His Leu Trp Arg
1               5                   10                  15

<210> SEQ ID NO 200
<211> LENGTH: 20
<212> TYPE: PRT
<213> ORGANISM: Homo sapiens

<400> SEQUENCE: 200

Gly Ala Thr Asp Asn Lys Gly Pro Val Leu Ala Trp Ile Asn Ala Val
1               5                   10                  15
```

Ser Ala Phe Arg
            20

<210> SEQ ID NO 201
<211> LENGTH: 13
<212> TYPE: PRT
<213> ORGANISM: Homo sapiens

<400> SEQUENCE: 201

Leu Phe Ala Ala Phe Phe Leu Glu Met Ala Gln Leu His
1               5                   10

<210> SEQ ID NO 202
<211> LENGTH: 11
<212> TYPE: PRT
<213> ORGANISM: Homo sapiens

<400> SEQUENCE: 202

Met Met Ala Val Ala Ala Asp Thr Leu Gln Arg
1               5                   10

<210> SEQ ID NO 203
<211> LENGTH: 20
<212> TYPE: PRT
<213> ORGANISM: Homo sapiens

<400> SEQUENCE: 203

Ser Val Val Leu Ile Pro Leu Gly Ala Val Asp Asp Gly Glu His Ser
1               5                   10                  15

Gln Asn Glu Lys
            20

<210> SEQ ID NO 204
<211> LENGTH: 17
<212> TYPE: PRT
<213> ORGANISM: Homo sapiens

<400> SEQUENCE: 204

Val Phe Gln Tyr Ile Asp Leu His Gln Asp Glu Phe Val Gln Thr Leu
1               5                   10                  15

Lys

<210> SEQ ID NO 205
<211> LENGTH: 19
<212> TYPE: PRT
<213> ORGANISM: Homo sapiens

<400> SEQUENCE: 205

Tyr Pro Ser Leu Ser Ile His Gly Ile Glu Gly Ala Phe Asp Glu Pro
1               5                   10                  15

Gly Thr Lys

<210> SEQ ID NO 206
<211> LENGTH: 18
<212> TYPE: PRT
<213> ORGANISM: Homo sapiens

<400> SEQUENCE: 206

Ala Ile His Cys Pro Arg Pro His Asp Phe Glu Asn Gly Glu Tyr Trp
1               5                   10                  15

Pro Arg

<210> SEQ ID NO 207
<211> LENGTH: 10
<212> TYPE: PRT
<213> ORGANISM: Homo sapiens

<400> SEQUENCE: 207

Ala Leu Phe Val Ser Glu Glu Glu Lys Lys
1               5                   10

<210> SEQ ID NO 208
<211> LENGTH: 14
<212> TYPE: PRT
<213> ORGANISM: Homo sapiens

<400> SEQUENCE: 208

Ala Leu Arg Leu Pro Pro Thr Thr Thr Cys Gln Gln Gln Lys
1               5                   10

<210> SEQ ID NO 209
<211> LENGTH: 24
<212> TYPE: PRT
<213> ORGANISM: Homo sapiens

<400> SEQUENCE: 209

Ala Leu Arg Leu Pro Pro Thr Thr Thr Cys Gln Gln Gln Lys Glu Glu
1               5                   10                  15

Leu Leu Pro Ala Gln Asp Ile Lys
            20

<210> SEQ ID NO 210
<211> LENGTH: 8
<212> TYPE: PRT
<213> ORGANISM: Homo sapiens

<400> SEQUENCE: 210

Cys Leu Val Asn Leu Ile Glu Lys
1               5

<210> SEQ ID NO 211
<211> LENGTH: 10
<212> TYPE: PRT
<213> ORGANISM: Homo sapiens

<400> SEQUENCE: 211

Asp Ala Gln Tyr Ala Pro Gly Tyr Asp Lys
1               5                   10

<210> SEQ ID NO 212
<211> LENGTH: 12
<212> TYPE: PRT
<213> ORGANISM: Homo sapiens

<400> SEQUENCE: 212

Asp Ala Gln Tyr Ala Pro Gly Tyr Asp Lys Val Lys
1               5                   10

<210> SEQ ID NO 213
<211> LENGTH: 21
<212> TYPE: PRT
<213> ORGANISM: Homo sapiens

<400> SEQUENCE: 213

Asp Ala Gln Tyr Ala Pro Gly Tyr Asp Lys Val Lys Asp Ile Ser Glu
1               5                   10                  15

Val Val Thr Pro Arg

```
            20

<210> SEQ ID NO 214
<211> LENGTH: 14
<212> TYPE: PRT
<213> ORGANISM: Homo sapiens

<400> SEQUENCE: 214

Asp Phe His Ile Asn Leu Phe Gln Val Leu Pro Trp Leu Lys
1               5                   10

<210> SEQ ID NO 215
<211> LENGTH: 9
<212> TYPE: PRT
<213> ORGANISM: Homo sapiens

<400> SEQUENCE: 215

Asp Ile Ser Glu Val Val Thr Pro Arg
1               5

<210> SEQ ID NO 216
<211> LENGTH: 18
<212> TYPE: PRT
<213> ORGANISM: Homo sapiens

<400> SEQUENCE: 216

Asp Leu Glu Ile Glu Val Val Leu Phe His Pro Asn Tyr Asn Ile Asn
1               5                   10                  15

Gly Lys

<210> SEQ ID NO 217
<211> LENGTH: 9
<212> TYPE: PRT
<213> ORGANISM: Homo sapiens

<400> SEQUENCE: 217

Asp Leu Leu Tyr Ile Gly Lys Asp Arg
1               5

<210> SEQ ID NO 218
<211> LENGTH: 8
<212> TYPE: PRT
<213> ORGANISM: Homo sapiens

<400> SEQUENCE: 218

Asp Asn Glu Gln His Val Phe Lys
1               5

<210> SEQ ID NO 219
<211> LENGTH: 16
<212> TYPE: PRT
<213> ORGANISM: Homo sapiens

<400> SEQUENCE: 219

Glu Ala Gly Ile Pro Glu Phe Tyr Asp Tyr Asp Val Ala Leu Ile Lys
1               5                   10                  15

<210> SEQ ID NO 220
<211> LENGTH: 26
<212> TYPE: PRT
<213> ORGANISM: Homo sapiens

<400> SEQUENCE: 220

Glu Asp Tyr Leu Asp Val Tyr Val Phe Gly Val Gly Pro Leu Val Asn
1               5                   10                  15
```

Gln Val Asn Ile Asn Ala Leu Ala Ser Lys
            20                  25

<210> SEQ ID NO 221
<211> LENGTH: 27
<212> TYPE: PRT
<213> ORGANISM: Homo sapiens

<400> SEQUENCE: 221

Glu Asp Tyr Leu Asp Val Tyr Val Phe Gly Val Gly Pro Leu Val Asn
1               5                   10                  15

Gln Val Asn Ile Asn Ala Leu Ala Ser Lys Lys
            20                  25

<210> SEQ ID NO 222
<211> LENGTH: 10
<212> TYPE: PRT
<213> ORGANISM: Homo sapiens

<400> SEQUENCE: 222

Glu Glu Leu Leu Pro Ala Gln Asp Ile Lys
1               5                   10

<210> SEQ ID NO 223
<211> LENGTH: 11
<212> TYPE: PRT
<213> ORGANISM: Homo sapiens

<400> SEQUENCE: 223

Glu Lys Leu Gln Asp Glu Asp Leu Gly Phe Leu
1               5                   10

<210> SEQ ID NO 224
<211> LENGTH: 17
<212> TYPE: PRT
<213> ORGANISM: Homo sapiens

<400> SEQUENCE: 224

Phe Leu Cys Thr Gly Gly Val Ser Pro Tyr Ala Asp Pro Asn Thr Cys
1               5                   10                  15

Arg

<210> SEQ ID NO 225
<211> LENGTH: 29
<212> TYPE: PRT
<213> ORGANISM: Homo sapiens

<400> SEQUENCE: 225

Phe Leu Cys Thr Gly Gly Val Ser Pro Tyr Ala Asp Pro Asn Thr Cys
1               5                   10                  15

Arg Gly Asp Ser Gly Gly Pro Leu Ile Val His Lys Arg
            20                  25

<210> SEQ ID NO 226
<211> LENGTH: 11
<212> TYPE: PRT
<213> ORGANISM: Homo sapiens

<400> SEQUENCE: 226

Gly Asp Ser Gly Gly Pro Leu Ile Val His Lys
1               5                   10

<210> SEQ ID NO 227

```
<211> LENGTH: 12
<212> TYPE: PRT
<213> ORGANISM: Homo sapiens

<400> SEQUENCE: 227

Gly Asp Ser Gly Gly Pro Leu Ile Val His Lys Arg
1               5                   10

<210> SEQ ID NO 228
<211> LENGTH: 32
<212> TYPE: PRT
<213> ORGANISM: Homo sapiens

<400> SEQUENCE: 228

Gly His Glu Ser Cys Met Gly Ala Val Val Ser Glu Tyr Phe Val Leu
1               5                   10                  15

Thr Ala Ala His Cys Phe Thr Val Asp Asp Lys Glu His Ser Ile Lys
            20                  25                  30

<210> SEQ ID NO 229
<211> LENGTH: 25
<212> TYPE: PRT
<213> ORGANISM: Homo sapiens

<400> SEQUENCE: 229

His Val Ile Ile Leu Met Thr Asp Gly Leu His Asn Met Gly Gly Asp
1               5                   10                  15

Pro Ile Thr Val Ile Asp Glu Ile Arg
            20                  25

<210> SEQ ID NO 230
<211> LENGTH: 32
<212> TYPE: PRT
<213> ORGANISM: Homo sapiens

<400> SEQUENCE: 230

His Val Ile Ile Leu Met Thr Asp Gly Leu His Asn Met Gly Gly Asp
1               5                   10                  15

Pro Ile Thr Val Ile Asp Glu Ile Arg Asp Leu Leu Tyr Ile Gly Lys
            20                  25                  30

<210> SEQ ID NO 231
<211> LENGTH: 9
<212> TYPE: PRT
<213> ORGANISM: Homo sapiens

<400> SEQUENCE: 231

Lys Cys Leu Val Asn Leu Ile Glu Lys
1               5

<210> SEQ ID NO 232
<211> LENGTH: 9
<212> TYPE: PRT
<213> ORGANISM: Homo sapiens

<400> SEQUENCE: 232

Lys Asp Asn Glu Gln His Val Phe Lys
1               5

<210> SEQ ID NO 233
<211> LENGTH: 6
<212> TYPE: PRT
<213> ORGANISM: Homo sapiens

<400> SEQUENCE: 233
```

```
Lys Glu Val Tyr Ile Lys
1               5

<210> SEQ ID NO 234
<211> LENGTH: 13
<212> TYPE: PRT
<213> ORGANISM: Homo sapiens

<400> SEQUENCE: 234

Lys Gly Thr Asp Tyr His Lys Gln Pro Trp Gln Ala Lys
1               5                   10

<210> SEQ ID NO 235
<211> LENGTH: 31
<212> TYPE: PRT
<213> ORGANISM: Homo sapiens

<400> SEQUENCE: 235

Lys Asn Pro Arg Glu Asp Tyr Leu Asp Val Tyr Val Phe Gly Val Gly
1               5                   10                  15

Pro Leu Val Asn Gln Val Asn Ile Asn Ala Leu Ala Ser Lys Lys
            20                  25                  30

<210> SEQ ID NO 236
<211> LENGTH: 7
<212> TYPE: PRT
<213> ORGANISM: Homo sapiens

<400> SEQUENCE: 236

Lys Val Gly Ser Gln Tyr Arg
1               5

<210> SEQ ID NO 237
<211> LENGTH: 18
<212> TYPE: PRT
<213> ORGANISM: Homo sapiens

<400> SEQUENCE: 237

Lys Val Gly Ser Gln Tyr Arg Leu Glu Asp Ser Val Thr Tyr His Cys
1               5                   10                  15

Ser Arg

<210> SEQ ID NO 238
<211> LENGTH: 11
<212> TYPE: PRT
<213> ORGANISM: Homo sapiens

<400> SEQUENCE: 238

Leu Glu Asp Ser Val Thr Tyr His Cys Ser Arg
1               5                   10

<210> SEQ ID NO 239
<211> LENGTH: 20
<212> TYPE: PRT
<213> ORGANISM: Homo sapiens

<400> SEQUENCE: 239

Leu Lys Tyr Gly Gln Thr Ile Arg Pro Ile Cys Leu Pro Cys Thr Glu
1               5                   10                  15

Gly Thr Thr Arg
            20

<210> SEQ ID NO 240
```

```
<211> LENGTH: 24
<212> TYPE: PRT
<213> ORGANISM: Homo sapiens

<400> SEQUENCE: 240

Leu Leu Gln Glu Gly Gln Ala Leu Glu Tyr Val Cys Pro Ser Gly Phe
1               5                   10                  15

Tyr Pro Tyr Pro Val Gln Thr Arg
            20

<210> SEQ ID NO 241
<211> LENGTH: 11
<212> TYPE: PRT
<213> ORGANISM: Homo sapiens

<400> SEQUENCE: 241

Leu Pro Pro Thr Thr Thr Cys Gln Gln Gln Lys
1               5                   10

<210> SEQ ID NO 242
<211> LENGTH: 21
<212> TYPE: PRT
<213> ORGANISM: Homo sapiens

<400> SEQUENCE: 242

Leu Pro Pro Thr Thr Thr Cys Gln Gln Gln Lys Glu Glu Leu Leu Pro
1               5                   10                  15

Ala Gln Asp Ile Lys
            20

<210> SEQ ID NO 243
<211> LENGTH: 29
<212> TYPE: PRT
<213> ORGANISM: Homo sapiens

<400> SEQUENCE: 243

Asn Pro Arg Glu Asp Tyr Leu Asp Val Tyr Val Phe Gly Val Gly Pro
1               5                   10                  15

Leu Val Asn Gln Val Asn Ile Asn Ala Leu Ala Ser Lys
            20                  25

<210> SEQ ID NO 244
<211> LENGTH: 30
<212> TYPE: PRT
<213> ORGANISM: Homo sapiens

<400> SEQUENCE: 244

Asn Pro Arg Glu Asp Tyr Leu Asp Val Tyr Val Phe Gly Val Gly Pro
1               5                   10                  15

Leu Val Asn Gln Val Asn Ile Asn Ala Leu Ala Ser Lys Lys
            20                  25                  30

<210> SEQ ID NO 245
<211> LENGTH: 16
<212> TYPE: PRT
<213> ORGANISM: Homo sapiens

<400> SEQUENCE: 245

Pro Ile Thr Val Ile Asp Glu Ile Arg Asp Leu Leu Tyr Ile Gly Lys
1               5                   10                  15

<210> SEQ ID NO 246
<211> LENGTH: 11
<212> TYPE: PRT
```

<213> ORGANISM: Homo sapiens

<400> SEQUENCE: 246

Gln Leu Asn Glu Ile Asn Tyr Glu Asp His Lys
1               5                   10

<210> SEQ ID NO 247
<211> LENGTH: 13
<212> TYPE: PRT
<213> ORGANISM: Homo sapiens

<400> SEQUENCE: 247

Gln Leu Asn Glu Ile Asn Tyr Glu Asp His Lys Leu Lys
1               5                   10

<210> SEQ ID NO 248
<211> LENGTH: 14
<212> TYPE: PRT
<213> ORGANISM: Homo sapiens

<400> SEQUENCE: 248

Arg Pro Gln Gly Ser Cys Ser Leu Glu Gly Val Glu Ile Lys
1               5                   10

<210> SEQ ID NO 249
<211> LENGTH: 9
<212> TYPE: PRT
<213> ORGANISM: Homo sapiens

<400> SEQUENCE: 249

Ser Thr Gly Ser Trp Ser Thr Leu Lys
1               5

<210> SEQ ID NO 250
<211> LENGTH: 20
<212> TYPE: PRT
<213> ORGANISM: Homo sapiens

<400> SEQUENCE: 250

Thr Pro Trp Ser Leu Ala Arg Pro Gln Gly Ser Cys Ser Leu Glu Gly
1               5                   10                  15

Val Glu Ile Lys
            20

<210> SEQ ID NO 251
<211> LENGTH: 9
<212> TYPE: PRT
<213> ORGANISM: Homo sapiens

<400> SEQUENCE: 251

Val Ala Ser Tyr Gly Val Lys Pro Arg
1               5

<210> SEQ ID NO 252
<211> LENGTH: 11
<212> TYPE: PRT
<213> ORGANISM: Homo sapiens

<400> SEQUENCE: 252

Val Lys Asp Ile Ser Glu Val Val Thr Pro Arg
1               5                   10

<210> SEQ ID NO 253
<211> LENGTH: 32
<212> TYPE: PRT

<213> ORGANISM: Homo sapiens

<400> SEQUENCE: 253

Val Lys Asp Met Glu Asn Leu Glu Asp Val Phe Tyr Gln Met Ile Asp
1               5                   10                  15

Glu Ser Gln Ser Leu Ser Leu Cys Gly Met Val Trp Glu His Arg Lys
            20                  25                  30

<210> SEQ ID NO 254
<211> LENGTH: 14
<212> TYPE: PRT
<213> ORGANISM: Homo sapiens

<400> SEQUENCE: 254

Val Ser Glu Ala Asp Ser Ser Asn Ala Asp Trp Val Thr Lys
1               5                   10

<210> SEQ ID NO 255
<211> LENGTH: 25
<212> TYPE: PRT
<213> ORGANISM: Homo sapiens

<400> SEQUENCE: 255

Trp Ser Gly Gln Thr Ala Ile Cys Asp Asn Gly Ala Gly Tyr Cys Ser
1               5                   10                  15

Asn Pro Gly Ile Pro Ile Gly Thr Arg
            20                  25

<210> SEQ ID NO 256
<211> LENGTH: 26
<212> TYPE: PRT
<213> ORGANISM: Homo sapiens

<400> SEQUENCE: 256

Trp Ser Gly Gln Thr Ala Ile Cys Asp Asn Gly Ala Gly Tyr Cys Ser
1               5                   10                  15

Asn Pro Gly Ile Pro Ile Gly Thr Arg Lys
            20                  25

<210> SEQ ID NO 257
<211> LENGTH: 18
<212> TYPE: PRT
<213> ORGANISM: Homo sapiens

<400> SEQUENCE: 257

Trp Ser Leu Ala Arg Pro Gln Gly Ser Cys Ser Leu Glu Gly Val Glu
1               5                   10                  15

Ile Lys

<210> SEQ ID NO 258
<211> LENGTH: 11
<212> TYPE: PRT
<213> ORGANISM: Homo sapiens

<400> SEQUENCE: 258

Tyr Gly Leu Val Thr Tyr Ala Thr Tyr Pro Lys
1               5                   10

<210> SEQ ID NO 259
<211> LENGTH: 18
<212> TYPE: PRT
<213> ORGANISM: Homo sapiens

<400> SEQUENCE: 259

Tyr Gly Gln Thr Ile Arg Pro Ile Cys Leu Pro Cys Thr Glu Gly Thr
1               5                   10                  15

Thr Arg

<210> SEQ ID NO 260
<211> LENGTH: 9
<212> TYPE: PRT
<213> ORGANISM: Homo sapiens

<400> SEQUENCE: 260

Leu Tyr His Ala Phe Ser Ala Met Lys
1               5

<210> SEQ ID NO 261
<211> LENGTH: 10
<212> TYPE: PRT
<213> ORGANISM: Homo sapiens

<400> SEQUENCE: 261

Leu Tyr His Ala Phe Ser Ala Met Lys Lys
1               5                   10

<210> SEQ ID NO 262
<211> LENGTH: 8
<212> TYPE: PRT
<213> ORGANISM: Homo sapiens

<400> SEQUENCE: 262

Val Ala Thr Thr Val Ile Ser Lys
1               5

<210> SEQ ID NO 263
<211> LENGTH: 19
<212> TYPE: PRT
<213> ORGANISM: Homo sapiens

<400> SEQUENCE: 263

Met Arg Pro Ser Thr Asp Thr Ile Thr Val Met Val Glu Asn Ser His
1               5                   10                  15

Gly Leu Arg

<210> SEQ ID NO 264
<211> LENGTH: 21
<212> TYPE: PRT
<213> ORGANISM: Homo sapiens

<400> SEQUENCE: 264

Ala Glu Phe Gln Asp Ala Leu Glu Lys Leu Asn Met Gly Ile Thr Asp
1               5                   10                  15

Leu Gln Gly Leu Arg
            20

<210> SEQ ID NO 265
<211> LENGTH: 13
<212> TYPE: PRT
<213> ORGANISM: Homo sapiens

<400> SEQUENCE: 265

Glu Met Ser Gly Ser Pro Ala Ser Gly Ile Pro Val Lys
1               5                   10

<210> SEQ ID NO 266
<211> LENGTH: 25

<212> TYPE: PRT
<213> ORGANISM: Homo sapiens

<400> SEQUENCE: 266

Glu Val Tyr Met Pro Ser Ser Ile Phe Gln Asp Asp Phe Val Ile Pro
1               5                   10                  15

Asp Ile Ser Glu Pro Gly Thr Trp Lys
            20                  25

<210> SEQ ID NO 267
<211> LENGTH: 11
<212> TYPE: PRT
<213> ORGANISM: Homo sapiens

<400> SEQUENCE: 267

Gly Gln Ile Val Phe Met Asn Arg Glu Pro Lys
1               5                   10

<210> SEQ ID NO 268
<211> LENGTH: 27
<212> TYPE: PRT
<213> ORGANISM: Homo sapiens

<400> SEQUENCE: 268

Lys Lys Glu Val Tyr Met Pro Ser Ser Ile Phe Gln Asp Asp Phe Val
1               5                   10                  15

Ile Pro Asp Ile Ser Glu Pro Gly Thr Trp Lys
            20                  25

<210> SEQ ID NO 269
<211> LENGTH: 42
<212> TYPE: PRT
<213> ORGANISM: Homo sapiens

<400> SEQUENCE: 269

Leu Arg Leu Glu Pro Gly Lys Glu Tyr Leu Ile Met Gly Leu Asp Gly
1               5                   10                  15

Ala Thr Tyr Asp Leu Glu Gly His Pro Gln Tyr Leu Leu Asp Ser Asn
            20                  25                  30

Ser Trp Ile Glu Glu Met Pro Ser Glu Arg
        35                  40

<210> SEQ ID NO 270
<211> LENGTH: 39
<212> TYPE: PRT
<213> ORGANISM: Homo sapiens

<400> SEQUENCE: 270

Ser Met Gln Gly Gly Leu Val Gly Asn Asp Glu Thr Val Ala Leu Thr
1               5                   10                  15

Ala Phe Val Thr Ile Ala Leu His His Gly Leu Ala Val Phe Gln Asp
            20                  25                  30

Glu Gly Ala Glu Pro Leu Lys
        35

<210> SEQ ID NO 271
<211> LENGTH: 41
<212> TYPE: PRT
<213> ORGANISM: Homo sapiens

<400> SEQUENCE: 271

Ser Met Gln Gly Gly Leu Val Gly Asn Asp Glu Thr Val Ala Leu Thr
1               5                   10                  15

Ala Phe Val Thr Ile Ala Leu His His Gly Leu Ala Val Phe Gln Asp
            20                  25                  30

Glu Gly Ala Glu Pro Leu Lys Gln Arg
        35                  40

<210> SEQ ID NO 272
<211> LENGTH: 23
<212> TYPE: PRT
<213> ORGANISM: Homo sapiens

<400> SEQUENCE: 272

Thr Leu Glu Ile Pro Gly Asn Ser Asp Pro Asn Met Ile Pro Asp Gly
1               5                   10                  15

Asp Phe Asn Ser Tyr Val Arg
            20

<210> SEQ ID NO 273
<211> LENGTH: 20
<212> TYPE: PRT
<213> ORGANISM: Homo sapiens

<400> SEQUENCE: 273

Ala Ala Cys Ala Gln Leu Asn Asp Phe Leu Gln Glu Tyr Gly Thr Gln
1               5                   10                  15

Gly Cys Gln Val
            20

<210> SEQ ID NO 274
<211> LENGTH: 35
<212> TYPE: PRT
<213> ORGANISM: Homo sapiens

<400> SEQUENCE: 274

Ala Asp Leu Glu Lys Leu Thr Ser Leu Ser Asp Arg Tyr Val Ser His
1               5                   10                  15

Phe Glu Thr Glu Gly Pro His Val Leu Leu Tyr Phe Asp Ser Val Pro
            20                  25                  30

Thr Ser Arg
        35

<210> SEQ ID NO 275
<211> LENGTH: 9
<212> TYPE: PRT
<213> ORGANISM: Homo sapiens

<400> SEQUENCE: 275

Ala Glu Phe Gln Asp Ala Leu Glu Lys
1               5

<210> SEQ ID NO 276
<211> LENGTH: 13
<212> TYPE: PRT
<213> ORGANISM: Homo sapiens

<400> SEQUENCE: 276

Ala Glu Met Ala Asp Gln Ala Ala Ala Trp Leu Thr Arg
1               5                   10

<210> SEQ ID NO 277
<211> LENGTH: 19
<212> TYPE: PRT
<213> ORGANISM: Homo sapiens

<400> SEQUENCE: 277

Ala Leu Glu Ile Leu Gln Glu Glu Asp Leu Ile Asp Glu Asp Asp Ile
1               5                   10                  15

Pro Val Arg

<210> SEQ ID NO 278
<211> LENGTH: 13
<212> TYPE: PRT
<213> ORGANISM: Homo sapiens

<400> SEQUENCE: 278

Ala Leu Leu Ser Leu Gln Val Pro Leu Lys Asp Ala Lys
1               5                   10

<210> SEQ ID NO 279
<211> LENGTH: 22
<212> TYPE: PRT
<213> ORGANISM: Homo sapiens

<400> SEQUENCE: 279

Ala Ser Ala Gly Leu Leu Gly Ala His Ala Ala Ile Thr Ala Tyr
1               5                   10                  15

Ala Leu Thr Leu Thr Lys
            20

<210> SEQ ID NO 280
<211> LENGTH: 8
<212> TYPE: PRT
<213> ORGANISM: Homo sapiens

<400> SEQUENCE: 280

Ala Ser Ser Phe Leu Gly Glu Lys
1               5

<210> SEQ ID NO 281
<211> LENGTH: 18
<212> TYPE: PRT
<213> ORGANISM: Homo sapiens

<400> SEQUENCE: 281

Ala Val Gly Ser Gly Ala Thr Phe Ser His Tyr Tyr Tyr Met Ile Leu
1               5                   10                  15

Ser Arg

<210> SEQ ID NO 282
<211> LENGTH: 10
<212> TYPE: PRT
<213> ORGANISM: Homo sapiens

<400> SEQUENCE: 282

Cys Ser Val Phe Tyr Gly Ala Pro Ser Lys
1               5                   10

<210> SEQ ID NO 283
<211> LENGTH: 15
<212> TYPE: PRT
<213> ORGANISM: Homo sapiens

<400> SEQUENCE: 283

Asp Phe Ala Leu Leu Ser Leu Gln Val Pro Leu Lys Asp Ala Lys
1               5                   10                  15

<210> SEQ ID NO 284

```
<211> LENGTH: 12
<212> TYPE: PRT
<213> ORGANISM: Homo sapiens

<400> SEQUENCE: 284

Glu Ala Pro Lys Val Val Glu Glu Gln Glu Ser Arg
1               5                   10

<210> SEQ ID NO 285
<211> LENGTH: 31
<212> TYPE: PRT
<213> ORGANISM: Homo sapiens

<400> SEQUENCE: 285

Glu Cys Val Gly Phe Glu Ala Val Gln Glu Val Pro Val Gly Leu Val
1               5                   10                  15

Gln Pro Ala Ser Ala Thr Leu Tyr Asp Tyr Tyr Asn Pro Glu Arg
            20                  25                  30

<210> SEQ ID NO 286
<211> LENGTH: 32
<212> TYPE: PRT
<213> ORGANISM: Homo sapiens

<400> SEQUENCE: 286

Glu Cys Val Gly Phe Glu Ala Val Gln Glu Val Pro Val Gly Leu Val
1               5                   10                  15

Gln Pro Ala Ser Ala Thr Leu Tyr Asp Tyr Tyr Asn Pro Glu Arg Arg
            20                  25                  30

<210> SEQ ID NO 287
<211> LENGTH: 7
<212> TYPE: PRT
<213> ORGANISM: Homo sapiens

<400> SEQUENCE: 287

Glu Phe His Leu His Leu Arg
1               5

<210> SEQ ID NO 288
<211> LENGTH: 18
<212> TYPE: PRT
<213> ORGANISM: Homo sapiens

<400> SEQUENCE: 288

Glu Gly Ala Ile His Arg Glu Glu Leu Val Tyr Glu Leu Asn Pro Leu
1               5                   10                  15

Asp His

<210> SEQ ID NO 289
<211> LENGTH: 19
<212> TYPE: PRT
<213> ORGANISM: Homo sapiens

<400> SEQUENCE: 289

Glu Gly Ala Ile His Arg Glu Glu Leu Val Tyr Glu Leu Asn Pro Leu
1               5                   10                  15

Asp His Arg

<210> SEQ ID NO 290
<211> LENGTH: 20
<212> TYPE: PRT
<213> ORGANISM: Homo sapiens
```

```
<400> SEQUENCE: 290

Glu Gly Ala Ile His Arg Glu Glu Leu Val Tyr Glu Leu Asn Pro Leu
1               5                   10                  15

Asp His Arg Gly
            20

<210> SEQ ID NO 291
<211> LENGTH: 14
<212> TYPE: PRT
<213> ORGANISM: Homo sapiens

<400> SEQUENCE: 291

Glu Pro Phe Leu Ser Cys Cys Gln Phe Ala Glu Ser Leu Arg
1               5                   10

<210> SEQ ID NO 292
<211> LENGTH: 10
<212> TYPE: PRT
<213> ORGANISM: Homo sapiens

<400> SEQUENCE: 292

Phe Gly Leu Leu Asp Glu Asp Gly Lys Lys
1               5                   10

<210> SEQ ID NO 293
<211> LENGTH: 14
<212> TYPE: PRT
<213> ORGANISM: Homo sapiens

<400> SEQUENCE: 293

Phe Gly Leu Leu Asp Glu Asp Gly Lys Lys Thr Phe Phe Arg
1               5                   10

<210> SEQ ID NO 294
<211> LENGTH: 24
<212> TYPE: PRT
<213> ORGANISM: Homo sapiens

<400> SEQUENCE: 294

Phe Gln Ile Leu Thr Leu Trp Leu Pro Asp Ser Leu Thr Thr Trp Glu
1               5                   10                  15

Ile His Gly Leu Ser Leu Ser Lys
            20

<210> SEQ ID NO 295
<211> LENGTH: 17
<212> TYPE: PRT
<213> ORGANISM: Homo sapiens

<400> SEQUENCE: 295

Gly His Leu Phe Leu Gln Thr Asp Gln Pro Ile Tyr Asn Pro Gly Gln
1               5                   10                  15

Arg

<210> SEQ ID NO 296
<211> LENGTH: 13
<212> TYPE: PRT
<213> ORGANISM: Homo sapiens

<400> SEQUENCE: 296

Gly Leu Glu Glu Glu Leu Gln Phe Ser Leu Gly Ser Lys
1               5                   10
```

```
<210> SEQ ID NO 297
<211> LENGTH: 9
<212> TYPE: PRT
<213> ORGANISM: Homo sapiens

<400> SEQUENCE: 297

Gly Leu Gln Asp Glu Asp Gly Tyr Arg
1               5

<210> SEQ ID NO 298
<211> LENGTH: 14
<212> TYPE: PRT
<213> ORGANISM: Homo sapiens

<400> SEQUENCE: 298

Gly Pro Glu Val Gln Leu Val Ala His Ser Pro Trp Leu Lys
1               5                   10

<210> SEQ ID NO 299
<211> LENGTH: 19
<212> TYPE: PRT
<213> ORGANISM: Homo sapiens

<400> SEQUENCE: 299

Gly Pro Glu Val Gln Leu Val Ala His Ser Pro Trp Leu Lys Asp Ser
1               5                   10                  15

Leu Ser Arg

<210> SEQ ID NO 300
<211> LENGTH: 8
<212> TYPE: PRT
<213> ORGANISM: Homo sapiens

<400> SEQUENCE: 300

Gly Gln Ile Val Phe Met Asn Arg
1               5

<210> SEQ ID NO 301
<211> LENGTH: 13
<212> TYPE: PRT
<213> ORGANISM: Homo sapiens

<400> SEQUENCE: 301

Gly Ser Phe Glu Phe Pro Val Gly Asp Ala Val Ser Lys
1               5                   10

<210> SEQ ID NO 302
<211> LENGTH: 12
<212> TYPE: PRT
<213> ORGANISM: Homo sapiens

<400> SEQUENCE: 302

Gly Ser Ser Thr Trp Leu Thr Ala Phe Val Leu Lys
1               5                   10

<210> SEQ ID NO 303
<211> LENGTH: 10
<212> TYPE: PRT
<213> ORGANISM: Homo sapiens

<400> SEQUENCE: 303

Gly Ser Val Phe Leu Arg Asn Pro Ser Arg
1               5                   10

<210> SEQ ID NO 304
```

```
<211> LENGTH: 15
<212> TYPE: PRT
<213> ORGANISM: Homo sapiens

<400> SEQUENCE: 304

His Leu Val Pro Gly Ala Pro Phe Leu Gln Ala Leu Val Arg
1               5                   10                  15

<210> SEQ ID NO 305
<211> LENGTH: 25
<212> TYPE: PRT
<213> ORGANISM: Homo sapiens

<400> SEQUENCE: 305

Ile Thr Pro Gly Lys Pro Tyr Ile Leu Thr Val Pro Gly His Leu Asp
1               5                   10                  15

Glu Met Gln Leu Asp Ile Gln Ala Arg
            20                  25

<210> SEQ ID NO 306
<211> LENGTH: 12
<212> TYPE: PRT
<213> ORGANISM: Homo sapiens

<400> SEQUENCE: 306

Lys Ala Asp Gly Ser Tyr Ala Ala Trp Leu Ser Arg
1               5                   10

<210> SEQ ID NO 307
<211> LENGTH: 10
<212> TYPE: PRT
<213> ORGANISM: Homo sapiens

<400> SEQUENCE: 307

Lys Tyr Val Leu Pro Asn Phe Glu Val Lys
1               5                   10

<210> SEQ ID NO 308
<211> LENGTH: 9
<212> TYPE: PRT
<213> ORGANISM: Homo sapiens

<400> SEQUENCE: 308

Leu Glu Leu Ser Val Asp Gly Ala Lys
1               5

<210> SEQ ID NO 309
<211> LENGTH: 10
<212> TYPE: PRT
<213> ORGANISM: Homo sapiens

<400> SEQUENCE: 309

Leu Gly Gln Tyr Ala Ser Pro Thr Ala Lys
1               5                   10

<210> SEQ ID NO 310
<211> LENGTH: 11
<212> TYPE: PRT
<213> ORGANISM: Homo sapiens

<400> SEQUENCE: 310

Leu Gly Gln Tyr Ala Ser Pro Thr Ala Lys Arg
1               5                   10

<210> SEQ ID NO 311
```

```
<211> LENGTH: 26
<212> TYPE: PRT
<213> ORGANISM: Homo sapiens

<400> SEQUENCE: 311

Leu His Leu Glu Thr Asp Ser Leu Ala Leu Val Ala Leu Gly Ala Leu
1               5                   10                  15

Asp Thr Ala Leu Tyr Ala Ala Gly Ser Lys
            20                  25

<210> SEQ ID NO 312
<211> LENGTH: 17
<212> TYPE: PRT
<213> ORGANISM: Homo sapiens

<400> SEQUENCE: 312

Leu Leu Ala Thr Leu Cys Ser Ala Glu Val Cys Gln Cys Ala Glu Gly
1               5                   10                  15

Lys

<210> SEQ ID NO 313
<211> LENGTH: 26
<212> TYPE: PRT
<213> ORGANISM: Homo sapiens

<400> SEQUENCE: 313

Leu Leu Leu Phe Ser Pro Ser Val Val His Leu Gly Val Pro Leu Ser
1               5                   10                  15

Val Gly Val Gln Leu Gln Asp Val Pro Arg
            20                  25

<210> SEQ ID NO 314
<211> LENGTH: 31
<212> TYPE: PRT
<213> ORGANISM: Homo sapiens

<400> SEQUENCE: 314

Leu Leu Leu Phe Ser Pro Ser Val Val His Leu Gly Val Pro Leu Ser
1               5                   10                  15

Val Gly Val Gln Leu Gln Asp Val Pro Arg Gly Gln Val Val Lys
            20                  25                  30

<210> SEQ ID NO 315
<211> LENGTH: 12
<212> TYPE: PRT
<213> ORGANISM: Homo sapiens

<400> SEQUENCE: 315

Leu Asn Met Gly Ile Thr Asp Leu Gln Gly Leu Arg
1               5                   10

<210> SEQ ID NO 316
<211> LENGTH: 6
<212> TYPE: PRT
<213> ORGANISM: Homo sapiens

<400> SEQUENCE: 316

Leu Pro Met Ser Val Arg
1               5

<210> SEQ ID NO 317
<211> LENGTH: 27
<212> TYPE: PRT
<213> ORGANISM: Homo sapiens
```

-continued

```
<400> SEQUENCE: 317

Leu Gln Glu Thr Ser Asn Trp Leu Leu Ser Gln Gln Gln Ala Asp Gly
1               5                   10                  15

Ser Phe Gln Asp Leu Ser Pro Val Ile His Arg
            20                  25

<210> SEQ ID NO 318
<211> LENGTH: 30
<212> TYPE: PRT
<213> ORGANISM: Homo sapiens

<400> SEQUENCE: 318

Leu Thr Ser Leu Ser Asp Arg Tyr Val Ser His Phe Glu Thr Glu Gly
1               5                   10                  15

Pro His Val Leu Leu Tyr Phe Asp Ser Val Pro Thr Ser Arg
            20                  25                  30

<210> SEQ ID NO 319
<211> LENGTH: 25
<212> TYPE: PRT
<213> ORGANISM: Homo sapiens

<400> SEQUENCE: 319

Leu Thr Val Ala Ala Pro Pro Ser Gly Gly Pro Gly Phe Leu Ser Ile
1               5                   10                  15

Glu Arg Pro Asp Ser Arg Pro Pro Arg
            20                  25

<210> SEQ ID NO 320
<211> LENGTH: 12
<212> TYPE: PRT
<213> ORGANISM: Homo sapiens

<400> SEQUENCE: 320

Leu Val Asn Gly Gln Ser His Ile Ser Leu Ser Lys
1               5                   10

<210> SEQ ID NO 321
<211> LENGTH: 33
<212> TYPE: PRT
<213> ORGANISM: Homo sapiens

<400> SEQUENCE: 321

Leu Val Asn Gly Gln Ser His Ile Ser Leu Ser Lys Ala Glu Phe Gln
1               5                   10                  15

Asp Ala Leu Glu Lys Leu Asn Met Gly Ile Thr Asp Leu Gln Gly Leu
            20                  25                  30

Arg

<210> SEQ ID NO 322
<211> LENGTH: 9
<212> TYPE: PRT
<213> ORGANISM: Homo sapiens

<400> SEQUENCE: 322

Met Lys Phe Ala Cys Tyr Tyr Pro Arg
1               5

<210> SEQ ID NO 323
<211> LENGTH: 32
<212> TYPE: PRT
<213> ORGANISM: Homo sapiens
```

<400> SEQUENCE: 323

Asn Gly Glu Ser Val Lys Leu His Leu Glu Thr Asp Ser Leu Ala Leu
1               5                   10                  15

Val Ala Leu Gly Ala Leu Asp Thr Ala Leu Tyr Ala Ala Gly Ser Lys
            20                  25                  30

<210> SEQ ID NO 324
<211> LENGTH: 32
<212> TYPE: PRT
<213> ORGANISM: Homo sapiens

<400> SEQUENCE: 324

Asn Asn Val Pro Cys Ser Pro Lys Val Asp Phe Thr Leu Ser Ser Glu
1               5                   10                  15

Arg Asp Phe Ala Leu Leu Ser Leu Gln Val Pro Leu Lys Asp Ala Lys
            20                  25                  30

<210> SEQ ID NO 325
<211> LENGTH: 30
<212> TYPE: PRT
<213> ORGANISM: Homo sapiens

<400> SEQUENCE: 325

Asn Pro Ser Asp Pro Met Pro Gln Ala Pro Ala Leu Trp Ile Glu Thr
1               5                   10                  15

Thr Ala Tyr Ala Leu Leu His Leu Leu Leu His Glu Gly Lys
            20                  25                  30

<210> SEQ ID NO 326
<211> LENGTH: 6
<212> TYPE: PRT
<213> ORGANISM: Homo sapiens

<400> SEQUENCE: 326

Asn Val Asn Phe Gln Lys
1               5

<210> SEQ ID NO 327
<211> LENGTH: 9
<212> TYPE: PRT
<213> ORGANISM: Homo sapiens

<400> SEQUENCE: 327

Pro Phe Leu Leu Gln Ala Leu Val Arg
1               5

<210> SEQ ID NO 328
<211> LENGTH: 14
<212> TYPE: PRT
<213> ORGANISM: Homo sapiens

<400> SEQUENCE: 328

Pro Gly His Leu Asp Glu Met Gln Leu Asp Ile Gln Ala Arg
1               5                   10

<210> SEQ ID NO 329
<211> LENGTH: 23
<212> TYPE: PRT
<213> ORGANISM: Homo sapiens

<400> SEQUENCE: 329

Pro Gly Lys Pro Tyr Ile Leu Thr Val Pro Gly His Leu Asp Glu Met
1               5                   10                  15

Gln Leu Asp Ile Gln Ala Arg
            20

<210> SEQ ID NO 330
<211> LENGTH: 26
<212> TYPE: PRT
<213> ORGANISM: Homo sapiens

<400> SEQUENCE: 330

Pro Ile Ile Ile Pro Gln Thr Ile Ser Glu Leu Gln Leu Ser Val Ser
1               5                   10                  15

Ala Gly Ser Pro His Pro Ala Ile Ala Arg
            20                  25

<210> SEQ ID NO 331
<211> LENGTH: 21
<212> TYPE: PRT
<213> ORGANISM: Homo sapiens

<400> SEQUENCE: 331

Pro Leu Asp Thr Leu Gly Ser Glu Gly Ala Leu Ser Pro Gly Gly Val
1               5                   10                  15

Ala Ser Leu Leu Arg
            20

<210> SEQ ID NO 332
<211> LENGTH: 17
<212> TYPE: PRT
<213> ORGANISM: Homo sapiens

<400> SEQUENCE: 332

Pro Val Ala Phe Ser Val Val Pro Thr Ala Ala Thr Ala Val Ser Leu
1               5                   10                  15

Lys

<210> SEQ ID NO 333
<211> LENGTH: 9
<212> TYPE: PRT
<213> ORGANISM: Homo sapiens

<400> SEQUENCE: 333

Gln Gly Ser Phe Gln Gly Gly Phe Arg
1               5

<210> SEQ ID NO 334
<211> LENGTH: 9
<212> TYPE: PRT
<213> ORGANISM: Homo sapiens

<400> SEQUENCE: 334

Arg Cys Cys Gln Asp Gly Val Thr Arg
1               5

<210> SEQ ID NO 335
<211> LENGTH: 16
<212> TYPE: PRT
<213> ORGANISM: Homo sapiens

<400> SEQUENCE: 335

Arg His Leu Val Pro Gly Ala Pro Phe Leu Leu Gln Ala Leu Val Arg
1               5                   10                  15

<210> SEQ ID NO 336

```
<211> LENGTH: 23
<212> TYPE: PRT
<213> ORGANISM: Homo sapiens

<400> SEQUENCE: 336

Ser Cys Gly Leu His Gln Leu Leu Arg Gly Pro Glu Val Gln Leu Val
1               5                   10                  15

Ala His Ser Pro Trp Leu Lys
            20

<210> SEQ ID NO 337
<211> LENGTH: 10
<212> TYPE: PRT
<213> ORGANISM: Homo sapiens

<400> SEQUENCE: 337

Ser Phe Phe Pro Glu Asn Trp Leu Trp Arg
1               5                   10

<210> SEQ ID NO 338
<211> LENGTH: 9
<212> TYPE: PRT
<213> ORGANISM: Homo sapiens

<400> SEQUENCE: 338

Ser His Ala Leu Gln Leu Asn Asn Arg
1               5

<210> SEQ ID NO 339
<211> LENGTH: 9
<212> TYPE: PRT
<213> ORGANISM: Homo sapiens

<400> SEQUENCE: 339

Ser His Lys Pro Leu Asn Met Gly Lys
1               5

<210> SEQ ID NO 340
<211> LENGTH: 25
<212> TYPE: PRT
<213> ORGANISM: Homo sapiens

<400> SEQUENCE: 340

Ser Thr Gln Asp Thr Val Ile Ala Leu Asp Ala Leu Ser Ala Tyr Trp
1               5                   10                  15

Ile Ala Ser His Thr Thr Glu Glu Arg
            20                  25

<210> SEQ ID NO 341
<211> LENGTH: 13
<212> TYPE: PRT
<213> ORGANISM: Homo sapiens

<400> SEQUENCE: 341

Thr Lys Gly Leu Cys Val Ala Thr Pro Val Gln Leu Arg
1               5                   10

<210> SEQ ID NO 342
<211> LENGTH: 14
<212> TYPE: PRT
<213> ORGANISM: Homo sapiens

<400> SEQUENCE: 342

Thr Thr Asn Ile Gln Gly Ile Asn Leu Leu Phe Ser Ser Arg
1               5                   10
```

```
<210> SEQ ID NO 343
<211> LENGTH: 8
<212> TYPE: PRT
<213> ORGANISM: Homo sapiens

<400> SEQUENCE: 343

Thr Tyr Asn Val Leu Asp Met Lys
1               5

<210> SEQ ID NO 344
<211> LENGTH: 9
<212> TYPE: PRT
<213> ORGANISM: Homo sapiens

<400> SEQUENCE: 344

Val Asp Phe Thr Leu Ser Ser Glu Arg
1               5

<210> SEQ ID NO 345
<211> LENGTH: 24
<212> TYPE: PRT
<213> ORGANISM: Homo sapiens

<400> SEQUENCE: 345

Val Asp Phe Thr Leu Ser Ser Glu Arg Asp Phe Ala Leu Leu Ser Leu
1               5                   10                  15

Gln Val Pro Leu Lys Asp Ala Lys
            20

<210> SEQ ID NO 346
<211> LENGTH: 11
<212> TYPE: PRT
<213> ORGANISM: Homo sapiens

<400> SEQUENCE: 346

Val Asp Val Gln Ala Gly Ala Cys Glu Gly Lys
1               5                   10

<210> SEQ ID NO 347
<211> LENGTH: 20
<212> TYPE: PRT
<213> ORGANISM: Homo sapiens

<400> SEQUENCE: 347

Val Asp Val Gln Ala Gly Ala Cys Glu Gly Lys Leu Glu Leu Ser Val
1               5                   10                  15

Asp Gly Ala Lys
            20

<210> SEQ ID NO 348
<211> LENGTH: 30
<212> TYPE: PRT
<213> ORGANISM: Homo sapiens

<400> SEQUENCE: 348

Val Glu Thr Val Asp Arg Phe Gln Ile Leu Thr Leu Trp Leu Pro Asp
1               5                   10                  15

Ser Leu Thr Thr Trp Glu Ile His Gly Leu Ser Leu Ser Lys
            20                  25                  30

<210> SEQ ID NO 349
<211> LENGTH: 8
<212> TYPE: PRT
```

<213> ORGANISM: Homo sapiens

<400> SEQUENCE: 349

Val Glu Tyr Gly Phe Gln Val Lys
1               5

<210> SEQ ID NO 350
<211> LENGTH: 7
<212> TYPE: PRT
<213> ORGANISM: Homo sapiens

<400> SEQUENCE: 350

Val Phe Ala Leu Asp Gln Lys
1               5

<210> SEQ ID NO 351
<211> LENGTH: 10
<212> TYPE: PRT
<213> ORGANISM: Homo sapiens

<400> SEQUENCE: 351

Val Phe Arg Glu Phe His Leu His Leu Arg
1               5                   10

<210> SEQ ID NO 352
<211> LENGTH: 10
<212> TYPE: PRT
<213> ORGANISM: Homo sapiens

<400> SEQUENCE: 352

Val Gly Asp Thr Leu Asn Leu Asn Leu Arg
1               5                   10

<210> SEQ ID NO 353
<211> LENGTH: 26
<212> TYPE: PRT
<213> ORGANISM: Homo sapiens

<400> SEQUENCE: 353

Val Gly Leu Ser Gly Met Ala Ile Ala Asp Val Thr Leu Leu Ser Gly
1               5                   10                  15

Phe His Ala Leu Arg Ala Asp Leu Glu Lys
            20                  25

<210> SEQ ID NO 354
<211> LENGTH: 9
<212> TYPE: PRT
<213> ORGANISM: Homo sapiens

<400> SEQUENCE: 354

Val His Tyr Thr Val Cys Ile Trp Arg
1               5

<210> SEQ ID NO 355
<211> LENGTH: 15
<212> TYPE: PRT
<213> ORGANISM: Homo sapiens

<400> SEQUENCE: 355

Val Leu Ser Leu Ala Gln Glu Gln Val Gly Gly Ser Pro Glu Lys
1               5                   10                  15

<210> SEQ ID NO 356
<211> LENGTH: 42
<212> TYPE: PRT

<213> ORGANISM: Homo sapiens

<400> SEQUENCE: 356

Val Leu Ser Leu Ala Gln Glu Gln Val Gly Gly Ser Pro Glu Lys Leu
1               5                   10                  15

Gln Glu Thr Ser Asn Trp Leu Leu Ser Gln Gln Ala Asp Gly Ser
            20                  25                  30

Phe Gln Asp Leu Ser Pro Val Ile His Arg
        35                  40

<210> SEQ ID NO 357
<211> LENGTH: 21
<212> TYPE: PRT
<213> ORGANISM: Homo sapiens

<400> SEQUENCE: 357

Val Gln Gln Pro Asp Cys Arg Glu Pro Phe Leu Ser Cys Cys Gln Phe
1               5                   10                  15

Ala Glu Ser Leu Arg
            20

<210> SEQ ID NO 358
<211> LENGTH: 22
<212> TYPE: PRT
<213> ORGANISM: Homo sapiens

<400> SEQUENCE: 358

Val Gln Gln Pro Asp Cys Arg Glu Pro Phe Leu Ser Cys Cys Gln Phe
1               5                   10                  15

Ala Glu Ser Leu Arg Lys
            20

<210> SEQ ID NO 359
<211> LENGTH: 22
<212> TYPE: PRT
<213> ORGANISM: Homo sapiens

<400> SEQUENCE: 359

Val Ser Ala Thr Val Ser Ser Pro Gly Ser Val Pro Glu Val Gln Asp
1               5                   10                  15

Ile Gln Gln Asn Thr Asp
            20

<210> SEQ ID NO 360
<211> LENGTH: 26
<212> TYPE: PRT
<213> ORGANISM: Homo sapiens

<400> SEQUENCE: 360

Val Thr Ala Ser Asp Pro Leu Asp Thr Leu Gly Ser Glu Gly Ala Leu
1               5                   10                  15

Ser Pro Gly Gly Val Ala Ser Leu Leu Arg
            20                  25

<210> SEQ ID NO 361
<211> LENGTH: 14
<212> TYPE: PRT
<213> ORGANISM: Homo sapiens

<400> SEQUENCE: 361

Tyr Ile Tyr Gly Lys Pro Val Gln Gly Val Ala Tyr Val Arg
1               5                   10

```
<210> SEQ ID NO 362
<211> LENGTH: 16
<212> TYPE: PRT
<213> ORGANISM: Homo sapiens

<400> SEQUENCE: 362

Tyr Leu Asp Lys Thr Glu Gln Trp Ser Thr Leu Pro Pro Glu Thr Lys
1               5                   10                  15

<210> SEQ ID NO 363
<211> LENGTH: 25
<212> TYPE: PRT
<213> ORGANISM: Homo sapiens

<400> SEQUENCE: 363

Tyr Leu Asp Lys Thr Glu Gln Trp Ser Thr Leu Pro Pro Glu Thr Lys
1               5                   10                  15

Asp His Ala Val Asp Leu Ile Gln Lys
            20                  25

<210> SEQ ID NO 364
<211> LENGTH: 9
<212> TYPE: PRT
<213> ORGANISM: Homo sapiens

<400> SEQUENCE: 364

Tyr Arg Val Phe Ala Leu Asp Gln Lys
1               5

<210> SEQ ID NO 365
<211> LENGTH: 23
<212> TYPE: PRT
<213> ORGANISM: Homo sapiens

<400> SEQUENCE: 365

Tyr Val Ser His Phe Glu Thr Glu Gly Pro His Val Leu Leu Tyr Phe
1               5                   10                  15

Asp Ser Val Pro Thr Ser Arg
            20

<210> SEQ ID NO 366
<211> LENGTH: 20
<212> TYPE: PRT
<213> ORGANISM: Homo sapiens

<400> SEQUENCE: 366

Ser Val Val Leu Ile Pro Leu Gly Ala Val Asp Asp Gly Glu His Ser
1               5                   10                  15

Gln Asn Glu Lys
            20

<210> SEQ ID NO 367
<211> LENGTH: 19
<212> TYPE: PRT
<213> ORGANISM: Homo sapiens

<400> SEQUENCE: 367

Tyr Pro Ser Leu Ser Ile His Gly Ile Glu Gly Ala Phe Asp Glu Pro
1               5                   10                  15

Gly Thr Lys

<210> SEQ ID NO 368
<211> LENGTH: 16
```

```
<212> TYPE: PRT
<213> ORGANISM: Homo sapiens

<400> SEQUENCE: 368

Ala Ala Gly Asn Glu Cys Pro Glu Leu Gln Pro Pro Val His Gly Lys
1               5                   10                  15

<210> SEQ ID NO 369
<211> LENGTH: 15
<212> TYPE: PRT
<213> ORGANISM: Homo sapiens

<400> SEQUENCE: 369

Thr Gly Val Ile Thr Ser Pro Asp Phe Pro Asn Pro Tyr Pro Lys
1               5                   10                  15

<210> SEQ ID NO 370
<211> LENGTH: 16
<212> TYPE: PRT
<213> ORGANISM: Homo sapiens

<400> SEQUENCE: 370

Tyr Phe Phe Lys Asp Gln Val Leu Val Ser Cys Asp Thr Gly Tyr Lys
1               5                   10                  15

<210> SEQ ID NO 371
<211> LENGTH: 10
<212> TYPE: PRT
<213> ORGANISM: Homo sapiens

<400> SEQUENCE: 371

Ala Ile Met Glu Lys Leu Glu Met Ser Lys
1               5                   10

<210> SEQ ID NO 372
<211> LENGTH: 10
<212> TYPE: PRT
<213> ORGANISM: Homo sapiens

<400> SEQUENCE: 372

Asp Phe Thr Cys Val His Gln Ala Leu Lys
1               5                   10

<210> SEQ ID NO 373
<211> LENGTH: 10
<212> TYPE: PRT
<213> ORGANISM: Homo sapiens

<400> SEQUENCE: 373

Phe Gln Pro Thr Leu Leu Thr Leu Pro Arg
1               5                   10

<210> SEQ ID NO 374
<211> LENGTH: 17
<212> TYPE: PRT
<213> ORGANISM: Homo sapiens

<400> SEQUENCE: 374

Gly Val Thr Ser Val Ser Gln Ile Phe His Ser Pro Asp Leu Ala Ile
1               5                   10                  15

Arg

<210> SEQ ID NO 375
<211> LENGTH: 16
<212> TYPE: PRT
```

<213> ORGANISM: Homo sapiens

<400> SEQUENCE: 375

His Arg Leu Glu Asp Met Glu Gln Ala Leu Ser Pro Ser Val Phe Lys
1               5                   10                  15

<210> SEQ ID NO 376
<211> LENGTH: 15
<212> TYPE: PRT
<213> ORGANISM: Homo sapiens

<400> SEQUENCE: 376

Ile Lys Val Thr Thr Ser Gln Asp Met Leu Ser Ile Met Glu Lys
1               5                   10                  15

<210> SEQ ID NO 377
<211> LENGTH: 29
<212> TYPE: PRT
<213> ORGANISM: Homo sapiens

<400> SEQUENCE: 377

Lys Val Glu Thr Asn Met Ala Phe Ser Pro Phe Ser Ile Ala Ser Leu
1               5                   10                  15

Leu Thr Gln Val Leu Leu Gly Ala Gly Glu Asn Thr Lys
            20                  25

<210> SEQ ID NO 378
<211> LENGTH: 13
<212> TYPE: PRT
<213> ORGANISM: Homo sapiens

<400> SEQUENCE: 378

Lys Tyr Pro Val Ala His Phe Ile Asp Gln Thr Leu Lys
1               5                   10

<210> SEQ ID NO 379
<211> LENGTH: 14
<212> TYPE: PRT
<213> ORGANISM: Homo sapiens

<400> SEQUENCE: 379

Leu Glu Asp Met Glu Gln Ala Leu Ser Pro Ser Val Phe Lys
1               5                   10

<210> SEQ ID NO 380
<211> LENGTH: 10
<212> TYPE: PRT
<213> ORGANISM: Homo sapiens

<400> SEQUENCE: 380

Leu Leu Asp Ser Leu Pro Ser Asp Thr Arg
1               5                   10

<210> SEQ ID NO 381
<211> LENGTH: 9
<212> TYPE: PRT
<213> ORGANISM: Homo sapiens

<400> SEQUENCE: 381

Leu Tyr His Ala Phe Ser Ala Met Lys
1               5

<210> SEQ ID NO 382
<211> LENGTH: 10
<212> TYPE: PRT

<213> ORGANISM: Homo sapiens

<400> SEQUENCE: 382

Leu Tyr His Ala Phe Ser Ala Met Lys Lys
1               5                   10

<210> SEQ ID NO 383
<211> LENGTH: 18
<212> TYPE: PRT
<213> ORGANISM: Homo sapiens

<400> SEQUENCE: 383

Ser Ile Ala Ser Leu Leu Thr Gln Val Leu Leu Gly Ala Gly Glu Asn
1               5                   10                  15

Thr Lys

<210> SEQ ID NO 384
<211> LENGTH: 28
<212> TYPE: PRT
<213> ORGANISM: Homo sapiens

<400> SEQUENCE: 384

Thr Leu Leu Val Phe Glu Val Gln Gln Pro Phe Leu Phe Val Leu Trp
1               5                   10                  15

Asp Gln Gln His Lys Phe Pro Val Phe Met Gly Arg
            20                  25

<210> SEQ ID NO 385
<211> LENGTH: 8
<212> TYPE: PRT
<213> ORGANISM: Homo sapiens

<400> SEQUENCE: 385

Thr Leu Tyr Ser Ser Ser Pro Arg
1               5

<210> SEQ ID NO 386
<211> LENGTH: 21
<212> TYPE: PRT
<213> ORGANISM: Homo sapiens

<400> SEQUENCE: 386

Thr Asn Leu Glu Ser Ile Leu Ser Tyr Pro Lys Asp Phe Thr Cys Val
1               5                   10                  15

His Gln Ala Leu Lys
            20

<210> SEQ ID NO 387
<211> LENGTH: 8
<212> TYPE: PRT
<213> ORGANISM: Homo sapiens

<400> SEQUENCE: 387

Val Ala Thr Thr Val Ile Ser Lys
1               5

<210> SEQ ID NO 388
<211> LENGTH: 15
<212> TYPE: PRT
<213> ORGANISM: Homo sapiens

<400> SEQUENCE: 388

Ala Asp Ser Pro Met Asp Asp Phe Gln Cys Val Asn Gly Lys
1               5                   10                  15

```
<210> SEQ ID NO 389
<211> LENGTH: 12
<212> TYPE: PRT
<213> ORGANISM: Homo sapiens

<400> SEQUENCE: 389

Leu Val Asp Gln Asp Lys Thr Met Phe Ile Cys Lys
1               5                   10

<210> SEQ ID NO 390
<211> LENGTH: 16
<212> TYPE: PRT
<213> ORGANISM: Homo sapiens

<400> SEQUENCE: 390

Thr Met Gly Tyr Gln Asp Phe Ala Asp Val Val Cys Tyr Thr Gln Lys
1               5                   10                  15

<210> SEQ ID NO 391
<211> LENGTH: 18
<212> TYPE: PRT
<213> ORGANISM: Homo sapiens

<400> SEQUENCE: 391

Ala Cys Asp Gly Ile Asn Asp Cys Gly Asp Gln Ser Asp Glu Leu Cys
1               5                   10                  15

Cys Lys

<210> SEQ ID NO 392
<211> LENGTH: 9
<212> TYPE: PRT
<213> ORGANISM: Homo sapiens

<400> SEQUENCE: 392

Cys Ile Glu Gly Thr Cys Val Cys Lys
1               5

<210> SEQ ID NO 393
<211> LENGTH: 19
<212> TYPE: PRT
<213> ORGANISM: Homo sapiens

<400> SEQUENCE: 393

Glu Ala Asn Val Ala Cys Leu Asp Leu Gly Phe Gln Gln Gly Ala Asp
1               5                   10                  15

Thr Gln Arg

<210> SEQ ID NO 394
<211> LENGTH: 13
<212> TYPE: PRT
<213> ORGANISM: Homo sapiens

<400> SEQUENCE: 394

Gly Leu Glu Thr Ser Leu Ala Glu Cys Thr Phe Thr Lys
1               5                   10

<210> SEQ ID NO 395
<211> LENGTH: 13
<212> TYPE: PRT
<213> ORGANISM: Homo sapiens

<400> SEQUENCE: 395

His Gly Asn Thr Asp Ser Glu Gly Ile Val Glu Val Lys
```

```
                1               5                  10

<210> SEQ ID NO 396
<211> LENGTH: 14
<212> TYPE: PRT
<213> ORGANISM: Homo sapiens

<400> SEQUENCE: 396

Lys Val Thr Tyr Thr Ser Gln Glu Asp Leu Val Glu Lys Lys
1               5                  10

<210> SEQ ID NO 397
<211> LENGTH: 9
<212> TYPE: PRT
<213> ORGANISM: Homo sapiens

<400> SEQUENCE: 397

Lys Tyr Thr His Leu Ser Cys Asp Lys
1               5

<210> SEQ ID NO 398
<211> LENGTH: 17
<212> TYPE: PRT
<213> ORGANISM: Homo sapiens

<400> SEQUENCE: 398

Lys Tyr Thr His Leu Ser Cys Asp Lys Val Phe Cys Gln Pro Trp Gln
1               5                  10                 15

Arg

<210> SEQ ID NO 399
<211> LENGTH: 10
<212> TYPE: PRT
<213> ORGANISM: Homo sapiens

<400> SEQUENCE: 399

Arg Ser Phe Pro Thr Tyr Cys Gln Gln Lys
1               5                  10

<210> SEQ ID NO 400
<211> LENGTH: 17
<212> TYPE: PRT
<213> ORGANISM: Homo sapiens

<400> SEQUENCE: 400

Arg Thr Met Gly Tyr Gln Asp Phe Ala Asp Val Val Cys Tyr Thr Gln
1               5                  10                 15

Lys

<210> SEQ ID NO 401
<211> LENGTH: 9
<212> TYPE: PRT
<213> ORGANISM: Homo sapiens

<400> SEQUENCE: 401

Ser Phe Pro Thr Tyr Cys Gln Gln Lys
1               5

<210> SEQ ID NO 402
<211> LENGTH: 10
<212> TYPE: PRT
<213> ORGANISM: Homo sapiens

<400> SEQUENCE: 402
```

Ser Leu Glu Cys Leu His Pro Gly Thr Lys
1               5                   10

<210> SEQ ID NO 403
<211> LENGTH: 6
<212> TYPE: PRT
<213> ORGANISM: Homo sapiens

<400> SEQUENCE: 403

Thr Met Phe Ile Cys Lys
1               5

<210> SEQ ID NO 404
<211> LENGTH: 8
<212> TYPE: PRT
<213> ORGANISM: Homo sapiens

<400> SEQUENCE: 404

Tyr Thr His Leu Ser Cys Asp Lys
1               5

<210> SEQ ID NO 405
<211> LENGTH: 21
<212> TYPE: PRT
<213> ORGANISM: Homo sapiens

<400> SEQUENCE: 405

Glu Ala Leu Gly Asp Val Val Gly Asp Tyr Asn Phe Ile Cys Pro Ala
1               5                   10                  15

Leu Glu Phe Thr Lys
            20

<210> SEQ ID NO 406
<211> LENGTH: 7
<212> TYPE: PRT
<213> ORGANISM: Homo sapiens

<400> SEQUENCE: 406

Glu Phe Gln Glu Gly Leu Lys
1               5

<210> SEQ ID NO 407
<211> LENGTH: 20
<212> TYPE: PRT
<213> ORGANISM: Homo sapiens

<400> SEQUENCE: 407

Glu Ser Ile Leu Phe His Tyr Thr Asp Trp Val Asp Asp Gln Arg Pro
1               5                   10                  15

Glu Asn Tyr Arg
            20

<210> SEQ ID NO 408
<211> LENGTH: 9
<212> TYPE: PRT
<213> ORGANISM: Homo sapiens

<400> SEQUENCE: 408

Phe Lys Lys Pro Gln Ser Leu Thr Lys
1               5

<210> SEQ ID NO 409
<211> LENGTH: 16
<212> TYPE: PRT
<213> ORGANISM: Homo sapiens

<400> SEQUENCE: 409

Phe Ser Glu Trp Gly Asn Asn Ala Phe Phe Tyr Tyr Phe Glu His Arg
1               5                   10                  15

<210> SEQ ID NO 410
<211> LENGTH: 8
<212> TYPE: PRT
<213> ORGANISM: Homo sapiens

<400> SEQUENCE: 410

Phe Trp Thr Ser Phe Phe Pro Lys
1               5

<210> SEQ ID NO 411
<211> LENGTH: 11
<212> TYPE: PRT
<213> ORGANISM: Homo sapiens

<400> SEQUENCE: 411

Ile Phe Phe Pro Gly Val Ser Glu Phe Gly Lys
1               5                   10

<210> SEQ ID NO 412
<211> LENGTH: 26
<212> TYPE: PRT
<213> ORGANISM: Homo sapiens

<400> SEQUENCE: 412

Lys Thr Gln Ile Leu Val Gly Val Asn Lys Asp Glu Gly Thr Ala Phe
1               5                   10                  15

Leu Val Tyr Gly Ala Pro Gly Phe Ser Lys
            20                  25

<210> SEQ ID NO 413
<211> LENGTH: 10
<212> TYPE: PRT
<213> ORGANISM: Homo sapiens

<400> SEQUENCE: 413

Asn Ile Ala Ala Phe Gly Gly Asn Pro Lys
1               5                   10

<210> SEQ ID NO 414
<211> LENGTH: 29
<212> TYPE: PRT
<213> ORGANISM: Homo sapiens

<400> SEQUENCE: 414

Ser Val Thr Leu Phe Gly Glu Ser Ala Gly Ala Ala Ser Val Ser Leu
1               5                   10                  15

His Leu Leu Ser Pro Gly Ser His Ser Leu Phe Thr Arg
            20                  25

<210> SEQ ID NO 415
<211> LENGTH: 33
<212> TYPE: PRT
<213> ORGANISM: Homo sapiens

<400> SEQUENCE: 415

Val Gly Ala Leu Gly Phe Leu Ala Leu Pro Gly Asn Pro Glu Ala Pro
1               5                   10                  15

Gly Asn Met Gly Leu Phe Asp Gln Gln Leu Ala Leu Gln Trp Val Gln
            20                  25                  30

Lys

<210> SEQ ID NO 416
<211> LENGTH: 9
<212> TYPE: PRT
<213> ORGANISM: Homo sapiens

<400> SEQUENCE: 416

Val Ile Val Val Ser Met Asn Tyr Arg
1               5

<210> SEQ ID NO 417
<211> LENGTH: 16
<212> TYPE: PRT
<213> ORGANISM: Homo sapiens

<400> SEQUENCE: 417

Val Leu Glu Met Thr Gly Asn Ile Asp Glu Ala Glu Trp Glu Trp Lys
1               5                   10                  15

<210> SEQ ID NO 418
<211> LENGTH: 10
<212> TYPE: PRT
<213> ORGANISM: Homo sapiens

<400> SEQUENCE: 418

Tyr Leu Thr Leu Asn Thr Glu Ser Thr Arg
1               5                   10

<210> SEQ ID NO 419
<211> LENGTH: 6
<212> TYPE: PRT
<213> ORGANISM: Homo sapiens

<400> SEQUENCE: 419

Ala Leu Gln Glu Tyr Arg
1               5

<210> SEQ ID NO 420
<211> LENGTH: 12
<212> TYPE: PRT
<213> ORGANISM: Homo sapiens

<400> SEQUENCE: 420

Ala Ser Ser Ile Ile Asp Glu Leu Phe Gln Asp Arg
1               5                   10

<210> SEQ ID NO 421
<211> LENGTH: 16
<212> TYPE: PRT
<213> ORGANISM: Homo sapiens

<400> SEQUENCE: 421

Ala Ser Ser Ile Ile Asp Glu Leu Phe Gln Asp Arg Phe Phe Thr Arg
1               5                   10                  15

<210> SEQ ID NO 422
<211> LENGTH: 18
<212> TYPE: PRT
<213> ORGANISM: Homo sapiens

<400> SEQUENCE: 422

Cys Arg Glu Ile Leu Ser Val Asp Cys Ser Thr Asn Asn Pro Ser Gln
1               5                   10                  15

Ala Lys

<210> SEQ ID NO 423
<211> LENGTH: 18
<212> TYPE: PRT
<213> ORGANISM: Homo sapiens

<400> SEQUENCE: 423

Asp Gln Thr Val Ser Asp Asn Glu Leu Gln Glu Met Ser Asn Gln Gly
1               5                   10                  15

Ser Lys

<210> SEQ ID NO 424
<211> LENGTH: 16
<212> TYPE: PRT
<213> ORGANISM: Homo sapiens

<400> SEQUENCE: 424

Glu Ile Leu Ser Val Asp Cys Ser Thr Asn Asn Pro Ser Gln Ala Lys
1               5                   10                  15

<210> SEQ ID NO 425
<211> LENGTH: 10
<212> TYPE: PRT
<213> ORGANISM: Homo sapiens

<400> SEQUENCE: 425

Glu Ile Gln Asn Ala Val Asn Gly Val Lys
1               5                   10

<210> SEQ ID NO 426
<211> LENGTH: 11
<212> TYPE: PRT
<213> ORGANISM: Homo sapiens

<400> SEQUENCE: 426

Glu Leu Asp Glu Ser Leu Gln Val Ala Glu Arg
1               5                   10

<210> SEQ ID NO 427
<211> LENGTH: 16
<212> TYPE: PRT
<213> ORGANISM: Homo sapiens

<400> SEQUENCE: 427

Glu Pro Gln Asp Thr Tyr His Tyr Leu Pro Phe Ser Leu Pro His Arg
1               5                   10                  15

<210> SEQ ID NO 428
<211> LENGTH: 20
<212> TYPE: PRT
<213> ORGANISM: Homo sapiens

<400> SEQUENCE: 428

Phe Phe Thr Arg Glu Pro Gln Asp Thr Tyr His Tyr Leu Pro Phe Ser
1               5                   10                  15

Leu Pro His Arg
            20

<210> SEQ ID NO 429
<211> LENGTH: 8
<212> TYPE: PRT
<213> ORGANISM: Homo sapiens

<400> SEQUENCE: 429

```
Phe Met Glu Thr Val Ala Glu Lys
1               5

<210> SEQ ID NO 430
<211> LENGTH: 17
<212> TYPE: PRT
<213> ORGANISM: Homo sapiens

<400> SEQUENCE: 430

Leu Phe Asp Ser Asp Pro Ile Thr Val Thr Val Pro Val Glu Val Ser
1               5                   10                  15
Arg

<210> SEQ ID NO 431
<211> LENGTH: 15
<212> TYPE: PRT
<213> ORGANISM: Homo sapiens

<400> SEQUENCE: 431

Gln Gln Thr His Met Leu Asp Val Met Gln Asp His Phe Ser Arg
1               5                   10                  15

<210> SEQ ID NO 432
<211> LENGTH: 8
<212> TYPE: PRT
<213> ORGANISM: Homo sapiens

<400> SEQUENCE: 432

Arg Pro His Phe Phe Phe Pro Lys
1               5

<210> SEQ ID NO 433
<211> LENGTH: 10
<212> TYPE: PRT
<213> ORGANISM: Homo sapiens

<400> SEQUENCE: 433

Thr Leu Leu Ser Asn Leu Glu Glu Ala Lys
1               5                   10

<210> SEQ ID NO 434
<211> LENGTH: 11
<212> TYPE: PRT
<213> ORGANISM: Homo sapiens

<400> SEQUENCE: 434

Thr Leu Leu Ser Asn Leu Glu Glu Ala Lys Lys
1               5                   10

<210> SEQ ID NO 435
<211> LENGTH: 23
<212> TYPE: PRT
<213> ORGANISM: Homo sapiens

<400> SEQUENCE: 435

Val Thr Thr Val Ala Ser His Thr Ser Asp Ser Asp Val Pro Ser Gly
1               5                   10                  15
Val Thr Glu Val Val Val Lys
            20

<210> SEQ ID NO 436
<211> LENGTH: 6
<212> TYPE: PRT
<213> ORGANISM: Homo sapiens
```

```
<400> SEQUENCE: 436

Tyr Asn Glu Leu Leu Lys
1               5

<210> SEQ ID NO 437
<211> LENGTH: 14
<212> TYPE: PRT
<213> ORGANISM: Homo sapiens

<400> SEQUENCE: 437

Tyr Val Asn Lys Glu Ile Gln Asn Ala Val Asn Gly Val Lys
1               5                  10

<210> SEQ ID NO 438
<211> LENGTH: 6
<212> TYPE: PRT
<213> ORGANISM: Homo sapiens

<400> SEQUENCE: 438

Ala Leu Gln Glu Tyr Arg
1               5

<210> SEQ ID NO 439
<211> LENGTH: 12
<212> TYPE: PRT
<213> ORGANISM: Homo sapiens

<400> SEQUENCE: 439

Ala Ser Ser Ile Ile Asp Glu Leu Phe Gln Asp Arg
1               5                  10

<210> SEQ ID NO 440
<211> LENGTH: 16
<212> TYPE: PRT
<213> ORGANISM: Homo sapiens

<400> SEQUENCE: 440

Ala Ser Ser Ile Ile Asp Glu Leu Phe Gln Asp Arg Phe Phe Thr Arg
1               5                  10                  15

<210> SEQ ID NO 441
<211> LENGTH: 18
<212> TYPE: PRT
<213> ORGANISM: Homo sapiens

<400> SEQUENCE: 441

Cys Arg Glu Ile Leu Ser Val Asp Cys Ser Thr Asn Asn Pro Ser Gln
1               5                  10                  15

Ala Lys

<210> SEQ ID NO 442
<211> LENGTH: 18
<212> TYPE: PRT
<213> ORGANISM: Homo sapiens

<400> SEQUENCE: 442

Asp Gln Thr Val Ser Asp Asn Glu Leu Gln Glu Met Ser Asn Gln Gly
1               5                  10                  15

Ser Lys

<210> SEQ ID NO 443
<211> LENGTH: 16
<212> TYPE: PRT
```

<213> ORGANISM: Homo sapiens

<400> SEQUENCE: 443

Glu Ile Leu Ser Val Asp Cys Ser Thr Asn Asn Pro Ser Gln Ala Lys
1               5                   10                  15

<210> SEQ ID NO 444
<211> LENGTH: 10
<212> TYPE: PRT
<213> ORGANISM: Homo sapiens

<400> SEQUENCE: 444

Glu Ile Gln Asn Ala Val Asn Gly Val Lys
1               5                   10

<210> SEQ ID NO 445
<211> LENGTH: 11
<212> TYPE: PRT
<213> ORGANISM: Homo sapiens

<400> SEQUENCE: 445

Glu Leu Asp Glu Ser Leu Gln Val Ala Glu Arg
1               5                   10

<210> SEQ ID NO 446
<211> LENGTH: 16
<212> TYPE: PRT
<213> ORGANISM: Homo sapiens

<400> SEQUENCE: 446

Glu Pro Gln Asp Thr Tyr His Tyr Leu Pro Phe Ser Leu Pro His Arg
1               5                   10                  15

<210> SEQ ID NO 447
<211> LENGTH: 20
<212> TYPE: PRT
<213> ORGANISM: Homo sapiens

<400> SEQUENCE: 447

Phe Phe Thr Arg Glu Pro Gln Asp Thr Tyr His Tyr Leu Pro Phe Ser
1               5                   10                  15

Leu Pro His Arg
            20

<210> SEQ ID NO 448
<211> LENGTH: 8
<212> TYPE: PRT
<213> ORGANISM: Homo sapiens

<400> SEQUENCE: 448

Phe Met Glu Thr Val Ala Glu Lys
1               5

<210> SEQ ID NO 449
<211> LENGTH: 17
<212> TYPE: PRT
<213> ORGANISM: Homo sapiens

<400> SEQUENCE: 449

Leu Phe Asp Ser Asp Pro Ile Thr Val Thr Val Pro Val Glu Val Ser
1               5                   10                  15

Arg

<210> SEQ ID NO 450

```
<211> LENGTH: 15
<212> TYPE: PRT
<213> ORGANISM: Homo sapiens

<400> SEQUENCE: 450

Gln Gln Thr His Met Leu Asp Val Met Gln Asp His Phe Ser Arg
1               5                   10                  15

<210> SEQ ID NO 451
<211> LENGTH: 8
<212> TYPE: PRT
<213> ORGANISM: Homo sapiens

<400> SEQUENCE: 451

Arg Pro His Phe Phe Phe Pro Lys
1               5

<210> SEQ ID NO 452
<211> LENGTH: 10
<212> TYPE: PRT
<213> ORGANISM: Homo sapiens

<400> SEQUENCE: 452

Thr Leu Leu Ser Asn Leu Glu Glu Ala Lys
1               5                   10

<210> SEQ ID NO 453
<211> LENGTH: 11
<212> TYPE: PRT
<213> ORGANISM: Homo sapiens

<400> SEQUENCE: 453

Thr Leu Leu Ser Asn Leu Glu Glu Ala Lys Lys
1               5                   10

<210> SEQ ID NO 454
<211> LENGTH: 23
<212> TYPE: PRT
<213> ORGANISM: Homo sapiens

<400> SEQUENCE: 454

Val Thr Thr Val Ala Ser His Thr Ser Asp Ser Asp Val Pro Ser Gly
1               5                   10                  15

Val Thr Glu Val Val Val Lys
            20

<210> SEQ ID NO 455
<211> LENGTH: 6
<212> TYPE: PRT
<213> ORGANISM: Homo sapiens

<400> SEQUENCE: 455

Tyr Asn Glu Leu Leu Lys
1               5

<210> SEQ ID NO 456
<211> LENGTH: 14
<212> TYPE: PRT
<213> ORGANISM: Homo sapiens

<400> SEQUENCE: 456

Tyr Val Asn Lys Glu Ile Gln Asn Ala Val Asn Gly Val Lys
1               5                   10

<210> SEQ ID NO 457
```

```
<211> LENGTH: 12
<212> TYPE: PRT
<213> ORGANISM: Homo sapiens

<400> SEQUENCE: 457

Ala Ser Ser Ile Ile Asp Glu Leu Phe Gln Asp Arg
1               5                   10

<210> SEQ ID NO 458
<211> LENGTH: 18
<212> TYPE: PRT
<213> ORGANISM: Homo sapiens

<400> SEQUENCE: 458

Asp Gln Thr Val Ser Asp Asn Glu Leu Gln Glu Met Ser Asn Gln Gly
1               5                   10                  15

Ser Lys

<210> SEQ ID NO 459
<211> LENGTH: 11
<212> TYPE: PRT
<213> ORGANISM: Homo sapiens

<400> SEQUENCE: 459

Glu Leu Asp Glu Ser Leu Gln Val Ala Glu Arg
1               5                   10

<210> SEQ ID NO 460
<211> LENGTH: 8
<212> TYPE: PRT
<213> ORGANISM: Homo sapiens

<400> SEQUENCE: 460

Phe Met Glu Thr Val Ala Glu Lys
1               5

<210> SEQ ID NO 461
<211> LENGTH: 17
<212> TYPE: PRT
<213> ORGANISM: Homo sapiens

<400> SEQUENCE: 461

Leu Phe Asp Ser Asp Pro Ile Thr Val Thr Val Pro Val Glu Val Ser
1               5                   10                  15

Arg

<210> SEQ ID NO 462
<211> LENGTH: 8
<212> TYPE: PRT
<213> ORGANISM: Homo sapiens

<400> SEQUENCE: 462

Arg Pro His Phe Phe Phe Pro Lys
1               5

<210> SEQ ID NO 463
<211> LENGTH: 10
<212> TYPE: PRT
<213> ORGANISM: Homo sapiens

<400> SEQUENCE: 463

Thr Leu Leu Ser Asn Leu Glu Glu Ala Lys
1               5                   10
```

<210> SEQ ID NO 464
<211> LENGTH: 11
<212> TYPE: PRT
<213> ORGANISM: Homo sapiens

<400> SEQUENCE: 464

Thr Leu Leu Ser Asn Leu Glu Glu Ala Lys Lys
1               5                   10

<210> SEQ ID NO 465
<211> LENGTH: 23
<212> TYPE: PRT
<213> ORGANISM: Homo sapiens

<400> SEQUENCE: 465

Val Thr Thr Val Ala Ser His Thr Ser Asp Ser Asp Val Pro Ser Gly
1               5                   10                  15

Val Thr Glu Val Val Val Lys
            20

<210> SEQ ID NO 466
<211> LENGTH: 6
<212> TYPE: PRT
<213> ORGANISM: Homo sapiens

<400> SEQUENCE: 466

Ala Leu Gln Glu Tyr Arg
1               5

<210> SEQ ID NO 467
<211> LENGTH: 16
<212> TYPE: PRT
<213> ORGANISM: Homo sapiens

<400> SEQUENCE: 467

Ala Ser Ser Ile Ile Asp Glu Leu Phe Gln Asp Arg Phe Phe Thr Arg
1               5                   10                  15

<210> SEQ ID NO 468
<211> LENGTH: 18
<212> TYPE: PRT
<213> ORGANISM: Homo sapiens

<400> SEQUENCE: 468

Cys Arg Glu Ile Leu Ser Val Asp Cys Ser Thr Asn Asn Pro Ser Gln
1               5                   10                  15

Ala Lys

<210> SEQ ID NO 469
<211> LENGTH: 16
<212> TYPE: PRT
<213> ORGANISM: Homo sapiens

<400> SEQUENCE: 469

Glu Ile Leu Ser Val Asp Cys Ser Thr Asn Asn Pro Ser Gln Ala Lys
1               5                   10                  15

<210> SEQ ID NO 470
<211> LENGTH: 10
<212> TYPE: PRT
<213> ORGANISM: Homo sapiens

<400> SEQUENCE: 470

Glu Ile Gln Asn Ala Val Asn Gly Val Lys
1               5                   10

<210> SEQ ID NO 471
<211> LENGTH: 16
<212> TYPE: PRT
<213> ORGANISM: Homo sapiens

<400> SEQUENCE: 471

Glu Pro Gln Asp Thr Tyr His Tyr Leu Pro Phe Ser Leu Pro His Arg
1               5                   10                  15

<210> SEQ ID NO 472
<211> LENGTH: 20
<212> TYPE: PRT
<213> ORGANISM: Homo sapiens

<400> SEQUENCE: 472

Phe Phe Thr Arg Glu Pro Gln Asp Thr Tyr His Tyr Leu Pro Phe Ser
1               5                   10                  15

Leu Pro His Arg
            20

<210> SEQ ID NO 473
<211> LENGTH: 9
<212> TYPE: PRT
<213> ORGANISM: Homo sapiens

<400> SEQUENCE: 473

Ile Asp Ser Leu Leu Glu Asn Asp Arg
1               5

<210> SEQ ID NO 474
<211> LENGTH: 24
<212> TYPE: PRT
<213> ORGANISM: Homo sapiens

<400> SEQUENCE: 474

Ile Asp Ser Leu Leu Glu Asn Asp Arg Gln Gln Thr His Met Leu Asp
1               5                   10                  15

Val Met Gln Asp His Phe Ser Arg
            20

<210> SEQ ID NO 475
<211> LENGTH: 11
<212> TYPE: PRT
<213> ORGANISM: Homo sapiens

<400> SEQUENCE: 475

Lys Thr Leu Leu Ser Asn Leu Glu Glu Ala Lys
1               5                   10

<210> SEQ ID NO 476
<211> LENGTH: 12
<212> TYPE: PRT
<213> ORGANISM: Homo sapiens

<400> SEQUENCE: 476

Lys Thr Leu Leu Ser Asn Leu Glu Glu Ala Lys Lys
1               5                   10

<210> SEQ ID NO 477
<211> LENGTH: 7
<212> TYPE: PRT
<213> ORGANISM: Homo sapiens

<400> SEQUENCE: 477

Lys Tyr Asn Glu Leu Leu Lys
1               5

<210> SEQ ID NO 478
<211> LENGTH: 10
<212> TYPE: PRT
<213> ORGANISM: Homo sapiens

<400> SEQUENCE: 478

Pro Ser Gly Val Thr Glu Val Val Val Lys
1               5                   10

<210> SEQ ID NO 479
<211> LENGTH: 15
<212> TYPE: PRT
<213> ORGANISM: Homo sapiens

<400> SEQUENCE: 479

Gln Gln Thr His Met Leu Asp Val Met Gln Asp His Phe Ser Arg
1               5                   10                  15

<210> SEQ ID NO 480
<211> LENGTH: 6
<212> TYPE: PRT
<213> ORGANISM: Homo sapiens

<400> SEQUENCE: 480

Tyr Asn Glu Leu Leu Lys
1               5

<210> SEQ ID NO 481
<211> LENGTH: 14
<212> TYPE: PRT
<213> ORGANISM: Homo sapiens

<400> SEQUENCE: 481

Tyr Val Asn Lys Glu Ile Gln Asn Ala Val Asn Gly Val Lys
1               5                   10

<210> SEQ ID NO 482
<211> LENGTH: 13
<212> TYPE: PRT
<213> ORGANISM: Homo sapiens

<400> SEQUENCE: 482

Ile Ile Pro His His Asn Tyr Asn Ala Ala Ile Asn Lys
1               5                   10

<210> SEQ ID NO 483
<211> LENGTH: 20
<212> TYPE: PRT
<213> ORGANISM: Homo sapiens

<400> SEQUENCE: 483

Ile Thr Val Val Ala Gly Glu His Asn Ile Glu Glu Thr Glu His Thr
1               5                   10                  15

Glu Gln Lys Arg
            20

<210> SEQ ID NO 484
<211> LENGTH: 12
<212> TYPE: PRT
<213> ORGANISM: Homo sapiens

<400> SEQUENCE: 484

Ser Cys Glu Pro Ala Val Pro Phe Pro Cys Gly Arg
1               5                   10

<210> SEQ ID NO 485
<211> LENGTH: 14
<212> TYPE: PRT
<213> ORGANISM: Homo sapiens

<400> SEQUENCE: 485

Trp Ile Val Thr Ala Ala His Cys Val Glu Thr Gly Val Lys
1               5                   10

<210> SEQ ID NO 486
<211> LENGTH: 10
<212> TYPE: PRT
<213> ORGANISM: Homo sapiens

<400> SEQUENCE: 486

Cys Lys Ile Lys Asp Cys Gly Gln Pro Arg
1               5                   10

<210> SEQ ID NO 487
<211> LENGTH: 15
<212> TYPE: PRT
<213> ORGANISM: Homo sapiens

<400> SEQUENCE: 487

Cys Leu Pro Val Cys Gly Lys Pro Val Asn Pro Val Glu Gln Arg
1               5                   10                  15

<210> SEQ ID NO 488
<211> LENGTH: 16
<212> TYPE: PRT
<213> ORGANISM: Homo sapiens

<400> SEQUENCE: 488

Phe Cys Gly Gln Leu Gly Ser Pro Leu Gly Asn Pro Pro Gly Lys Lys
1               5                   10                  15

<210> SEQ ID NO 489
<211> LENGTH: 7
<212> TYPE: PRT
<213> ORGANISM: Homo sapiens

<400> SEQUENCE: 489

Gly Tyr Gly Phe Tyr Thr Lys
1               5

<210> SEQ ID NO 490
<211> LENGTH: 11
<212> TYPE: PRT
<213> ORGANISM: Homo sapiens

<400> SEQUENCE: 490

Ile Gln Tyr Tyr Cys His Glu Pro Tyr Tyr Lys
1               5                   10

<210> SEQ ID NO 491
<211> LENGTH: 9
<212> TYPE: PRT
<213> ORGANISM: Homo sapiens

<400> SEQUENCE: 491

Lys Glu Phe Met Ser Gln Gly Asn Lys
1               5

<210> SEQ ID NO 492
<211> LENGTH: 31
<212> TYPE: PRT
<213> ORGANISM: Homo sapiens

<400> SEQUENCE: 492

Leu Phe Gly Glu Val Thr Ser Pro Leu Phe Pro Lys Pro Tyr Pro Asn
1               5                   10                  15

Asn Phe Glu Thr Thr Thr Val Ile Thr Val Pro Thr Gly Tyr Arg
            20                  25                  30

<210> SEQ ID NO 493
<211> LENGTH: 14
<212> TYPE: PRT
<213> ORGANISM: Homo sapiens

<400> SEQUENCE: 493

Leu Pro Val Ala Asn Pro Gln Ala Cys Glu Asn Trp Leu Arg
1               5                   10

<210> SEQ ID NO 494
<211> LENGTH: 20
<212> TYPE: PRT
<213> ORGANISM: Homo sapiens

<400> SEQUENCE: 494

Leu Val Phe Gln Gln Phe Asp Leu Glu Pro Ser Glu Gly Cys Phe Tyr
1               5                   10                  15

Asp Tyr Val Lys
            20

<210> SEQ ID NO 495
<211> LENGTH: 8
<212> TYPE: PRT
<213> ORGANISM: Homo sapiens

<400> SEQUENCE: 495

Asn Ile Gly Glu Phe Cys Gly Lys
1               5

<210> SEQ ID NO 496
<211> LENGTH: 26
<212> TYPE: PRT
<213> ORGANISM: Homo sapiens

<400> SEQUENCE: 496

Gln Arg Pro Pro Asp Leu Asp Thr Ser Ser Asn Ala Val Asp Leu Leu
1               5                   10                  15

Phe Phe Thr Asp Glu Ser Gly Asp Ser Arg
            20                  25

<210> SEQ ID NO 497
<211> LENGTH: 18
<212> TYPE: PRT
<213> ORGANISM: Homo sapiens

<400> SEQUENCE: 497

Thr Leu Asp Glu Phe Thr Ile Ile Gln Asn Leu Gln Pro Gln Tyr Gln
1               5                   10                  15

Phe Arg

<210> SEQ ID NO 498

```
<211> LENGTH: 7
<212> TYPE: PRT
<213> ORGANISM: Homo sapiens

<400> SEQUENCE: 498

Tyr Thr Thr Glu Ile Ile Lys
1               5

<210> SEQ ID NO 499
<211> LENGTH: 14
<212> TYPE: PRT
<213> ORGANISM: Homo sapiens

<400> SEQUENCE: 499

Ala Gly Asp Phe Leu Glu Ala Asn Tyr Met Asn Leu Gln Arg
1               5                   10

<210> SEQ ID NO 500
<211> LENGTH: 22
<212> TYPE: PRT
<213> ORGANISM: Homo sapiens

<400> SEQUENCE: 500

Ile Leu Leu Gln Gly Thr Pro Val Ala Gln Met Thr Glu Asp Ala Val
1               5                   10                  15

Asp Ala Glu Arg Leu Lys
            20

<210> SEQ ID NO 501
<211> LENGTH: 38
<212> TYPE: PRT
<213> ORGANISM: Homo sapiens

<400> SEQUENCE: 501

Ala Gly Asp Phe Leu Glu Ala Asn Tyr Met Asn Leu Gln Arg Ser Tyr
1               5                   10                  15

Thr Val Ala Ile Ala Gly Tyr Ala Leu Ala Gln Met Gly Arg Leu Lys
            20                  25                  30

Gly Pro Leu Leu Asn Lys
        35

<210> SEQ ID NO 502
<211> LENGTH: 12
<212> TYPE: PRT
<213> ORGANISM: Homo sapiens

<400> SEQUENCE: 502

Ala Pro Ser Thr Trp Leu Thr Ala Tyr Val Val Lys
1               5                   10

<210> SEQ ID NO 503
<211> LENGTH: 18
<212> TYPE: PRT
<213> ORGANISM: Homo sapiens

<400> SEQUENCE: 503

Asp Ala Pro Asp His Gln Glu Leu Asn Leu Asp Val Ser Leu Gln Leu
1               5                   10                  15

Pro Ser

<210> SEQ ID NO 504
<211> LENGTH: 16
<212> TYPE: PRT
<213> ORGANISM: Homo sapiens
```

```
<400> SEQUENCE: 504

Asp Ile Cys Glu Glu Gln Val Asn Ser Leu Pro Gly Ser Ile Thr Lys
1               5                   10                  15

<210> SEQ ID NO 505
<211> LENGTH: 10
<212> TYPE: PRT
<213> ORGANISM: Homo sapiens

<400> SEQUENCE: 505

Asp Lys Asn Arg Trp Glu Asp Pro Gly Lys
1               5                   10

<210> SEQ ID NO 506
<211> LENGTH: 32
<212> TYPE: PRT
<213> ORGANISM: Homo sapiens

<400> SEQUENCE: 506

Asp Met Ala Leu Thr Ala Phe Val Leu Ile Ser Leu Gln Glu Ala Lys
1               5                   10                  15

Asp Ile Cys Glu Glu Gln Val Asn Ser Leu Pro Gly Ser Ile Thr Lys
                20                  25                  30

<210> SEQ ID NO 507
<211> LENGTH: 25
<212> TYPE: PRT
<213> ORGANISM: Homo sapiens

<400> SEQUENCE: 507

Glu Gly Val Gln Lys Glu Asp Ile Pro Pro Ala Asp Leu Ser Asp Gln
1               5                   10                  15

Val Pro Asp Thr Glu Ser Glu Thr Arg
                20                  25

<210> SEQ ID NO 508
<211> LENGTH: 10
<212> TYPE: PRT
<213> ORGANISM: Homo sapiens

<400> SEQUENCE: 508

Glu Leu Ser Glu Ala Glu Gln Ala Thr Arg
1               5                   10

<210> SEQ ID NO 509
<211> LENGTH: 9
<212> TYPE: PRT
<213> ORGANISM: Homo sapiens

<400> SEQUENCE: 509

Phe Ile Ser Leu Gly Glu Ala Cys Lys
1               5

<210> SEQ ID NO 510
<211> LENGTH: 10
<212> TYPE: PRT
<213> ORGANISM: Homo sapiens

<400> SEQUENCE: 510

Phe Ile Ser Leu Gly Glu Ala Cys Lys Lys
1               5                   10

<210> SEQ ID NO 511
```

```
<211> LENGTH: 6
<212> TYPE: PRT
<213> ORGANISM: Homo sapiens

<400> SEQUENCE: 511

Phe Leu Thr Thr Ala Lys
1               5

<210> SEQ ID NO 512
<211> LENGTH: 8
<212> TYPE: PRT
<213> ORGANISM: Homo sapiens

<400> SEQUENCE: 512

Phe Leu Thr Thr Ala Lys Asp Lys
1               5

<210> SEQ ID NO 513
<211> LENGTH: 9
<212> TYPE: PRT
<213> ORGANISM: Homo sapiens

<400> SEQUENCE: 513

Gly Tyr Thr Gln Gln Leu Ala Phe Arg
1               5

<210> SEQ ID NO 514
<211> LENGTH: 20
<212> TYPE: PRT
<213> ORGANISM: Homo sapiens

<400> SEQUENCE: 514

Gly Tyr Thr Gln Gln Leu Ala Phe Arg Gln Pro Ser Ser Ala Phe Ala
1               5                   10                  15

Ala Phe Val Lys
            20

<210> SEQ ID NO 515
<211> LENGTH: 35
<212> TYPE: PRT
<213> ORGANISM: Homo sapiens

<400> SEQUENCE: 515

His Leu Ile Val Thr Pro Ser Gly Cys Gly Glu Gln Asn Met Ile Gly
1               5                   10                  15

Met Thr Pro Thr Val Ile Ala Val His Tyr Leu Asp Glu Thr Glu Gln
            20                  25                  30

Trp Glu Lys
        35

<210> SEQ ID NO 516
<211> LENGTH: 20
<212> TYPE: PRT
<213> ORGANISM: Homo sapiens

<400> SEQUENCE: 516

Ile Leu Leu Gln Gly Thr Pro Val Ala Gln Met Thr Glu Asp Ala Val
1               5                   10                  15

Asp Ala Glu Arg
            20

<210> SEQ ID NO 517
<211> LENGTH: 13
<212> TYPE: PRT
```

<213> ORGANISM: Homo sapiens

<400> SEQUENCE: 517

Lys Cys Cys Glu Asp Gly Met Arg Glu Asn Pro Met Arg
1               5                   10

<210> SEQ ID NO 518
<211> LENGTH: 10
<212> TYPE: PRT
<213> ORGANISM: Homo sapiens

<400> SEQUENCE: 518

Lys Gly Tyr Thr Gln Gln Leu Ala Phe Arg
1               5                   10

<210> SEQ ID NO 519
<211> LENGTH: 14
<212> TYPE: PRT
<213> ORGANISM: Homo sapiens

<400> SEQUENCE: 519

Lys Val Phe Leu Asp Cys Cys Asn Tyr Ile Thr Glu Leu Arg
1               5                   10

<210> SEQ ID NO 520
<211> LENGTH: 15
<212> TYPE: PRT
<213> ORGANISM: Homo sapiens

<400> SEQUENCE: 520

Lys Val Phe Leu Asp Cys Cys Asn Tyr Ile Thr Glu Leu Arg Arg
1               5                   10                  15

<210> SEQ ID NO 521
<211> LENGTH: 8
<212> TYPE: PRT
<213> ORGANISM: Homo sapiens

<400> SEQUENCE: 521

Leu Lys Gly Pro Leu Leu Asn Lys
1               5

<210> SEQ ID NO 522
<211> LENGTH: 14
<212> TYPE: PRT
<213> ORGANISM: Homo sapiens

<400> SEQUENCE: 522

Leu Lys Gly Pro Leu Leu Asn Lys Phe Leu Thr Thr Ala Lys
1               5                   10

<210> SEQ ID NO 523
<211> LENGTH: 21
<212> TYPE: PRT
<213> ORGANISM: Homo sapiens

<400> SEQUENCE: 523

Asn Asn Asn Glu Lys Asp Met Ala Leu Thr Ala Phe Val Leu Ile Ser
1               5                   10                  15

Leu Gln Glu Ala Lys
            20

<210> SEQ ID NO 524
<211> LENGTH: 37
<212> TYPE: PRT

-continued

<213> ORGANISM: Homo sapiens

<400> SEQUENCE: 524

Asn Asn Asn Glu Lys Asp Met Ala Leu Thr Ala Phe Val Leu Ile Ser
1               5                   10                  15

Leu Gln Glu Ala Lys Asp Ile Cys Glu Glu Gln Val Asn Ser Leu Pro
            20                  25                  30

Gly Ser Ile Thr Lys
        35

<210> SEQ ID NO 525
<211> LENGTH: 27
<212> TYPE: PRT
<213> ORGANISM: Homo sapiens

<400> SEQUENCE: 525

Asn Arg Trp Glu Asp Pro Gly Lys Gln Leu Tyr Asn Val Glu Ala Thr
1               5                   10                  15

Ser Tyr Ala Leu Leu Ala Leu Leu Gln Leu Lys
            20                  25

<210> SEQ ID NO 526
<211> LENGTH: 23
<212> TYPE: PRT
<213> ORGANISM: Homo sapiens

<400> SEQUENCE: 526

Gln Lys Pro Asp Gly Val Phe Gln Glu Asp Ala Pro Val Ile His Gln
1               5                   10                  15

Glu Met Ile Gly Gly Leu Arg
            20

<210> SEQ ID NO 527
<211> LENGTH: 19
<212> TYPE: PRT
<213> ORGANISM: Homo sapiens

<400> SEQUENCE: 527

Gln Leu Tyr Asn Val Glu Ala Thr Ser Tyr Ala Leu Leu Ala Leu Leu
1               5                   10                  15

Gln Leu Lys

<210> SEQ ID NO 528
<211> LENGTH: 29
<212> TYPE: PRT
<213> ORGANISM: Homo sapiens

<400> SEQUENCE: 528

Gln Leu Tyr Asn Val Glu Ala Thr Ser Tyr Ala Leu Leu Ala Leu Leu
1               5                   10                  15

Gln Leu Lys Asp Phe Asp Phe Val Pro Pro Val Val Arg
            20                  25

<210> SEQ ID NO 529
<211> LENGTH: 11
<212> TYPE: PRT
<213> ORGANISM: Homo sapiens

<400> SEQUENCE: 529

Gln Pro Ser Ser Ala Phe Ala Ala Phe Val Lys
1               5                   10

```
<210> SEQ ID NO 530
<211> LENGTH: 12
<212> TYPE: PRT
<213> ORGANISM: Homo sapiens

<400> SEQUENCE: 530

Gln Pro Ser Ser Ala Phe Ala Ala Phe Val Lys Arg
1               5                   10

<210> SEQ ID NO 531
<211> LENGTH: 13
<212> TYPE: PRT
<213> ORGANISM: Homo sapiens

<400> SEQUENCE: 531

Arg Ala Pro Ser Thr Trp Leu Thr Ala Tyr Val Val Lys
1               5                   10

<210> SEQ ID NO 532
<211> LENGTH: 9
<212> TYPE: PRT
<213> ORGANISM: Homo sapiens

<400> SEQUENCE: 532

Arg Gln Gly Ala Leu Glu Leu Ile Lys
1               5

<210> SEQ ID NO 533
<211> LENGTH: 10
<212> TYPE: PRT
<213> ORGANISM: Homo sapiens

<400> SEQUENCE: 533

Arg Gln Gly Ala Leu Glu Leu Ile Lys Lys
1               5                   10

<210> SEQ ID NO 534
<211> LENGTH: 7
<212> TYPE: PRT
<213> ORGANISM: Homo sapiens

<400> SEQUENCE: 534

Ser Val Gln Leu Thr Glu Lys
1               5

<210> SEQ ID NO 535
<211> LENGTH: 8
<212> TYPE: PRT
<213> ORGANISM: Homo sapiens

<400> SEQUENCE: 535

Ser Val Gln Leu Thr Glu Lys Arg
1               5

<210> SEQ ID NO 536
<211> LENGTH: 16
<212> TYPE: PRT
<213> ORGANISM: Homo sapiens

<400> SEQUENCE: 536

Ser Tyr Thr Val Ala Ile Ala Gly Tyr Ala Leu Ala Gln Met Gly Arg
1               5                   10                  15

<210> SEQ ID NO 537
<211> LENGTH: 12
<212> TYPE: PRT
```

<213> ORGANISM: Homo sapiens

<400> SEQUENCE: 537

Thr Arg Phe Ile Ser Leu Gly Glu Ala Cys Lys Lys
1               5                   10

<210> SEQ ID NO 538
<211> LENGTH: 13
<212> TYPE: PRT
<213> ORGANISM: Homo sapiens

<400> SEQUENCE: 538

Val Phe Leu Asp Cys Cys Asn Tyr Ile Thr Glu Leu Arg
1               5                   10

<210> SEQ ID NO 539
<211> LENGTH: 25
<212> TYPE: PRT
<213> ORGANISM: Homo sapiens

<400> SEQUENCE: 539

Trp Glu Asp Pro Gly Lys Gln Leu Tyr Asn Val Glu Ala Thr Ser Tyr
1               5                   10                  15

Ala Leu Leu Ala Leu Leu Gln Leu Lys
            20                  25

<210> SEQ ID NO 540
<211> LENGTH: 35
<212> TYPE: PRT
<213> ORGANISM: Homo sapiens

<400> SEQUENCE: 540

Trp Glu Asp Pro Gly Lys Gln Leu Tyr Asn Val Glu Ala Thr Ser Tyr
1               5                   10                  15

Ala Leu Leu Ala Leu Leu Gln Leu Lys Asp Phe Asp Phe Val Pro Pro
            20                  25                  30

Val Val Arg
        35

<210> SEQ ID NO 541
<211> LENGTH: 6
<212> TYPE: PRT
<213> ORGANISM: Homo sapiens

<400> SEQUENCE: 541

Trp Leu Ile Leu Glu Lys
1               5

<210> SEQ ID NO 542
<211> LENGTH: 24
<212> TYPE: PRT
<213> ORGANISM: Homo sapiens

<400> SEQUENCE: 542

Tyr Tyr Gly Gly Gly Tyr Gly Ser Thr Gln Ala Thr Phe Met Val Phe
1               5                   10                  15

Gln Ala Leu Ala Gln Tyr Gln Lys
            20

<210> SEQ ID NO 543
<211> LENGTH: 19
<212> TYPE: PRT
<213> ORGANISM: Homo sapiens -continued

```
<400> SEQUENCE: 543

Met Arg Pro Ser Thr Asp Thr Ile Thr Val Met Val Glu Asn Ser His
1               5                   10                  15

Gly Leu Arg

<210> SEQ ID NO 544
<211> LENGTH: 21
<212> TYPE: PRT
<213> ORGANISM: Homo sapiens

<400> SEQUENCE: 544

Ala Glu Phe Gln Asp Ala Leu Glu Lys Leu Asn Met Gly Ile Thr Asp
1               5                   10                  15

Leu Gln Gly Leu Arg
            20

<210> SEQ ID NO 545
<211> LENGTH: 13
<212> TYPE: PRT
<213> ORGANISM: Homo sapiens

<400> SEQUENCE: 545

Glu Met Ser Gly Ser Pro Ala Ser Gly Ile Pro Val Lys
1               5                   10

<210> SEQ ID NO 546
<211> LENGTH: 25
<212> TYPE: PRT
<213> ORGANISM: Homo sapiens

<400> SEQUENCE: 546

Glu Val Tyr Met Pro Ser Ser Ile Phe Gln Asp Phe Val Ile Pro
1               5                   10                  15

Asp Ile Ser Glu Pro Gly Thr Trp Lys
            20                  25

<210> SEQ ID NO 547
<211> LENGTH: 11
<212> TYPE: PRT
<213> ORGANISM: Homo sapiens

<400> SEQUENCE: 547

Gly Gln Ile Val Phe Met Asn Arg Glu Pro Lys
1               5                   10

<210> SEQ ID NO 548
<211> LENGTH: 27
<212> TYPE: PRT
<213> ORGANISM: Homo sapiens

<400> SEQUENCE: 548

Lys Lys Glu Val Tyr Met Pro Ser Ser Ile Phe Gln Asp Asp Phe Val
1               5                   10                  15

Ile Pro Asp Ile Ser Glu Pro Gly Thr Trp Lys
            20                  25

<210> SEQ ID NO 549
<211> LENGTH: 42
<212> TYPE: PRT
<213> ORGANISM: Homo sapiens

<400> SEQUENCE: 549

Leu Arg Leu Glu Pro Gly Lys Glu Tyr Leu Ile Met Gly Leu Asp Gly
```

```
                1               5                  10                 15
Ala Thr Tyr Asp Leu Glu Gly His Pro Gln Tyr Leu Leu Asp Ser Asn
                20                 25                 30

Ser Trp Ile Glu Glu Met Pro Ser Glu Arg
        35                 40

<210> SEQ ID NO 550
<211> LENGTH: 39
<212> TYPE: PRT
<213> ORGANISM: Homo sapiens

<400> SEQUENCE: 550

Ser Met Gln Gly Gly Leu Val Gly Asn Asp Glu Thr Val Ala Leu Thr
1               5                  10                 15

Ala Phe Val Thr Ile Ala Leu His His Gly Leu Ala Val Phe Gln Asp
                20                 25                 30

Glu Gly Ala Glu Pro Leu Lys
        35

<210> SEQ ID NO 551
<211> LENGTH: 41
<212> TYPE: PRT
<213> ORGANISM: Homo sapiens

<400> SEQUENCE: 551

Ser Met Gln Gly Gly Leu Val Gly Asn Asp Glu Thr Val Ala Leu Thr
1               5                  10                 15

Ala Phe Val Thr Ile Ala Leu His His Gly Leu Ala Val Phe Gln Asp
                20                 25                 30

Glu Gly Ala Glu Pro Leu Lys Gln Arg
        35                 40

<210> SEQ ID NO 552
<211> LENGTH: 23
<212> TYPE: PRT
<213> ORGANISM: Homo sapiens

<400> SEQUENCE: 552

Thr Leu Glu Ile Pro Gly Asn Ser Asp Pro Asn Met Ile Pro Asp Gly
1               5                  10                 15

Asp Phe Asn Ser Tyr Val Arg
        20

<210> SEQ ID NO 553
<211> LENGTH: 20
<212> TYPE: PRT
<213> ORGANISM: Homo sapiens

<400> SEQUENCE: 553

Ala Ala Cys Ala Gln Leu Asn Asp Phe Leu Gln Glu Tyr Gly Thr Gln
1               5                  10                 15

Gly Cys Gln Val
        20

<210> SEQ ID NO 554
<211> LENGTH: 35
<212> TYPE: PRT
<213> ORGANISM: Homo sapiens

<400> SEQUENCE: 554

Ala Asp Leu Glu Lys Leu Thr Ser Leu Ser Asp Arg Tyr Val Ser His
1               5                  10                 15
```

```
Phe Glu Thr Glu Gly Pro His Val Leu Leu Tyr Phe Asp Ser Val Pro
             20                  25                  30
Thr Ser Arg
         35

<210> SEQ ID NO 555
<211> LENGTH: 9
<212> TYPE: PRT
<213> ORGANISM: Homo sapiens

<400> SEQUENCE: 555

Ala Glu Phe Gln Asp Ala Leu Glu Lys
1               5

<210> SEQ ID NO 556
<211> LENGTH: 19
<212> TYPE: PRT
<213> ORGANISM: Homo sapiens

<400> SEQUENCE: 556

Ala Leu Glu Ile Leu Gln Glu Glu Asp Leu Ile Asp Glu Asp Asp Ile
1               5                   10                  15
Pro Val Arg

<210> SEQ ID NO 557
<211> LENGTH: 13
<212> TYPE: PRT
<213> ORGANISM: Homo sapiens

<400> SEQUENCE: 557

Ala Leu Leu Ser Leu Gln Val Pro Leu Lys Asp Ala Lys
1               5                   10

<210> SEQ ID NO 558
<211> LENGTH: 18
<212> TYPE: PRT
<213> ORGANISM: Homo sapiens

<400> SEQUENCE: 558

Ala Val Gly Ser Gly Ala Thr Phe Ser His Tyr Tyr Met Ile Leu
1               5                   10                  15
Ser Arg

<210> SEQ ID NO 559
<211> LENGTH: 10
<212> TYPE: PRT
<213> ORGANISM: Homo sapiens

<400> SEQUENCE: 559

Cys Ser Val Phe Tyr Gly Ala Pro Ser Lys
1               5                   10

<210> SEQ ID NO 560
<211> LENGTH: 15
<212> TYPE: PRT
<213> ORGANISM: Homo sapiens

<400> SEQUENCE: 560

Asp Phe Ala Leu Leu Ser Leu Gln Val Pro Leu Lys Asp Ala Lys
1               5                   10                  15

<210> SEQ ID NO 561
<211> LENGTH: 12
```

```
<212> TYPE: PRT
<213> ORGANISM: Homo sapiens

<400> SEQUENCE: 561

Asp Ser Ser Thr Trp Leu Thr Ala Phe Val Leu Lys
1               5                   10

<210> SEQ ID NO 562
<211> LENGTH: 12
<212> TYPE: PRT
<213> ORGANISM: Homo sapiens

<400> SEQUENCE: 562

Glu Ala Pro Lys Val Val Glu Glu Gln Glu Ser Arg
1               5                   10

<210> SEQ ID NO 563
<211> LENGTH: 31
<212> TYPE: PRT
<213> ORGANISM: Homo sapiens

<400> SEQUENCE: 563

Glu Cys Val Gly Phe Glu Ala Val Gln Glu Val Pro Val Gly Leu Val
1               5                   10                  15

Gln Pro Ala Ser Ala Thr Leu Tyr Asp Tyr Tyr Asn Pro Glu Arg
            20                  25                  30

<210> SEQ ID NO 564
<211> LENGTH: 32
<212> TYPE: PRT
<213> ORGANISM: Homo sapiens

<400> SEQUENCE: 564

Glu Cys Val Gly Phe Glu Ala Val Gln Glu Val Pro Val Gly Leu Val
1               5                   10                  15

Gln Pro Ala Ser Ala Thr Leu Tyr Asp Tyr Tyr Asn Pro Glu Arg Arg
            20                  25                  30

<210> SEQ ID NO 565
<211> LENGTH: 7
<212> TYPE: PRT
<213> ORGANISM: Homo sapiens

<400> SEQUENCE: 565

Glu Phe His Leu His Leu Arg
1               5

<210> SEQ ID NO 566
<211> LENGTH: 18
<212> TYPE: PRT
<213> ORGANISM: Homo sapiens

<400> SEQUENCE: 566

Glu Gly Ala Ile His Arg Glu Glu Leu Val Tyr Glu Leu Asn Pro Leu
1               5                   10                  15

Asp His

<210> SEQ ID NO 567
<211> LENGTH: 19
<212> TYPE: PRT
<213> ORGANISM: Homo sapiens

<400> SEQUENCE: 567

Glu Gly Ala Ile His Arg Glu Glu Leu Val Tyr Glu Leu Asn Pro Leu
```

```
                1               5                  10                 15

Asp His Arg

<210> SEQ ID NO 568
<211> LENGTH: 20
<212> TYPE: PRT
<213> ORGANISM: Homo sapiens

<400> SEQUENCE: 568

Glu Gly Ala Ile His Arg Glu Glu Leu Val Tyr Glu Leu Asn Pro Leu
1               5                  10                 15

Asp His Arg Gly
            20

<210> SEQ ID NO 569
<211> LENGTH: 14
<212> TYPE: PRT
<213> ORGANISM: Homo sapiens

<400> SEQUENCE: 569

Glu Pro Phe Leu Ser Cys Cys Gln Phe Ala Glu Ser Leu Arg
1               5                  10

<210> SEQ ID NO 570
<211> LENGTH: 10
<212> TYPE: PRT
<213> ORGANISM: Homo sapiens

<400> SEQUENCE: 570

Phe Gly Leu Leu Asp Glu Asp Gly Lys Lys
1               5                  10

<210> SEQ ID NO 571
<211> LENGTH: 14
<212> TYPE: PRT
<213> ORGANISM: Homo sapiens

<400> SEQUENCE: 571

Phe Gly Leu Leu Asp Glu Asp Gly Lys Lys Thr Phe Phe Arg
1               5                  10

<210> SEQ ID NO 572
<211> LENGTH: 24
<212> TYPE: PRT
<213> ORGANISM: Homo sapiens

<400> SEQUENCE: 572

Phe Gln Ile Leu Thr Leu Trp Leu Pro Asp Ser Leu Thr Thr Trp Glu
1               5                  10                 15

Ile His Gly Leu Ser Leu Ser Lys
            20

<210> SEQ ID NO 573
<211> LENGTH: 17
<212> TYPE: PRT
<213> ORGANISM: Homo sapiens

<400> SEQUENCE: 573

Gly His Leu Phe Leu Gln Thr Asp Gln Pro Ile Tyr Asn Pro Gly Gln
1               5                  10                 15

Arg

<210> SEQ ID NO 574
```

```
<211> LENGTH: 13
<212> TYPE: PRT
<213> ORGANISM: Homo sapiens

<400> SEQUENCE: 574

Gly Leu Glu Glu Glu Leu Gln Phe Ser Leu Gly Ser Lys
1               5                   10

<210> SEQ ID NO 575
<211> LENGTH: 9
<212> TYPE: PRT
<213> ORGANISM: Homo sapiens

<400> SEQUENCE: 575

Gly Leu Gln Asp Glu Asp Gly Tyr Arg
1               5

<210> SEQ ID NO 576
<211> LENGTH: 14
<212> TYPE: PRT
<213> ORGANISM: Homo sapiens

<400> SEQUENCE: 576

Gly Pro Glu Val Gln Leu Val Ala His Ser Pro Trp Leu Lys
1               5                   10

<210> SEQ ID NO 577
<211> LENGTH: 19
<212> TYPE: PRT
<213> ORGANISM: Homo sapiens

<400> SEQUENCE: 577

Gly Pro Glu Val Gln Leu Val Ala His Ser Pro Trp Leu Lys Asp Ser
1               5                   10                  15

Leu Ser Arg

<210> SEQ ID NO 578
<211> LENGTH: 8
<212> TYPE: PRT
<213> ORGANISM: Homo sapiens

<400> SEQUENCE: 578

Gly Gln Ile Val Phe Met Asn Arg
1               5

<210> SEQ ID NO 579
<211> LENGTH: 13
<212> TYPE: PRT
<213> ORGANISM: Homo sapiens

<400> SEQUENCE: 579

Gly Ser Phe Glu Phe Pro Val Gly Asp Ala Val Ser Lys
1               5                   10

<210> SEQ ID NO 580
<211> LENGTH: 10
<212> TYPE: PRT
<213> ORGANISM: Homo sapiens

<400> SEQUENCE: 580

Gly Ser Val Phe Leu Arg Asn Pro Ser Arg
1               5                   10

<210> SEQ ID NO 581
<211> LENGTH: 15
```

```
<212> TYPE: PRT
<213> ORGANISM: Homo sapiens

<400> SEQUENCE: 581

His Leu Val Pro Gly Ala Pro Phe Leu Gln Ala Leu Val Arg
1               5                   10                  15

<210> SEQ ID NO 582
<211> LENGTH: 25
<212> TYPE: PRT
<213> ORGANISM: Homo sapiens

<400> SEQUENCE: 582

Ile Thr Pro Gly Lys Pro Tyr Ile Leu Thr Val Pro Gly His Leu Asp
1               5                   10                  15

Glu Met Gln Leu Asp Ile Gln Ala Arg
            20                  25

<210> SEQ ID NO 583
<211> LENGTH: 12
<212> TYPE: PRT
<213> ORGANISM: Homo sapiens

<400> SEQUENCE: 583

Lys Ala Asp Gly Ser Tyr Ala Ala Trp Leu Ser Arg
1               5                   10

<210> SEQ ID NO 584
<211> LENGTH: 10
<212> TYPE: PRT
<213> ORGANISM: Homo sapiens

<400> SEQUENCE: 584

Lys Tyr Val Leu Pro Asn Phe Glu Val Lys
1               5                   10

<210> SEQ ID NO 585
<211> LENGTH: 9
<212> TYPE: PRT
<213> ORGANISM: Homo sapiens

<400> SEQUENCE: 585

Leu Glu Leu Ser Val Asp Gly Ala Lys
1               5

<210> SEQ ID NO 586
<211> LENGTH: 10
<212> TYPE: PRT
<213> ORGANISM: Homo sapiens

<400> SEQUENCE: 586

Leu Gly Gln Tyr Ala Ser Pro Thr Ala Lys
1               5                   10

<210> SEQ ID NO 587
<211> LENGTH: 11
<212> TYPE: PRT
<213> ORGANISM: Homo sapiens

<400> SEQUENCE: 587

Leu Gly Gln Tyr Ala Ser Pro Thr Ala Lys Arg
1               5                   10

<210> SEQ ID NO 588
<211> LENGTH: 26
```

```
<212> TYPE: PRT
<213> ORGANISM: Homo sapiens

<400> SEQUENCE: 588

Leu His Leu Glu Thr Asp Ser Leu Ala Leu Val Ala Leu Gly Ala Leu
1               5                   10                  15

Asp Thr Ala Leu Tyr Ala Ala Gly Ser Lys
            20                  25

<210> SEQ ID NO 589
<211> LENGTH: 17
<212> TYPE: PRT
<213> ORGANISM: Homo sapiens

<400> SEQUENCE: 589

Leu Leu Ala Thr Leu Cys Ser Ala Glu Val Cys Gln Cys Ala Glu Gly
1               5                   10                  15

Lys

<210> SEQ ID NO 590
<211> LENGTH: 26
<212> TYPE: PRT
<213> ORGANISM: Homo sapiens

<400> SEQUENCE: 590

Leu Leu Leu Phe Ser Pro Ser Val Val His Leu Gly Val Pro Leu Ser
1               5                   10                  15

Val Gly Val Gln Leu Gln Asp Val Pro Arg
            20                  25

<210> SEQ ID NO 591
<211> LENGTH: 31
<212> TYPE: PRT
<213> ORGANISM: Homo sapiens

<400> SEQUENCE: 591

Leu Leu Leu Phe Ser Pro Ser Val Val His Leu Gly Val Pro Leu Ser
1               5                   10                  15

Val Gly Val Gln Leu Gln Asp Val Pro Arg Gly Gln Val Val Lys
            20                  25                  30

<210> SEQ ID NO 592
<211> LENGTH: 12
<212> TYPE: PRT
<213> ORGANISM: Homo sapiens

<400> SEQUENCE: 592

Leu Asn Met Gly Ile Thr Asp Leu Gln Gly Leu Arg
1               5                   10

<210> SEQ ID NO 593
<211> LENGTH: 6
<212> TYPE: PRT
<213> ORGANISM: Homo sapiens

<400> SEQUENCE: 593

Leu Pro Met Ser Val Arg
1               5

<210> SEQ ID NO 594
<211> LENGTH: 27
<212> TYPE: PRT
<213> ORGANISM: Homo sapiens
```

```
<400> SEQUENCE: 594

Leu Gln Glu Thr Ser Asn Trp Leu Leu Ser Gln Gln Gln Ala Asp Gly
1               5                   10                  15

Ser Phe Gln Asp Pro Cys Pro Val Leu Asp Arg
            20                  25

<210> SEQ ID NO 595
<211> LENGTH: 30
<212> TYPE: PRT
<213> ORGANISM: Homo sapiens

<400> SEQUENCE: 595

Leu Thr Ser Leu Ser Asp Arg Tyr Val Ser His Phe Glu Thr Glu Gly
1               5                   10                  15

Pro His Val Leu Leu Tyr Phe Asp Ser Val Pro Thr Ser Arg
            20                  25                  30

<210> SEQ ID NO 596
<211> LENGTH: 25
<212> TYPE: PRT
<213> ORGANISM: Homo sapiens

<400> SEQUENCE: 596

Leu Thr Val Ala Ala Pro Pro Ser Gly Gly Pro Gly Phe Leu Ser Ile
1               5                   10                  15

Glu Arg Pro Asp Ser Arg Pro Pro Arg
            20                  25

<210> SEQ ID NO 597
<211> LENGTH: 12
<212> TYPE: PRT
<213> ORGANISM: Homo sapiens

<400> SEQUENCE: 597

Leu Val Asn Gly Gln Ser His Ile Ser Leu Ser Lys
1               5                   10

<210> SEQ ID NO 598
<211> LENGTH: 33
<212> TYPE: PRT
<213> ORGANISM: Homo sapiens

<400> SEQUENCE: 598

Leu Val Asn Gly Gln Ser His Ile Ser Leu Ser Lys Ala Glu Phe Gln
1               5                   10                  15

Asp Ala Leu Glu Lys Leu Asn Met Gly Ile Thr Asp Leu Gln Gly Leu
            20                  25                  30

Arg

<210> SEQ ID NO 599
<211> LENGTH: 9
<212> TYPE: PRT
<213> ORGANISM: Homo sapiens

<400> SEQUENCE: 599

Met Lys Phe Ala Cys Tyr Tyr Pro Arg
1               5

<210> SEQ ID NO 600
<211> LENGTH: 32
<212> TYPE: PRT
<213> ORGANISM: Homo sapiens
```

```
<400> SEQUENCE: 600

Asn Gly Glu Ser Val Lys Leu His Leu Glu Thr Asp Ser Leu Ala Leu
1               5                   10                  15

Val Ala Leu Gly Ala Leu Asp Thr Ala Leu Tyr Ala Ala Gly Ser Lys
            20                  25                  30

<210> SEQ ID NO 601
<211> LENGTH: 32
<212> TYPE: PRT
<213> ORGANISM: Homo sapiens

<400> SEQUENCE: 601

Asn Asn Val Pro Cys Ser Pro Lys Val Asp Phe Thr Leu Ser Ser Glu
1               5                   10                  15

Arg Asp Phe Ala Leu Leu Ser Leu Gln Val Pro Leu Lys Asp Ala Lys
            20                  25                  30

<210> SEQ ID NO 602
<211> LENGTH: 30
<212> TYPE: PRT
<213> ORGANISM: Homo sapiens

<400> SEQUENCE: 602

Asn Pro Ser Asp Pro Met Pro Gln Ala Pro Ala Leu Trp Ile Glu Thr
1               5                   10                  15

Thr Ala Tyr Ala Leu Leu His Leu Leu His Glu Gly Lys
            20                  25                  30

<210> SEQ ID NO 603
<211> LENGTH: 6
<212> TYPE: PRT
<213> ORGANISM: Homo sapiens

<400> SEQUENCE: 603

Asn Val Asn Phe Gln Lys
1               5

<210> SEQ ID NO 604
<211> LENGTH: 9
<212> TYPE: PRT
<213> ORGANISM: Homo sapiens

<400> SEQUENCE: 604

Pro Phe Leu Leu Gln Ala Leu Val Arg
1               5

<210> SEQ ID NO 605
<211> LENGTH: 14
<212> TYPE: PRT
<213> ORGANISM: Homo sapiens

<400> SEQUENCE: 605

Pro Gly His Leu Asp Glu Met Gln Leu Asp Ile Gln Ala Arg
1               5                   10

<210> SEQ ID NO 606
<211> LENGTH: 23
<212> TYPE: PRT
<213> ORGANISM: Homo sapiens

<400> SEQUENCE: 606

Pro Gly Lys Pro Tyr Ile Leu Thr Val Pro Gly His Leu Asp Glu Met
1               5                   10                  15
```

Gln Leu Asp Ile Gln Ala Arg
            20

<210> SEQ ID NO 607
<211> LENGTH: 26
<212> TYPE: PRT
<213> ORGANISM: Homo sapiens

<400> SEQUENCE: 607

Pro Ile Ile Ile Pro Gln Thr Ile Ser Glu Leu Gln Leu Ser Val Ser
1               5                   10                  15

Ala Gly Ser Pro His Pro Ala Ile Ala Arg
            20                  25

<210> SEQ ID NO 608
<211> LENGTH: 21
<212> TYPE: PRT
<213> ORGANISM: Homo sapiens

<400> SEQUENCE: 608

Pro Leu Asp Thr Leu Gly Ser Glu Gly Ala Leu Ser Pro Gly Gly Val
1               5                   10                  15

Ala Ser Leu Leu Arg
            20

<210> SEQ ID NO 609
<211> LENGTH: 17
<212> TYPE: PRT
<213> ORGANISM: Homo sapiens

<400> SEQUENCE: 609

Pro Val Ala Phe Ser Val Val Pro Thr Ala Ala Ala Val Ser Leu
1               5                   10                  15

Lys

<210> SEQ ID NO 610
<211> LENGTH: 9
<212> TYPE: PRT
<213> ORGANISM: Homo sapiens

<400> SEQUENCE: 610

Gln Gly Ser Phe Gln Gly Gly Phe Arg
1               5

<210> SEQ ID NO 611
<211> LENGTH: 9
<212> TYPE: PRT
<213> ORGANISM: Homo sapiens

<400> SEQUENCE: 611

Arg Cys Cys Gln Asp Gly Val Thr Arg
1               5

<210> SEQ ID NO 612
<211> LENGTH: 16
<212> TYPE: PRT
<213> ORGANISM: Homo sapiens

<400> SEQUENCE: 612

Arg His Leu Val Pro Gly Ala Pro Phe Leu Leu Gln Ala Leu Val Arg
1               5                   10                  15

<210> SEQ ID NO 613
<211> LENGTH: 23

```
<212> TYPE: PRT
<213> ORGANISM: Homo sapiens

<400> SEQUENCE: 613

Ser Cys Gly Leu His Gln Leu Leu Arg Gly Pro Glu Val Gln Leu Val
1               5                   10                  15
Ala His Ser Pro Trp Leu Lys
            20

<210> SEQ ID NO 614
<211> LENGTH: 10
<212> TYPE: PRT
<213> ORGANISM: Homo sapiens

<400> SEQUENCE: 614

Ser Phe Phe Pro Glu Asn Trp Leu Trp Arg
1               5                   10

<210> SEQ ID NO 615
<211> LENGTH: 9
<212> TYPE: PRT
<213> ORGANISM: Homo sapiens

<400> SEQUENCE: 615

Ser His Ala Leu Gln Leu Asn Asn Arg
1               5

<210> SEQ ID NO 616
<211> LENGTH: 9
<212> TYPE: PRT
<213> ORGANISM: Homo sapiens

<400> SEQUENCE: 616

Ser His Lys Pro Leu Asn Met Gly Lys
1               5

<210> SEQ ID NO 617
<211> LENGTH: 25
<212> TYPE: PRT
<213> ORGANISM: Homo sapiens

<400> SEQUENCE: 617

Ser Thr Gln Asp Thr Val Ile Ala Leu Asp Ala Leu Ser Ala Tyr Trp
1               5                   10                  15
Ile Ala Ser His Thr Thr Glu Glu Arg
            20                  25

<210> SEQ ID NO 618
<211> LENGTH: 13
<212> TYPE: PRT
<213> ORGANISM: Homo sapiens

<400> SEQUENCE: 618

Thr Lys Gly Leu Cys Val Ala Thr Pro Val Gln Leu Arg
1               5                   10

<210> SEQ ID NO 619
<211> LENGTH: 14
<212> TYPE: PRT
<213> ORGANISM: Homo sapiens

<400> SEQUENCE: 619

Thr Thr Asn Ile Gln Gly Ile Asn Leu Leu Phe Ser Ser Arg
1               5                   10
```

```
<210> SEQ ID NO 620
<211> LENGTH: 8
<212> TYPE: PRT
<213> ORGANISM: Homo sapiens

<400> SEQUENCE: 620

Thr Tyr Asn Val Leu Asp Met Lys
1               5

<210> SEQ ID NO 621
<211> LENGTH: 9
<212> TYPE: PRT
<213> ORGANISM: Homo sapiens

<400> SEQUENCE: 621

Val Asp Phe Thr Leu Ser Ser Glu Arg
1               5

<210> SEQ ID NO 622
<211> LENGTH: 24
<212> TYPE: PRT
<213> ORGANISM: Homo sapiens

<400> SEQUENCE: 622

Val Asp Phe Thr Leu Ser Ser Glu Arg Asp Phe Ala Leu Leu Ser Leu
1               5                   10                  15

Gln Val Pro Leu Lys Asp Ala Lys
            20

<210> SEQ ID NO 623
<211> LENGTH: 11
<212> TYPE: PRT
<213> ORGANISM: Homo sapiens

<400> SEQUENCE: 623

Val Asp Val Gln Ala Gly Ala Cys Glu Gly Lys
1               5                   10

<210> SEQ ID NO 624
<211> LENGTH: 20
<212> TYPE: PRT
<213> ORGANISM: Homo sapiens

<400> SEQUENCE: 624

Val Asp Val Gln Ala Gly Ala Cys Glu Gly Lys Leu Glu Leu Ser Val
1               5                   10                  15

Asp Gly Ala Lys
            20

<210> SEQ ID NO 625
<211> LENGTH: 30
<212> TYPE: PRT
<213> ORGANISM: Homo sapiens

<400> SEQUENCE: 625

Val Glu Thr Val Asp Arg Phe Gln Ile Leu Thr Leu Trp Leu Pro Asp
1               5                   10                  15

Ser Leu Thr Thr Trp Glu Ile His Gly Leu Ser Leu Ser Lys
            20                  25                  30

<210> SEQ ID NO 626
<211> LENGTH: 8
<212> TYPE: PRT
<213> ORGANISM: Homo sapiens
```

<400> SEQUENCE: 626

Val Glu Tyr Gly Phe Gln Val Lys
1               5

<210> SEQ ID NO 627
<211> LENGTH: 7
<212> TYPE: PRT
<213> ORGANISM: Homo sapiens

<400> SEQUENCE: 627

Val Phe Ala Leu Asp Gln Lys
1               5

<210> SEQ ID NO 628
<211> LENGTH: 10
<212> TYPE: PRT
<213> ORGANISM: Homo sapiens

<400> SEQUENCE: 628

Val Phe Arg Glu Phe His Leu His Leu Arg
1               5                   10

<210> SEQ ID NO 629
<211> LENGTH: 10
<212> TYPE: PRT
<213> ORGANISM: Homo sapiens

<400> SEQUENCE: 629

Val Gly Asp Thr Leu Asn Leu Asn Leu Arg
1               5                   10

<210> SEQ ID NO 630
<211> LENGTH: 26
<212> TYPE: PRT
<213> ORGANISM: Homo sapiens

<400> SEQUENCE: 630

Val Gly Leu Ser Gly Met Ala Ile Ala Asp Val Thr Leu Leu Ser Gly
1               5                   10                  15

Phe His Ala Leu Arg Ala Asp Leu Glu Lys
            20                  25

<210> SEQ ID NO 631
<211> LENGTH: 9
<212> TYPE: PRT
<213> ORGANISM: Homo sapiens

<400> SEQUENCE: 631

Val His Tyr Thr Val Cys Ile Trp Arg
1               5

<210> SEQ ID NO 632
<211> LENGTH: 15
<212> TYPE: PRT
<213> ORGANISM: Homo sapiens

<400> SEQUENCE: 632

Val Leu Ser Leu Ala Gln Glu Gln Val Gly Gly Ser Pro Glu Lys
1               5                   10                  15

<210> SEQ ID NO 633
<211> LENGTH: 42
<212> TYPE: PRT
<213> ORGANISM: Homo sapiens

<400> SEQUENCE: 633

Val Leu Ser Leu Ala Gln Glu Gln Val Gly Gly Ser Pro Glu Lys Leu
1               5                   10                  15

Gln Glu Thr Ser Asn Trp Leu Leu Ser Gln Gln Ala Asp Gly Ser
            20                  25                  30

Phe Gln Asp Pro Cys Pro Val Leu Asp Arg
        35                  40

<210> SEQ ID NO 634
<211> LENGTH: 21
<212> TYPE: PRT
<213> ORGANISM: Homo sapiens

<400> SEQUENCE: 634

Val Gln Gln Pro Asp Cys Arg Glu Pro Phe Leu Ser Cys Cys Gln Phe
1               5                   10                  15

Ala Glu Ser Leu Arg
            20

<210> SEQ ID NO 635
<211> LENGTH: 22
<212> TYPE: PRT
<213> ORGANISM: Homo sapiens

<400> SEQUENCE: 635

Val Gln Gln Pro Asp Cys Arg Glu Pro Phe Leu Ser Cys Cys Gln Phe
1               5                   10                  15

Ala Glu Ser Leu Arg Lys
            20

<210> SEQ ID NO 636
<211> LENGTH: 22
<212> TYPE: PRT
<213> ORGANISM: Homo sapiens

<400> SEQUENCE: 636

Val Ser Ala Thr Val Ser Ser Pro Gly Ser Val Pro Glu Val Gln Asp
1               5                   10                  15

Ile Gln Gln Asn Thr Asp
            20

<210> SEQ ID NO 637
<211> LENGTH: 26
<212> TYPE: PRT
<213> ORGANISM: Homo sapiens

<400> SEQUENCE: 637

Val Thr Ala Ser Asp Pro Leu Asp Thr Leu Gly Ser Glu Gly Ala Leu
1               5                   10                  15

Ser Pro Gly Gly Val Ala Ser Leu Leu Arg
            20                  25

<210> SEQ ID NO 638
<211> LENGTH: 14
<212> TYPE: PRT
<213> ORGANISM: Homo sapiens

<400> SEQUENCE: 638

Tyr Ile Tyr Gly Lys Pro Val Gln Gly Val Ala Tyr Val Arg
1               5                   10

```
<210> SEQ ID NO 639
<211> LENGTH: 16
<212> TYPE: PRT
<213> ORGANISM: Homo sapiens

<400> SEQUENCE: 639

Tyr Leu Asp Lys Thr Glu Gln Trp Ser Thr Leu Pro Pro Glu Thr Lys
1               5                   10                  15

<210> SEQ ID NO 640
<211> LENGTH: 25
<212> TYPE: PRT
<213> ORGANISM: Homo sapiens

<400> SEQUENCE: 640

Tyr Leu Asp Lys Thr Glu Gln Trp Ser Thr Leu Pro Pro Glu Thr Lys
1               5                   10                  15

Asp His Ala Val Asp Leu Ile Gln Lys
            20                  25

<210> SEQ ID NO 641
<211> LENGTH: 9
<212> TYPE: PRT
<213> ORGANISM: Homo sapiens

<400> SEQUENCE: 641

Tyr Arg Val Phe Ala Leu Asp Gln Lys
1               5

<210> SEQ ID NO 642
<211> LENGTH: 23
<212> TYPE: PRT
<213> ORGANISM: Homo sapiens

<400> SEQUENCE: 642

Tyr Val Ser His Phe Glu Thr Glu Gly Pro His Val Leu Leu Tyr Phe
1               5                   10                  15

Asp Ser Val Pro Thr Ser Arg
            20

<210> SEQ ID NO 643
<211> LENGTH: 19
<212> TYPE: PRT
<213> ORGANISM: Homo sapiens

<400> SEQUENCE: 643

Met Arg Pro Ser Thr Asp Thr Ile Thr Val Met Val Glu Asn Ser His
1               5                   10                  15

Gly Leu Arg

<210> SEQ ID NO 644
<211> LENGTH: 21
<212> TYPE: PRT
<213> ORGANISM: Homo sapiens

<400> SEQUENCE: 644

Ala Glu Phe Gln Asp Ala Leu Glu Lys Leu Asn Met Gly Ile Thr Asp
1               5                   10                  15

Leu Gln Gly Leu Arg
            20

<210> SEQ ID NO 645
<211> LENGTH: 13
<212> TYPE: PRT
```

<213> ORGANISM: Homo sapiens

<400> SEQUENCE: 645

Glu Met Ser Gly Ser Pro Ala Ser Gly Ile Pro Val Lys
1               5                   10

<210> SEQ ID NO 646
<211> LENGTH: 25
<212> TYPE: PRT
<213> ORGANISM: Homo sapiens

<400> SEQUENCE: 646

Glu Val Tyr Met Pro Ser Ser Ile Phe Gln Asp Asp Phe Val Ile Pro
1               5                   10                  15

Asp Ile Ser Glu Pro Gly Thr Trp Lys
            20                  25

<210> SEQ ID NO 647
<211> LENGTH: 11
<212> TYPE: PRT
<213> ORGANISM: Homo sapiens

<400> SEQUENCE: 647

Gly Gln Ile Val Phe Met Asn Arg Glu Pro Lys
1               5                   10

<210> SEQ ID NO 648
<211> LENGTH: 27
<212> TYPE: PRT
<213> ORGANISM: Homo sapiens

<400> SEQUENCE: 648

Lys Lys Glu Val Tyr Met Pro Ser Ser Ile Phe Gln Asp Asp Phe Val
1               5                   10                  15

Ile Pro Asp Ile Ser Glu Pro Gly Thr Trp Lys
            20                  25

<210> SEQ ID NO 649
<211> LENGTH: 42
<212> TYPE: PRT
<213> ORGANISM: Homo sapiens

<400> SEQUENCE: 649

Leu Arg Leu Glu Pro Gly Lys Glu Tyr Leu Ile Met Gly Leu Asp Gly
1               5                   10                  15

Ala Thr Tyr Asp Leu Glu Gly His Pro Gln Tyr Leu Leu Asp Ser Asn
            20                  25                  30

Ser Trp Ile Glu Glu Met Pro Ser Glu Arg
        35                  40

<210> SEQ ID NO 650
<211> LENGTH: 39
<212> TYPE: PRT
<213> ORGANISM: Homo sapiens

<400> SEQUENCE: 650

Ser Met Gln Gly Gly Leu Val Gly Asn Asp Glu Thr Val Ala Leu Thr
1               5                   10                  15

Ala Phe Val Thr Ile Ala Leu His His Gly Leu Ala Val Phe Gln Asp
            20                  25                  30

Glu Gly Ala Glu Pro Leu Lys
        35

<210> SEQ ID NO 651
<211> LENGTH: 41
<212> TYPE: PRT
<213> ORGANISM: Homo sapiens

<400> SEQUENCE: 651

Ser Met Gln Gly Gly Leu Val Gly Asn Asp Glu Thr Val Ala Leu Thr
1               5                   10                  15

Ala Phe Val Thr Ile Ala Leu His His Gly Leu Ala Val Phe Gln Asp
            20                  25                  30

Glu Gly Ala Glu Pro Leu Lys Gln Arg
        35                  40

<210> SEQ ID NO 652
<211> LENGTH: 23
<212> TYPE: PRT
<213> ORGANISM: Homo sapiens

<400> SEQUENCE: 652

Thr Leu Glu Ile Pro Gly Asn Ser Asp Pro Asn Met Ile Pro Asp Gly
1               5                   10                  15

Asp Phe Asn Ser Tyr Val Arg
            20

<210> SEQ ID NO 653
<211> LENGTH: 20
<212> TYPE: PRT
<213> ORGANISM: Homo sapiens

<400> SEQUENCE: 653

Ala Ala Cys Ala Gln Leu Asn Asp Phe Leu Gln Glu Tyr Gly Thr Gln
1               5                   10                  15

Gly Cys Gln Val
            20

<210> SEQ ID NO 654
<211> LENGTH: 35
<212> TYPE: PRT
<213> ORGANISM: Homo sapiens

<400> SEQUENCE: 654

Ala Asp Leu Glu Lys Leu Thr Ser Leu Ser Asp Arg Tyr Val Ser His
1               5                   10                  15

Phe Glu Thr Glu Gly Pro His Val Leu Leu Tyr Phe Ser Val Pro
            20                  25                  30

Thr Ser Arg
        35

<210> SEQ ID NO 655
<211> LENGTH: 9
<212> TYPE: PRT
<213> ORGANISM: Homo sapiens

<400> SEQUENCE: 655

Ala Glu Phe Gln Asp Ala Leu Glu Lys
1               5

<210> SEQ ID NO 656
<211> LENGTH: 19
<212> TYPE: PRT
<213> ORGANISM: Homo sapiens

<400> SEQUENCE: 656

```
Ala Leu Glu Ile Leu Gln Glu Glu Asp Leu Ile Asp Glu Asp Asp Ile
1               5                   10                  15

Pro Val Arg
```

<210> SEQ ID NO 657
<211> LENGTH: 13
<212> TYPE: PRT
<213> ORGANISM: Homo sapiens

<400> SEQUENCE: 657

```
Ala Leu Leu Ser Leu Gln Val Pro Leu Lys Asp Ala Lys
1               5                   10
```

<210> SEQ ID NO 658
<211> LENGTH: 18
<212> TYPE: PRT
<213> ORGANISM: Homo sapiens

<400> SEQUENCE: 658

```
Ala Val Gly Ser Gly Ala Thr Phe Ser His Tyr Tyr Tyr Met Ile Leu
1               5                   10                  15

Ser Arg
```

<210> SEQ ID NO 659
<211> LENGTH: 10
<212> TYPE: PRT
<213> ORGANISM: Homo sapiens

<400> SEQUENCE: 659

```
Cys Ser Val Phe Tyr Gly Ala Pro Ser Lys
1               5                   10
```

<210> SEQ ID NO 660
<211> LENGTH: 15
<212> TYPE: PRT
<213> ORGANISM: Homo sapiens

<400> SEQUENCE: 660

```
Asp Phe Ala Leu Leu Ser Leu Gln Val Pro Leu Lys Asp Ala Lys
1               5                   10                  15
```

<210> SEQ ID NO 661
<211> LENGTH: 12
<212> TYPE: PRT
<213> ORGANISM: Homo sapiens

<400> SEQUENCE: 661

```
Asp Ser Ser Thr Trp Leu Thr Ala Phe Val Leu Lys
1               5                   10
```

<210> SEQ ID NO 662
<211> LENGTH: 12
<212> TYPE: PRT
<213> ORGANISM: Homo sapiens

<400> SEQUENCE: 662

```
Glu Ala Pro Lys Val Val Glu Gln Glu Ser Arg
1               5                   10
```

<210> SEQ ID NO 663
<211> LENGTH: 31
<212> TYPE: PRT
<213> ORGANISM: Homo sapiens

<400> SEQUENCE: 663

Glu Cys Val Gly Phe Glu Ala Val Gln Glu Val Pro Val Gly Leu Val
1               5                   10                  15

Gln Pro Ala Ser Ala Thr Leu Tyr Asp Tyr Tyr Asn Pro Glu Arg
            20                  25                  30

<210> SEQ ID NO 664
<211> LENGTH: 32
<212> TYPE: PRT
<213> ORGANISM: Homo sapiens

<400> SEQUENCE: 664

Glu Cys Val Gly Phe Glu Ala Val Gln Glu Val Pro Val Gly Leu Val
1               5                   10                  15

Gln Pro Ala Ser Ala Thr Leu Tyr Asp Tyr Tyr Asn Pro Glu Arg Arg
            20                  25                  30

<210> SEQ ID NO 665
<211> LENGTH: 7
<212> TYPE: PRT
<213> ORGANISM: Homo sapiens

<400> SEQUENCE: 665

Glu Phe His Leu His Leu Arg
1               5

<210> SEQ ID NO 666
<211> LENGTH: 18
<212> TYPE: PRT
<213> ORGANISM: Homo sapiens

<400> SEQUENCE: 666

Glu Gly Ala Ile His Arg Glu Glu Leu Val Tyr Glu Leu Asn Pro Leu
1               5                   10                  15

Asp His

<210> SEQ ID NO 667
<211> LENGTH: 19
<212> TYPE: PRT
<213> ORGANISM: Homo sapiens

<400> SEQUENCE: 667

Glu Gly Ala Ile His Arg Glu Glu Leu Val Tyr Glu Leu Asn Pro Leu
1               5                   10                  15

Asp His Arg

<210> SEQ ID NO 668
<211> LENGTH: 20
<212> TYPE: PRT
<213> ORGANISM: Homo sapiens

<400> SEQUENCE: 668

Glu Gly Ala Ile His Arg Glu Glu Leu Val Tyr Glu Leu Asn Pro Leu
1               5                   10                  15

Asp His Arg Gly
            20

<210> SEQ ID NO 669
<211> LENGTH: 14
<212> TYPE: PRT
<213> ORGANISM: Homo sapiens

<400> SEQUENCE: 669

Glu Pro Phe Leu Ser Cys Cys Gln Phe Ala Glu Ser Leu Arg
1               5                   10

<210> SEQ ID NO 670
<211> LENGTH: 10
<212> TYPE: PRT
<213> ORGANISM: Homo sapiens

<400> SEQUENCE: 670

Phe Gly Leu Leu Asp Glu Asp Gly Lys Lys
1               5                   10

<210> SEQ ID NO 671
<211> LENGTH: 14
<212> TYPE: PRT
<213> ORGANISM: Homo sapiens

<400> SEQUENCE: 671

Phe Gly Leu Leu Asp Glu Asp Gly Lys Lys Thr Phe Phe Arg
1               5                   10

<210> SEQ ID NO 672
<211> LENGTH: 24
<212> TYPE: PRT
<213> ORGANISM: Homo sapiens

<400> SEQUENCE: 672

Phe Gln Ile Leu Thr Leu Trp Leu Pro Asp Ser Leu Thr Thr Trp Glu
1               5                   10                  15

Ile His Gly Leu Ser Leu Ser Lys
            20

<210> SEQ ID NO 673
<211> LENGTH: 17
<212> TYPE: PRT
<213> ORGANISM: Homo sapiens

<400> SEQUENCE: 673

Gly His Leu Phe Leu Gln Thr Asp Gln Pro Ile Tyr Asn Pro Gly Gln
1               5                   10                  15

Arg

<210> SEQ ID NO 674
<211> LENGTH: 13
<212> TYPE: PRT
<213> ORGANISM: Homo sapiens

<400> SEQUENCE: 674

Gly Leu Glu Glu Glu Leu Gln Phe Ser Leu Gly Ser Lys
1               5                   10

<210> SEQ ID NO 675
<211> LENGTH: 9
<212> TYPE: PRT
<213> ORGANISM: Homo sapiens

<400> SEQUENCE: 675

Gly Leu Gln Asp Glu Asp Gly Tyr Arg
1               5

<210> SEQ ID NO 676
<211> LENGTH: 14
<212> TYPE: PRT
<213> ORGANISM: Homo sapiens

```
<400> SEQUENCE: 676

Gly Pro Glu Val Gln Leu Val Ala His Ser Pro Trp Leu Lys
1               5                   10

<210> SEQ ID NO 677
<211> LENGTH: 19
<212> TYPE: PRT
<213> ORGANISM: Homo sapiens

<400> SEQUENCE: 677

Gly Pro Glu Val Gln Leu Val Ala His Ser Pro Trp Leu Lys Asp Ser
1               5                   10                  15

Leu Ser Arg

<210> SEQ ID NO 678
<211> LENGTH: 8
<212> TYPE: PRT
<213> ORGANISM: Homo sapiens

<400> SEQUENCE: 678

Gly Gln Ile Val Phe Met Asn Arg
1               5

<210> SEQ ID NO 679
<211> LENGTH: 13
<212> TYPE: PRT
<213> ORGANISM: Homo sapiens

<400> SEQUENCE: 679

Gly Ser Phe Glu Phe Pro Val Gly Asp Ala Val Ser Lys
1               5                   10

<210> SEQ ID NO 680
<211> LENGTH: 10
<212> TYPE: PRT
<213> ORGANISM: Homo sapiens

<400> SEQUENCE: 680

Gly Ser Val Phe Leu Arg Asn Pro Ser Arg
1               5                   10

<210> SEQ ID NO 681
<211> LENGTH: 15
<212> TYPE: PRT
<213> ORGANISM: Homo sapiens

<400> SEQUENCE: 681

His Leu Val Pro Gly Ala Pro Phe Leu Leu Gln Ala Leu Val Arg
1               5                   10                  15

<210> SEQ ID NO 682
<211> LENGTH: 25
<212> TYPE: PRT
<213> ORGANISM: Homo sapiens

<400> SEQUENCE: 682

Ile Thr Pro Gly Lys Pro Tyr Ile Leu Thr Val Pro Gly His Leu Asp
1               5                   10                  15

Glu Met Gln Leu Asp Ile Gln Ala Arg
            20                  25

<210> SEQ ID NO 683
<211> LENGTH: 12
```

```
<212> TYPE: PRT
<213> ORGANISM: Homo sapiens

<400> SEQUENCE: 683

Lys Ala Asp Gly Ser Tyr Ala Ala Trp Leu Ser Arg
1               5                   10

<210> SEQ ID NO 684
<211> LENGTH: 10
<212> TYPE: PRT
<213> ORGANISM: Homo sapiens

<400> SEQUENCE: 684

Lys Tyr Val Leu Pro Asn Phe Glu Val Lys
1               5                   10

<210> SEQ ID NO 685
<211> LENGTH: 9
<212> TYPE: PRT
<213> ORGANISM: Homo sapiens

<400> SEQUENCE: 685

Leu Glu Leu Ser Val Asp Gly Ala Lys
1               5

<210> SEQ ID NO 686
<211> LENGTH: 10
<212> TYPE: PRT
<213> ORGANISM: Homo sapiens

<400> SEQUENCE: 686

Leu Gly Gln Tyr Ala Ser Pro Thr Ala Lys
1               5                   10

<210> SEQ ID NO 687
<211> LENGTH: 11
<212> TYPE: PRT
<213> ORGANISM: Homo sapiens

<400> SEQUENCE: 687

Leu Gly Gln Tyr Ala Ser Pro Thr Ala Lys Arg
1               5                   10

<210> SEQ ID NO 688
<211> LENGTH: 26
<212> TYPE: PRT
<213> ORGANISM: Homo sapiens

<400> SEQUENCE: 688

Leu His Leu Glu Thr Asp Ser Leu Ala Leu Val Ala Leu Gly Ala Leu
1               5                   10                  15

Asp Thr Ala Leu Tyr Ala Ala Gly Ser Lys
            20                  25

<210> SEQ ID NO 689
<211> LENGTH: 17
<212> TYPE: PRT
<213> ORGANISM: Homo sapiens

<400> SEQUENCE: 689

Leu Leu Ala Thr Leu Cys Ser Ala Glu Val Cys Gln Cys Ala Glu Gly
1               5                   10                  15

Lys
```

-continued

```
<210> SEQ ID NO 690
<211> LENGTH: 26
<212> TYPE: PRT
<213> ORGANISM: Homo sapiens

<400> SEQUENCE: 690

Leu Leu Leu Phe Ser Pro Ser Val Val His Leu Gly Val Pro Leu Ser
1               5                  10                  15

Val Gly Val Gln Leu Gln Asp Val Pro Arg
            20                  25

<210> SEQ ID NO 691
<211> LENGTH: 31
<212> TYPE: PRT
<213> ORGANISM: Homo sapiens

<400> SEQUENCE: 691

Leu Leu Leu Phe Ser Pro Ser Val Val His Leu Gly Val Pro Leu Ser
1               5                  10                  15

Val Gly Val Gln Leu Gln Asp Val Pro Arg Gly Gln Val Val Lys
            20                  25                  30

<210> SEQ ID NO 692
<211> LENGTH: 12
<212> TYPE: PRT
<213> ORGANISM: Homo sapiens

<400> SEQUENCE: 692

Leu Asn Met Gly Ile Thr Asp Leu Gln Gly Leu Arg
1               5                  10

<210> SEQ ID NO 693
<211> LENGTH: 6
<212> TYPE: PRT
<213> ORGANISM: Homo sapiens

<400> SEQUENCE: 693

Leu Pro Met Ser Val Arg
1               5

<210> SEQ ID NO 694
<211> LENGTH: 27
<212> TYPE: PRT
<213> ORGANISM: Homo sapiens

<400> SEQUENCE: 694

Leu Gln Glu Thr Ser Asn Trp Leu Leu Ser Gln Gln Ala Asp Gly
1               5                  10                  15

Ser Phe Gln Asp Leu Ser Pro Val Ile His Arg
            20                  25

<210> SEQ ID NO 695
<211> LENGTH: 30
<212> TYPE: PRT
<213> ORGANISM: Homo sapiens

<400> SEQUENCE: 695

Leu Thr Ser Leu Ser Asp Arg Tyr Val Ser His Phe Glu Thr Glu Gly
1               5                  10                  15

Pro His Val Leu Leu Tyr Phe Asp Ser Val Pro Thr Ser Arg
            20                  25                  30

<210> SEQ ID NO 696
<211> LENGTH: 25
```

```
<212> TYPE: PRT
<213> ORGANISM: Homo sapiens

<400> SEQUENCE: 696

Leu Thr Val Ala Ala Pro Pro Ser Gly Gly Pro Gly Phe Leu Ser Ile
1               5                   10                  15

Glu Arg Pro Asp Ser Arg Pro Pro Arg
            20                  25

<210> SEQ ID NO 697
<211> LENGTH: 12
<212> TYPE: PRT
<213> ORGANISM: Homo sapiens

<400> SEQUENCE: 697

Leu Val Asn Gly Gln Ser His Ile Ser Leu Ser Lys
1               5                   10

<210> SEQ ID NO 698
<211> LENGTH: 33
<212> TYPE: PRT
<213> ORGANISM: Homo sapiens

<400> SEQUENCE: 698

Leu Val Asn Gly Gln Ser His Ile Ser Leu Ser Lys Ala Glu Phe Gln
1               5                   10                  15

Asp Ala Leu Glu Lys Leu Asn Met Gly Ile Thr Asp Leu Gln Gly Leu
            20                  25                  30

Arg

<210> SEQ ID NO 699
<211> LENGTH: 9
<212> TYPE: PRT
<213> ORGANISM: Homo sapiens

<400> SEQUENCE: 699

Met Lys Phe Ala Cys Tyr Tyr Pro Arg
1               5

<210> SEQ ID NO 700
<211> LENGTH: 32
<212> TYPE: PRT
<213> ORGANISM: Homo sapiens

<400> SEQUENCE: 700

Asn Gly Glu Ser Val Lys Leu His Leu Glu Thr Asp Ser Leu Ala Leu
1               5                   10                  15

Val Ala Leu Gly Ala Leu Asp Thr Ala Leu Tyr Ala Ala Gly Ser Lys
            20                  25                  30

<210> SEQ ID NO 701
<211> LENGTH: 32
<212> TYPE: PRT
<213> ORGANISM: Homo sapiens

<400> SEQUENCE: 701

Asn Asn Val Pro Cys Ser Pro Lys Val Asp Phe Thr Leu Ser Ser Glu
1               5                   10                  15

Arg Asp Phe Ala Leu Leu Ser Leu Gln Val Pro Leu Lys Asp Ala Lys
            20                  25                  30

<210> SEQ ID NO 702
<211> LENGTH: 30
```

<212> TYPE: PRT
<213> ORGANISM: Homo sapiens

<400> SEQUENCE: 702

Asn Pro Ser Asp Pro Met Pro Gln Ala Pro Ala Leu Trp Ile Glu Thr
1               5                   10                  15

Thr Ala Tyr Ala Leu Leu His Leu Leu Leu His Glu Gly Lys
            20                  25                  30

<210> SEQ ID NO 703
<211> LENGTH: 6
<212> TYPE: PRT
<213> ORGANISM: Homo sapiens

<400> SEQUENCE: 703

Asn Val Asn Phe Gln Lys
1               5

<210> SEQ ID NO 704
<211> LENGTH: 9
<212> TYPE: PRT
<213> ORGANISM: Homo sapiens

<400> SEQUENCE: 704

Pro Phe Leu Leu Gln Ala Leu Val Arg
1               5

<210> SEQ ID NO 705
<211> LENGTH: 14
<212> TYPE: PRT
<213> ORGANISM: Homo sapiens

<400> SEQUENCE: 705

Pro Gly His Leu Asp Glu Met Gln Leu Asp Ile Gln Ala Arg
1               5                   10

<210> SEQ ID NO 706
<211> LENGTH: 23
<212> TYPE: PRT
<213> ORGANISM: Homo sapiens

<400> SEQUENCE: 706

Pro Gly Lys Pro Tyr Ile Leu Thr Val Pro Gly His Leu Asp Glu Met
1               5                   10                  15

Gln Leu Asp Ile Gln Ala Arg
            20

<210> SEQ ID NO 707
<211> LENGTH: 26
<212> TYPE: PRT
<213> ORGANISM: Homo sapiens

<400> SEQUENCE: 707

Pro Ile Ile Ile Pro Gln Thr Ile Ser Glu Leu Gln Leu Ser Val Ser
1               5                   10                  15

Ala Gly Ser Pro His Pro Ala Ile Ala Arg
            20                  25

<210> SEQ ID NO 708
<211> LENGTH: 21
<212> TYPE: PRT
<213> ORGANISM: Homo sapiens

<400> SEQUENCE: 708

Pro Leu Asp Thr Leu Gly Ser Glu Gly Ala Leu Ser Pro Gly Gly Val
1               5                   10                  15

Ala Ser Leu Leu Arg
            20

<210> SEQ ID NO 709
<211> LENGTH: 17
<212> TYPE: PRT
<213> ORGANISM: Homo sapiens

<400> SEQUENCE: 709

Pro Val Ala Phe Ser Val Val Pro Thr Ala Ala Ala Val Ser Leu
1               5                   10                  15

Lys

<210> SEQ ID NO 710
<211> LENGTH: 9
<212> TYPE: PRT
<213> ORGANISM: Homo sapiens

<400> SEQUENCE: 710

Gln Gly Ser Phe Gln Gly Gly Phe Arg
1               5

<210> SEQ ID NO 711
<211> LENGTH: 9
<212> TYPE: PRT
<213> ORGANISM: Homo sapiens

<400> SEQUENCE: 711

Arg Cys Cys Gln Asp Gly Val Thr Arg
1               5

<210> SEQ ID NO 712
<211> LENGTH: 16
<212> TYPE: PRT
<213> ORGANISM: Homo sapiens

<400> SEQUENCE: 712

Arg His Leu Val Pro Gly Ala Pro Phe Leu Leu Gln Ala Leu Val Arg
1               5                   10                  15

<210> SEQ ID NO 713
<211> LENGTH: 23
<212> TYPE: PRT
<213> ORGANISM: Homo sapiens

<400> SEQUENCE: 713

Ser Cys Gly Leu His Gln Leu Leu Arg Gly Pro Glu Val Gln Leu Val
1               5                   10                  15

Ala His Ser Pro Trp Leu Lys
            20

<210> SEQ ID NO 714
<211> LENGTH: 10
<212> TYPE: PRT
<213> ORGANISM: Homo sapiens

<400> SEQUENCE: 714

Ser Phe Phe Pro Glu Asn Trp Leu Trp Arg
1               5                   10

<210> SEQ ID NO 715
<211> LENGTH: 9

```
<212> TYPE: PRT
<213> ORGANISM: Homo sapiens

<400> SEQUENCE: 715

Ser His Ala Leu Gln Leu Asn Asn Arg
1               5

<210> SEQ ID NO 716
<211> LENGTH: 9
<212> TYPE: PRT
<213> ORGANISM: Homo sapiens

<400> SEQUENCE: 716

Ser His Lys Pro Leu Asn Met Gly Lys
1               5

<210> SEQ ID NO 717
<211> LENGTH: 25
<212> TYPE: PRT
<213> ORGANISM: Homo sapiens

<400> SEQUENCE: 717

Ser Thr Gln Asp Thr Val Ile Ala Leu Asp Ala Leu Ser Ala Tyr Trp
1               5                   10                  15

Ile Ala Ser His Thr Thr Glu Glu Arg
            20                  25

<210> SEQ ID NO 718
<211> LENGTH: 13
<212> TYPE: PRT
<213> ORGANISM: Homo sapiens

<400> SEQUENCE: 718

Thr Lys Gly Leu Cys Val Ala Thr Pro Val Gln Leu Arg
1               5                   10

<210> SEQ ID NO 719
<211> LENGTH: 14
<212> TYPE: PRT
<213> ORGANISM: Homo sapiens

<400> SEQUENCE: 719

Thr Thr Asn Ile Gln Gly Ile Asn Leu Leu Phe Ser Ser Arg
1               5                   10

<210> SEQ ID NO 720
<211> LENGTH: 8
<212> TYPE: PRT
<213> ORGANISM: Homo sapiens

<400> SEQUENCE: 720

Thr Tyr Asn Val Leu Asp Met Lys
1               5

<210> SEQ ID NO 721
<211> LENGTH: 9
<212> TYPE: PRT
<213> ORGANISM: Homo sapiens

<400> SEQUENCE: 721

Val Asp Phe Thr Leu Ser Ser Glu Arg
1               5

<210> SEQ ID NO 722
<211> LENGTH: 24
```

```
<212> TYPE: PRT
<213> ORGANISM: Homo sapiens

<400> SEQUENCE: 722

Val Asp Phe Thr Leu Ser Ser Glu Arg Asp Phe Ala Leu Leu Ser Leu
1               5                   10                  15

Gln Val Pro Leu Lys Asp Ala Lys
            20

<210> SEQ ID NO 723
<211> LENGTH: 11
<212> TYPE: PRT
<213> ORGANISM: Homo sapiens

<400> SEQUENCE: 723

Val Asp Val Gln Ala Gly Ala Cys Glu Gly Lys
1               5                   10

<210> SEQ ID NO 724
<211> LENGTH: 20
<212> TYPE: PRT
<213> ORGANISM: Homo sapiens

<400> SEQUENCE: 724

Val Asp Val Gln Ala Gly Ala Cys Glu Gly Lys Leu Glu Leu Ser Val
1               5                   10                  15

Asp Gly Ala Lys
            20

<210> SEQ ID NO 725
<211> LENGTH: 30
<212> TYPE: PRT
<213> ORGANISM: Homo sapiens

<400> SEQUENCE: 725

Val Glu Thr Val Asp Arg Phe Gln Ile Leu Thr Leu Trp Leu Pro Asp
1               5                   10                  15

Ser Leu Thr Thr Trp Glu Ile His Gly Leu Ser Leu Ser Lys
            20                  25                  30

<210> SEQ ID NO 726
<211> LENGTH: 8
<212> TYPE: PRT
<213> ORGANISM: Homo sapiens

<400> SEQUENCE: 726

Val Glu Tyr Gly Phe Gln Val Lys
1               5

<210> SEQ ID NO 727
<211> LENGTH: 7
<212> TYPE: PRT
<213> ORGANISM: Homo sapiens

<400> SEQUENCE: 727

Val Phe Ala Leu Asp Gln Lys
1               5

<210> SEQ ID NO 728
<211> LENGTH: 10
<212> TYPE: PRT
<213> ORGANISM: Homo sapiens

<400> SEQUENCE: 728
```

Val Phe Arg Glu Phe His Leu His Leu Arg
1               5                   10

<210> SEQ ID NO 729
<211> LENGTH: 10
<212> TYPE: PRT
<213> ORGANISM: Homo sapiens

<400> SEQUENCE: 729

Val Gly Asp Thr Leu Asn Leu Asn Leu Arg
1               5                   10

<210> SEQ ID NO 730
<211> LENGTH: 26
<212> TYPE: PRT
<213> ORGANISM: Homo sapiens

<400> SEQUENCE: 730

Val Gly Leu Ser Gly Met Ala Ile Ala Asp Val Thr Leu Leu Ser Gly
1               5                   10                  15

Phe His Ala Leu Arg Ala Asp Leu Glu Lys
            20                  25

<210> SEQ ID NO 731
<211> LENGTH: 9
<212> TYPE: PRT
<213> ORGANISM: Homo sapiens

<400> SEQUENCE: 731

Val His Tyr Thr Val Cys Ile Trp Arg
1               5

<210> SEQ ID NO 732
<211> LENGTH: 15
<212> TYPE: PRT
<213> ORGANISM: Homo sapiens

<400> SEQUENCE: 732

Val Leu Ser Leu Ala Gln Glu Gln Val Gly Gly Ser Pro Glu Lys
1               5                   10                  15

<210> SEQ ID NO 733
<211> LENGTH: 42
<212> TYPE: PRT
<213> ORGANISM: Homo sapiens

<400> SEQUENCE: 733

Val Leu Ser Leu Ala Gln Glu Gln Val Gly Gly Ser Pro Glu Lys Leu
1               5                   10                  15

Gln Glu Thr Ser Asn Trp Leu Leu Ser Gln Gln Ala Asp Gly Ser
            20                  25                  30

Phe Gln Asp Leu Ser Pro Val Ile His Arg
        35                  40

<210> SEQ ID NO 734
<211> LENGTH: 21
<212> TYPE: PRT
<213> ORGANISM: Homo sapiens

<400> SEQUENCE: 734

Val Gln Gln Pro Asp Cys Arg Glu Pro Phe Leu Ser Cys Cys Gln Phe
1               5                   10                  15

Ala Glu Ser Leu Arg
            20

```
<210> SEQ ID NO 735
<211> LENGTH: 22
<212> TYPE: PRT
<213> ORGANISM: Homo sapiens

<400> SEQUENCE: 735

Val Gln Gln Pro Asp Cys Arg Glu Pro Phe Leu Ser Cys Cys Gln Phe
1               5                   10                  15

Ala Glu Ser Leu Arg Lys
            20

<210> SEQ ID NO 736
<211> LENGTH: 22
<212> TYPE: PRT
<213> ORGANISM: Homo sapiens

<400> SEQUENCE: 736

Val Ser Ala Thr Val Ser Ser Pro Gly Ser Val Pro Glu Val Gln Asp
1               5                   10                  15

Ile Gln Gln Asn Thr Asp
            20

<210> SEQ ID NO 737
<211> LENGTH: 26
<212> TYPE: PRT
<213> ORGANISM: Homo sapiens

<400> SEQUENCE: 737

Val Thr Ala Ser Asp Pro Leu Asp Thr Leu Gly Ser Glu Gly Ala Leu
1               5                   10                  15

Ser Pro Gly Gly Val Ala Ser Leu Leu Arg
            20                  25

<210> SEQ ID NO 738
<211> LENGTH: 14
<212> TYPE: PRT
<213> ORGANISM: Homo sapiens

<400> SEQUENCE: 738

Tyr Ile Tyr Gly Lys Pro Val Gln Gly Val Ala Tyr Val Arg
1               5                   10

<210> SEQ ID NO 739
<211> LENGTH: 16
<212> TYPE: PRT
<213> ORGANISM: Homo sapiens

<400> SEQUENCE: 739

Tyr Leu Asp Lys Thr Glu Gln Trp Ser Thr Leu Pro Pro Glu Thr Lys
1               5                   10                  15

<210> SEQ ID NO 740
<211> LENGTH: 25
<212> TYPE: PRT
<213> ORGANISM: Homo sapiens

<400> SEQUENCE: 740

Tyr Leu Asp Lys Thr Glu Gln Trp Ser Thr Leu Pro Pro Glu Thr Lys
1               5                   10                  15

Asp His Ala Val Asp Leu Ile Gln Lys
            20                  25
```

```
<210> SEQ ID NO 741
<211> LENGTH: 9
<212> TYPE: PRT
<213> ORGANISM: Homo sapiens

<400> SEQUENCE: 741

Tyr Arg Val Phe Ala Leu Asp Gln Lys
1               5

<210> SEQ ID NO 742
<211> LENGTH: 23
<212> TYPE: PRT
<213> ORGANISM: Homo sapiens

<400> SEQUENCE: 742

Tyr Val Ser His Phe Glu Thr Glu Gly Pro His Val Leu Leu Tyr Phe
1               5                   10                  15

Asp Ser Val Pro Thr Ser Arg
            20

<210> SEQ ID NO 743
<211> LENGTH: 13
<212> TYPE: PRT
<213> ORGANISM: Homo sapiens

<400> SEQUENCE: 743

Cys Ser Ser Asn Leu Val Leu Thr Gly Ser Ser Glu Arg
1               5                   10

<210> SEQ ID NO 744
<211> LENGTH: 16
<212> TYPE: PRT
<213> ORGANISM: Homo sapiens

<400> SEQUENCE: 744

Glu Cys Gln Gly Asn Gly Val Trp Ser Gly Thr Glu Pro Ile Cys Arg
1               5                   10                  15

<210> SEQ ID NO 745
<211> LENGTH: 6
<212> TYPE: PRT
<213> ORGANISM: Homo sapiens

<400> SEQUENCE: 745

Lys Ile Gln Ile Gln Arg
1               5

<210> SEQ ID NO 746
<211> LENGTH: 31
<212> TYPE: PRT
<213> ORGANISM: Homo sapiens

<400> SEQUENCE: 746

Gln Pro Tyr Ser Tyr Asp Phe Pro Glu Asp Val Ala Pro Ala Leu Gly
1               5                   10                  15

Thr Ser Phe Ser His Met Leu Gly Ala Thr Asn Pro Thr Gln Lys
            20                  25                  30

<210> SEQ ID NO 747
<211> LENGTH: 12
<212> TYPE: PRT
<213> ORGANISM: Homo sapiens

<400> SEQUENCE: 747

Ser Ser Gly Gln Trp Gln Thr Pro Gly Ala Thr Arg
```

-continued

<210> SEQ ID NO 748
<211> LENGTH: 19
<212> TYPE: PRT
<213> ORGANISM: Homo sapiens

<400> SEQUENCE: 748

Met Arg Pro Ser Thr Asp Thr Ile Thr Val Met Val Glu Asn Ser His
1               5                   10                  15

Gly Leu Arg

<210> SEQ ID NO 749
<211> LENGTH: 21
<212> TYPE: PRT
<213> ORGANISM: Homo sapiens

<400> SEQUENCE: 749

Ala Glu Phe Gln Asp Ala Leu Glu Lys Leu Asn Met Gly Ile Thr Asp
1               5                   10                  15

Leu Gln Gly Leu Arg
            20

<210> SEQ ID NO 750
<211> LENGTH: 13
<212> TYPE: PRT
<213> ORGANISM: Homo sapiens

<400> SEQUENCE: 750

Glu Met Ser Gly Ser Pro Ala Ser Gly Ile Pro Val Lys
1               5                   10

<210> SEQ ID NO 751
<211> LENGTH: 25
<212> TYPE: PRT
<213> ORGANISM: Homo sapiens

<400> SEQUENCE: 751

Glu Val Tyr Met Pro Ser Ser Ile Phe Gln Asp Asp Phe Val Ile Pro
1               5                   10                  15

Asp Ile Ser Glu Pro Gly Thr Trp Lys
            20                  25

<210> SEQ ID NO 752
<211> LENGTH: 11
<212> TYPE: PRT
<213> ORGANISM: Homo sapiens

<400> SEQUENCE: 752

Gly Gln Ile Val Phe Met Asn Arg Glu Pro Lys
1               5                   10

<210> SEQ ID NO 753
<211> LENGTH: 27
<212> TYPE: PRT
<213> ORGANISM: Homo sapiens

<400> SEQUENCE: 753

Lys Lys Glu Val Tyr Met Pro Ser Ser Ile Phe Gln Asp Asp Phe Val
1               5                   10                  15

Ile Pro Asp Ile Ser Glu Pro Gly Thr Trp Lys
            20                  25

<210> SEQ ID NO 754
<211> LENGTH: 42
<212> TYPE: PRT
<213> ORGANISM: Homo sapiens

<400> SEQUENCE: 754

Leu Arg Leu Glu Pro Gly Lys Glu Tyr Leu Ile Met Gly Leu Asp Gly
1               5                   10                  15

Ala Thr Tyr Asp Leu Glu Gly His Pro Gln Tyr Leu Leu Asp Ser Asn
            20                  25                  30

Ser Trp Ile Glu Glu Met Pro Ser Glu Arg
        35                  40

<210> SEQ ID NO 755
<211> LENGTH: 39
<212> TYPE: PRT
<213> ORGANISM: Homo sapiens

<400> SEQUENCE: 755

Ser Met Gln Gly Gly Leu Val Gly Asn Asp Glu Thr Val Ala Leu Thr
1               5                   10                  15

Ala Phe Val Thr Ile Ala Leu His His Gly Leu Ala Val Phe Gln Asp
            20                  25                  30

Glu Gly Ala Glu Pro Leu Lys
        35

<210> SEQ ID NO 756
<211> LENGTH: 41
<212> TYPE: PRT
<213> ORGANISM: Homo sapiens

<400> SEQUENCE: 756

Ser Met Gln Gly Gly Leu Val Gly Asn Asp Glu Thr Val Ala Leu Thr
1               5                   10                  15

Ala Phe Val Thr Ile Ala Leu His His Gly Leu Ala Val Phe Gln Asp
            20                  25                  30

Glu Gly Ala Glu Pro Leu Lys Gln Arg
        35                  40

<210> SEQ ID NO 757
<211> LENGTH: 23
<212> TYPE: PRT
<213> ORGANISM: Homo sapiens

<400> SEQUENCE: 757

Thr Leu Glu Ile Pro Gly Asn Ser Asp Pro Asn Met Ile Pro Asp Gly
1               5                   10                  15

Asp Phe Asn Ser Tyr Val Arg
            20

<210> SEQ ID NO 758
<211> LENGTH: 20
<212> TYPE: PRT
<213> ORGANISM: Homo sapiens

<400> SEQUENCE: 758

Ala Ala Cys Ala Gln Leu Asn Asp Phe Leu Gln Glu Tyr Gly Thr Gln
1               5                   10                  15

Gly Cys Gln Val
            20

<210> SEQ ID NO 759

```
<211> LENGTH: 35
<212> TYPE: PRT
<213> ORGANISM: Homo sapiens

<400> SEQUENCE: 759

Ala Asp Leu Glu Lys Leu Thr Ser Leu Ser Asp Arg Tyr Val Ser His
1               5                   10                  15

Phe Glu Thr Glu Gly Pro His Val Leu Leu Tyr Phe Asp Ser Val Pro
                20                  25                  30

Thr Ser Arg
        35

<210> SEQ ID NO 760
<211> LENGTH: 9
<212> TYPE: PRT
<213> ORGANISM: Homo sapiens

<400> SEQUENCE: 760

Ala Glu Phe Gln Asp Ala Leu Glu Lys
1               5

<210> SEQ ID NO 761
<211> LENGTH: 13
<212> TYPE: PRT
<213> ORGANISM: Homo sapiens

<400> SEQUENCE: 761

Ala Glu Met Ala Asp Gln Ala Ala Ala Trp Leu Thr Arg
1               5                   10

<210> SEQ ID NO 762
<211> LENGTH: 19
<212> TYPE: PRT
<213> ORGANISM: Homo sapiens

<400> SEQUENCE: 762

Ala Leu Glu Ile Leu Gln Glu Glu Asp Leu Ile Asp Glu Asp Asp Ile
1               5                   10                  15

Pro Val Arg

<210> SEQ ID NO 763
<211> LENGTH: 13
<212> TYPE: PRT
<213> ORGANISM: Homo sapiens

<400> SEQUENCE: 763

Ala Leu Leu Ser Leu Gln Val Pro Leu Lys Asp Ala Lys
1               5                   10

<210> SEQ ID NO 764
<211> LENGTH: 22
<212> TYPE: PRT
<213> ORGANISM: Homo sapiens

<400> SEQUENCE: 764

Ala Ser Ala Gly Leu Leu Gly Ala His Ala Ala Ile Thr Ala Tyr
1               5                   10                  15

Ala Leu Thr Leu Thr Lys
            20

<210> SEQ ID NO 765
<211> LENGTH: 8
<212> TYPE: PRT
<213> ORGANISM: Homo sapiens
```

<400> SEQUENCE: 765

Ala Ser Ser Phe Leu Gly Glu Lys
1               5

<210> SEQ ID NO 766
<211> LENGTH: 18
<212> TYPE: PRT
<213> ORGANISM: Homo sapiens

<400> SEQUENCE: 766

Ala Val Gly Ser Gly Ala Thr Phe Ser His Tyr Tyr Tyr Met Ile Leu
1               5                   10                  15

Ser Arg

<210> SEQ ID NO 767
<211> LENGTH: 10
<212> TYPE: PRT
<213> ORGANISM: Homo sapiens

<400> SEQUENCE: 767

Cys Ser Val Phe Tyr Gly Ala Pro Ser Lys
1               5                   10

<210> SEQ ID NO 768
<211> LENGTH: 15
<212> TYPE: PRT
<213> ORGANISM: Homo sapiens

<400> SEQUENCE: 768

Asp Phe Ala Leu Leu Ser Leu Gln Val Pro Leu Lys Asp Ala Lys
1               5                   10                  15

<210> SEQ ID NO 769
<211> LENGTH: 12
<212> TYPE: PRT
<213> ORGANISM: Homo sapiens

<400> SEQUENCE: 769

Asp Ser Ser Thr Trp Leu Thr Ala Phe Val Leu Lys
1               5                   10

<210> SEQ ID NO 770
<211> LENGTH: 12
<212> TYPE: PRT
<213> ORGANISM: Homo sapiens

<400> SEQUENCE: 770

Glu Ala Pro Lys Val Val Glu Glu Gln Glu Ser Arg
1               5                   10

<210> SEQ ID NO 771
<211> LENGTH: 31
<212> TYPE: PRT
<213> ORGANISM: Homo sapiens

<400> SEQUENCE: 771

Glu Cys Val Gly Phe Glu Ala Val Gln Glu Val Pro Val Gly Leu Val
1               5                   10                  15

Gln Pro Ala Ser Ala Thr Leu Tyr Asp Tyr Tyr Asn Pro Glu Arg
            20                  25                  30

<210> SEQ ID NO 772
<211> LENGTH: 32

```
<212> TYPE: PRT
<213> ORGANISM: Homo sapiens

<400> SEQUENCE: 772

Glu Cys Val Gly Phe Glu Ala Val Gln Glu Val Pro Val Gly Leu Val
1               5                   10                  15

Gln Pro Ala Ser Ala Thr Leu Tyr Asp Tyr Tyr Asn Pro Glu Arg Arg
            20                  25                  30

<210> SEQ ID NO 773
<211> LENGTH: 7
<212> TYPE: PRT
<213> ORGANISM: Homo sapiens

<400> SEQUENCE: 773

Glu Phe His Leu His Leu Arg
1               5

<210> SEQ ID NO 774
<211> LENGTH: 18
<212> TYPE: PRT
<213> ORGANISM: Homo sapiens

<400> SEQUENCE: 774

Glu Gly Ala Ile His Arg Glu Glu Leu Val Tyr Glu Leu Asn Pro Leu
1               5                   10                  15

Asp His

<210> SEQ ID NO 775
<211> LENGTH: 19
<212> TYPE: PRT
<213> ORGANISM: Homo sapiens

<400> SEQUENCE: 775

Glu Gly Ala Ile His Arg Glu Glu Leu Val Tyr Glu Leu Asn Pro Leu
1               5                   10                  15

Asp His Arg

<210> SEQ ID NO 776
<211> LENGTH: 20
<212> TYPE: PRT
<213> ORGANISM: Homo sapiens

<400> SEQUENCE: 776

Glu Gly Ala Ile His Arg Glu Glu Leu Val Tyr Glu Leu Asn Pro Leu
1               5                   10                  15

Asp His Arg Gly
            20

<210> SEQ ID NO 777
<211> LENGTH: 14
<212> TYPE: PRT
<213> ORGANISM: Homo sapiens

<400> SEQUENCE: 777

Glu Pro Phe Leu Ser Cys Cys Gln Phe Ala Glu Ser Leu Arg
1               5                   10

<210> SEQ ID NO 778
<211> LENGTH: 10
<212> TYPE: PRT
<213> ORGANISM: Homo sapiens

<400> SEQUENCE: 778
```

Phe Gly Leu Leu Asp Glu Asp Gly Lys Lys
1               5                   10

<210> SEQ ID NO 779
<211> LENGTH: 14
<212> TYPE: PRT
<213> ORGANISM: Homo sapiens

<400> SEQUENCE: 779

Phe Gly Leu Leu Asp Glu Asp Gly Lys Lys Thr Phe Phe Arg
1               5                   10

<210> SEQ ID NO 780
<211> LENGTH: 24
<212> TYPE: PRT
<213> ORGANISM: Homo sapiens

<400> SEQUENCE: 780

Phe Gln Ile Leu Thr Leu Trp Leu Pro Asp Ser Leu Thr Thr Trp Glu
1               5                   10                  15

Ile His Gly Leu Ser Leu Ser Lys
            20

<210> SEQ ID NO 781
<211> LENGTH: 17
<212> TYPE: PRT
<213> ORGANISM: Homo sapiens

<400> SEQUENCE: 781

Gly His Leu Phe Leu Gln Thr Asp Gln Pro Ile Tyr Asn Pro Gly Gln
1               5                   10                  15

Arg

<210> SEQ ID NO 782
<211> LENGTH: 13
<212> TYPE: PRT
<213> ORGANISM: Homo sapiens

<400> SEQUENCE: 782

Gly Leu Glu Glu Glu Leu Gln Phe Ser Leu Gly Ser Lys
1               5                   10

<210> SEQ ID NO 783
<211> LENGTH: 9
<212> TYPE: PRT
<213> ORGANISM: Homo sapiens

<400> SEQUENCE: 783

Gly Leu Gln Asp Glu Asp Gly Tyr Arg
1               5

<210> SEQ ID NO 784
<211> LENGTH: 14
<212> TYPE: PRT
<213> ORGANISM: Homo sapiens

<400> SEQUENCE: 784

Gly Pro Glu Val Gln Leu Val Ala His Ser Pro Trp Leu Lys
1               5                   10

<210> SEQ ID NO 785
<211> LENGTH: 19
<212> TYPE: PRT
<213> ORGANISM: Homo sapiens

```
<400> SEQUENCE: 785

Gly Pro Glu Val Gln Leu Val Ala His Ser Pro Trp Leu Lys Asp Ser
1               5                   10                  15

Leu Ser Arg

<210> SEQ ID NO 786
<211> LENGTH: 8
<212> TYPE: PRT
<213> ORGANISM: Homo sapiens

<400> SEQUENCE: 786

Gly Gln Ile Val Phe Met Asn Arg
1               5

<210> SEQ ID NO 787
<211> LENGTH: 13
<212> TYPE: PRT
<213> ORGANISM: Homo sapiens

<400> SEQUENCE: 787

Gly Ser Phe Glu Phe Pro Val Gly Asp Ala Val Ser Lys
1               5                   10

<210> SEQ ID NO 788
<211> LENGTH: 10
<212> TYPE: PRT
<213> ORGANISM: Homo sapiens

<400> SEQUENCE: 788

Gly Ser Val Phe Leu Arg Asn Pro Ser Arg
1               5                   10

<210> SEQ ID NO 789
<211> LENGTH: 15
<212> TYPE: PRT
<213> ORGANISM: Homo sapiens

<400> SEQUENCE: 789

His Leu Val Pro Gly Ala Pro Phe Leu Leu Gln Ala Leu Val Arg
1               5                   10                  15

<210> SEQ ID NO 790
<211> LENGTH: 25
<212> TYPE: PRT
<213> ORGANISM: Homo sapiens

<400> SEQUENCE: 790

Ile Thr Pro Gly Lys Pro Tyr Ile Leu Thr Val Pro Gly His Leu Asp
1               5                   10                  15

Glu Met Gln Leu Asp Ile Gln Ala Arg
            20                  25

<210> SEQ ID NO 791
<211> LENGTH: 12
<212> TYPE: PRT
<213> ORGANISM: Homo sapiens

<400> SEQUENCE: 791

Lys Ala Asp Gly Ser Tyr Ala Ala Trp Leu Ser Arg
1               5                   10

<210> SEQ ID NO 792
<211> LENGTH: 10
```

```
<212> TYPE: PRT
<213> ORGANISM: Homo sapiens

<400> SEQUENCE: 792

Lys Tyr Val Leu Pro Asn Phe Glu Val Lys
1               5                   10

<210> SEQ ID NO 793
<211> LENGTH: 9
<212> TYPE: PRT
<213> ORGANISM: Homo sapiens

<400> SEQUENCE: 793

Leu Glu Leu Ser Val Asp Gly Ala Lys
1               5

<210> SEQ ID NO 794
<211> LENGTH: 10
<212> TYPE: PRT
<213> ORGANISM: Homo sapiens

<400> SEQUENCE: 794

Leu Gly Gln Tyr Ala Ser Pro Thr Ala Lys
1               5                   10

<210> SEQ ID NO 795
<211> LENGTH: 11
<212> TYPE: PRT
<213> ORGANISM: Homo sapiens

<400> SEQUENCE: 795

Leu Gly Gln Tyr Ala Ser Pro Thr Ala Lys Arg
1               5                   10

<210> SEQ ID NO 796
<211> LENGTH: 26
<212> TYPE: PRT
<213> ORGANISM: Homo sapiens

<400> SEQUENCE: 796

Leu His Leu Glu Thr Asp Ser Leu Ala Leu Val Ala Leu Gly Ala Leu
1               5                   10                  15

Asp Thr Ala Leu Tyr Ala Ala Gly Ser Lys
            20                  25

<210> SEQ ID NO 797
<211> LENGTH: 17
<212> TYPE: PRT
<213> ORGANISM: Homo sapiens

<400> SEQUENCE: 797

Leu Leu Ala Thr Leu Cys Ser Ala Glu Val Cys Gln Cys Ala Glu Gly
1               5                   10                  15

Lys

<210> SEQ ID NO 798
<211> LENGTH: 26
<212> TYPE: PRT
<213> ORGANISM: Homo sapiens

<400> SEQUENCE: 798

Leu Leu Leu Phe Ser Pro Ser Val Val His Leu Gly Val Pro Leu Ser
1               5                   10                  15

Val Gly Val Gln Leu Gln Asp Val Pro Arg
```

-continued

```
                20                  25

<210> SEQ ID NO 799
<211> LENGTH: 31
<212> TYPE: PRT
<213> ORGANISM: Homo sapiens

<400> SEQUENCE: 799

Leu Leu Leu Phe Ser Pro Ser Val Val His Leu Gly Val Pro Leu Ser
1               5                   10                  15

Val Gly Val Gln Leu Gln Asp Val Pro Arg Gly Gln Val Val Lys
            20                  25                  30

<210> SEQ ID NO 800
<211> LENGTH: 12
<212> TYPE: PRT
<213> ORGANISM: Homo sapiens

<400> SEQUENCE: 800

Leu Asn Met Gly Ile Thr Asp Leu Gln Gly Leu Arg
1               5                   10

<210> SEQ ID NO 801
<211> LENGTH: 6
<212> TYPE: PRT
<213> ORGANISM: Homo sapiens

<400> SEQUENCE: 801

Leu Pro Met Ser Val Arg
1               5

<210> SEQ ID NO 802
<211> LENGTH: 27
<212> TYPE: PRT
<213> ORGANISM: Homo sapiens

<400> SEQUENCE: 802

Leu Gln Glu Thr Ser Asn Trp Leu Leu Ser Gln Gln Ala Asp Gly
1               5                   10                  15

Ser Phe Gln Asp Pro Cys Pro Val Leu Asp Arg
            20                  25

<210> SEQ ID NO 803
<211> LENGTH: 30
<212> TYPE: PRT
<213> ORGANISM: Homo sapiens

<400> SEQUENCE: 803

Leu Thr Ser Leu Ser Asp Arg Tyr Val Ser His Phe Glu Thr Glu Gly
1               5                   10                  15

Pro His Val Leu Leu Tyr Phe Asp Ser Val Pro Thr Ser Arg
            20                  25                  30

<210> SEQ ID NO 804
<211> LENGTH: 25
<212> TYPE: PRT
<213> ORGANISM: Homo sapiens

<400> SEQUENCE: 804

Leu Thr Val Ala Ala Pro Pro Ser Gly Gly Pro Gly Phe Leu Ser Ile
1               5                   10                  15

Glu Arg Pro Asp Ser Arg Pro Pro Arg
            20                  25
```

```
<210> SEQ ID NO 805
<211> LENGTH: 12
<212> TYPE: PRT
<213> ORGANISM: Homo sapiens

<400> SEQUENCE: 805

Leu Val Asn Gly Gln Ser His Ile Ser Leu Ser Lys
1               5                   10

<210> SEQ ID NO 806
<211> LENGTH: 33
<212> TYPE: PRT
<213> ORGANISM: Homo sapiens

<400> SEQUENCE: 806

Leu Val Asn Gly Gln Ser His Ile Ser Leu Ser Lys Ala Glu Phe Gln
1               5                   10                  15

Asp Ala Leu Glu Lys Leu Asn Met Gly Ile Thr Asp Leu Gln Gly Leu
            20                  25                  30

Arg

<210> SEQ ID NO 807
<211> LENGTH: 9
<212> TYPE: PRT
<213> ORGANISM: Homo sapiens

<400> SEQUENCE: 807

Met Lys Phe Ala Cys Tyr Tyr Pro Arg
1               5

<210> SEQ ID NO 808
<211> LENGTH: 32
<212> TYPE: PRT
<213> ORGANISM: Homo sapiens

<400> SEQUENCE: 808

Asn Gly Glu Ser Val Lys Leu His Leu Glu Thr Asp Ser Leu Ala Leu
1               5                   10                  15

Val Ala Leu Gly Ala Leu Asp Thr Ala Leu Tyr Ala Ala Gly Ser Lys
            20                  25                  30

<210> SEQ ID NO 809
<211> LENGTH: 32
<212> TYPE: PRT
<213> ORGANISM: Homo sapiens

<400> SEQUENCE: 809

Asn Asn Val Pro Cys Ser Pro Lys Val Asp Phe Thr Leu Ser Ser Glu
1               5                   10                  15

Arg Asp Phe Ala Leu Leu Ser Leu Gln Val Pro Leu Lys Asp Ala Lys
            20                  25                  30

<210> SEQ ID NO 810
<211> LENGTH: 30
<212> TYPE: PRT
<213> ORGANISM: Homo sapiens

<400> SEQUENCE: 810

Asn Pro Ser Asp Pro Met Pro Gln Ala Pro Ala Leu Trp Ile Glu Thr
1               5                   10                  15

Thr Ala Tyr Ala Leu Leu His Leu Leu His Glu Gly Lys
            20                  25                  30
```

<210> SEQ ID NO 811
<211> LENGTH: 6
<212> TYPE: PRT
<213> ORGANISM: Homo sapiens

<400> SEQUENCE: 811

Asn Val Asn Phe Gln Lys
1               5

<210> SEQ ID NO 812
<211> LENGTH: 9
<212> TYPE: PRT
<213> ORGANISM: Homo sapiens

<400> SEQUENCE: 812

Pro Phe Leu Leu Gln Ala Leu Val Arg
1               5

<210> SEQ ID NO 813
<211> LENGTH: 14
<212> TYPE: PRT
<213> ORGANISM: Homo sapiens

<400> SEQUENCE: 813

Pro Gly His Leu Asp Glu Met Gln Leu Asp Ile Gln Ala Arg
1               5                   10

<210> SEQ ID NO 814
<211> LENGTH: 23
<212> TYPE: PRT
<213> ORGANISM: Homo sapiens

<400> SEQUENCE: 814

Pro Gly Lys Pro Tyr Ile Leu Thr Val Pro Gly His Leu Asp Glu Met
1               5                   10                  15

Gln Leu Asp Ile Gln Ala Arg
            20

<210> SEQ ID NO 815
<211> LENGTH: 26
<212> TYPE: PRT
<213> ORGANISM: Homo sapiens

<400> SEQUENCE: 815

Pro Ile Ile Ile Pro Gln Thr Ile Ser Glu Leu Gln Leu Ser Val Ser
1               5                   10                  15

Ala Gly Ser Pro His Pro Ala Ile Ala Arg
            20                  25

<210> SEQ ID NO 816
<211> LENGTH: 21
<212> TYPE: PRT
<213> ORGANISM: Homo sapiens

<400> SEQUENCE: 816

Pro Leu Asp Thr Leu Gly Ser Glu Gly Ala Leu Ser Pro Gly Gly Val
1               5                   10                  15

Ala Ser Leu Leu Arg
            20

<210> SEQ ID NO 817
<211> LENGTH: 17
<212> TYPE: PRT
<213> ORGANISM: Homo sapiens

```
<400> SEQUENCE: 817

Pro Val Ala Phe Ser Val Val Pro Thr Ala Ala Ala Val Ser Leu
1               5                   10                  15

Lys

<210> SEQ ID NO 818
<211> LENGTH: 9
<212> TYPE: PRT
<213> ORGANISM: Homo sapiens

<400> SEQUENCE: 818

Gln Gly Ser Phe Gln Gly Gly Phe Arg
1               5

<210> SEQ ID NO 819
<211> LENGTH: 9
<212> TYPE: PRT
<213> ORGANISM: Homo sapiens

<400> SEQUENCE: 819

Arg Cys Cys Gln Asp Gly Val Thr Arg
1               5

<210> SEQ ID NO 820
<211> LENGTH: 16
<212> TYPE: PRT
<213> ORGANISM: Homo sapiens

<400> SEQUENCE: 820

Arg His Leu Val Pro Gly Ala Pro Phe Leu Leu Gln Ala Leu Val Arg
1               5                   10                  15

<210> SEQ ID NO 821
<211> LENGTH: 23
<212> TYPE: PRT
<213> ORGANISM: Homo sapiens

<400> SEQUENCE: 821

Ser Cys Gly Leu His Gln Leu Leu Arg Gly Pro Glu Val Gln Leu Val
1               5                   10                  15

Ala His Ser Pro Trp Leu Lys
            20

<210> SEQ ID NO 822
<211> LENGTH: 10
<212> TYPE: PRT
<213> ORGANISM: Homo sapiens

<400> SEQUENCE: 822

Ser Phe Phe Pro Glu Asn Trp Leu Trp Arg
1               5                   10

<210> SEQ ID NO 823
<211> LENGTH: 9
<212> TYPE: PRT
<213> ORGANISM: Homo sapiens

<400> SEQUENCE: 823

Ser His Ala Leu Gln Leu Asn Asn Arg
1               5

<210> SEQ ID NO 824
<211> LENGTH: 9
```

```
<212> TYPE: PRT
<213> ORGANISM: Homo sapiens

<400> SEQUENCE: 824

Ser His Lys Pro Leu Asn Met Gly Lys
1               5

<210> SEQ ID NO 825
<211> LENGTH: 25
<212> TYPE: PRT
<213> ORGANISM: Homo sapiens

<400> SEQUENCE: 825

Ser Thr Gln Asp Thr Val Ile Ala Leu Asp Ala Leu Ser Ala Tyr Trp
1               5                   10                  15

Ile Ala Ser His Thr Thr Glu Glu Arg
            20                  25

<210> SEQ ID NO 826
<211> LENGTH: 13
<212> TYPE: PRT
<213> ORGANISM: Homo sapiens

<400> SEQUENCE: 826

Thr Lys Gly Leu Cys Val Ala Thr Pro Val Gln Leu Arg
1               5                   10

<210> SEQ ID NO 827
<211> LENGTH: 14
<212> TYPE: PRT
<213> ORGANISM: Homo sapiens

<400> SEQUENCE: 827

Thr Thr Asn Ile Gln Gly Ile Asn Leu Leu Phe Ser Ser Arg
1               5                   10

<210> SEQ ID NO 828
<211> LENGTH: 8
<212> TYPE: PRT
<213> ORGANISM: Homo sapiens

<400> SEQUENCE: 828

Thr Tyr Asn Val Leu Asp Met Lys
1               5

<210> SEQ ID NO 829
<211> LENGTH: 9
<212> TYPE: PRT
<213> ORGANISM: Homo sapiens

<400> SEQUENCE: 829

Val Asp Phe Thr Leu Ser Ser Glu Arg
1               5

<210> SEQ ID NO 830
<211> LENGTH: 24
<212> TYPE: PRT
<213> ORGANISM: Homo sapiens

<400> SEQUENCE: 830

Val Asp Phe Thr Leu Ser Ser Glu Arg Asp Phe Ala Leu Leu Ser Leu
1               5                   10                  15

Gln Val Pro Leu Lys Asp Ala Lys
            20
```

```
<210> SEQ ID NO 831
<211> LENGTH: 11
<212> TYPE: PRT
<213> ORGANISM: Homo sapiens

<400> SEQUENCE: 831

Val Asp Val Gln Ala Gly Ala Cys Glu Gly Lys
1               5                   10

<210> SEQ ID NO 832
<211> LENGTH: 20
<212> TYPE: PRT
<213> ORGANISM: Homo sapiens

<400> SEQUENCE: 832

Val Asp Val Gln Ala Gly Ala Cys Glu Gly Lys Leu Glu Leu Ser Val
1               5                   10                  15

Asp Gly Ala Lys
            20

<210> SEQ ID NO 833
<211> LENGTH: 30
<212> TYPE: PRT
<213> ORGANISM: Homo sapiens

<400> SEQUENCE: 833

Val Glu Thr Val Asp Arg Phe Gln Ile Leu Thr Leu Trp Leu Pro Asp
1               5                   10                  15

Ser Leu Thr Thr Trp Glu Ile His Gly Leu Ser Leu Ser Lys
            20                  25                  30

<210> SEQ ID NO 834
<211> LENGTH: 8
<212> TYPE: PRT
<213> ORGANISM: Homo sapiens

<400> SEQUENCE: 834

Val Glu Tyr Gly Phe Gln Val Lys
1               5

<210> SEQ ID NO 835
<211> LENGTH: 7
<212> TYPE: PRT
<213> ORGANISM: Homo sapiens

<400> SEQUENCE: 835

Val Phe Ala Leu Asp Gln Lys
1               5

<210> SEQ ID NO 836
<211> LENGTH: 10
<212> TYPE: PRT
<213> ORGANISM: Homo sapiens

<400> SEQUENCE: 836

Val Phe Arg Glu Phe His Leu His Leu Arg
1               5                   10

<210> SEQ ID NO 837
<211> LENGTH: 10
<212> TYPE: PRT
<213> ORGANISM: Homo sapiens

<400> SEQUENCE: 837
```

```
Val Gly Asp Thr Leu Asn Leu Asn Leu Arg
1               5                   10

<210> SEQ ID NO 838
<211> LENGTH: 26
<212> TYPE: PRT
<213> ORGANISM: Homo sapiens

<400> SEQUENCE: 838

Val Gly Leu Ser Gly Met Ala Ile Ala Asp Val Thr Leu Leu Ser Gly
1               5                   10                  15

Phe His Ala Leu Arg Ala Asp Leu Glu Lys
            20                  25

<210> SEQ ID NO 839
<211> LENGTH: 9
<212> TYPE: PRT
<213> ORGANISM: Homo sapiens

<400> SEQUENCE: 839

Val His Tyr Thr Val Cys Ile Trp Arg
1               5

<210> SEQ ID NO 840
<211> LENGTH: 15
<212> TYPE: PRT
<213> ORGANISM: Homo sapiens

<400> SEQUENCE: 840

Val Leu Ser Leu Ala Gln Glu Gln Val Gly Gly Ser Pro Glu Lys
1               5                   10                  15

<210> SEQ ID NO 841
<211> LENGTH: 42
<212> TYPE: PRT
<213> ORGANISM: Homo sapiens

<400> SEQUENCE: 841

Val Leu Ser Leu Ala Gln Glu Gln Val Gly Gly Ser Pro Glu Lys Leu
1               5                   10                  15

Gln Glu Thr Ser Asn Trp Leu Leu Ser Gln Gln Gln Ala Asp Gly Ser
            20                  25                  30

Phe Gln Asp Pro Cys Pro Val Leu Asp Arg
            35                  40

<210> SEQ ID NO 842
<211> LENGTH: 21
<212> TYPE: PRT
<213> ORGANISM: Homo sapiens

<400> SEQUENCE: 842

Val Gln Gln Pro Asp Cys Arg Glu Pro Phe Leu Ser Cys Cys Gln Phe
1               5                   10                  15

Ala Glu Ser Leu Arg
            20

<210> SEQ ID NO 843
<211> LENGTH: 22
<212> TYPE: PRT
<213> ORGANISM: Homo sapiens

<400> SEQUENCE: 843

Val Gln Gln Pro Asp Cys Arg Glu Pro Phe Leu Ser Cys Cys Gln Phe
1               5                   10                  15
```

Ala Glu Ser Leu Arg Lys
            20

<210> SEQ ID NO 844
<211> LENGTH: 22
<212> TYPE: PRT
<213> ORGANISM: Homo sapiens

<400> SEQUENCE: 844

Val Ser Ala Thr Val Ser Ser Pro Gly Ser Val Pro Glu Val Gln Asp
1               5                   10                  15

Ile Gln Gln Asn Thr Asp
            20

<210> SEQ ID NO 845
<211> LENGTH: 26
<212> TYPE: PRT
<213> ORGANISM: Homo sapiens

<400> SEQUENCE: 845

Val Thr Ala Ser Asp Pro Leu Asp Thr Leu Gly Ser Glu Gly Ala Leu
1               5                   10                  15

Ser Pro Gly Gly Val Ala Ser Leu Leu Arg
            20                  25

<210> SEQ ID NO 846
<211> LENGTH: 14
<212> TYPE: PRT
<213> ORGANISM: Homo sapiens

<400> SEQUENCE: 846

Tyr Ile Tyr Gly Lys Pro Val Gln Gly Val Ala Tyr Val Arg
1               5                   10

<210> SEQ ID NO 847
<211> LENGTH: 16
<212> TYPE: PRT
<213> ORGANISM: Homo sapiens

<400> SEQUENCE: 847

Tyr Leu Asp Lys Thr Glu Gln Trp Ser Thr Leu Pro Pro Glu Thr Lys
1               5                   10                  15

<210> SEQ ID NO 848
<211> LENGTH: 25
<212> TYPE: PRT
<213> ORGANISM: Homo sapiens

<400> SEQUENCE: 848

Tyr Leu Asp Lys Thr Glu Gln Trp Ser Thr Leu Pro Pro Glu Thr Lys
1               5                   10                  15

Asp His Ala Val Asp Leu Ile Gln Lys
            20                  25

<210> SEQ ID NO 849
<211> LENGTH: 9
<212> TYPE: PRT
<213> ORGANISM: Homo sapiens

<400> SEQUENCE: 849

Tyr Arg Val Phe Ala Leu Asp Gln Lys
1               5

```
<210> SEQ ID NO 850
<211> LENGTH: 23
<212> TYPE: PRT
<213> ORGANISM: Homo sapiens

<400> SEQUENCE: 850

Tyr Val Ser His Phe Glu Thr Glu Gly Pro His Val Leu Leu Tyr Phe
1               5                   10                  15

Asp Ser Val Pro Thr Ser Arg
            20

<210> SEQ ID NO 851
<211> LENGTH: 19
<212> TYPE: PRT
<213> ORGANISM: Homo sapiens

<400> SEQUENCE: 851

Cys Asp Cys Ile Cys Pro Val Gly Ser Gln Gly Leu Ala Cys Glu Val
1               5                   10                  15

Ser Tyr Arg

<210> SEQ ID NO 852
<211> LENGTH: 20
<212> TYPE: PRT
<213> ORGANISM: Homo sapiens

<400> SEQUENCE: 852

Cys Asp Cys Ile Cys Pro Val Gly Ser Gln Gly Leu Ala Cys Glu Val
1               5                   10                  15

Ser Tyr Arg Lys
            20

<210> SEQ ID NO 853
<211> LENGTH: 11
<212> TYPE: PRT
<213> ORGANISM: Homo sapiens

<400> SEQUENCE: 853

Cys Glu Gly Phe Val Cys Ala Gln Thr Gly Arg
1               5                   10

<210> SEQ ID NO 854
<211> LENGTH: 33
<212> TYPE: PRT
<213> ORGANISM: Homo sapiens

<400> SEQUENCE: 854

Cys Gln His Glu Met Asp Gln Tyr Trp Gly Ile Gly Ser Leu Ala Ser
1               5                   10                  15

Gly Ile Asn Leu Phe Thr Asn Ser Phe Glu Gly Pro Val Leu Asp His
            20                  25                  30

Arg

<210> SEQ ID NO 855
<211> LENGTH: 24
<212> TYPE: PRT
<213> ORGANISM: Homo sapiens

<400> SEQUENCE: 855

Asp Phe Gly Thr His Tyr Ile Thr Glu Ala Val Leu Gly Gly Ile Tyr
1               5                   10                  15

Glu Tyr Thr Leu Val Met Asn Lys
            20
```

<210> SEQ ID NO 856
<211> LENGTH: 12
<212> TYPE: PRT
<213> ORGANISM: Homo sapiens

<400> SEQUENCE: 856

Asp Thr Met Val Glu Asp Leu Val Val Leu Val Arg
1               5                   10

<210> SEQ ID NO 857
<211> LENGTH: 19
<212> TYPE: PRT
<213> ORGANISM: Homo sapiens

<400> SEQUENCE: 857

Glu Val Ser Ser Cys His Cys Ala Pro Cys Gln Gly Asn Gly Val Pro
1               5                   10                  15

Val Leu Lys

<210> SEQ ID NO 858
<211> LENGTH: 17
<212> TYPE: PRT
<213> ORGANISM: Homo sapiens

<400> SEQUENCE: 858

Phe Arg Lys Pro Tyr Asn Val Glu Ser Tyr Thr Pro Gln Thr Gln Gly
1               5                   10                  15

Lys

<210> SEQ ID NO 859
<211> LENGTH: 13
<212> TYPE: PRT
<213> ORGANISM: Homo sapiens

<400> SEQUENCE: 859

Gly Asp Tyr Thr Leu Asn Asn Val His Ala Cys Ala Lys
1               5                   10

<210> SEQ ID NO 860
<211> LENGTH: 9
<212> TYPE: PRT
<213> ORGANISM: Homo sapiens

<400> SEQUENCE: 860

Gly Ile Leu Asn Glu Ile Lys Asp Arg
1               5

<210> SEQ ID NO 861
<211> LENGTH: 18
<212> TYPE: PRT
<213> ORGANISM: Homo sapiens

<400> SEQUENCE: 861

Ile Gly Gly Ala Ile Glu Glu Val Tyr Val Ser Leu Gly Val Ser Val
1               5                   10                  15

Gly Lys

<210> SEQ ID NO 862
<211> LENGTH: 15
<212> TYPE: PRT
<213> ORGANISM: Homo sapiens

<400> SEQUENCE: 862

Ile Pro Gly Ile Phe Glu Leu Gly Ile Ser Ser Gln Ser Asp Arg
1               5                   10                  15

<210> SEQ ID NO 863
<211> LENGTH: 15
<212> TYPE: PRT
<213> ORGANISM: Homo sapiens

<400> SEQUENCE: 863

Lys Pro Tyr Asn Val Glu Ser Tyr Thr Pro Gln Thr Gln Gly Lys
1               5                   10                  15

<210> SEQ ID NO 864
<211> LENGTH: 19
<212> TYPE: PRT
<213> ORGANISM: Homo sapiens

<400> SEQUENCE: 864

Leu Leu Cys Asn Gly Asp Asn Asp Cys Gly Asp Gln Ser Asp Glu Ala
1               5                   10                  15

Asn Cys Arg

<210> SEQ ID NO 865
<211> LENGTH: 11
<212> TYPE: PRT
<213> ORGANISM: Homo sapiens

<400> SEQUENCE: 865

Leu Pro Leu Glu Tyr Ser Tyr Gly Glu Tyr Arg
1               5                   10

<210> SEQ ID NO 866
<211> LENGTH: 8
<212> TYPE: PRT
<213> ORGANISM: Homo sapiens

<400> SEQUENCE: 866

Gln Ala Leu Glu Glu Phe Gln Lys
1               5

<210> SEQ ID NO 867
<211> LENGTH: 27
<212> TYPE: PRT
<213> ORGANISM: Homo sapiens

<400> SEQUENCE: 867

Gln Ala Leu Glu Glu Phe Gln Lys Glu Val Ser Ser Cys His Cys Ala
1               5                   10                  15

Pro Cys Gln Gly Asn Gly Val Pro Val Leu Lys
                20                  25

<210> SEQ ID NO 868
<211> LENGTH: 20
<212> TYPE: PRT
<213> ORGANISM: Homo sapiens

<400> SEQUENCE: 868

Arg Leu Leu Cys Asn Gly Asp Asn Asp Cys Gly Asp Gln Ser Asp Glu
1               5                   10                  15

Ala Asn Cys Arg
                20

<210> SEQ ID NO 869

-continued

```
<211> LENGTH: 12
<212> TYPE: PRT
<213> ORGANISM: Homo sapiens

<400> SEQUENCE: 869

Arg Leu Pro Leu Glu Tyr Ser Tyr Gly Glu Tyr Arg
1               5                   10

<210> SEQ ID NO 870
<211> LENGTH: 9
<212> TYPE: PRT
<213> ORGANISM: Homo sapiens

<400> SEQUENCE: 870

Ser Asp Leu Glu Val Ala His Tyr Lys
1               5

<210> SEQ ID NO 871
<211> LENGTH: 8
<212> TYPE: PRT
<213> ORGANISM: Homo sapiens

<400> SEQUENCE: 871

Ser Gly Phe Ser Phe Gly Phe Lys
1               5

<210> SEQ ID NO 872
<211> LENGTH: 11
<212> TYPE: PRT
<213> ORGANISM: Homo sapiens

<400> SEQUENCE: 872

Ser Leu Met Leu His Tyr Glu Phe Leu Gln Arg
1               5                   10

<210> SEQ ID NO 873
<211> LENGTH: 20
<212> TYPE: PRT
<213> ORGANISM: Homo sapiens

<400> SEQUENCE: 873

Val Glu Pro Leu Tyr Glu Leu Val Thr Ala Thr Asp Phe Ala Tyr Ser
1               5                   10                  15

Ser Thr Val Arg
            20

<210> SEQ ID NO 874
<211> LENGTH: 22
<212> TYPE: PRT
<213> ORGANISM: Homo sapiens

<400> SEQUENCE: 874

Val Lys Val Glu Pro Leu Tyr Glu Leu Val Thr Ala Thr Asp Phe Ala
1               5                   10                  15

Tyr Ser Ser Thr Val Arg
            20

<210> SEQ ID NO 875
<211> LENGTH: 32
<212> TYPE: PRT
<213> ORGANISM: Homo sapiens

<400> SEQUENCE: 875

Tyr Ala Tyr Leu Leu Gln Pro Ser Gln Phe His Gly Glu Pro Cys Asn
1               5                   10                  15
```

Phe Ser Asp Lys Glu Val Glu Asp Cys Val Thr Asn Arg Pro Cys Arg
            20                  25                  30

<210> SEQ ID NO 876
<211> LENGTH: 6
<212> TYPE: PRT
<213> ORGANISM: Homo sapiens

<400> SEQUENCE: 876

Tyr Glu Phe Ile Leu Lys
1               5

<210> SEQ ID NO 877
<211> LENGTH: 15
<212> TYPE: PRT
<213> ORGANISM: Homo sapiens

<400> SEQUENCE: 877

Tyr Tyr Ala Gly Gly Cys Ser Pro His Tyr Ile Leu Asn Thr Arg
1               5                   10                  15

<210> SEQ ID NO 878
<211> LENGTH: 14
<212> TYPE: PRT
<213> ORGANISM: Homo sapiens

<400> SEQUENCE: 878

Ala Thr Leu Gly Pro Ala Val Arg Pro Leu Pro Trp Gln Arg
1               5                   10

<210> SEQ ID NO 879
<211> LENGTH: 24
<212> TYPE: PRT
<213> ORGANISM: Homo sapiens

<400> SEQUENCE: 879

Ala Val Pro His Pro Asp Ser Gln Pro Asp Thr Ile Asp His Asp Leu
1               5                   10                  15

Leu Leu Leu Gln Leu Ser Glu Lys
            20

<210> SEQ ID NO 880
<211> LENGTH: 26
<212> TYPE: PRT
<213> ORGANISM: Homo sapiens

<400> SEQUENCE: 880

Asp Ser Cys Lys Gly Asp Ser Gly Gly Pro Leu Val Cys Gly Gly Val
1               5                   10                  15

Leu Glu Gly Val Val Thr Ser Gly Ser Arg
            20                  25

<210> SEQ ID NO 881
<211> LENGTH: 6
<212> TYPE: PRT
<213> ORGANISM: Homo sapiens

<400> SEQUENCE: 881

Leu Tyr Asp Val Leu Arg
1               5

<210> SEQ ID NO 882
<211> LENGTH: 15
<212> TYPE: PRT

```
<213> ORGANISM: Homo sapiens

<400> SEQUENCE: 882

Arg Pro Asp Ser Leu Gln His Val Leu Leu Pro Val Leu Asp Arg
1               5                   10                  15

<210> SEQ ID NO 883
<211> LENGTH: 24
<212> TYPE: PRT
<213> ORGANISM: Homo sapiens

<400> SEQUENCE: 883

Val Asp Arg Asp Val Ala Pro Gly Thr Leu Cys Asp Val Ala Gly Trp
1               5                   10                  15

Gly Ile Val Asn His Ala Gly Arg
            20

<210> SEQ ID NO 884
<211> LENGTH: 18
<212> TYPE: PRT
<213> ORGANISM: Homo sapiens

<400> SEQUENCE: 884

Val Gln Val Leu Leu Gly Ala His Ser Leu Ser Gln Pro Glu Pro Ser
1               5                   10                  15

Lys Arg

<210> SEQ ID NO 885
<211> LENGTH: 16
<212> TYPE: PRT
<213> ORGANISM: Homo sapiens

<400> SEQUENCE: 885

Ala Ala Gly Asn Glu Cys Pro Glu Leu Gln Pro Pro Val His Gly Lys
1               5                   10                  15

<210> SEQ ID NO 886
<211> LENGTH: 15
<212> TYPE: PRT
<213> ORGANISM: Homo sapiens

<400> SEQUENCE: 886

Thr Gly Val Ile Thr Ser Pro Asp Phe Pro Asn Pro Tyr Pro Lys
1               5                   10                  15

<210> SEQ ID NO 887
<211> LENGTH: 16
<212> TYPE: PRT
<213> ORGANISM: Homo sapiens

<400> SEQUENCE: 887

Tyr Phe Phe Lys Asp Gln Val Leu Val Ser Cys Asp Thr Gly Tyr Lys
1               5                   10                  15

<210> SEQ ID NO 888
<211> LENGTH: 8
<212> TYPE: PRT
<213> ORGANISM: Homo sapiens

<400> SEQUENCE: 888

Ile Thr Gln Asp Ala Gln Leu Lys
1               5

<210> SEQ ID NO 889
```

```
<211> LENGTH: 18
<212> TYPE: PRT
<213> ORGANISM: Homo sapiens

<400> SEQUENCE: 889

Ser Glu Thr Glu Ile His Gln Gly Phe Gln His Leu His Gln Leu Phe
1               5                   10                  15

Ala Lys

<210> SEQ ID NO 890
<211> LENGTH: 16
<212> TYPE: PRT
<213> ORGANISM: Homo sapiens

<400> SEQUENCE: 890

Trp Ser Ala Gly Leu Thr Ser Ser Gln Val Asp Leu Tyr Ile Pro Lys
1               5                   10                  15

<210> SEQ ID NO 891
<211> LENGTH: 6
<212> TYPE: PRT
<213> ORGANISM: Homo sapiens

<400> SEQUENCE: 891

Ala Phe Val Phe Pro Lys
1               5

<210> SEQ ID NO 892
<211> LENGTH: 18
<212> TYPE: PRT
<213> ORGANISM: Homo sapiens

<400> SEQUENCE: 892

Ala Leu Lys Tyr Glu Val Gln Gly Glu Val Phe Thr Lys Pro Gln Leu
1               5                   10                  15

Trp Pro

<210> SEQ ID NO 893
<211> LENGTH: 7
<212> TYPE: PRT
<213> ORGANISM: Homo sapiens

<400> SEQUENCE: 893

Lys Tyr Ala Phe Glu Leu Lys
1               5

<210> SEQ ID NO 894
<211> LENGTH: 6
<212> TYPE: PRT
<213> ORGANISM: Homo sapiens

<400> SEQUENCE: 894

Tyr Ala Phe Glu Leu Lys
1               5

<210> SEQ ID NO 895
<211> LENGTH: 28
<212> TYPE: PRT
<213> ORGANISM: Homo sapiens

<400> SEQUENCE: 895

Ala Cys Pro Ser His Gln Pro Asp Ile Ser Ser Gly Leu Glu Leu Pro
1               5                   10                  15

Phe Pro Pro Gly Val Pro Thr Leu Asp Asn Ile Lys
```

<210> SEQ ID NO 896
<211> LENGTH: 9
<212> TYPE: PRT
<213> ORGANISM: Homo sapiens

<400> SEQUENCE: 896

Phe Cys Glu Ala Glu Phe Ser Val Lys
1               5

<210> SEQ ID NO 897
<211> LENGTH: 16
<212> TYPE: PRT
<213> ORGANISM: Homo sapiens

<400> SEQUENCE: 897

Phe Ser Cys Phe Gln Glu Ala Pro Gln Pro His Tyr Gln Leu Arg
1               5                   10                  15

<210> SEQ ID NO 898
<211> LENGTH: 13
<212> TYPE: PRT
<213> ORGANISM: Homo sapiens

<400> SEQUENCE: 898

His Pro Pro Ser Pro Thr Arg Asp Glu Cys Phe Ala Arg
1               5                   10

<210> SEQ ID NO 899
<211> LENGTH: 22
<212> TYPE: PRT
<213> ORGANISM: Homo sapiens

<400> SEQUENCE: 899

Leu Asp Gly Phe Pro Pro Gly Arg Pro Ser Pro Asp Asn Leu Asn Gln
1               5                   10                  15

Ile Cys Leu Pro Asn Arg
            20

<210> SEQ ID NO 900
<211> LENGTH: 25
<212> TYPE: PRT
<213> ORGANISM: Homo sapiens

<400> SEQUENCE: 900

Leu Leu Pro Ala Gln Leu Pro Ala Glu Lys Glu Val Gly Pro Pro Leu
1               5                   10                  15

Pro Gln Glu Ala Val Pro Leu Gln Lys
            20                  25

<210> SEQ ID NO 901
<211> LENGTH: 9
<212> TYPE: PRT
<213> ORGANISM: Homo sapiens

<400> SEQUENCE: 901

Leu Val Trp Glu Glu Ala Met Ser Arg
1               5

<210> SEQ ID NO 902
<211> LENGTH: 10
<212> TYPE: PRT
<213> ORGANISM: Homo sapiens

```
<400> SEQUENCE: 902

Asn Leu Pro Ala Thr Asp Pro Leu Gln Arg
1               5                   10

<210> SEQ ID NO 903
<211> LENGTH: 14
<212> TYPE: PRT
<213> ORGANISM: Homo sapiens

<400> SEQUENCE: 903

Gln Gly Glu Thr Leu Asn Phe Leu Glu Ile Gly Tyr Ser Arg
1               5                   10

<210> SEQ ID NO 904
<211> LENGTH: 20
<212> TYPE: PRT
<213> ORGANISM: Homo sapiens

<400> SEQUENCE: 904

Gln His Val Val Tyr Gly Pro Trp Asn Leu Pro Gln Ser Ser Tyr Ser
1               5                   10                  15

His Leu Thr Arg
            20

<210> SEQ ID NO 905
<211> LENGTH: 18
<212> TYPE: PRT
<213> ORGANISM: Homo sapiens

<400> SEQUENCE: 905

Arg Ala Pro Tyr Pro Asn Tyr Asp Arg Asp Ile Leu Thr Ile Asp Ile
1               5                   10                  15

Gly Arg

<210> SEQ ID NO 906
<211> LENGTH: 29
<212> TYPE: PRT
<213> ORGANISM: Homo sapiens

<400> SEQUENCE: 906

Arg Asn Ile Trp Arg Asp Pro Ala Leu Cys Cys Tyr Leu Ser Pro Gly
1               5                   10                  15

Asp Glu Gln Val Asn Cys Phe Asn Ile Asn Tyr Leu Arg
                20                  25

<210> SEQ ID NO 907
<211> LENGTH: 14
<212> TYPE: PRT
<213> ORGANISM: Homo sapiens

<400> SEQUENCE: 907

Val Thr Pro Asn Leu Met Gly His Leu Cys Gly Asn Gln Arg
1               5                   10

<210> SEQ ID NO 908
<211> LENGTH: 28
<212> TYPE: PRT
<213> ORGANISM: Homo sapiens

<400> SEQUENCE: 908

Ala Cys Pro Ser His Gln Pro Asp Ile Ser Ser Gly Leu Glu Leu Pro
1               5                   10                  15

Phe Pro Pro Gly Val Pro Thr Leu Asp Asn Ile Lys
```

20          25

<210> SEQ ID NO 909
<211> LENGTH: 9
<212> TYPE: PRT
<213> ORGANISM: Homo sapiens

<400> SEQUENCE: 909

Phe Cys Glu Ala Glu Phe Ser Val Lys
1               5

<210> SEQ ID NO 910
<211> LENGTH: 16
<212> TYPE: PRT
<213> ORGANISM: Homo sapiens

<400> SEQUENCE: 910

Phe Ser Cys Phe Gln Glu Ala Pro Gln Pro His Tyr Gln Leu Arg
1               5                   10                  15

<210> SEQ ID NO 911
<211> LENGTH: 13
<212> TYPE: PRT
<213> ORGANISM: Homo sapiens

<400> SEQUENCE: 911

His Pro Pro Ser Pro Thr Arg Asp Glu Cys Phe Ala Arg
1               5                   10

<210> SEQ ID NO 912
<211> LENGTH: 22
<212> TYPE: PRT
<213> ORGANISM: Homo sapiens

<400> SEQUENCE: 912

Leu Asp Gly Phe Pro Pro Gly Arg Pro Ser Pro Asp Asn Leu Asn Gln
1               5                   10                  15

Ile Cys Leu Pro Asn Arg
            20

<210> SEQ ID NO 913
<211> LENGTH: 25
<212> TYPE: PRT
<213> ORGANISM: Homo sapiens

<400> SEQUENCE: 913

Leu Leu Pro Ala Gln Leu Pro Ala Glu Lys Glu Val Gly Pro Pro Leu
1               5                   10                  15

Pro Gln Glu Ala Val Pro Leu Gln Lys
            20                  25

<210> SEQ ID NO 914
<211> LENGTH: 9
<212> TYPE: PRT
<213> ORGANISM: Homo sapiens

<400> SEQUENCE: 914

Leu Val Trp Glu Glu Ala Met Ser Arg
1               5

<210> SEQ ID NO 915
<211> LENGTH: 10
<212> TYPE: PRT
<213> ORGANISM: Homo sapiens

```
<400> SEQUENCE: 915

Asn Leu Pro Ala Thr Asp Pro Leu Gln Arg
1               5                   10

<210> SEQ ID NO 916
<211> LENGTH: 14
<212> TYPE: PRT
<213> ORGANISM: Homo sapiens

<400> SEQUENCE: 916

Gln Gly Glu Thr Leu Asn Phe Leu Glu Ile Gly Tyr Ser Arg
1               5                   10

<210> SEQ ID NO 917
<211> LENGTH: 20
<212> TYPE: PRT
<213> ORGANISM: Homo sapiens

<400> SEQUENCE: 917

Gln His Val Val Tyr Gly Pro Trp Asn Leu Pro Gln Ser Ser Tyr Ser
1               5                   10                  15

His Leu Thr Arg
            20

<210> SEQ ID NO 918
<211> LENGTH: 18
<212> TYPE: PRT
<213> ORGANISM: Homo sapiens

<400> SEQUENCE: 918

Arg Ala Pro Tyr Pro Asn Tyr Asp Arg Asp Ile Leu Thr Ile Asp Ile
1               5                   10                  15

Gly Arg

<210> SEQ ID NO 919
<211> LENGTH: 29
<212> TYPE: PRT
<213> ORGANISM: Homo sapiens

<400> SEQUENCE: 919

Arg Asn Ile Trp Arg Asp Pro Ala Leu Cys Cys Tyr Leu Ser Pro Gly
1               5                   10                  15

Asp Glu Gln Val Asn Cys Phe Asn Ile Asn Tyr Leu Arg
            20                  25

<210> SEQ ID NO 920
<211> LENGTH: 37
<212> TYPE: PRT
<213> ORGANISM: Homo sapiens

<400> SEQUENCE: 920

Ser Leu Pro Met Asp His Pro Asp Ser Ser Gln His Gly Pro Pro Phe
1               5                   10                  15

Glu Gly Gln Ser Gln Val Gln Pro Pro Ser Gln Glu Ala Thr Pro
            20                  25                  30

Leu Gln Gln Glu Lys
        35

<210> SEQ ID NO 921
<211> LENGTH: 14
<212> TYPE: PRT
<213> ORGANISM: Homo sapiens
```

```
<400> SEQUENCE: 921

Val Thr Pro Asn Leu Met Gly His Leu Cys Gly Asn Gln Arg
1               5                   10

<210> SEQ ID NO 922
<211> LENGTH: 16
<212> TYPE: PRT
<213> ORGANISM: Homo sapiens

<400> SEQUENCE: 922

Met Ser Pro Pro Gln Leu Ala Leu Asn Pro Ser Ala Leu Leu Ser Arg
1               5                   10                  15

<210> SEQ ID NO 923
<211> LENGTH: 10
<212> TYPE: PRT
<213> ORGANISM: Homo sapiens

<400> SEQUENCE: 923

Ala Ile Phe Tyr Met Asn Asn Pro Ser Arg
1               5                   10

<210> SEQ ID NO 924
<211> LENGTH: 18
<212> TYPE: PRT
<213> ORGANISM: Homo sapiens

<400> SEQUENCE: 924

Ala Ser Ser Gln Trp Val Val Gly Pro Ser Tyr Phe Val Glu Tyr Leu
1               5                   10                  15

Ile Lys

<210> SEQ ID NO 925
<211> LENGTH: 6
<212> TYPE: PRT
<213> ORGANISM: Homo sapiens

<400> SEQUENCE: 925

Asp Gly Tyr Val Leu Arg
1               5

<210> SEQ ID NO 926
<211> LENGTH: 11
<212> TYPE: PRT
<213> ORGANISM: Homo sapiens

<400> SEQUENCE: 926

Ile Phe Phe Glu Ser Val Tyr Gly Gln Cys Lys
1               5                   10

<210> SEQ ID NO 927
<211> LENGTH: 31
<212> TYPE: PRT
<213> ORGANISM: Homo sapiens

<400> SEQUENCE: 927

Ile Tyr Met Thr Cys Pro Asp Cys Pro Ser Ser Ile Pro Thr Asp Ser
1               5                   10                  15

Ser Asn His Gln Val Leu Glu Ala Ala Thr Glu Ser Leu Ala Lys
                20                  25                  30

<210> SEQ ID NO 928
<211> LENGTH: 8
<212> TYPE: PRT
```

<213> ORGANISM: Homo sapiens

<400> SEQUENCE: 928

Leu Val Val Leu Pro Phe Pro Lys
1               5

<210> SEQ ID NO 929
<211> LENGTH: 10
<212> TYPE: PRT
<213> ORGANISM: Homo sapiens

<400> SEQUENCE: 929

Leu Val Val Leu Pro Phe Pro Lys Glu Lys
1               5                   10

<210> SEQ ID NO 930
<211> LENGTH: 6
<212> TYPE: PRT
<213> ORGANISM: Homo sapiens

<400> SEQUENCE: 930

Gln Tyr Ser Leu Phe Lys
1               5

<210> SEQ ID NO 931
<211> LENGTH: 23
<212> TYPE: PRT
<213> ORGANISM: Homo sapiens

<400> SEQUENCE: 931

Arg Gly Gly Leu Gly Ser Leu Phe Tyr Leu Thr Leu Asp Val Leu Glu
1               5                   10                  15

Thr Asp Cys His Val Leu Arg
            20

<210> SEQ ID NO 932
<211> LENGTH: 15
<212> TYPE: PRT
<213> ORGANISM: Homo sapiens

<400> SEQUENCE: 932

Ser Pro Pro Gln Leu Ala Leu Asn Pro Ser Ala Leu Leu Ser Arg
1               5                   10                  15

<210> SEQ ID NO 933
<211> LENGTH: 18
<212> TYPE: PRT
<213> ORGANISM: Homo sapiens

<400> SEQUENCE: 933

Thr Ala Glu Cys Pro Gly Pro Ala Gln Asn Ala Ser Pro Leu Val Leu
1               5                   10                  15

Pro Pro

<210> SEQ ID NO 934
<211> LENGTH: 13
<212> TYPE: PRT
<213> ORGANISM: Homo sapiens

<400> SEQUENCE: 934

Ala Gly Ala Leu Asn Ser Asn Asp Ala Phe Val Leu Lys
1               5                   10

<210> SEQ ID NO 935

```
<211> LENGTH: 7
<212> TYPE: PRT
<213> ORGANISM: Homo sapiens

<400> SEQUENCE: 935

Thr Pro Ile Thr Val Val Lys
1               5

<210> SEQ ID NO 936
<211> LENGTH: 18
<212> TYPE: PRT
<213> ORGANISM: Homo sapiens

<400> SEQUENCE: 936

Thr Pro Ser Ala Ala Tyr Leu Trp Val Gly Thr Gly Ala Ser Glu Ala
1               5                   10                  15

Glu Lys

<210> SEQ ID NO 937
<211> LENGTH: 9
<212> TYPE: PRT
<213> ORGANISM: Homo sapiens

<400> SEQUENCE: 937

Tyr Ile Glu Thr Asp Pro Ala Asn Arg
1               5

<210> SEQ ID NO 938
<211> LENGTH: 13
<212> TYPE: PRT
<213> ORGANISM: Homo sapiens

<400> SEQUENCE: 938

Ala Gly Ala Leu Asn Ser Asn Asp Ala Phe Val Leu Lys
1               5                   10

<210> SEQ ID NO 939
<211> LENGTH: 7
<212> TYPE: PRT
<213> ORGANISM: Homo sapiens

<400> SEQUENCE: 939

Ala Val Glu Val Leu Pro Lys
1               5

<210> SEQ ID NO 940
<211> LENGTH: 18
<212> TYPE: PRT
<213> ORGANISM: Homo sapiens

<400> SEQUENCE: 940

Glu Pro Ala His Leu Met Ser Leu Phe Gly Gly Lys Pro Met Ile Ile
1               5                   10                  15

Tyr Lys

<210> SEQ ID NO 941
<211> LENGTH: 27
<212> TYPE: PRT
<213> ORGANISM: Homo sapiens

<400> SEQUENCE: 941

Met Leu Gln Val Leu Gly Pro Lys Pro Ala Leu Pro Ala Gly Thr Glu
1               5                   10                  15

Asp Thr Ala Lys Glu Asp Ala Ala Asn Arg Lys
```

20                  25

<210> SEQ ID NO 942
<211> LENGTH: 25
<212> TYPE: PRT
<213> ORGANISM: Homo sapiens

<400> SEQUENCE: 942

Asn Trp Arg Asp Pro Asp Gln Thr Asp Gly Leu Gly Leu Ser Tyr Leu
1               5                   10                  15

Ser Ser His Ile Ala Asn Val Glu Arg
            20                  25

<210> SEQ ID NO 943
<211> LENGTH: 17
<212> TYPE: PRT
<213> ORGANISM: Homo sapiens

<400> SEQUENCE: 943

Gln Thr Gln Val Ser Val Leu Pro Glu Gly Gly Glu Thr Pro Leu Phe
1               5                   10                  15

Lys

<210> SEQ ID NO 944
<211> LENGTH: 14
<212> TYPE: PRT
<213> ORGANISM: Homo sapiens

<400> SEQUENCE: 944

Ser Glu Asp Cys Phe Ile Leu Asp His Gly Lys Asp Gly Lys
1               5                   10

<210> SEQ ID NO 945
<211> LENGTH: 8
<212> TYPE: PRT
<213> ORGANISM: Homo sapiens

<400> SEQUENCE: 945

Thr Ala Ser Asp Phe Ile Thr Lys
1               5

<210> SEQ ID NO 946
<211> LENGTH: 18
<212> TYPE: PRT
<213> ORGANISM: Homo sapiens

<400> SEQUENCE: 946

Thr Pro Ser Ala Ala Tyr Leu Trp Val Gly Thr Gly Ala Ser Glu Ala
1               5                   10                  15

Glu Lys

<210> SEQ ID NO 947
<211> LENGTH: 28
<212> TYPE: PRT
<213> ORGANISM: Homo sapiens

<400> SEQUENCE: 947

Val Pro Phe Asp Ala Ala Thr Leu His Thr Ser Thr Ala Met Ala Ala
1               5                   10                  15

Gln His Gly Met Asp Asp Asp Gly Thr Gly Gln Lys
            20                  25

<210> SEQ ID NO 948

```
<211> LENGTH: 23
<212> TYPE: PRT
<213> ORGANISM: Homo sapiens

<400> SEQUENCE: 948

Val Val Gln Gly Lys Glu Pro Ala His Leu Met Ser Leu Phe Gly Gly
1               5                   10                  15

Lys Pro Met Ile Ile Tyr Lys
            20

<210> SEQ ID NO 949
<211> LENGTH: 13
<212> TYPE: PRT
<213> ORGANISM: Homo sapiens

<400> SEQUENCE: 949

Ala Gly Ala Leu Asn Ser Asn Asp Ala Phe Val Leu Lys
1               5                   10

<210> SEQ ID NO 950
<211> LENGTH: 16
<212> TYPE: PRT
<213> ORGANISM: Homo sapiens

<400> SEQUENCE: 950

Asp Ser Gln Glu Glu Lys Thr Glu Ala Leu Thr Ser Ala Lys Arg
1               5                   10                  15

<210> SEQ ID NO 951
<211> LENGTH: 7
<212> TYPE: PRT
<213> ORGANISM: Homo sapiens

<400> SEQUENCE: 951

Thr Pro Ile Thr Val Val Lys
1               5

<210> SEQ ID NO 952
<211> LENGTH: 18
<212> TYPE: PRT
<213> ORGANISM: Homo sapiens

<400> SEQUENCE: 952

Thr Pro Ser Ala Ala Tyr Leu Trp Val Gly Thr Gly Ala Ser Glu Ala
1               5                   10                  15

Glu Lys

<210> SEQ ID NO 953
<211> LENGTH: 9
<212> TYPE: PRT
<213> ORGANISM: Homo sapiens

<400> SEQUENCE: 953

Tyr Ile Glu Thr Asp Pro Ala Asn Arg
1               5

<210> SEQ ID NO 954
<211> LENGTH: 21
<212> TYPE: PRT
<213> ORGANISM: Homo sapiens

<400> SEQUENCE: 954

Val Ile Ile Ser Ala Pro Ser Ala Asp Ala Pro Met Phe Val Met Gly
1               5                   10                  15
```

Val Asn His Glu Lys
        20

<210> SEQ ID NO 955
<211> LENGTH: 27
<212> TYPE: PRT
<213> ORGANISM: Homo sapiens

<400> SEQUENCE: 955

Val Ile Ile Ser Ala Pro Ser Ala Asp Ala Pro Met Phe Val Met Gly
1               5                   10                  15

Val Asn His Glu Lys Tyr Asp Asn Ser Leu Lys
        20                  25

<210> SEQ ID NO 956
<211> LENGTH: 21
<212> TYPE: PRT
<213> ORGANISM: Homo sapiens

<400> SEQUENCE: 956

Val Ile Ile Ser Ala Pro Ser Ala Asp Ala Pro Met Phe Val Met Gly
1               5                   10                  15

Val Asn His Glu Lys
        20

<210> SEQ ID NO 957
<211> LENGTH: 27
<212> TYPE: PRT
<213> ORGANISM: Homo sapiens

<400> SEQUENCE: 957

Val Ile Ile Ser Ala Pro Ser Ala Asp Ala Pro Met Phe Val Met Gly
1               5                   10                  15

Val Asn His Glu Lys Tyr Asp Asn Ser Leu Lys
        20                  25

<210> SEQ ID NO 958
<211> LENGTH: 16
<212> TYPE: PRT
<213> ORGANISM: Homo sapiens

<400> SEQUENCE: 958

Met Ser Pro Pro Gln Leu Ala Leu Asn Pro Ser Ala Leu Leu Ser Arg
1               5                   10                  15

<210> SEQ ID NO 959
<211> LENGTH: 10
<212> TYPE: PRT
<213> ORGANISM: Homo sapiens

<400> SEQUENCE: 959

Ala Ile Phe Tyr Met Asn Asn Pro Ser Arg
1               5                   10

<210> SEQ ID NO 960
<211> LENGTH: 18
<212> TYPE: PRT
<213> ORGANISM: Homo sapiens

<400> SEQUENCE: 960

Ala Ser Ser Gln Trp Val Val Gly Pro Ser Tyr Phe Val Glu Tyr Leu
1               5                   10                  15

Ile Lys

<210> SEQ ID NO 961
<211> LENGTH: 6
<212> TYPE: PRT
<213> ORGANISM: Homo sapiens

<400> SEQUENCE: 961

Asp Gly Tyr Val Leu Arg
1               5

<210> SEQ ID NO 962
<211> LENGTH: 31
<212> TYPE: PRT
<213> ORGANISM: Homo sapiens

<400> SEQUENCE: 962

Ile Tyr Met Thr Cys Pro Asp Cys Pro Ser Ser Ile Pro Thr Asp Ser
1               5                   10                  15

Ser Asn His Gln Val Leu Glu Ala Ala Thr Glu Ser Leu Ala Lys
            20                  25                  30

<210> SEQ ID NO 963
<211> LENGTH: 8
<212> TYPE: PRT
<213> ORGANISM: Homo sapiens

<400> SEQUENCE: 963

Leu Val Val Leu Pro Phe Pro Lys
1               5

<210> SEQ ID NO 964
<211> LENGTH: 10
<212> TYPE: PRT
<213> ORGANISM: Homo sapiens

<400> SEQUENCE: 964

Leu Val Val Leu Pro Phe Pro Lys Glu Lys
1               5                   10

<210> SEQ ID NO 965
<211> LENGTH: 6
<212> TYPE: PRT
<213> ORGANISM: Homo sapiens

<400> SEQUENCE: 965

Gln Tyr Ser Leu Phe Lys
1               5

<210> SEQ ID NO 966
<211> LENGTH: 15
<212> TYPE: PRT
<213> ORGANISM: Homo sapiens

<400> SEQUENCE: 966

Ser Pro Pro Gln Leu Ala Leu Asn Pro Ser Ala Leu Leu Ser Arg
1               5                   10                  15

<210> SEQ ID NO 967
<211> LENGTH: 18
<212> TYPE: PRT
<213> ORGANISM: Homo sapiens

<400> SEQUENCE: 967

Thr Ala Glu Cys Pro Gly Pro Ala Gln Asn Ala Ser Pro Leu Val Leu
1               5                   10                  15

Pro Pro

<210> SEQ ID NO 968
<211> LENGTH: 16
<212> TYPE: PRT
<213> ORGANISM: Homo sapiens

<400> SEQUENCE: 968

Met Ser Pro Pro Gln Leu Ala Leu Asn Pro Ser Ala Leu Leu Ser Arg
1               5                   10                  15

<210> SEQ ID NO 969
<211> LENGTH: 18
<212> TYPE: PRT
<213> ORGANISM: Homo sapiens

<400> SEQUENCE: 969

Ala Ser Ser Gln Trp Val Val Gly Pro Ser Tyr Phe Val Glu Tyr Leu
1               5                   10                  15

Ile Lys

<210> SEQ ID NO 970
<211> LENGTH: 6
<212> TYPE: PRT
<213> ORGANISM: Homo sapiens

<400> SEQUENCE: 970

Asp Gly Tyr Val Leu Arg
1               5

<210> SEQ ID NO 971
<211> LENGTH: 31
<212> TYPE: PRT
<213> ORGANISM: Homo sapiens

<400> SEQUENCE: 971

Ile Tyr Met Thr Cys Pro Asp Cys Pro Ser Ser Ile Pro Thr Asp Ser
1               5                   10                  15

Ser Asn His Gln Val Leu Glu Ala Ala Thr Glu Ser Leu Ala Lys
            20                  25                  30

<210> SEQ ID NO 972
<211> LENGTH: 8
<212> TYPE: PRT
<213> ORGANISM: Homo sapiens

<400> SEQUENCE: 972

Leu Val Val Leu Pro Phe Pro Lys
1               5

<210> SEQ ID NO 973
<211> LENGTH: 10
<212> TYPE: PRT
<213> ORGANISM: Homo sapiens

<400> SEQUENCE: 973

Leu Val Val Leu Pro Phe Pro Lys Glu Lys
1               5                   10

<210> SEQ ID NO 974
<211> LENGTH: 6
<212> TYPE: PRT
<213> ORGANISM: Homo sapiens

<400> SEQUENCE: 974

```
Gln Tyr Ser Leu Phe Lys
1               5
```

```
<210> SEQ ID NO 975
<211> LENGTH: 15
<212> TYPE: PRT
<213> ORGANISM: Homo sapiens

<400> SEQUENCE: 975

Ser Pro Pro Gln Leu Ala Leu Asn Pro Ser Ala Leu Leu Ser Arg
1               5                   10                  15
```

```
<210> SEQ ID NO 976
<211> LENGTH: 18
<212> TYPE: PRT
<213> ORGANISM: Homo sapiens

<400> SEQUENCE: 976

Thr Ala Glu Cys Pro Gly Pro Ala Gln Asn Ala Ser Pro Leu Val Leu
1               5                   10                  15

Pro Pro
```

```
<210> SEQ ID NO 977
<211> LENGTH: 15
<212> TYPE: PRT
<213> ORGANISM: Homo sapiens

<400> SEQUENCE: 977

Phe Thr Val Asp Arg Pro Phe Leu Phe Leu Ile Tyr Glu His Arg
1               5                   10                  15
```

```
<210> SEQ ID NO 978
<211> LENGTH: 18
<212> TYPE: PRT
<213> ORGANISM: Homo sapiens

<400> SEQUENCE: 978

Gly Ser Trp Val Asn Lys Phe Pro Val Glu Met Thr His Asn His Asn
1               5                   10                  15

Phe Arg
```

```
<210> SEQ ID NO 979
<211> LENGTH: 15
<212> TYPE: PRT
<213> ORGANISM: Homo sapiens

<400> SEQUENCE: 979

Leu Phe Asp Lys Asn Gly Asn Met Ala Gly Ile Ser Asp Gln Arg
1               5                   10                  15
```

```
<210> SEQ ID NO 980
<211> LENGTH: 7
<212> TYPE: PRT
<213> ORGANISM: Homo sapiens

<400> SEQUENCE: 980

Asn Phe Gly Tyr Thr Leu Arg
1               5
```

```
<210> SEQ ID NO 981
<211> LENGTH: 9
<212> TYPE: PRT
<213> ORGANISM: Homo sapiens
```

```
<400> SEQUENCE: 981

Ser Val Asn Asp Leu Tyr Ile Gln Lys
1               5

<210> SEQ ID NO 982
<211> LENGTH: 13
<212> TYPE: PRT
<213> ORGANISM: Homo sapiens

<400> SEQUENCE: 982

Thr Arg Glu Val Leu Leu Pro Lys Phe Lys Leu Glu Lys
1               5                   10

<210> SEQ ID NO 983
<211> LENGTH: 11
<212> TYPE: PRT
<213> ORGANISM: Homo sapiens

<400> SEQUENCE: 983

Glu Ala Leu Val Pro Leu Val Ala Asp His Lys
1               5                   10

<210> SEQ ID NO 984
<211> LENGTH: 21
<212> TYPE: PRT
<213> ORGANISM: Homo sapiens

<400> SEQUENCE: 984

Ser Gln Phe Val Gln Pro Ile Cys Leu Pro Glu Pro Gly Ser Thr Phe
1               5                   10                  15

Pro Ala Gly His Lys
            20

<210> SEQ ID NO 985
<211> LENGTH: 12
<212> TYPE: PRT
<213> ORGANISM: Homo sapiens

<400> SEQUENCE: 985

Thr Thr Asp Val Thr Gln Thr Phe Gly Ile Glu Lys
1               5                   10

<210> SEQ ID NO 986
<211> LENGTH: 21
<212> TYPE: PRT
<213> ORGANISM: Homo sapiens

<400> SEQUENCE: 986

Tyr Ile Pro Tyr Thr Leu Tyr Ser Val Phe Asn Pro Ser Asp His Asp
1               5                   10                  15

Leu Val Leu Ile Arg
            20

<210> SEQ ID NO 987
<211> LENGTH: 8
<212> TYPE: PRT
<213> ORGANISM: Homo sapiens

<400> SEQUENCE: 987

Ala Ala Phe Cys Tyr Gln Ile Arg
1               5

<210> SEQ ID NO 988
<211> LENGTH: 29
```

-continued

<212> TYPE: PRT
<213> ORGANISM: Homo sapiens

<400> SEQUENCE: 988

Gly Thr Glu Leu Gln His Leu Leu His Ala Val Val Pro Gly Pro Trp
1               5                   10                  15

Gln Glu Asp Val Ala Asp Ala Glu Glu Cys Ala Gly Arg
            20                  25

<210> SEQ ID NO 989
<211> LENGTH: 11
<212> TYPE: PRT
<213> ORGANISM: Homo sapiens

<400> SEQUENCE: 989

Thr Cys Ile Met Asn Asn Gly Val Gly Tyr Arg
1               5                   10

<210> SEQ ID NO 990
<211> LENGTH: 16
<212> TYPE: PRT
<213> ORGANISM: Homo sapiens

<400> SEQUENCE: 990

Val Val Gly Gly His Pro Gly Asn Ser Pro Trp Thr Val Ser Leu Arg
1               5                   10                  15

<210> SEQ ID NO 991
<211> LENGTH: 16
<212> TYPE: PRT
<213> ORGANISM: Homo sapiens

<400> SEQUENCE: 991

Ser Gly Phe Pro Gln Val Ser Met Phe Phe Thr His Thr Phe Pro Lys
1               5                   10                  15

<210> SEQ ID NO 992
<211> LENGTH: 16
<212> TYPE: PRT
<213> ORGANISM: Homo sapiens

<400> SEQUENCE: 992

Ala Asp Leu Phe Tyr Asp Val Glu Ala Leu Asp Leu Glu Ser Pro Lys
1               5                   10                  15

<210> SEQ ID NO 993
<211> LENGTH: 9
<212> TYPE: PRT
<213> ORGANISM: Homo sapiens

<400> SEQUENCE: 993

Asp Gly Tyr Leu Phe Gln Leu Leu Arg
1               5

<210> SEQ ID NO 994
<211> LENGTH: 14
<212> TYPE: PRT
<213> ORGANISM: Homo sapiens

<400> SEQUENCE: 994

Asp Ser Pro Val Leu Ile Asp Phe Phe Glu Asp Thr Glu Arg
1               5                   10

<210> SEQ ID NO 995
<211> LENGTH: 16

```
<212> TYPE: PRT
<213> ORGANISM: Homo sapiens

<400> SEQUENCE: 995

Asp Ser Pro Val Leu Ile Asp Phe Phe Glu Asp Thr Glu Arg Tyr Arg
1               5                   10                  15

<210> SEQ ID NO 996
<211> LENGTH: 20
<212> TYPE: PRT
<213> ORGANISM: Homo sapiens

<400> SEQUENCE: 996

Gly Glu Val Leu Pro Leu Pro Glu Ala Asn Phe Pro Ser Phe Pro Leu
1               5                   10                  15

Pro His His Lys
            20

<210> SEQ ID NO 997
<211> LENGTH: 14
<212> TYPE: PRT
<213> ORGANISM: Homo sapiens

<400> SEQUENCE: 997

Gly Gly Glu Gly Thr Gly Tyr Phe Val Asp Phe Ser Val Arg
1               5                   10

<210> SEQ ID NO 998
<211> LENGTH: 9
<212> TYPE: PRT
<213> ORGANISM: Homo sapiens

<400> SEQUENCE: 998

His Pro Asn Val Phe Gly Phe Cys Arg
1               5

<210> SEQ ID NO 999
<211> LENGTH: 9
<212> TYPE: PRT
<213> ORGANISM: Homo sapiens

<400> SEQUENCE: 999

His Ser His Glu Ser Gln Asp Leu Arg
1               5

<210> SEQ ID NO 1000
<211> LENGTH: 21
<212> TYPE: PRT
<213> ORGANISM: Homo sapiens

<400> SEQUENCE: 1000

Lys Gly Glu Val Leu Pro Leu Pro Glu Ala Asn Phe Pro Ser Phe Pro
1               5                   10                  15

Leu Pro His His Lys
            20

<210> SEQ ID NO 1001
<211> LENGTH: 12
<212> TYPE: PRT
<213> ORGANISM: Homo sapiens

<400> SEQUENCE: 1001

Lys Tyr Trp Asn Asp Cys Glu Pro Pro Asp Ser Arg
1               5                   10
```

```
<210> SEQ ID NO 1002
<211> LENGTH: 10
<212> TYPE: PRT
<213> ORGANISM: Homo sapiens

<400> SEQUENCE: 1002

Arg Asp Gly Tyr Leu Phe Gln Leu Leu Arg
1               5                   10

<210> SEQ ID NO 1003
<211> LENGTH: 11
<212> TYPE: PRT
<213> ORGANISM: Homo sapiens

<400> SEQUENCE: 1003

Arg Pro Ser Glu Ile Val Ile Gly Gln Cys Lys
1               5                   10

<210> SEQ ID NO 1004
<211> LENGTH: 14
<212> TYPE: PRT
<213> ORGANISM: Homo sapiens

<400> SEQUENCE: 1004

Ser Ser Thr Thr Lys Pro Pro Phe Lys Pro His Gly Ser Arg
1               5                   10

<210> SEQ ID NO 1005
<211> LENGTH: 16
<212> TYPE: PRT
<213> ORGANISM: Homo sapiens

<400> SEQUENCE: 1005

Val Arg Gly Gly Glu Gly Thr Gly Tyr Phe Val Asp Phe Ser Val Arg
1               5                   10                  15

<210> SEQ ID NO 1006
<211> LENGTH: 23
<212> TYPE: PRT
<213> ORGANISM: Homo sapiens

<400> SEQUENCE: 1006

Val Ser Pro Thr Asp Cys Ser Ala Val Glu Pro Glu Ala Glu Lys Ala
1               5                   10                  15

Leu Asp Leu Ile Asn Lys Arg
            20

<210> SEQ ID NO 1007
<211> LENGTH: 12
<212> TYPE: PRT
<213> ORGANISM: Homo sapiens

<400> SEQUENCE: 1007

Tyr Lys Glu Glu Asn Asp Asp Phe Ala Ser Phe Arg
1               5                   10

<210> SEQ ID NO 1008
<211> LENGTH: 15
<212> TYPE: PRT
<213> ORGANISM: Homo sapiens

<400> SEQUENCE: 1008

Tyr Lys Glu Glu Asn Asp Asp Phe Ala Ser Phe Arg Val Asp Arg
1               5                   10                  15
```

```
<210> SEQ ID NO 1009
<211> LENGTH: 15
<212> TYPE: PRT
<213> ORGANISM: Homo sapiens

<400> SEQUENCE: 1009

Phe Thr Cys Thr Val Thr His Thr Asp Leu Pro Ser Pro Leu Lys
1               5                   10                  15

<210> SEQ ID NO 1010
<211> LENGTH: 11
<212> TYPE: PRT
<213> ORGANISM: Homo sapiens

<400> SEQUENCE: 1010

Leu Ile Cys Gln Ala Thr Gly Phe Ser Pro Arg
1               5                   10

<210> SEQ ID NO 1011
<211> LENGTH: 15
<212> TYPE: PRT
<213> ORGANISM: Homo sapiens

<400> SEQUENCE: 1011

Val Phe Ala Ile Pro Pro Ser Phe Ala Ser Ile Phe Leu Thr Lys
1               5                   10                  15

<210> SEQ ID NO 1012
<211> LENGTH: 15
<212> TYPE: PRT
<213> ORGANISM: Homo sapiens

<400> SEQUENCE: 1012

Tyr Val Thr Ser Ala Pro Met Pro Glu Pro Gln Ala Pro Gly Arg
1               5                   10                  15

<210> SEQ ID NO 1013
<211> LENGTH: 15
<212> TYPE: PRT
<213> ORGANISM: Homo sapiens

<400> SEQUENCE: 1013

Phe Thr Cys Thr Val Thr His Thr Asp Leu Pro Ser Pro Leu Lys
1               5                   10                  15

<210> SEQ ID NO 1014
<211> LENGTH: 11
<212> TYPE: PRT
<213> ORGANISM: Homo sapiens

<400> SEQUENCE: 1014

Leu Ile Cys Gln Ala Thr Gly Phe Ser Pro Arg
1               5                   10

<210> SEQ ID NO 1015
<211> LENGTH: 15
<212> TYPE: PRT
<213> ORGANISM: Homo sapiens

<400> SEQUENCE: 1015

Phe Thr Cys Thr Val Thr His Thr Asp Leu Pro Ser Pro Leu Lys
1               5                   10                  15

<210> SEQ ID NO 1016
<211> LENGTH: 11
```

```
<212> TYPE: PRT
<213> ORGANISM: Homo sapiens

<400> SEQUENCE: 1016

Leu Ile Cys Gln Ala Thr Gly Phe Ser Pro Arg
1               5                   10

<210> SEQ ID NO 1017
<211> LENGTH: 15
<212> TYPE: PRT
<213> ORGANISM: Homo sapiens

<400> SEQUENCE: 1017

Phe Thr Cys Thr Val Thr His Thr Asp Leu Pro Ser Pro Leu Lys
1               5                   10                  15

<210> SEQ ID NO 1018
<211> LENGTH: 11
<212> TYPE: PRT
<213> ORGANISM: Homo sapiens

<400> SEQUENCE: 1018

Leu Ile Cys Gln Ala Thr Gly Phe Ser Pro Arg
1               5                   10

<210> SEQ ID NO 1019
<211> LENGTH: 15
<212> TYPE: PRT
<213> ORGANISM: Homo sapiens

<400> SEQUENCE: 1019

Phe Thr Cys Thr Val Thr His Thr Asp Leu Pro Ser Pro Leu Lys
1               5                   10                  15

<210> SEQ ID NO 1020
<211> LENGTH: 11
<212> TYPE: PRT
<213> ORGANISM: Homo sapiens

<400> SEQUENCE: 1020

Leu Ile Cys Gln Ala Thr Gly Phe Ser Pro Arg
1               5                   10

<210> SEQ ID NO 1021
<211> LENGTH: 15
<212> TYPE: PRT
<213> ORGANISM: Homo sapiens

<400> SEQUENCE: 1021

Phe Thr Cys Thr Val Thr His Thr Asp Leu Pro Ser Pro Leu Lys
1               5                   10                  15

<210> SEQ ID NO 1022
<211> LENGTH: 11
<212> TYPE: PRT
<213> ORGANISM: Homo sapiens

<400> SEQUENCE: 1022

Leu Ile Cys Gln Ala Thr Gly Phe Ser Pro Arg
1               5                   10

<210> SEQ ID NO 1023
<211> LENGTH: 15
<212> TYPE: PRT
<213> ORGANISM: Homo sapiens
```

```
<400> SEQUENCE: 1023

Phe Thr Cys Thr Val Thr His Thr Asp Leu Pro Ser Pro Leu Lys
 1               5                  10                  15

<210> SEQ ID NO 1024
<211> LENGTH: 11
<212> TYPE: PRT
<213> ORGANISM: Homo sapiens

<400> SEQUENCE: 1024

Leu Ile Cys Gln Ala Thr Gly Phe Ser Pro Arg
 1               5                  10

<210> SEQ ID NO 1025
<211> LENGTH: 15
<212> TYPE: PRT
<213> ORGANISM: Homo sapiens

<400> SEQUENCE: 1025

Phe Thr Cys Thr Val Thr His Thr Asp Leu Pro Ser Pro Leu Lys
 1               5                  10                  15

<210> SEQ ID NO 1026
<211> LENGTH: 11
<212> TYPE: PRT
<213> ORGANISM: Homo sapiens

<400> SEQUENCE: 1026

Leu Ile Cys Gln Ala Thr Gly Phe Ser Pro Arg
 1               5                  10

<210> SEQ ID NO 1027
<211> LENGTH: 15
<212> TYPE: PRT
<213> ORGANISM: Homo sapiens

<400> SEQUENCE: 1027

Phe Thr Cys Thr Val Thr His Thr Asp Leu Pro Ser Pro Leu Lys
 1               5                  10                  15

<210> SEQ ID NO 1028
<211> LENGTH: 11
<212> TYPE: PRT
<213> ORGANISM: Homo sapiens

<400> SEQUENCE: 1028

Leu Ile Cys Gln Ala Thr Gly Phe Ser Pro Arg
 1               5                  10

<210> SEQ ID NO 1029
<211> LENGTH: 15
<212> TYPE: PRT
<213> ORGANISM: Homo sapiens

<400> SEQUENCE: 1029

Phe Thr Cys Thr Val Thr His Thr Asp Leu Pro Ser Pro Leu Lys
 1               5                  10                  15

<210> SEQ ID NO 1030
<211> LENGTH: 11
<212> TYPE: PRT
<213> ORGANISM: Homo sapiens

<400> SEQUENCE: 1030

Leu Ile Cys Gln Ala Thr Gly Phe Ser Pro Arg
```

```
1               5                   10

<210> SEQ ID NO 1031
<211> LENGTH: 28
<212> TYPE: PRT
<213> ORGANISM: Homo sapiens

<400> SEQUENCE: 1031

Gly Met Ala Asp Gln Asp Gly Leu Lys Pro Thr Ile Asp Lys Pro Ser
1               5                   10                  15

Glu Asp Ser Pro Pro Leu Glu Met Leu Gly Pro Arg
            20                  25

<210> SEQ ID NO 1032
<211> LENGTH: 25
<212> TYPE: PRT
<213> ORGANISM: Homo sapiens

<400> SEQUENCE: 1032

Ala Asp Val Gln Ala His Gly Glu Gly Gln Glu Phe Ser Ile Thr Cys
1               5                   10                  15

Leu Val Asp Glu Glu Glu Met Lys Lys
            20                  25

<210> SEQ ID NO 1033
<211> LENGTH: 12
<212> TYPE: PRT
<213> ORGANISM: Homo sapiens

<400> SEQUENCE: 1033

Glu Arg Gly His Met Leu Glu Asn His Val Glu Arg
1               5                   10

<210> SEQ ID NO 1034
<211> LENGTH: 19
<212> TYPE: PRT
<213> ORGANISM: Homo sapiens

<400> SEQUENCE: 1034

Ile Leu Gly Asp Met Gln Pro Gly Asp Tyr Phe Asp Leu Val Leu Phe
1               5                   10                  15

Gly Thr Arg

<210> SEQ ID NO 1035
<211> LENGTH: 17
<212> TYPE: PRT
<213> ORGANISM: Homo sapiens

<400> SEQUENCE: 1035

Met Ser Leu Asp Tyr Gly Phe Val Thr Pro Leu Thr Ser Met Ser Ile
1               5                   10                  15

Arg

<210> SEQ ID NO 1036
<211> LENGTH: 10
<212> TYPE: PRT
<213> ORGANISM: Homo sapiens

<400> SEQUENCE: 1036

Asn His Met Gln Tyr Glu Ile Val Ile Lys
1               5                   10

<210> SEQ ID NO 1037
```

```
<211> LENGTH: 16
<212> TYPE: PRT
<213> ORGANISM: Homo sapiens

<400> SEQUENCE: 1037

Thr Met Glu Gln Phe Thr Ile His Leu Thr Val Asn Pro Gln Ser Lys
1               5                   10                  15

<210> SEQ ID NO 1038
<211> LENGTH: 24
<212> TYPE: PRT
<213> ORGANISM: Homo sapiens

<400> SEQUENCE: 1038

Ala Asp Val Gln Ala His Gly Glu Gly Gln Glu Phe Ser Ile Thr Cys
1               5                   10                  15

Leu Val Asp Glu Glu Glu Met Lys
            20

<210> SEQ ID NO 1039
<211> LENGTH: 7
<212> TYPE: PRT
<213> ORGANISM: Homo sapiens

<400> SEQUENCE: 1039

Asp Lys Val Thr Ala Trp Lys
1               5

<210> SEQ ID NO 1040
<211> LENGTH: 9
<212> TYPE: PRT
<213> ORGANISM: Homo sapiens

<400> SEQUENCE: 1040

Glu Leu Ala Ala Gln Thr Ile Lys Lys
1               5

<210> SEQ ID NO 1041
<211> LENGTH: 10
<212> TYPE: PRT
<213> ORGANISM: Homo sapiens

<400> SEQUENCE: 1041

Glu Val Ala Phe Asp Leu Glu Ile Pro Lys
1               5                   10

<210> SEQ ID NO 1042
<211> LENGTH: 16
<212> TYPE: PRT
<213> ORGANISM: Homo sapiens

<400> SEQUENCE: 1042

Gly Phe Ser Leu Asp Glu Ala Thr Asn Leu Asn Gly Gly Leu Leu Arg
1               5                   10                  15

<210> SEQ ID NO 1043
<211> LENGTH: 10
<212> TYPE: PRT
<213> ORGANISM: Homo sapiens

<400> SEQUENCE: 1043

Gly His Met Leu Glu Asn His Val Glu Arg
1               5                   10

<210> SEQ ID NO 1044
```

```
<211> LENGTH: 28
<212> TYPE: PRT
<213> ORGANISM: Homo sapiens

<400> SEQUENCE: 1044

Gly His Val Leu Phe Arg Pro Thr Val Ser Gln Gln Gln Ser Cys Pro
1               5                   10                  15

Thr Cys Ser Thr Ser Leu Leu Asn Gly His Phe Lys
            20                  25

<210> SEQ ID NO 1045
<211> LENGTH: 37
<212> TYPE: PRT
<213> ORGANISM: Homo sapiens

<400> SEQUENCE: 1045

Gly Ile Glu Ile Leu Asn Gln Val Gln Glu Ser Leu Pro Glu Leu Ser
1               5                   10                  15

Asn His Ala Ser Ile Leu Ile Met Leu Thr Asp Gly Asp Pro Thr Glu
            20                  25                  30

Gly Val Thr Asp Arg
        35

<210> SEQ ID NO 1046
<211> LENGTH: 29
<212> TYPE: PRT
<213> ORGANISM: Homo sapiens

<400> SEQUENCE: 1046

Gly Arg Phe Pro Leu Tyr Asn Leu Gly Phe Gly His Asn Val Asp Phe
1               5                   10                  15

Asn Phe Leu Glu Val Met Ser Met Glu Asn Asn Gly Arg
            20                  25

<210> SEQ ID NO 1047
<211> LENGTH: 19
<212> TYPE: PRT
<213> ORGANISM: Homo sapiens

<400> SEQUENCE: 1047

Gly Ser Leu Val Gln Ala Ser Glu Ala Asn Leu Gln Ala Ala Gln Asp
1               5                   10                  15

Phe Val Arg

<210> SEQ ID NO 1048
<211> LENGTH: 10
<212> TYPE: PRT
<213> ORGANISM: Homo sapiens

<400> SEQUENCE: 1048

Ile Ala Asp Asn Lys Gln Ser Ser Phe Lys
1               5                   10

<210> SEQ ID NO 1049
<211> LENGTH: 20
<212> TYPE: PRT
<213> ORGANISM: Homo sapiens

<400> SEQUENCE: 1049

Ile Tyr Glu Asp His Asp Ala Thr Gln Gln Leu Gln Gly Phe Tyr Ser
1               5                   10                  15

Gln Val Ala Lys
        20
```

```
<210> SEQ ID NO 1050
<211> LENGTH: 13
<212> TYPE: PRT
<213> ORGANISM: Homo sapiens

<400> SEQUENCE: 1050

Lys Ala Ala Ile Ser Gly Glu Asn Ala Gly Leu Val Arg
1               5                   10

<210> SEQ ID NO 1051
<211> LENGTH: 29
<212> TYPE: PRT
<213> ORGANISM: Homo sapiens

<400> SEQUENCE: 1051

Lys Gly His Val Leu Phe Arg Pro Thr Val Ser Gln Gln Gln Ser Cys
1               5                   10                  15

Pro Thr Cys Ser Thr Ser Leu Leu Asn Gly His Phe Lys
            20                  25

<210> SEQ ID NO 1052
<211> LENGTH: 14
<212> TYPE: PRT
<213> ORGANISM: Homo sapiens

<400> SEQUENCE: 1052

Leu Trp Ala Tyr Leu Thr Ile Gln Glu Leu Leu Ala Lys Arg
1               5                   10

<210> SEQ ID NO 1053
<211> LENGTH: 8
<212> TYPE: PRT
<213> ORGANISM: Homo sapiens

<400> SEQUENCE: 1053

Met Lys Val Asp Arg Glu Glu Arg
1               5

<210> SEQ ID NO 1054
<211> LENGTH: 24
<212> TYPE: PRT
<213> ORGANISM: Homo sapiens

<400> SEQUENCE: 1054

Pro Leu Leu Val Asp Val Asp Leu Gln Tyr Pro Gln Asp Ala Val Leu
1               5                   10                  15

Ala Leu Thr Gln Asn His His Lys
            20

<210> SEQ ID NO 1055
<211> LENGTH: 20
<212> TYPE: PRT
<213> ORGANISM: Homo sapiens

<400> SEQUENCE: 1055

Gln Leu Val His His Phe Glu Ile Asp Val Asp Ile Phe Glu Pro Gln
1               5                   10                  15

Gly Ile Ser Lys
            20

<210> SEQ ID NO 1056
<211> LENGTH: 14
<212> TYPE: PRT
```

<213> ORGANISM: Homo sapiens

<400> SEQUENCE: 1056

Arg Gln Ala Val Asp Thr Ala Val Asp Gly Val Phe Ile Arg
1               5                   10

<210> SEQ ID NO 1057
<211> LENGTH: 7
<212> TYPE: PRT
<213> ORGANISM: Homo sapiens

<400> SEQUENCE: 1057

Ser Leu Lys Val Asn Cys Lys
1               5

<210> SEQ ID NO 1058
<211> LENGTH: 23
<212> TYPE: PRT
<213> ORGANISM: Homo sapiens

<400> SEQUENCE: 1058

Thr Ala Phe Ile Ser Asp Phe Ala Val Thr Ala Asp Gly Asn Ala Phe
1               5                   10                  15

Ile Gly Asp Ile Lys Asp Lys
            20

<210> SEQ ID NO 1059
<211> LENGTH: 28
<212> TYPE: PRT
<213> ORGANISM: Homo sapiens

<400> SEQUENCE: 1059

Thr Ala Phe Ile Ser Asp Phe Ala Val Thr Ala Asp Gly Asn Ala Phe
1               5                   10                  15

Ile Gly Asp Ile Lys Asp Lys Val Thr Ala Trp Lys
            20                  25

<210> SEQ ID NO 1060
<211> LENGTH: 13
<212> TYPE: PRT
<213> ORGANISM: Homo sapiens

<400> SEQUENCE: 1060

Val Thr Phe Gln Leu Thr Tyr Glu Glu Val Leu Lys Arg
1               5                   10

<210> SEQ ID NO 1061
<211> LENGTH: 9
<212> TYPE: PRT
<213> ORGANISM: Homo sapiens

<400> SEQUENCE: 1061

Val Thr Tyr Asp Val Ser Arg Asp Lys
1               5

<210> SEQ ID NO 1062
<211> LENGTH: 22
<212> TYPE: PRT
<213> ORGANISM: Homo sapiens

<400> SEQUENCE: 1062

Phe Asn Arg Pro Phe Leu Met Ile Ile Val Pro Thr Asp Thr Gln Asn
1               5                   10                  15

Ile Phe Phe Met Ser Lys

-continued

<210> SEQ ID NO 1063
<211> LENGTH: 16
<212> TYPE: PRT
<213> ORGANISM: Homo sapiens

<400> SEQUENCE: 1063

Ala Lys Trp Glu Met Pro Phe Asp Pro Gln Asp Thr His Gln Ser Arg
1               5                   10                  15

<210> SEQ ID NO 1064
<211> LENGTH: 10
<212> TYPE: PRT
<213> ORGANISM: Homo sapiens

<400> SEQUENCE: 1064

Ala Asp Leu Ser Gly Ile Thr Gly Ala Arg
1               5                   10

<210> SEQ ID NO 1065
<211> LENGTH: 19
<212> TYPE: PRT
<213> ORGANISM: Homo sapiens

<400> SEQUENCE: 1065

Ala Val Leu Asp Val Phe Glu Glu Gly Thr Glu Ala Ser Ala Ala Thr
1               5                   10                  15

Ala Val Lys

<210> SEQ ID NO 1066
<211> LENGTH: 12
<212> TYPE: PRT
<213> ORGANISM: Homo sapiens

<400> SEQUENCE: 1066

Asp Glu Glu Leu Ser Cys Thr Val Val Glu Leu Lys
1               5                   10

<210> SEQ ID NO 1067
<211> LENGTH: 20
<212> TYPE: PRT
<213> ORGANISM: Homo sapiens

<400> SEQUENCE: 1067

Asp Tyr Asn Leu Asn Asp Ile Leu Leu Gln Leu Gly Ile Glu Glu Ala
1               5                   10                  15

Phe Thr Ser Lys
            20

<210> SEQ ID NO 1068
<211> LENGTH: 9
<212> TYPE: PRT
<213> ORGANISM: Homo sapiens

<400> SEQUENCE: 1068

Glu Ile Gly Glu Leu Tyr Leu Pro Lys
1               5

<210> SEQ ID NO 1069
<211> LENGTH: 8
<212> TYPE: PRT
<213> ORGANISM: Homo sapiens

<400> SEQUENCE: 1069

```
Glu Gln Leu Ser Leu Leu Asp Arg
1               5

<210> SEQ ID NO 1070
<211> LENGTH: 14
<212> TYPE: PRT
<213> ORGANISM: Homo sapiens

<400> SEQUENCE: 1070

Glu Gln Leu Ser Leu Leu Asp Arg Phe Thr Glu Asp Ala Lys
1               5                   10

<210> SEQ ID NO 1071
<211> LENGTH: 8
<212> TYPE: PRT
<213> ORGANISM: Homo sapiens

<400> SEQUENCE: 1071

Gly Lys Ile Thr Asp Leu Ile Lys
1               5

<210> SEQ ID NO 1072
<211> LENGTH: 25
<212> TYPE: PRT
<213> ORGANISM: Homo sapiens

<400> SEQUENCE: 1072

Gly Lys Ile Thr Asp Leu Ile Lys Asp Leu Asp Ser Gln Thr Met Met
1               5                   10                  15

Val Leu Val Asn Tyr Ile Phe Phe Lys
            20                  25

<210> SEQ ID NO 1073
<211> LENGTH: 18
<212> TYPE: PRT
<213> ORGANISM: Homo sapiens

<400> SEQUENCE: 1073

His Pro Asn Ser Pro Leu Asp Glu Glu Asn Leu Thr Gln Glu Asn Gln
1               5                   10                  15

Asp Arg

<210> SEQ ID NO 1074
<211> LENGTH: 23
<212> TYPE: PRT
<213> ORGANISM: Homo sapiens

<400> SEQUENCE: 1074

Ile Thr Asp Leu Ile Lys Asp Leu Asp Ser Gln Thr Met Met Val Leu
1               5                   10                  15

Val Asn Tyr Ile Phe Phe Lys
            20

<210> SEQ ID NO 1075
<211> LENGTH: 11
<212> TYPE: PRT
<213> ORGANISM: Homo sapiens

<400> SEQUENCE: 1075

Ile Thr Leu Leu Ser Ala Leu Val Glu Thr Arg
1               5                   10

<210> SEQ ID NO 1076
```

```
<211> LENGTH: 7
<212> TYPE: PRT
<213> ORGANISM: Homo sapiens

<400> SEQUENCE: 1076

Leu Ile Asn Asp Tyr Val Lys
1               5

<210> SEQ ID NO 1077
<211> LENGTH: 18
<212> TYPE: PRT
<213> ORGANISM: Homo sapiens

<400> SEQUENCE: 1077

Leu Tyr Gly Ser Glu Ala Phe Ala Thr Asp Phe Gln Asp Ser Ala Ala
1               5                   10                  15

Ala Lys

<210> SEQ ID NO 1078
<211> LENGTH: 19
<212> TYPE: PRT
<213> ORGANISM: Homo sapiens

<400> SEQUENCE: 1078

Leu Tyr Gly Ser Glu Ala Phe Ala Thr Asp Phe Gln Asp Ser Ala Ala
1               5                   10                  15

Ala Lys Lys

<210> SEQ ID NO 1079
<211> LENGTH: 15
<212> TYPE: PRT
<213> ORGANISM: Homo sapiens

<400> SEQUENCE: 1079

Met Glu Glu Val Glu Ala Met Leu Leu Pro Glu Thr Leu Lys Arg
1               5                   10                  15

<210> SEQ ID NO 1080
<211> LENGTH: 24
<212> TYPE: PRT
<213> ORGANISM: Homo sapiens

<400> SEQUENCE: 1080

Met Ser Leu His His Leu Thr Ile Pro Tyr Phe Arg Asp Glu Glu Leu
1               5                   10                  15

Ser Cys Thr Val Val Glu Leu Lys
            20

<210> SEQ ID NO 1081
<211> LENGTH: 16
<212> TYPE: PRT
<213> ORGANISM: Homo sapiens

<400> SEQUENCE: 1081

Asn Ser Pro Leu Asp Glu Glu Asn Leu Thr Gln Glu Asn Gln Asp Arg
1               5                   10                  15

<210> SEQ ID NO 1082
<211> LENGTH: 19
<212> TYPE: PRT
<213> ORGANISM: Homo sapiens

<400> SEQUENCE: 1082

Arg Leu Tyr Gly Ser Glu Ala Phe Ala Thr Asp Phe Gln Asp Ser Ala
```

```
                1               5                  10                 15
Ala Ala Lys

<210> SEQ ID NO 1083
<211> LENGTH: 20
<212> TYPE: PRT
<213> ORGANISM: Homo sapiens

<400> SEQUENCE: 1083

Arg Leu Tyr Gly Ser Glu Ala Phe Ala Thr Asp Phe Gln Asp Ser Ala
1               5                  10                 15

Ala Ala Lys Lys
            20

<210> SEQ ID NO 1084
<211> LENGTH: 26
<212> TYPE: PRT
<213> ORGANISM: Homo sapiens

<400> SEQUENCE: 1084

Thr Ile Val Arg Phe Asn Arg Pro Phe Leu Met Ile Ile Val Pro Thr
1               5                  10                 15

Asp Thr Gln Asn Ile Phe Phe Met Ser Lys
            20                  25

<210> SEQ ID NO 1085
<211> LENGTH: 14
<212> TYPE: PRT
<213> ORGANISM: Homo sapiens

<400> SEQUENCE: 1085

Trp Glu Met Pro Phe Asp Pro Gln Asp Thr His Gln Ser Arg
1               5                  10

<210> SEQ ID NO 1086
<211> LENGTH: 8
<212> TYPE: PRT
<213> ORGANISM: Homo sapiens

<400> SEQUENCE: 1086

Trp Arg Asp Ser Leu Glu Phe Arg
1               5

<210> SEQ ID NO 1087
<211> LENGTH: 32
<212> TYPE: PRT
<213> ORGANISM: Homo sapiens

<400> SEQUENCE: 1087

Ala Ser Ala Ser Tyr Tyr Glu Gln Tyr His Ser Leu Asn Glu Ile Tyr
1               5                  10                 15

Ser Trp Ile Glu Phe Ile Thr Glu Arg His Pro Asp Met Leu Thr Lys
            20                  25                 30

<210> SEQ ID NO 1088
<211> LENGTH: 20
<212> TYPE: PRT
<213> ORGANISM: Homo sapiens

<400> SEQUENCE: 1088

Ala Tyr Ile Ser Met His Ser Tyr Ser Gln His Ile Val Phe Pro Tyr
1               5                  10                 15

Ser Tyr Thr Arg
```

<210> SEQ ID NO 1089
<211> LENGTH: 8
<212> TYPE: PRT
<213> ORGANISM: Homo sapiens

<400> SEQUENCE: 1089

Glu Ala Phe Ala Ala Val Ser Lys
1               5

<210> SEQ ID NO 1090
<211> LENGTH: 30
<212> TYPE: PRT
<213> ORGANISM: Homo sapiens

<400> SEQUENCE: 1090

Glu Trp Ile Ser Pro Ala Phe Cys Leu Trp Phe Ile Gly His Ile Thr
1               5                   10                  15

Gln Phe Tyr Gly Ile Ile Gly Gln Tyr Thr Asn Leu Leu Arg
            20                  25                  30

<210> SEQ ID NO 1091
<211> LENGTH: 12
<212> TYPE: PRT
<213> ORGANISM: Homo sapiens

<400> SEQUENCE: 1091

Phe Gln Ser Gly Gln Val Leu Ala Ala Leu Pro Arg
1               5                   10

<210> SEQ ID NO 1092
<211> LENGTH: 28
<212> TYPE: PRT
<213> ORGANISM: Homo sapiens

<400> SEQUENCE: 1092

His Trp Cys Glu Glu Gly Ala Ser Ser Ser Cys Ser Gly Thr Tyr
1               5                   10                  15

Cys Gly Leu Tyr Pro Glu Ser Glu Pro Glu Val Lys
            20                  25

<210> SEQ ID NO 1093
<211> LENGTH: 7
<212> TYPE: PRT
<213> ORGANISM: Homo sapiens

<400> SEQUENCE: 1093

Ile Ala Trp His Val Ile Arg
1               5

<210> SEQ ID NO 1094
<211> LENGTH: 16
<212> TYPE: PRT
<213> ORGANISM: Homo sapiens

<400> SEQUENCE: 1094

Ile His Ile Gly Ser Ser Phe Glu Lys Tyr Pro Leu Tyr Val Leu Lys
1               5                   10                  15

<210> SEQ ID NO 1095
<211> LENGTH: 12
<212> TYPE: PRT
<213> ORGANISM: Homo sapiens

```
<400> SEQUENCE: 1095

Asn Ala Ile Trp Ile Asp Cys Gly Ile His Ala Arg
1               5                   10

<210> SEQ ID NO 1096
<211> LENGTH: 15
<212> TYPE: PRT
<213> ORGANISM: Homo sapiens

<400> SEQUENCE: 1096

Ser Phe Tyr Ala Asn Asn His Cys Ile Gly Thr Asp Leu Asn Arg
1               5                   10                  15

<210> SEQ ID NO 1097
<211> LENGTH: 16
<212> TYPE: PRT
<213> ORGANISM: Homo sapiens

<400> SEQUENCE: 1097

Ser Lys Asp His Glu Glu Leu Ser Leu Val Ala Ser Glu Ala Val Arg
1               5                   10                  15

<210> SEQ ID NO 1098
<211> LENGTH: 18
<212> TYPE: PRT
<213> ORGANISM: Homo sapiens

<400> SEQUENCE: 1098

Ser Lys Ser Lys Asp His Glu Glu Leu Ser Leu Val Ala Ser Glu Ala
1               5                   10                  15

Val Arg

<210> SEQ ID NO 1099
<211> LENGTH: 27
<212> TYPE: PRT
<213> ORGANISM: Homo sapiens

<400> SEQUENCE: 1099

Tyr Thr His Gly His Gly Ser Glu Thr Leu Tyr Leu Ala Pro Gly Gly
1               5                   10                  15

Gly Asp Asp Trp Ile Tyr Asp Leu Gly Ile Lys
            20                  25

<210> SEQ ID NO 1100
<211> LENGTH: 18
<212> TYPE: PRT
<213> ORGANISM: Homo sapiens

<400> SEQUENCE: 1100

Ala Ile His Cys Pro Arg Pro His Asp Phe Glu Asn Gly Glu Tyr Trp
1               5                   10                  15

Pro Arg

<210> SEQ ID NO 1101
<211> LENGTH: 10
<212> TYPE: PRT
<213> ORGANISM: Homo sapiens

<400> SEQUENCE: 1101

Ala Leu Phe Val Ser Glu Glu Glu Lys Lys
1               5                   10

<210> SEQ ID NO 1102
```

```
<211> LENGTH: 14
<212> TYPE: PRT
<213> ORGANISM: Homo sapiens

<400> SEQUENCE: 1102

Ala Leu Arg Leu Pro Pro Thr Thr Thr Cys Gln Gln Gln Lys
1               5                   10

<210> SEQ ID NO 1103
<211> LENGTH: 24
<212> TYPE: PRT
<213> ORGANISM: Homo sapiens

<400> SEQUENCE: 1103

Ala Leu Arg Leu Pro Pro Thr Thr Thr Cys Gln Gln Gln Lys Glu Glu
1               5                   10                  15

Leu Leu Pro Ala Gln Asp Ile Lys
            20

<210> SEQ ID NO 1104
<211> LENGTH: 8
<212> TYPE: PRT
<213> ORGANISM: Homo sapiens

<400> SEQUENCE: 1104

Cys Leu Val Asn Leu Ile Glu Lys
1               5

<210> SEQ ID NO 1105
<211> LENGTH: 10
<212> TYPE: PRT
<213> ORGANISM: Homo sapiens

<400> SEQUENCE: 1105

Asp Ala Gln Tyr Ala Pro Gly Tyr Asp Lys
1               5                   10

<210> SEQ ID NO 1106
<211> LENGTH: 12
<212> TYPE: PRT
<213> ORGANISM: Homo sapiens

<400> SEQUENCE: 1106

Asp Ala Gln Tyr Ala Pro Gly Tyr Asp Lys Val Lys
1               5                   10

<210> SEQ ID NO 1107
<211> LENGTH: 21
<212> TYPE: PRT
<213> ORGANISM: Homo sapiens

<400> SEQUENCE: 1107

Asp Ala Gln Tyr Ala Pro Gly Tyr Asp Lys Val Lys Asp Ile Ser Glu
1               5                   10                  15

Val Val Thr Pro Arg
            20

<210> SEQ ID NO 1108
<211> LENGTH: 14
<212> TYPE: PRT
<213> ORGANISM: Homo sapiens

<400> SEQUENCE: 1108

Asp Phe His Ile Asn Leu Phe Gln Val Leu Pro Trp Leu Lys
1               5                   10
```

<210> SEQ ID NO 1109
<211> LENGTH: 9
<212> TYPE: PRT
<213> ORGANISM: Homo sapiens

<400> SEQUENCE: 1109

Asp Ile Ser Glu Val Val Thr Pro Arg
1               5

<210> SEQ ID NO 1110
<211> LENGTH: 18
<212> TYPE: PRT
<213> ORGANISM: Homo sapiens

<400> SEQUENCE: 1110

Asp Leu Glu Ile Glu Val Val Leu Phe His Pro Asn Tyr Asn Ile Asn
1               5                   10                  15

Gly Lys

<210> SEQ ID NO 1111
<211> LENGTH: 19
<212> TYPE: PRT
<213> ORGANISM: Homo sapiens

<400> SEQUENCE: 1111

Asp Leu Glu Ile Glu Val Val Leu Phe His Pro Asn Tyr Asn Ile Asn
1               5                   10                  15

Gly Lys Lys

<210> SEQ ID NO 1112
<211> LENGTH: 9
<212> TYPE: PRT
<213> ORGANISM: Homo sapiens

<400> SEQUENCE: 1112

Asp Leu Leu Tyr Ile Gly Lys Asp Arg
1               5

<210> SEQ ID NO 1113
<211> LENGTH: 8
<212> TYPE: PRT
<213> ORGANISM: Homo sapiens

<400> SEQUENCE: 1113

Asp Asn Glu Gln His Val Phe Lys
1               5

<210> SEQ ID NO 1114
<211> LENGTH: 16
<212> TYPE: PRT
<213> ORGANISM: Homo sapiens

<400> SEQUENCE: 1114

Glu Ala Gly Ile Pro Glu Phe Tyr Asp Tyr Asp Val Ala Leu Ile Lys
1               5                   10                  15

<210> SEQ ID NO 1115
<211> LENGTH: 26
<212> TYPE: PRT
<213> ORGANISM: Homo sapiens

<400> SEQUENCE: 1115

Glu Asp Tyr Leu Asp Val Tyr Val Phe Gly Val Gly Pro Leu Val Asn

```
                1               5                  10                  15
Gln Val Asn Ile Asn Ala Leu Ala Ser Lys
            20                  25

<210> SEQ ID NO 1116
<211> LENGTH: 27
<212> TYPE: PRT
<213> ORGANISM: Homo sapiens

<400> SEQUENCE: 1116

Glu Asp Tyr Leu Asp Val Tyr Val Phe Gly Val Gly Pro Leu Val Asn
1               5                   10                  15

Gln Val Asn Ile Asn Ala Leu Ala Ser Lys Lys
            20                  25

<210> SEQ ID NO 1117
<211> LENGTH: 10
<212> TYPE: PRT
<213> ORGANISM: Homo sapiens

<400> SEQUENCE: 1117

Glu Glu Leu Leu Pro Ala Gln Asp Ile Lys
1               5                   10

<210> SEQ ID NO 1118
<211> LENGTH: 11
<212> TYPE: PRT
<213> ORGANISM: Homo sapiens

<400> SEQUENCE: 1118

Glu Lys Leu Gln Asp Glu Asp Leu Gly Phe Leu
1               5                   10

<210> SEQ ID NO 1119
<211> LENGTH: 17
<212> TYPE: PRT
<213> ORGANISM: Homo sapiens

<400> SEQUENCE: 1119

Phe Leu Cys Thr Gly Gly Val Ser Pro Tyr Ala Asp Pro Asn Thr Cys
1               5                   10                  15

Arg

<210> SEQ ID NO 1120
<211> LENGTH: 29
<212> TYPE: PRT
<213> ORGANISM: Homo sapiens

<400> SEQUENCE: 1120

Phe Leu Cys Thr Gly Gly Val Ser Pro Tyr Ala Asp Pro Asn Thr Cys
1               5                   10                  15

Arg Gly Asp Ser Gly Gly Pro Leu Ile Val His Lys Arg
            20                  25

<210> SEQ ID NO 1121
<211> LENGTH: 11
<212> TYPE: PRT
<213> ORGANISM: Homo sapiens

<400> SEQUENCE: 1121

Gly Asp Ser Gly Gly Pro Leu Ile Val His Lys
1               5                   10
```

```
<210> SEQ ID NO 1122
<211> LENGTH: 12
<212> TYPE: PRT
<213> ORGANISM: Homo sapiens

<400> SEQUENCE: 1122

Gly Asp Ser Gly Gly Pro Leu Ile Val His Lys Arg
1               5                   10

<210> SEQ ID NO 1123
<211> LENGTH: 32
<212> TYPE: PRT
<213> ORGANISM: Homo sapiens

<400> SEQUENCE: 1123

Gly His Glu Ser Cys Met Gly Ala Val Val Ser Glu Tyr Phe Val Leu
1               5                   10                  15

Thr Ala Ala His Cys Phe Thr Val Asp Asp Lys Glu His Ser Ile Lys
            20                  25                  30

<210> SEQ ID NO 1124
<211> LENGTH: 25
<212> TYPE: PRT
<213> ORGANISM: Homo sapiens

<400> SEQUENCE: 1124

His Val Ile Ile Leu Met Thr Asp Gly Leu His Asn Met Gly Gly Asp
1               5                   10                  15

Pro Ile Thr Val Ile Asp Glu Ile Arg
            20                  25

<210> SEQ ID NO 1125
<211> LENGTH: 32
<212> TYPE: PRT
<213> ORGANISM: Homo sapiens

<400> SEQUENCE: 1125

His Val Ile Ile Leu Met Thr Asp Gly Leu His Asn Met Gly Gly Asp
1               5                   10                  15

Pro Ile Thr Val Ile Asp Glu Ile Arg Asp Leu Leu Tyr Ile Gly Lys
            20                  25                  30

<210> SEQ ID NO 1126
<211> LENGTH: 9
<212> TYPE: PRT
<213> ORGANISM: Homo sapiens

<400> SEQUENCE: 1126

Lys Cys Leu Val Asn Leu Ile Glu Lys
1               5

<210> SEQ ID NO 1127
<211> LENGTH: 9
<212> TYPE: PRT
<213> ORGANISM: Homo sapiens

<400> SEQUENCE: 1127

Lys Asp Asn Glu Gln His Val Phe Lys
1               5

<210> SEQ ID NO 1128
<211> LENGTH: 17
<212> TYPE: PRT
<213> ORGANISM: Homo sapiens
```

```
<400> SEQUENCE: 1128

Lys Glu Ala Gly Ile Pro Glu Phe Tyr Asp Tyr Asp Val Ala Leu Ile
1               5                   10                  15

Lys

<210> SEQ ID NO 1129
<211> LENGTH: 6
<212> TYPE: PRT
<213> ORGANISM: Homo sapiens

<400> SEQUENCE: 1129

Lys Glu Val Tyr Ile Lys
1               5

<210> SEQ ID NO 1130
<211> LENGTH: 13
<212> TYPE: PRT
<213> ORGANISM: Homo sapiens

<400> SEQUENCE: 1130

Lys Gly Thr Asp Tyr His Lys Gln Pro Trp Gln Ala Lys
1               5                   10

<210> SEQ ID NO 1131
<211> LENGTH: 31
<212> TYPE: PRT
<213> ORGANISM: Homo sapiens

<400> SEQUENCE: 1131

Lys Asn Pro Arg Glu Asp Tyr Leu Asp Val Tyr Val Phe Gly Val Gly
1               5                   10                  15

Pro Leu Val Asn Gln Val Asn Ile Asn Ala Leu Ala Ser Lys Lys
            20                  25                  30

<210> SEQ ID NO 1132
<211> LENGTH: 7
<212> TYPE: PRT
<213> ORGANISM: Homo sapiens

<400> SEQUENCE: 1132

Lys Val Gly Ser Gln Tyr Arg
1               5

<210> SEQ ID NO 1133
<211> LENGTH: 18
<212> TYPE: PRT
<213> ORGANISM: Homo sapiens

<400> SEQUENCE: 1133

Lys Val Gly Ser Gln Tyr Arg Leu Glu Asp Ser Val Thr Tyr His Cys
1               5                   10                  15

Ser Arg

<210> SEQ ID NO 1134
<211> LENGTH: 11
<212> TYPE: PRT
<213> ORGANISM: Homo sapiens

<400> SEQUENCE: 1134

Leu Glu Asp Ser Val Thr Tyr His Cys Ser Arg
1               5                   10

<210> SEQ ID NO 1135
```

```
<211> LENGTH: 20
<212> TYPE: PRT
<213> ORGANISM: Homo sapiens

<400> SEQUENCE: 1135

Leu Lys Tyr Gly Gln Thr Ile Arg Pro Ile Cys Leu Pro Cys Thr Glu
1               5                   10                  15

Gly Thr Thr Arg
            20

<210> SEQ ID NO 1136
<211> LENGTH: 24
<212> TYPE: PRT
<213> ORGANISM: Homo sapiens

<400> SEQUENCE: 1136

Leu Leu Gln Glu Gly Gln Ala Leu Glu Tyr Val Cys Pro Ser Gly Phe
1               5                   10                  15

Tyr Pro Tyr Pro Val Gln Thr Arg
            20

<210> SEQ ID NO 1137
<211> LENGTH: 11
<212> TYPE: PRT
<213> ORGANISM: Homo sapiens

<400> SEQUENCE: 1137

Leu Pro Pro Thr Thr Thr Cys Gln Gln Gln Lys
1               5                   10

<210> SEQ ID NO 1138
<211> LENGTH: 21
<212> TYPE: PRT
<213> ORGANISM: Homo sapiens

<400> SEQUENCE: 1138

Leu Pro Pro Thr Thr Thr Cys Gln Gln Gln Lys Glu Glu Leu Leu Pro
1               5                   10                  15

Ala Gln Asp Ile Lys
            20

<210> SEQ ID NO 1139
<211> LENGTH: 29
<212> TYPE: PRT
<213> ORGANISM: Homo sapiens

<400> SEQUENCE: 1139

Asn Pro Arg Glu Asp Tyr Leu Asp Val Tyr Val Phe Gly Val Gly Pro
1               5                   10                  15

Leu Val Asn Gln Val Asn Ile Asn Ala Leu Ala Ser Lys
            20                  25

<210> SEQ ID NO 1140
<211> LENGTH: 30
<212> TYPE: PRT
<213> ORGANISM: Homo sapiens

<400> SEQUENCE: 1140

Asn Pro Arg Glu Asp Tyr Leu Asp Val Tyr Val Phe Gly Val Gly Pro
1               5                   10                  15

Leu Val Asn Gln Val Asn Ile Asn Ala Leu Ala Ser Lys Lys
            20                  25                  30
```

```
<210> SEQ ID NO 1141
<211> LENGTH: 16
<212> TYPE: PRT
<213> ORGANISM: Homo sapiens

<400> SEQUENCE: 1141

Pro Ile Thr Val Ile Asp Glu Ile Arg Asp Leu Leu Tyr Ile Gly Lys
1               5                   10                  15

<210> SEQ ID NO 1142
<211> LENGTH: 11
<212> TYPE: PRT
<213> ORGANISM: Homo sapiens

<400> SEQUENCE: 1142

Gln Leu Asn Glu Ile Asn Tyr Glu Asp His Lys
1               5                   10

<210> SEQ ID NO 1143
<211> LENGTH: 13
<212> TYPE: PRT
<213> ORGANISM: Homo sapiens

<400> SEQUENCE: 1143

Gln Leu Asn Glu Ile Asn Tyr Glu Asp His Lys Leu Lys
1               5                   10

<210> SEQ ID NO 1144
<211> LENGTH: 14
<212> TYPE: PRT
<213> ORGANISM: Homo sapiens

<400> SEQUENCE: 1144

Arg Pro Gln Gly Ser Cys Ser Leu Glu Gly Val Glu Ile Lys
1               5                   10

<210> SEQ ID NO 1145
<211> LENGTH: 9
<212> TYPE: PRT
<213> ORGANISM: Homo sapiens

<400> SEQUENCE: 1145

Ser Thr Gly Ser Trp Ser Thr Leu Lys
1               5

<210> SEQ ID NO 1146
<211> LENGTH: 20
<212> TYPE: PRT
<213> ORGANISM: Homo sapiens

<400> SEQUENCE: 1146

Thr Pro Trp Ser Leu Ala Arg Pro Gln Gly Ser Cys Ser Leu Glu Gly
1               5                   10                  15

Val Glu Ile Lys
            20

<210> SEQ ID NO 1147
<211> LENGTH: 9
<212> TYPE: PRT
<213> ORGANISM: Homo sapiens

<400> SEQUENCE: 1147

Val Ala Ser Tyr Gly Val Lys Pro Arg
1               5
```

```
<210> SEQ ID NO 1148
<211> LENGTH: 11
<212> TYPE: PRT
<213> ORGANISM: Homo sapiens

<400> SEQUENCE: 1148

Val Lys Asp Ile Ser Glu Val Val Thr Pro Arg
1               5                   10

<210> SEQ ID NO 1149
<211> LENGTH: 32
<212> TYPE: PRT
<213> ORGANISM: Homo sapiens

<400> SEQUENCE: 1149

Val Lys Asp Met Glu Asn Leu Glu Asp Val Phe Tyr Gln Met Ile Asp
1               5                   10                  15

Glu Ser Gln Ser Leu Ser Leu Cys Gly Met Val Trp Glu His Arg Lys
                20                  25                  30

<210> SEQ ID NO 1150
<211> LENGTH: 14
<212> TYPE: PRT
<213> ORGANISM: Homo sapiens

<400> SEQUENCE: 1150

Val Ser Glu Ala Asp Ser Ser Asn Ala Asp Trp Val Thr Lys
1               5                   10

<210> SEQ ID NO 1151
<211> LENGTH: 25
<212> TYPE: PRT
<213> ORGANISM: Homo sapiens

<400> SEQUENCE: 1151

Trp Ser Gly Gln Thr Ala Ile Cys Asp Asn Gly Ala Gly Tyr Cys Ser
1               5                   10                  15

Asn Pro Gly Ile Pro Ile Gly Thr Arg
                20                  25

<210> SEQ ID NO 1152
<211> LENGTH: 26
<212> TYPE: PRT
<213> ORGANISM: Homo sapiens

<400> SEQUENCE: 1152

Trp Ser Gly Gln Thr Ala Ile Cys Asp Asn Gly Ala Gly Tyr Cys Ser
1               5                   10                  15

Asn Pro Gly Ile Pro Ile Gly Thr Arg Lys
                20                  25

<210> SEQ ID NO 1153
<211> LENGTH: 18
<212> TYPE: PRT
<213> ORGANISM: Homo sapiens

<400> SEQUENCE: 1153

Trp Ser Leu Ala Arg Pro Gln Gly Ser Cys Ser Leu Glu Gly Val Glu
1               5                   10                  15

Ile Lys

<210> SEQ ID NO 1154
<211> LENGTH: 11
<212> TYPE: PRT
```

<213> ORGANISM: Homo sapiens

<400> SEQUENCE: 1154

Tyr Gly Leu Val Thr Tyr Ala Thr Tyr Pro Lys
1               5                   10

<210> SEQ ID NO 1155
<211> LENGTH: 18
<212> TYPE: PRT
<213> ORGANISM: Homo sapiens

<400> SEQUENCE: 1155

Tyr Gly Gln Thr Ile Arg Pro Ile Cys Leu Pro Cys Thr Glu Gly Thr
1               5                   10                  15

Thr Arg

<210> SEQ ID NO 1156
<211> LENGTH: 17
<212> TYPE: PRT
<213> ORGANISM: Homo sapiens

<400> SEQUENCE: 1156

Ala Gln Thr Thr Val Thr Cys Met Glu Asn Gly Trp Ser Pro Thr Pro
1               5                   10                  15

Arg

<210> SEQ ID NO 1157
<211> LENGTH: 10
<212> TYPE: PRT
<213> ORGANISM: Homo sapiens

<400> SEQUENCE: 1157

Cys Asn Met Gly Tyr Glu Tyr Ser Glu Arg
1               5                   10

<210> SEQ ID NO 1158
<211> LENGTH: 11
<212> TYPE: PRT
<213> ORGANISM: Homo sapiens

<400> SEQUENCE: 1158

Glu Ile Met Glu Asn Tyr Asn Ile Ala Leu Arg
1               5                   10

<210> SEQ ID NO 1159
<211> LENGTH: 10
<212> TYPE: PRT
<213> ORGANISM: Homo sapiens

<400> SEQUENCE: 1159

His Gly Gly Leu Tyr His Glu Asn Met Arg
1               5                   10

<210> SEQ ID NO 1160
<211> LENGTH: 19
<212> TYPE: PRT
<213> ORGANISM: Homo sapiens

<400> SEQUENCE: 1160

Ile Val Ser Ser Ala Met Glu Pro Asp Arg Glu Tyr His Phe Gly Gln
1               5                   10                  15

Ala Val Arg

-continued

<210> SEQ ID NO 1161
<211> LENGTH: 11
<212> TYPE: PRT
<213> ORGANISM: Homo sapiens

<400> SEQUENCE: 1161

Ser Cys Asp Ile Pro Val Phe Met Asn Ala Arg
1               5                   10

<210> SEQ ID NO 1162
<211> LENGTH: 18
<212> TYPE: PRT
<213> ORGANISM: Homo sapiens

<400> SEQUENCE: 1162

Thr Asp Cys Leu Ser Leu Pro Ser Phe Glu Asn Ala Ile Pro Met Gly
1               5                   10                  15

Glu Lys

<210> SEQ ID NO 1163
<211> LENGTH: 14
<212> TYPE: PRT
<213> ORGANISM: Homo sapiens

<400> SEQUENCE: 1163

Ala Gly Glu Gln Val Thr Tyr Thr Cys Ala Thr Tyr Tyr Lys
1               5                   10

<210> SEQ ID NO 1164
<211> LENGTH: 18
<212> TYPE: PRT
<213> ORGANISM: Homo sapiens

<400> SEQUENCE: 1164

Ala Val Tyr Thr Cys Asn Glu Gly Tyr Gln Leu Leu Gly Glu Ile Asn
1               5                   10                  15

Tyr Arg

<210> SEQ ID NO 1165
<211> LENGTH: 14
<212> TYPE: PRT
<213> ORGANISM: Homo sapiens

<400> SEQUENCE: 1165

Cys Phe Glu Gly Phe Gly Ile Asp Gly Pro Ala Ile Ala Lys
1               5                   10

<210> SEQ ID NO 1166
<211> LENGTH: 41
<212> TYPE: PRT
<213> ORGANISM: Homo sapiens

<400> SEQUENCE: 1166

Cys Gly Pro Pro Pro Ile Asp Asn Gly Asp Ile Thr Ser Phe Pro
1               5                   10                  15

Leu Ser Val Tyr Ala Pro Ala Ser Ser Val Glu Tyr Gln Cys Gln Asn
                20                  25                  30

Leu Tyr Gln Leu Glu Gly Asn Lys Arg
        35                  40

<210> SEQ ID NO 1167
<211> LENGTH: 14
<212> TYPE: PRT
<213> ORGANISM: Homo sapiens

```
<400> SEQUENCE: 1167

Cys Lys Ser Ser Asn Leu Ile Ile Leu Glu Glu His Leu Lys
1               5                   10

<210> SEQ ID NO 1168
<211> LENGTH: 9
<212> TYPE: PRT
<213> ORGANISM: Homo sapiens

<400> SEQUENCE: 1168

Cys Leu His Pro Cys Val Ile Ser Arg
1               5

<210> SEQ ID NO 1169
<211> LENGTH: 11
<212> TYPE: PRT
<213> ORGANISM: Homo sapiens

<400> SEQUENCE: 1169

Cys Leu Pro Val Thr Ala Pro Glu Asn Gly Lys
1               5                   10

<210> SEQ ID NO 1170
<211> LENGTH: 29
<212> TYPE: PRT
<213> ORGANISM: Homo sapiens

<400> SEQUENCE: 1170

Cys Asn Met Gly Tyr Glu Tyr Ser Glu Arg Gly Asp Ala Val Cys Thr
1               5                   10                  15

Glu Ser Gly Trp Arg Pro Leu Pro Ser Cys Glu Glu Lys
            20                  25

<210> SEQ ID NO 1171
<211> LENGTH: 12
<212> TYPE: PRT
<213> ORGANISM: Homo sapiens

<400> SEQUENCE: 1171

Cys Thr Leu Lys Pro Cys Asp Tyr Pro Asp Ile Lys
1               5                   10

<210> SEQ ID NO 1172
<211> LENGTH: 11
<212> TYPE: PRT
<213> ORGANISM: Homo sapiens

<400> SEQUENCE: 1172

Cys Thr Ser Thr Gly Trp Ile Pro Ala Pro Arg
1               5                   10

<210> SEQ ID NO 1173
<211> LENGTH: 7
<212> TYPE: PRT
<213> ORGANISM: Homo sapiens

<400> SEQUENCE: 1173

Cys Val Glu Ile Ser Cys Lys
1               5

<210> SEQ ID NO 1174
<211> LENGTH: 20
<212> TYPE: PRT
<213> ORGANISM: Homo sapiens
```

```
<400> SEQUENCE: 1174

Cys Val Glu Ile Ser Cys Lys Ser Pro Asp Val Ile Asn Gly Ser Pro
1               5                  10                  15

Ile Ser Gln Lys
            20

<210> SEQ ID NO 1175
<211> LENGTH: 16
<212> TYPE: PRT
<213> ORGANISM: Homo sapiens

<400> SEQUENCE: 1175

Cys Tyr Phe Pro Tyr Leu Glu Asn Gly Tyr Asn Gln Asn Tyr Gly Arg
1               5                  10                  15

<210> SEQ ID NO 1176
<211> LENGTH: 11
<212> TYPE: PRT
<213> ORGANISM: Homo sapiens

<400> SEQUENCE: 1176

Asp Gly Trp Ser Ala Gln Pro Thr Cys Ile Lys
1               5                  10

<210> SEQ ID NO 1177
<211> LENGTH: 10
<212> TYPE: PRT
<213> ORGANISM: Homo sapiens

<400> SEQUENCE: 1177

Asp Gln Tyr Lys Val Gly Glu Val Leu Lys
1               5                  10

<210> SEQ ID NO 1178
<211> LENGTH: 18
<212> TYPE: PRT
<213> ORGANISM: Homo sapiens

<400> SEQUENCE: 1178

Glu Cys Asp Thr Asp Gly Trp Thr Asn Asp Ile Pro Ile Cys Glu Val
1               5                  10                  15

Val Lys

<210> SEQ ID NO 1179
<211> LENGTH: 16
<212> TYPE: PRT
<213> ORGANISM: Homo sapiens

<400> SEQUENCE: 1179

Glu Cys Glu Leu Pro Lys Ile Asp Val His Leu Val Pro Asp Arg Lys
1               5                  10                  15

<210> SEQ ID NO 1180
<211> LENGTH: 9
<212> TYPE: PRT
<213> ORGANISM: Homo sapiens

<400> SEQUENCE: 1180

Glu Phe Asp His Asn Ser Asn Ile Arg
1               5

<210> SEQ ID NO 1181
<211> LENGTH: 12
```

```
<212> TYPE: PRT
<213> ORGANISM: Homo sapiens

<400> SEQUENCE: 1181

Glu Gly Trp Ile His Thr Val Cys Ile Asn Gly Arg
1               5                   10

<210> SEQ ID NO 1182
<211> LENGTH: 20
<212> TYPE: PRT
<213> ORGANISM: Homo sapiens

<400> SEQUENCE: 1182

Glu Lys Thr Lys Glu Glu Tyr Gly His Ser Glu Val Val Glu Tyr Tyr
1               5                   10                  15

Cys Asn Pro Arg
            20

<210> SEQ ID NO 1183
<211> LENGTH: 18
<212> TYPE: PRT
<213> ORGANISM: Homo sapiens

<400> SEQUENCE: 1183

Glu Gln Val Gln Ser Cys Gly Pro Pro Glu Leu Leu Asn Gly Asn
1               5                   10                  15

Val Lys

<210> SEQ ID NO 1184
<211> LENGTH: 8
<212> TYPE: PRT
<213> ORGANISM: Homo sapiens

<400> SEQUENCE: 1184

Phe Leu Met Lys Gly Pro Asn Lys
1               5

<210> SEQ ID NO 1185
<211> LENGTH: 30
<212> TYPE: PRT
<213> ORGANISM: Homo sapiens

<400> SEQUENCE: 1185

Phe Ser Cys Lys Pro Gly Phe Thr Ile Val Gly Pro Asn Ser Val Gln
1               5                   10                  15

Cys Tyr His Phe Gly Leu Ser Pro Asp Leu Pro Ile Cys Lys
            20                  25                  30

<210> SEQ ID NO 1186
<211> LENGTH: 8
<212> TYPE: PRT
<213> ORGANISM: Homo sapiens

<400> SEQUENCE: 1186

Phe Val Cys Asn Ser Gly Tyr Lys
1               5

<210> SEQ ID NO 1187
<211> LENGTH: 19
<212> TYPE: PRT
<213> ORGANISM: Homo sapiens

<400> SEQUENCE: 1187

Gly Asp Ala Val Cys Thr Glu Ser Gly Trp Arg Pro Leu Pro Ser Cys
```

Glu Glu Lys

<210> SEQ ID NO 1188
<211> LENGTH: 14
<212> TYPE: PRT
<213> ORGANISM: Homo sapiens

<400> SEQUENCE: 1188

Gly Lys Glu Gly Trp Ile His Thr Val Cys Ile Asn Gly Arg
1               5                   10

<210> SEQ ID NO 1189
<211> LENGTH: 12
<212> TYPE: PRT
<213> ORGANISM: Homo sapiens

<400> SEQUENCE: 1189

His Arg Thr Gly Asp Glu Ile Thr Tyr Gln Cys Arg
1               5                   10

<210> SEQ ID NO 1190
<211> LENGTH: 10
<212> TYPE: PRT
<213> ORGANISM: Homo sapiens

<400> SEQUENCE: 1190

Ile Asp Val His Leu Val Pro Asp Arg Lys
1               5                   10

<210> SEQ ID NO 1191
<211> LENGTH: 17
<212> TYPE: PRT
<213> ORGANISM: Homo sapiens

<400> SEQUENCE: 1191

Ile Glu Gly Asp Glu Glu Met His Cys Ser Asp Asp Gly Phe Trp Ser
1               5                   10                  15
Lys

<210> SEQ ID NO 1192
<211> LENGTH: 8
<212> TYPE: PRT
<213> ORGANISM: Homo sapiens

<400> SEQUENCE: 1192

Ile Ile Tyr Lys Glu Asn Glu Arg
1               5

<210> SEQ ID NO 1193
<211> LENGTH: 17
<212> TYPE: PRT
<213> ORGANISM: Homo sapiens

<400> SEQUENCE: 1193

Lys Cys Tyr Phe Pro Tyr Leu Glu Asn Gly Tyr Asn Gln Asn Tyr Gly
1               5                   10                  15
Arg

<210> SEQ ID NO 1194
<211> LENGTH: 18
<212> TYPE: PRT
<213> ORGANISM: Homo sapiens

```
<400> SEQUENCE: 1194

Lys Cys Tyr Phe Pro Tyr Leu Glu Asn Gly Tyr Asn Gln Asn Tyr Gly
1               5                   10                  15

Arg Lys

<210> SEQ ID NO 1195
<211> LENGTH: 10
<212> TYPE: PRT
<213> ORGANISM: Homo sapiens

<400> SEQUENCE: 1195

Lys Glu Phe Asp His Asn Ser Asn Ile Arg
1               5                   10

<210> SEQ ID NO 1196
<211> LENGTH: 12
<212> TYPE: PRT
<213> ORGANISM: Homo sapiens

<400> SEQUENCE: 1196

Lys Gly Glu Trp Val Ala Leu Asn Pro Leu Arg Lys
1               5                   10

<210> SEQ ID NO 1197
<211> LENGTH: 18
<212> TYPE: PRT
<213> ORGANISM: Homo sapiens

<400> SEQUENCE: 1197

Leu Gly Tyr Val Thr Ala Asp Gly Glu Thr Ser Gly Ser Ile Thr Cys
1               5                   10                  15

Gly Lys

<210> SEQ ID NO 1198
<211> LENGTH: 8
<212> TYPE: PRT
<213> ORGANISM: Homo sapiens

<400> SEQUENCE: 1198

Asn Gly Phe Tyr Pro Ala Thr Arg
1               5

<210> SEQ ID NO 1199
<211> LENGTH: 9
<212> TYPE: PRT
<213> ORGANISM: Homo sapiens

<400> SEQUENCE: 1199

Asn Gly Gln Trp Ser Glu Pro Pro Lys
1               5

<210> SEQ ID NO 1200
<211> LENGTH: 12
<212> TYPE: PRT
<213> ORGANISM: Homo sapiens

<400> SEQUENCE: 1200

Asn Lys Lys Glu Phe Asp His Asn Ser Asn Ile Arg
1               5                   10

<210> SEQ ID NO 1201
<211> LENGTH: 23
<212> TYPE: PRT
<213> ORGANISM: Homo sapiens
```

```
<400> SEQUENCE: 1201

Asn Thr Glu Ile Leu Thr Gly Ser Trp Ser Asp Gln Thr Tyr Pro Glu
1               5                   10                  15
Gly Thr Gln Ala Ile Tyr Lys
            20

<210> SEQ ID NO 1202
<211> LENGTH: 26
<212> TYPE: PRT
<213> ORGANISM: Homo sapiens

<400> SEQUENCE: 1202

Pro Gly Phe Thr Ile Val Gly Pro Asn Ser Val Gln Cys Tyr His Phe
1               5                   10                  15
Gly Leu Ser Pro Asp Leu Pro Ile Cys Lys
            20                  25

<210> SEQ ID NO 1203
<211> LENGTH: 12
<212> TYPE: PRT
<213> ORGANISM: Homo sapiens

<400> SEQUENCE: 1203

Pro Pro Thr Val Gln Asn Ala Tyr Ile Val Ser Arg
1               5                   10

<210> SEQ ID NO 1204
<211> LENGTH: 10
<212> TYPE: PRT
<213> ORGANISM: Homo sapiens

<400> SEQUENCE: 1204

Gln Met Ser Lys Tyr Pro Ser Gly Glu Arg
1               5                   10

<210> SEQ ID NO 1205
<211> LENGTH: 24
<212> TYPE: PRT
<213> ORGANISM: Homo sapiens

<400> SEQUENCE: 1205

Arg Asn Thr Glu Ile Leu Thr Gly Ser Trp Ser Asp Gln Thr Tyr Pro
1               5                   10                  15
Glu Gly Thr Gln Ala Ile Tyr Lys
            20

<210> SEQ ID NO 1206
<211> LENGTH: 27
<212> TYPE: PRT
<213> ORGANISM: Homo sapiens

<400> SEQUENCE: 1206

Arg Pro Cys Gly His Pro Gly Asp Thr Pro Phe Gly Thr Phe Thr Leu
1               5                   10                  15
Thr Gly Gly Asn Val Phe Glu Tyr Gly Val Lys
            20                  25

<210> SEQ ID NO 1207
<211> LENGTH: 10
<212> TYPE: PRT
<213> ORGANISM: Homo sapiens

<400> SEQUENCE: 1207
```

```
Arg Pro Tyr Phe Pro Val Ala Val Gly Lys
1               5                   10

<210> SEQ ID NO 1208
<211> LENGTH: 16
<212> TYPE: PRT
<213> ORGANISM: Homo sapiens

<400> SEQUENCE: 1208

Ser Cys Asp Asn Pro Tyr Ile Pro Asn Gly Asp Tyr Ser Pro Leu Arg
1               5                   10                  15

<210> SEQ ID NO 1209
<211> LENGTH: 20
<212> TYPE: PRT
<213> ORGANISM: Homo sapiens

<400> SEQUENCE: 1209

Ser Ile Thr Cys Ile His Gly Val Trp Thr Gln Leu Pro Gln Cys Val
1               5                   10                  15

Ala Ile Asp Lys
            20

<210> SEQ ID NO 1210
<211> LENGTH: 22
<212> TYPE: PRT
<213> ORGANISM: Homo sapiens

<400> SEQUENCE: 1210

Ser Ile Thr Cys Ile His Gly Val Trp Thr Gln Leu Pro Gln Cys Val
1               5                   10                  15

Ala Ile Asp Lys Leu Lys
            20

<210> SEQ ID NO 1211
<211> LENGTH: 23
<212> TYPE: PRT
<213> ORGANISM: Homo sapiens

<400> SEQUENCE: 1211

Ser Ile Thr Cys Ile His Gly Val Trp Thr Gln Leu Pro Gln Cys Val
1               5                   10                  15

Ala Ile Asp Lys Leu Lys Lys
            20

<210> SEQ ID NO 1212
<211> LENGTH: 10
<212> TYPE: PRT
<213> ORGANISM: Homo sapiens

<400> SEQUENCE: 1212

Ser Leu Gly Asn Val Ile Met Val Cys Arg
1               5                   10

<210> SEQ ID NO 1213
<211> LENGTH: 13
<212> TYPE: PRT
<213> ORGANISM: Homo sapiens

<400> SEQUENCE: 1213

Ser Pro Asp Val Ile Asn Gly Ser Pro Ile Ser Gln Lys
1               5                   10
```

```
<210> SEQ ID NO 1214
<211> LENGTH: 20
<212> TYPE: PRT
<213> ORGANISM: Homo sapiens

<400> SEQUENCE: 1214

Ser Ser Ile Asp Ile Glu Asn Gly Phe Ile Ser Glu Ser Gln Tyr Thr
1               5                   10                  15
Tyr Ala Leu Lys
            20

<210> SEQ ID NO 1215
<211> LENGTH: 12
<212> TYPE: PRT
<213> ORGANISM: Homo sapiens

<400> SEQUENCE: 1215

Ser Ser Asn Leu Ile Ile Leu Glu Glu His Leu Lys
1               5                   10

<210> SEQ ID NO 1216
<211> LENGTH: 11
<212> TYPE: PRT
<213> ORGANISM: Homo sapiens

<400> SEQUENCE: 1216

Ser Ser Gln Glu Ser Tyr Ala His Gly Thr Lys
1               5                   10

<210> SEQ ID NO 1217
<211> LENGTH: 10
<212> TYPE: PRT
<213> ORGANISM: Homo sapiens

<400> SEQUENCE: 1217

Thr Gly Glu Ser Val Glu Phe Val Cys Lys
1               5                   10

<210> SEQ ID NO 1218
<211> LENGTH: 11
<212> TYPE: PRT
<213> ORGANISM: Homo sapiens

<400> SEQUENCE: 1218

Thr Gly Glu Ser Val Glu Phe Val Cys Lys Arg
1               5                   10

<210> SEQ ID NO 1219
<211> LENGTH: 18
<212> TYPE: PRT
<213> ORGANISM: Homo sapiens

<400> SEQUENCE: 1219

Thr Lys Glu Glu Tyr Gly His Ser Glu Val Val Glu Tyr Tyr Cys Asn
1               5                   10                  15
Pro Arg

<210> SEQ ID NO 1220
<211> LENGTH: 9
<212> TYPE: PRT
<213> ORGANISM: Homo sapiens

<400> SEQUENCE: 1220

Thr Lys Asn Asp Phe Thr Trp Phe Lys
1               5
```

```
<210> SEQ ID NO 1221
<211> LENGTH: 15
<212> TYPE: PRT
<213> ORGANISM: Homo sapiens

<400> SEQUENCE: 1221

Thr Thr Cys Trp Asp Gly Lys Leu Glu Tyr Pro Thr Cys Ala Lys
1               5                   10                  15

<210> SEQ ID NO 1222
<211> LENGTH: 20
<212> TYPE: PRT
<213> ORGANISM: Homo sapiens

<400> SEQUENCE: 1222

Val Ser Val Leu Cys Gln Glu Asn Tyr Leu Ile Gln Glu Gly Glu Glu
1               5                   10                  15

Ile Thr Cys Lys
            20

<210> SEQ ID NO 1223
<211> LENGTH: 23
<212> TYPE: PRT
<213> ORGANISM: Homo sapiens

<400> SEQUENCE: 1223

Val Ser Val Leu Cys Gln Glu Asn Tyr Leu Ile Gln Glu Gly Glu Glu
1               5                   10                  15

Ile Thr Cys Lys Asp Gly Arg
            20

<210> SEQ ID NO 1224
<211> LENGTH: 10
<212> TYPE: PRT
<213> ORGANISM: Homo sapiens

<400> SEQUENCE: 1224

Trp Gln Ser Ile Pro Leu Cys Val Glu Lys
1               5                   10

<210> SEQ ID NO 1225
<211> LENGTH: 36
<212> TYPE: PRT
<213> ORGANISM: Homo sapiens

<400> SEQUENCE: 1225

Tyr Tyr Ser Tyr Tyr Cys Asp Glu His Phe Glu Thr Pro Ser Gly Ser
1               5                   10                  15

Tyr Trp Asp His Ile His Cys Thr Gln Asp Gly Trp Ser Pro Ala Val
            20                  25                  30

Pro Cys Leu Arg
        35

<210> SEQ ID NO 1226
<211> LENGTH: 6
<212> TYPE: PRT
<213> ORGANISM: Homo sapiens

<400> SEQUENCE: 1226

Ala Phe Val Phe Pro Lys
1               5
```

<210> SEQ ID NO 1227
<211> LENGTH: 18
<212> TYPE: PRT
<213> ORGANISM: Homo sapiens

<400> SEQUENCE: 1227

Ala Leu Lys Tyr Glu Val Gln Gly Glu Val Phe Thr Lys Pro Gln Leu
1               5                   10                  15

Trp Pro

<210> SEQ ID NO 1228
<211> LENGTH: 13
<212> TYPE: PRT
<213> ORGANISM: Homo sapiens

<400> SEQUENCE: 1228

Ala Gly Ala Leu Asn Ser Asn Asp Ala Phe Val Leu Lys
1               5                   10

<210> SEQ ID NO 1229
<211> LENGTH: 11
<212> TYPE: PRT
<213> ORGANISM: Homo sapiens

<400> SEQUENCE: 1229

Ala Gly Lys Glu Pro Gly Leu Gln Ile Trp Arg
1               5                   10

<210> SEQ ID NO 1230
<211> LENGTH: 7
<212> TYPE: PRT
<213> ORGANISM: Homo sapiens

<400> SEQUENCE: 1230

Ala Val Glu Val Leu Pro Lys
1               5

<210> SEQ ID NO 1231
<211> LENGTH: 16
<212> TYPE: PRT
<213> ORGANISM: Homo sapiens

<400> SEQUENCE: 1231

Asp Ser Gln Glu Glu Lys Thr Glu Ala Leu Thr Ser Ala Lys Arg
1               5                   10                  15

<210> SEQ ID NO 1232
<211> LENGTH: 18
<212> TYPE: PRT
<213> ORGANISM: Homo sapiens

<400> SEQUENCE: 1232

Glu Pro Ala His Leu Met Ser Leu Phe Gly Gly Lys Pro Met Ile Ile
1               5                   10                  15

Tyr Lys

<210> SEQ ID NO 1233
<211> LENGTH: 15
<212> TYPE: PRT
<213> ORGANISM: Homo sapiens

<400> SEQUENCE: 1233

Glu Val Gln Gly Phe Glu Ser Ala Thr Phe Leu Gly Tyr Phe Lys
1               5                   10                  15

```
<210> SEQ ID NO 1234
<211> LENGTH: 11
<212> TYPE: PRT
<213> ORGANISM: Homo sapiens

<400> SEQUENCE: 1234

His Val Val Pro Asn Glu Val Val Val Gln Arg
1               5                   10

<210> SEQ ID NO 1235
<211> LENGTH: 9
<212> TYPE: PRT
<213> ORGANISM: Homo sapiens

<400> SEQUENCE: 1235

Lys Gly Gly Val Ala Ser Gly Phe Lys
1               5

<210> SEQ ID NO 1236
<211> LENGTH: 27
<212> TYPE: PRT
<213> ORGANISM: Homo sapiens

<400> SEQUENCE: 1236

Met Leu Gln Val Leu Gly Pro Lys Pro Ala Leu Pro Ala Gly Thr Glu
1               5                   10                  15

Asp Thr Ala Lys Glu Asp Ala Ala Asn Arg Lys
            20                  25

<210> SEQ ID NO 1237
<211> LENGTH: 25
<212> TYPE: PRT
<213> ORGANISM: Homo sapiens

<400> SEQUENCE: 1237

Asn Trp Arg Asp Pro Asp Gln Thr Asp Gly Leu Gly Leu Ser Tyr Leu
1               5                   10                  15

Ser Ser His Ile Ala Asn Val Glu Arg
            20                  25

<210> SEQ ID NO 1238
<211> LENGTH: 17
<212> TYPE: PRT
<213> ORGANISM: Homo sapiens

<400> SEQUENCE: 1238

Gln Thr Gln Val Ser Val Leu Pro Glu Gly Gly Glu Thr Pro Leu Phe
1               5                   10                  15

Lys

<210> SEQ ID NO 1239
<211> LENGTH: 14
<212> TYPE: PRT
<213> ORGANISM: Homo sapiens

<400> SEQUENCE: 1239

Ser Glu Asp Cys Phe Ile Leu Asp His Gly Lys Asp Gly Lys
1               5                   10

<210> SEQ ID NO 1240
<211> LENGTH: 8
<212> TYPE: PRT
<213> ORGANISM: Homo sapiens
```

```
<400> SEQUENCE: 1240

Thr Ala Ser Asp Phe Ile Thr Lys
1               5

<210> SEQ ID NO 1241
<211> LENGTH: 7
<212> TYPE: PRT
<213> ORGANISM: Homo sapiens

<400> SEQUENCE: 1241

Thr Pro Ile Thr Val Val Lys
1               5

<210> SEQ ID NO 1242
<211> LENGTH: 18
<212> TYPE: PRT
<213> ORGANISM: Homo sapiens

<400> SEQUENCE: 1242

Thr Pro Ser Ala Ala Tyr Leu Trp Val Gly Thr Gly Ala Ser Glu Ala
1               5                   10                  15

Glu Lys

<210> SEQ ID NO 1243
<211> LENGTH: 18
<212> TYPE: PRT
<213> ORGANISM: Homo sapiens

<400> SEQUENCE: 1243

Val Pro Glu Ala Arg Pro Asn Ser Met Val Val Glu His Pro Glu Phe
1               5                   10                  15

Leu Lys

<210> SEQ ID NO 1244
<211> LENGTH: 28
<212> TYPE: PRT
<213> ORGANISM: Homo sapiens

<400> SEQUENCE: 1244

Val Pro Phe Asp Ala Ala Thr Leu His Thr Ser Thr Ala Met Ala Ala
1               5                   10                  15

Gln His Gly Met Asp Asp Asp Gly Thr Gly Gln Lys
            20                  25

<210> SEQ ID NO 1245
<211> LENGTH: 23
<212> TYPE: PRT
<213> ORGANISM: Homo sapiens

<400> SEQUENCE: 1245

Val Val Gln Gly Lys Glu Pro Ala His Leu Met Ser Leu Phe Gly Gly
1               5                   10                  15

Lys Pro Met Ile Ile Tyr Lys
            20

<210> SEQ ID NO 1246
<211> LENGTH: 9
<212> TYPE: PRT
<213> ORGANISM: Homo sapiens

<400> SEQUENCE: 1246

Tyr Ile Glu Thr Asp Pro Ala Asn Arg
1               5
```

<210> SEQ ID NO 1247
<211> LENGTH: 22
<212> TYPE: PRT
<213> ORGANISM: Homo sapiens

<400> SEQUENCE: 1247

Ser Thr Ser Ile Val Ile Met Leu Thr Asp Gly Asp Ala Asn Val Gly
1               5                   10                  15

Glu Ser Arg Pro Glu Lys
            20

<210> SEQ ID NO 1248
<211> LENGTH: 10
<212> TYPE: PRT
<213> ORGANISM: Homo sapiens

<400> SEQUENCE: 1248

Ala Arg Glu Glu His Arg Ile Pro Glu Arg
1               5                   10

<210> SEQ ID NO 1249
<211> LENGTH: 10
<212> TYPE: PRT
<213> ORGANISM: Homo sapiens

<400> SEQUENCE: 1249

Asp Tyr Ile Phe Gly Asn Tyr Ile Glu Arg
1               5                   10

<210> SEQ ID NO 1250
<211> LENGTH: 15
<212> TYPE: PRT
<213> ORGANISM: Homo sapiens

<400> SEQUENCE: 1250

Glu His Leu Val Gln Ala Thr Pro Glu Asn Leu Gln Glu Ala Arg
1               5                   10                  15

<210> SEQ ID NO 1251
<211> LENGTH: 27
<212> TYPE: PRT
<213> ORGANISM: Homo sapiens

<400> SEQUENCE: 1251

Glu Ser Pro Gly Asn Val Gln Ile Val Asn Gly Tyr Phe Val His Phe
1               5                   10                  15

Phe Ala Pro Gln Gly Leu Pro Val Val Pro Lys
            20                  25

<210> SEQ ID NO 1252
<211> LENGTH: 21
<212> TYPE: PRT
<213> ORGANISM: Homo sapiens

<400> SEQUENCE: 1252

Gly His Gly Ala Thr Asn Asp Leu Thr Phe Thr Glu Glu Val Asp Met
1               5                   10                  15

Lys Glu Met Glu Lys
            20

<210> SEQ ID NO 1253
<211> LENGTH: 13
<212> TYPE: PRT

<213> ORGANISM: Homo sapiens

<400> SEQUENCE: 1253

Gly His Val Ser Phe Lys Pro Ser Leu Asp Gln Gln Arg
1               5                   10

<210> SEQ ID NO 1254
<211> LENGTH: 7
<212> TYPE: PRT
<213> ORGANISM: Homo sapiens

<400> SEQUENCE: 1254

Gly Ile Ser Met Leu Asn Lys
1               5

<210> SEQ ID NO 1255
<211> LENGTH: 11
<212> TYPE: PRT
<213> ORGANISM: Homo sapiens

<400> SEQUENCE: 1255

Gly Met Thr Asn Ile Asn Asp Gly Leu Leu Arg
1               5                   10

<210> SEQ ID NO 1256
<211> LENGTH: 14
<212> TYPE: PRT
<213> ORGANISM: Homo sapiens

<400> SEQUENCE: 1256

Lys Gly His Val Ser Phe Lys Pro Ser Leu Asp Gln Gln Arg
1               5                   10

<210> SEQ ID NO 1257
<211> LENGTH: 10
<212> TYPE: PRT
<213> ORGANISM: Homo sapiens

<400> SEQUENCE: 1257

Leu Val Asp Glu Asp Met Asn Ser Phe Lys
1               5                   10

<210> SEQ ID NO 1258
<211> LENGTH: 14
<212> TYPE: PRT
<213> ORGANISM: Homo sapiens

<400> SEQUENCE: 1258

Leu Val Asp Glu Asp Met Asn Ser Phe Lys Ala Asp Val Lys
1               5                   10

<210> SEQ ID NO 1259
<211> LENGTH: 13
<212> TYPE: PRT
<213> ORGANISM: Homo sapiens

<400> SEQUENCE: 1259

Leu Trp Ala Tyr Leu Thr Ile Glu Gln Leu Leu Glu Lys
1               5                   10

<210> SEQ ID NO 1260
<211> LENGTH: 16
<212> TYPE: PRT
<213> ORGANISM: Homo sapiens

<400> SEQUENCE: 1260

Ser Leu Pro Glu Gly Val Ala Asn Gly Ile Glu Val Tyr Ser Thr Lys
1               5                   10                  15

<210> SEQ ID NO 1261
<211> LENGTH: 6
<212> TYPE: PRT
<213> ORGANISM: Homo sapiens

<400> SEQUENCE: 1261

Thr Ala Gly Leu Val Lys
1               5

<210> SEQ ID NO 1262
<211> LENGTH: 22
<212> TYPE: PRT
<213> ORGANISM: Homo sapiens

<400> SEQUENCE: 1262

Tyr His Phe Val Thr Pro Leu Thr Ser Met Val Val Thr Lys Pro Glu
1               5                   10                  15

Asp Asn Glu Asp Glu Arg
            20

<210> SEQ ID NO 1263
<211> LENGTH: 14
<212> TYPE: PRT
<213> ORGANISM: Homo sapiens

<400> SEQUENCE: 1263

Ala Gly Leu Leu Arg Pro Asp Tyr Ala Leu Leu Gly His Arg
1               5                   10

<210> SEQ ID NO 1264
<211> LENGTH: 32
<212> TYPE: PRT
<213> ORGANISM: Homo sapiens

<400> SEQUENCE: 1264

Glu Gly Lys Glu Tyr Gly Val Val Leu Ala Pro Asp Gly Ser Thr Val
1               5                   10                  15

Ala Val Glu Pro Leu Leu Ala Gly Leu Glu Ala Gly Leu Gln Gly Arg
            20                  25                  30

<210> SEQ ID NO 1265
<211> LENGTH: 23
<212> TYPE: PRT
<213> ORGANISM: Homo sapiens

<400> SEQUENCE: 1265

Gly Ser Gln Thr Gln Ser His Pro Asp Leu Gly Thr Glu Gly Cys Trp
1               5                   10                  15

Asp Gln Leu Ser Ala Pro Arg
            20

<210> SEQ ID NO 1266
<211> LENGTH: 15
<212> TYPE: PRT
<213> ORGANISM: Homo sapiens

<400> SEQUENCE: 1266

Gly Trp His Trp Val Gly Ala His Thr Leu Gly His Asn Ser Arg
1               5                   10                  15

```
<210> SEQ ID NO 1267
<211> LENGTH: 19
<212> TYPE: PRT
<213> ORGANISM: Homo sapiens

<400> SEQUENCE: 1267

Ser Leu Pro Leu Leu Met Asp Ser Val Ile Gln Ala Leu Ala Glu Leu
1               5                   10                  15

Glu Gln Lys

<210> SEQ ID NO 1268
<211> LENGTH: 24
<212> TYPE: PRT
<213> ORGANISM: Homo sapiens

<400> SEQUENCE: 1268

Ser Leu Pro Leu Leu Met Asp Ser Val Ile Gln Ala Leu Ala Glu Leu
1               5                   10                  15

Glu Gln Lys Val Pro Ala Ala Lys
            20

<210> SEQ ID NO 1269
<211> LENGTH: 13
<212> TYPE: PRT
<213> ORGANISM: Homo sapiens

<400> SEQUENCE: 1269

Thr Asp Cys Pro Gly Asp Ala Leu Phe Asp Leu Leu Arg
1               5                   10

<210> SEQ ID NO 1270
<211> LENGTH: 14
<212> TYPE: PRT
<213> ORGANISM: Homo sapiens

<400> SEQUENCE: 1270

Thr Trp Pro His Phe Thr Ala Thr Val Lys Pro Arg Pro Ala
1               5                   10

<210> SEQ ID NO 1271
<211> LENGTH: 18
<212> TYPE: PRT
<213> ORGANISM: Homo sapiens

<400> SEQUENCE: 1271

Ala Phe Leu Asn Gly Ala Leu Asp Gly Val Ile Leu Gly Asp Tyr Leu
1               5                   10                  15

Ser Arg

<210> SEQ ID NO 1272
<211> LENGTH: 26
<212> TYPE: PRT
<213> ORGANISM: Homo sapiens

<400> SEQUENCE: 1272

Ala Lys Ser Pro Pro Thr Met Val Asp Ser Leu Leu Ala Val Thr Leu
1               5                   10                  15

Ala Gly Asn Leu Gly Leu Thr Phe Leu Arg
            20                  25

<210> SEQ ID NO 1273
<211> LENGTH: 15
<212> TYPE: PRT
<213> ORGANISM: Homo sapiens
```

```
<400> SEQUENCE: 1273

Glu Phe Thr Glu Ala Phe Leu Gly Cys Pro Ala Ile His Pro Arg
1               5                   10                  15

<210> SEQ ID NO 1274
<211> LENGTH: 13
<212> TYPE: PRT
<213> ORGANISM: Homo sapiens

<400> SEQUENCE: 1274

Gly Cys Pro Asp Val Gln Ala Ser Leu Pro Asp Ala Lys
1               5                   10

<210> SEQ ID NO 1275
<211> LENGTH: 18
<212> TYPE: PRT
<213> ORGANISM: Homo sapiens

<400> SEQUENCE: 1275

His Thr Ala Ser Ala Trp Leu Met Ser Ala Pro Asn Ser Gly Pro His
1               5                   10                  15

Asn Arg

<210> SEQ ID NO 1276
<211> LENGTH: 22
<212> TYPE: PRT
<213> ORGANISM: Homo sapiens

<400> SEQUENCE: 1276

Pro Leu Leu Met Asp Ser Val Ile Gln Ala Leu Ala Glu Leu Glu Gln
1               5                   10                  15

Lys Val Pro Ala Ala Lys
            20

<210> SEQ ID NO 1277
<211> LENGTH: 25
<212> TYPE: PRT
<213> ORGANISM: Homo sapiens

<400> SEQUENCE: 1277

Gln Asn Gly Ala Ala Leu Thr Ser Ala Ser Ile Leu Ala Gln Gln Val
1               5                   10                  15

Trp Gly Thr Leu Val Leu Leu Gln Arg
            20                  25

<210> SEQ ID NO 1278
<211> LENGTH: 26
<212> TYPE: PRT
<213> ORGANISM: Homo sapiens

<400> SEQUENCE: 1278

Arg Gln Asn Gly Ala Ala Leu Thr Ser Ala Ser Ile Leu Ala Gln Gln
1               5                   10                  15

Val Trp Gly Thr Leu Val Leu Leu Gln Arg
            20                  25

<210> SEQ ID NO 1279
<211> LENGTH: 31
<212> TYPE: PRT
<213> ORGANISM: Homo sapiens

<400> SEQUENCE: 1279
```

Arg Val Ile Asn Leu Pro Leu Asp Ser Met Ala Ala Pro Trp Glu Thr
1               5                   10                  15

Gly Asp Thr Phe Pro Asp Val Val Ala Ile Ala Pro Asp Val Arg
            20                  25                  30

<210> SEQ ID NO 1280
<211> LENGTH: 22
<212> TYPE: PRT
<213> ORGANISM: Homo sapiens

<400> SEQUENCE: 1280

Thr Pro Glu Pro Arg Pro Ser Leu Ser His Leu Leu Ser Gln Tyr Tyr
1               5                   10                  15

Gly Ala Gly Val Ala Arg
            20

<210> SEQ ID NO 1281
<211> LENGTH: 12
<212> TYPE: PRT
<213> ORGANISM: Homo sapiens

<400> SEQUENCE: 1281

Thr Val Arg Asp Thr Leu Pro Ser Cys Ala Val Arg
1               5                   10

<210> SEQ ID NO 1282
<211> LENGTH: 7
<212> TYPE: PRT
<213> ORGANISM: Homo sapiens

<400> SEQUENCE: 1282

Trp Gly Ala Ala Pro Tyr Arg
1               5

<210> SEQ ID NO 1283
<211> LENGTH: 32
<212> TYPE: PRT
<213> ORGANISM: Homo sapiens

<400> SEQUENCE: 1283

Ala Ser Ala Ser Tyr Tyr Glu Gln Tyr His Ser Leu Asn Glu Ile Tyr
1               5                   10                  15

Ser Trp Ile Glu Phe Ile Thr Glu Arg His Pro Asp Met Leu Thr Lys
            20                  25                  30

<210> SEQ ID NO 1284
<211> LENGTH: 20
<212> TYPE: PRT
<213> ORGANISM: Homo sapiens

<400> SEQUENCE: 1284

Ala Tyr Ile Ser Met His Ser Tyr Ser Gln His Ile Val Phe Pro Tyr
1               5                   10                  15

Ser Tyr Thr Arg
            20

<210> SEQ ID NO 1285
<211> LENGTH: 12
<212> TYPE: PRT
<213> ORGANISM: Homo sapiens

<400> SEQUENCE: 1285

Phe Gln Ser Gly Gln Val Leu Ala Ala Leu Pro Arg
1               5                   10

<210> SEQ ID NO 1286
<211> LENGTH: 28
<212> TYPE: PRT
<213> ORGANISM: Homo sapiens

<400> SEQUENCE: 1286

His Trp Cys Glu Glu Gly Ala Ser Ser Ser Cys Ser Glu Thr Tyr
1               5                   10                  15

Cys Gly Leu Tyr Pro Glu Ser Glu Pro Glu Val Lys
            20                  25

<210> SEQ ID NO 1287
<211> LENGTH: 16
<212> TYPE: PRT
<213> ORGANISM: Homo sapiens

<400> SEQUENCE: 1287

Ile His Ile Gly Ser Ser Phe Glu Lys Tyr Pro Leu Tyr Val Leu Lys
1               5                   10                  15

<210> SEQ ID NO 1288
<211> LENGTH: 12
<212> TYPE: PRT
<213> ORGANISM: Homo sapiens

<400> SEQUENCE: 1288

Asn Ala Ile Trp Ile Asp Cys Gly Ile His Ala Arg
1               5                   10

<210> SEQ ID NO 1289
<211> LENGTH: 15
<212> TYPE: PRT
<213> ORGANISM: Homo sapiens

<400> SEQUENCE: 1289

Ser Phe Tyr Ala Asn Asn His Cys Ile Gly Thr Asp Leu Asn Arg
1               5                   10                  15

<210> SEQ ID NO 1290
<211> LENGTH: 16
<212> TYPE: PRT
<213> ORGANISM: Homo sapiens

<400> SEQUENCE: 1290

Ser Lys Asp His Glu Glu Leu Ser Leu Val Ala Ser Glu Ala Val Arg
1               5                   10                  15

<210> SEQ ID NO 1291
<211> LENGTH: 18
<212> TYPE: PRT
<213> ORGANISM: Homo sapiens

<400> SEQUENCE: 1291

Ser Lys Ser Lys Asp His Glu Glu Leu Ser Leu Val Ala Ser Glu Ala
1               5                   10                  15

Val Arg

<210> SEQ ID NO 1292
<211> LENGTH: 27
<212> TYPE: PRT
<213> ORGANISM: Homo sapiens

<400> SEQUENCE: 1292

Tyr Thr His Gly His Gly Ser Glu Thr Leu Tyr Leu Ala Pro Gly Gly
1               5                   10                  15

Gly Asp Asp Trp Ile Tyr Asp Leu Gly Ile Lys
            20                  25

<210> SEQ ID NO 1293
<211> LENGTH: 17
<212> TYPE: PRT
<213> ORGANISM: Homo sapiens

<400> SEQUENCE: 1293

Ala Gln Thr Thr Val Thr Cys Met Glu Asn Gly Trp Ser Pro Thr Pro
1               5                   10                  15

Arg

<210> SEQ ID NO 1294
<211> LENGTH: 10
<212> TYPE: PRT
<213> ORGANISM: Homo sapiens

<400> SEQUENCE: 1294

Cys Asn Met Gly Tyr Glu Tyr Ser Glu Arg
1               5                   10

<210> SEQ ID NO 1295
<211> LENGTH: 10
<212> TYPE: PRT
<213> ORGANISM: Homo sapiens

<400> SEQUENCE: 1295

His Gly Gly Leu Tyr His Glu Asn Met Arg
1               5                   10

<210> SEQ ID NO 1296
<211> LENGTH: 19
<212> TYPE: PRT
<213> ORGANISM: Homo sapiens

<400> SEQUENCE: 1296

Ile Val Ser Ser Ala Met Glu Pro Asp Arg Glu Tyr His Phe Gly Gln
1               5                   10                  15

Ala Val Arg

<210> SEQ ID NO 1297
<211> LENGTH: 18
<212> TYPE: PRT
<213> ORGANISM: Homo sapiens

<400> SEQUENCE: 1297

Ala Val Tyr Thr Cys Asn Glu Gly Tyr Gln Leu Leu Gly Glu Ile Asn
1               5                   10                  15

Tyr Arg

<210> SEQ ID NO 1298
<211> LENGTH: 11
<212> TYPE: PRT
<213> ORGANISM: Homo sapiens

<400> SEQUENCE: 1298

Cys Leu Pro Val Thr Ala Pro Glu Asn Gly Lys
1               5                   10

<210> SEQ ID NO 1299

<211> LENGTH: 29
<212> TYPE: PRT
<213> ORGANISM: Homo sapiens

<400> SEQUENCE: 1299

Cys Asn Met Gly Tyr Glu Tyr Ser Glu Arg Gly Asp Ala Val Cys Thr
1               5                   10                  15
Glu Ser Gly Trp Arg Pro Leu Pro Ser Cys Glu Glu Lys
            20                  25

<210> SEQ ID NO 1300
<211> LENGTH: 12
<212> TYPE: PRT
<213> ORGANISM: Homo sapiens

<400> SEQUENCE: 1300

Cys Thr Leu Lys Pro Cys Asp Tyr Pro Asp Ile Lys
1               5                   10

<210> SEQ ID NO 1301
<211> LENGTH: 11
<212> TYPE: PRT
<213> ORGANISM: Homo sapiens

<400> SEQUENCE: 1301

Cys Thr Ser Thr Gly Trp Ile Pro Ala Pro Arg
1               5                   10

<210> SEQ ID NO 1302
<211> LENGTH: 7
<212> TYPE: PRT
<213> ORGANISM: Homo sapiens

<400> SEQUENCE: 1302

Cys Val Glu Ile Ser Cys Lys
1               5

<210> SEQ ID NO 1303
<211> LENGTH: 20
<212> TYPE: PRT
<213> ORGANISM: Homo sapiens

<400> SEQUENCE: 1303

Cys Val Glu Ile Ser Cys Lys Ser Pro Asp Val Ile Asn Gly Ser Pro
1               5                   10                  15
Ile Ser Gln Lys
            20

<210> SEQ ID NO 1304
<211> LENGTH: 16
<212> TYPE: PRT
<213> ORGANISM: Homo sapiens

<400> SEQUENCE: 1304

Cys Tyr Phe Pro Tyr Leu Glu Asn Gly Tyr Asn Gln Asn Tyr Gly Arg
1               5                   10                  15

<210> SEQ ID NO 1305
<211> LENGTH: 18
<212> TYPE: PRT
<213> ORGANISM: Homo sapiens

<400> SEQUENCE: 1305

Glu Cys Asp Thr Asp Gly Trp Thr Asn Asp Ile Pro Ile Cys Glu Val
1               5                   10                  15

Val Lys

<210> SEQ ID NO 1306
<211> LENGTH: 8
<212> TYPE: PRT
<213> ORGANISM: Homo sapiens

<400> SEQUENCE: 1306

Phe Val Cys Asn Ser Gly Tyr Lys
1               5

<210> SEQ ID NO 1307
<211> LENGTH: 19
<212> TYPE: PRT
<213> ORGANISM: Homo sapiens

<400> SEQUENCE: 1307

Gly Asp Ala Val Cys Thr Glu Ser Gly Trp Arg Pro Leu Pro Ser Cys
1               5                   10                  15

Glu Glu Lys

<210> SEQ ID NO 1308
<211> LENGTH: 12
<212> TYPE: PRT
<213> ORGANISM: Homo sapiens

<400> SEQUENCE: 1308

His Arg Thr Gly Asp Glu Ile Thr Tyr Gln Cys Arg
1               5                   10

<210> SEQ ID NO 1309
<211> LENGTH: 17
<212> TYPE: PRT
<213> ORGANISM: Homo sapiens

<400> SEQUENCE: 1309

Ile Glu Gly Asp Glu Glu Met His Cys Ser Asp Asp Gly Phe Trp Ser
1               5                   10                  15

Lys

<210> SEQ ID NO 1310
<211> LENGTH: 8
<212> TYPE: PRT
<213> ORGANISM: Homo sapiens

<400> SEQUENCE: 1310

Ile Ile Tyr Lys Glu Asn Glu Arg
1               5

<210> SEQ ID NO 1311
<211> LENGTH: 17
<212> TYPE: PRT
<213> ORGANISM: Homo sapiens

<400> SEQUENCE: 1311

Lys Cys Tyr Phe Pro Tyr Leu Glu Asn Gly Tyr Asn Gln Asn Tyr Gly
1               5                   10                  15

Arg

<210> SEQ ID NO 1312
<211> LENGTH: 18
<212> TYPE: PRT
<213> ORGANISM: Homo sapiens

```
<400> SEQUENCE: 1312

Lys Cys Tyr Phe Pro Tyr Leu Glu Asn Gly Tyr Asn Gln Asn Tyr Gly
1               5                   10                  15

Arg Lys

<210> SEQ ID NO 1313
<211> LENGTH: 12
<212> TYPE: PRT
<213> ORGANISM: Homo sapiens

<400> SEQUENCE: 1313

Lys Gly Glu Trp Val Ala Leu Asn Pro Leu Arg Lys
1               5                   10

<210> SEQ ID NO 1314
<211> LENGTH: 8
<212> TYPE: PRT
<213> ORGANISM: Homo sapiens

<400> SEQUENCE: 1314

Asn Gly Phe Tyr Pro Ala Thr Arg
1               5

<210> SEQ ID NO 1315
<211> LENGTH: 23
<212> TYPE: PRT
<213> ORGANISM: Homo sapiens

<400> SEQUENCE: 1315

Asn Thr Glu Ile Leu Thr Gly Ser Trp Ser Asp Gln Thr Tyr Pro Glu
1               5                   10                  15

Gly Thr Gln Ala Ile Tyr Lys
            20

<210> SEQ ID NO 1316
<211> LENGTH: 24
<212> TYPE: PRT
<213> ORGANISM: Homo sapiens

<400> SEQUENCE: 1316

Arg Asn Thr Glu Ile Leu Thr Gly Ser Trp Ser Asp Gln Thr Tyr Pro
1               5                   10                  15

Glu Gly Thr Gln Ala Ile Tyr Lys
            20

<210> SEQ ID NO 1317
<211> LENGTH: 27
<212> TYPE: PRT
<213> ORGANISM: Homo sapiens

<400> SEQUENCE: 1317

Arg Pro Cys Gly His Pro Gly Asp Thr Pro Phe Gly Thr Phe Thr Leu
1               5                   10                  15

Thr Gly Gly Asn Val Phe Glu Tyr Gly Val Lys
            20                  25

<210> SEQ ID NO 1318
<211> LENGTH: 10
<212> TYPE: PRT
<213> ORGANISM: Homo sapiens

<400> SEQUENCE: 1318
```

Arg Pro Tyr Phe Pro Val Ala Val Gly Lys
1               5                   10

<210> SEQ ID NO 1319
<211> LENGTH: 16
<212> TYPE: PRT
<213> ORGANISM: Homo sapiens

<400> SEQUENCE: 1319

Ser Cys Asp Asn Pro Tyr Ile Pro Asn Gly Asp Tyr Ser Pro Leu Arg
1               5                   10                  15

<210> SEQ ID NO 1320
<211> LENGTH: 10
<212> TYPE: PRT
<213> ORGANISM: Homo sapiens

<400> SEQUENCE: 1320

Ser Leu Gly Asn Val Ile Met Val Cys Arg
1               5                   10

<210> SEQ ID NO 1321
<211> LENGTH: 13
<212> TYPE: PRT
<213> ORGANISM: Homo sapiens

<400> SEQUENCE: 1321

Ser Pro Asp Val Ile Asn Gly Ser Pro Ile Ser Gln Lys
1               5                   10

<210> SEQ ID NO 1322
<211> LENGTH: 36
<212> TYPE: PRT
<213> ORGANISM: Homo sapiens

<400> SEQUENCE: 1322

Tyr Tyr Ser Tyr Tyr Cys Asp Glu His Phe Glu Thr Pro Ser Gly Ser
1               5                   10                  15

Tyr Trp Asp His Ile His Cys Thr Gln Asp Gly Trp Ser Pro Ala Val
            20                  25                  30

Pro Cys Leu Arg
        35

<210> SEQ ID NO 1323
<211> LENGTH: 6
<212> TYPE: PRT
<213> ORGANISM: Homo sapiens

<400> SEQUENCE: 1323

Ala Phe Val Phe Pro Lys
1               5

<210> SEQ ID NO 1324
<211> LENGTH: 18
<212> TYPE: PRT
<213> ORGANISM: Homo sapiens

<400> SEQUENCE: 1324

Ala Leu Lys Tyr Glu Val Gln Gly Glu Val Phe Thr Lys Pro Gln Leu
1               5                   10                  15

Trp Pro

<210> SEQ ID NO 1325
<211> LENGTH: 7

<212> TYPE: PRT
<213> ORGANISM: Homo sapiens

<400> SEQUENCE: 1325

Lys Tyr Ala Phe Glu Leu Lys
1               5

<210> SEQ ID NO 1326
<211> LENGTH: 6
<212> TYPE: PRT
<213> ORGANISM: Homo sapiens

<400> SEQUENCE: 1326

Tyr Ala Phe Glu Leu Lys
1               5

<210> SEQ ID NO 1327
<211> LENGTH: 13
<212> TYPE: PRT
<213> ORGANISM: Homo sapiens

<400> SEQUENCE: 1327

Ala Gly Ala Leu Asn Ser Asn Asp Ala Phe Val Leu Lys
1               5                   10

<210> SEQ ID NO 1328
<211> LENGTH: 11
<212> TYPE: PRT
<213> ORGANISM: Homo sapiens

<400> SEQUENCE: 1328

Ala Gly Lys Glu Pro Gly Leu Gln Ile Trp Arg
1               5                   10

<210> SEQ ID NO 1329
<211> LENGTH: 7
<212> TYPE: PRT
<213> ORGANISM: Homo sapiens

<400> SEQUENCE: 1329

Ala Val Glu Val Leu Pro Lys
1               5

<210> SEQ ID NO 1330
<211> LENGTH: 16
<212> TYPE: PRT
<213> ORGANISM: Homo sapiens

<400> SEQUENCE: 1330

Asp Ser Gln Glu Glu Lys Thr Glu Ala Leu Thr Ser Ala Lys Arg
1               5                   10                  15

<210> SEQ ID NO 1331
<211> LENGTH: 18
<212> TYPE: PRT
<213> ORGANISM: Homo sapiens

<400> SEQUENCE: 1331

Glu Pro Ala His Leu Met Ser Leu Phe Gly Gly Lys Pro Met Ile Ile
1               5                   10                  15

Tyr Lys

<210> SEQ ID NO 1332
<211> LENGTH: 15
<212> TYPE: PRT

<213> ORGANISM: Homo sapiens

<400> SEQUENCE: 1332

Glu Val Gln Gly Phe Glu Ser Ala Thr Phe Leu Gly Tyr Phe Lys
1               5                   10                  15

<210> SEQ ID NO 1333
<211> LENGTH: 11
<212> TYPE: PRT
<213> ORGANISM: Homo sapiens

<400> SEQUENCE: 1333

His Val Val Pro Asn Glu Val Val Gln Arg
1               5                   10

<210> SEQ ID NO 1334
<211> LENGTH: 9
<212> TYPE: PRT
<213> ORGANISM: Homo sapiens

<400> SEQUENCE: 1334

Lys Gly Gly Val Ala Ser Gly Phe Lys
1               5

<210> SEQ ID NO 1335
<211> LENGTH: 27
<212> TYPE: PRT
<213> ORGANISM: Homo sapiens

<400> SEQUENCE: 1335

Met Leu Gln Val Leu Gly Pro Lys Pro Ala Leu Pro Ala Gly Thr Glu
1               5                   10                  15

Asp Thr Ala Lys Glu Asp Ala Ala Asn Arg Lys
            20                  25

<210> SEQ ID NO 1336
<211> LENGTH: 25
<212> TYPE: PRT
<213> ORGANISM: Homo sapiens

<400> SEQUENCE: 1336

Asn Trp Arg Asp Pro Asp Gln Thr Asp Gly Leu Gly Leu Ser Tyr Leu
1               5                   10                  15

Ser Ser His Ile Ala Asn Val Glu Arg
            20                  25

<210> SEQ ID NO 1337
<211> LENGTH: 17
<212> TYPE: PRT
<213> ORGANISM: Homo sapiens

<400> SEQUENCE: 1337

Gln Thr Gln Val Ser Val Leu Pro Glu Gly Gly Glu Thr Pro Leu Phe
1               5                   10                  15

Lys

<210> SEQ ID NO 1338
<211> LENGTH: 14
<212> TYPE: PRT
<213> ORGANISM: Homo sapiens

<400> SEQUENCE: 1338

Ser Glu Asp Cys Phe Ile Leu Asp His Gly Lys Asp Gly Lys
1               5                   10

<210> SEQ ID NO 1339
<211> LENGTH: 8
<212> TYPE: PRT
<213> ORGANISM: Homo sapiens

<400> SEQUENCE: 1339

Thr Ala Ser Asp Phe Ile Thr Lys
1               5

<210> SEQ ID NO 1340
<211> LENGTH: 7
<212> TYPE: PRT
<213> ORGANISM: Homo sapiens

<400> SEQUENCE: 1340

Thr Pro Ile Thr Val Val Lys
1               5

<210> SEQ ID NO 1341
<211> LENGTH: 18
<212> TYPE: PRT
<213> ORGANISM: Homo sapiens

<400> SEQUENCE: 1341

Thr Pro Ser Ala Ala Tyr Leu Trp Val Gly Thr Gly Ala Ser Glu Ala
1               5                   10                  15

Glu Lys

<210> SEQ ID NO 1342
<211> LENGTH: 28
<212> TYPE: PRT
<213> ORGANISM: Homo sapiens

<400> SEQUENCE: 1342

Val Pro Phe Asp Ala Ala Thr Leu His Thr Ser Thr Ala Met Ala Ala
1               5                   10                  15

Gln His Gly Met Asp Asp Asp Gly Thr Gly Gln Lys
            20                  25

<210> SEQ ID NO 1343
<211> LENGTH: 23
<212> TYPE: PRT
<213> ORGANISM: Homo sapiens

<400> SEQUENCE: 1343

Val Val Gln Gly Lys Glu Pro Ala His Leu Met Ser Leu Phe Gly Gly
1               5                   10                  15

Lys Pro Met Ile Ile Tyr Lys
            20

<210> SEQ ID NO 1344
<211> LENGTH: 9
<212> TYPE: PRT
<213> ORGANISM: Homo sapiens

<400> SEQUENCE: 1344

Tyr Ile Glu Thr Asp Pro Ala Asn Arg
1               5

<210> SEQ ID NO 1345
<211> LENGTH: 22
<212> TYPE: PRT
<213> ORGANISM: Homo sapiens

<400> SEQUENCE: 1345

Ser Thr Ser Ile Val Ile Met Leu Thr Asp Gly Asp Ala Asn Val Gly
1               5                   10                  15

Glu Ser Arg Pro Glu Lys
            20

<210> SEQ ID NO 1346
<211> LENGTH: 10
<212> TYPE: PRT
<213> ORGANISM: Homo sapiens

<400> SEQUENCE: 1346

Ala Arg Glu Glu His Arg Ile Pro Glu Arg
1               5                   10

<210> SEQ ID NO 1347
<211> LENGTH: 10
<212> TYPE: PRT
<213> ORGANISM: Homo sapiens

<400> SEQUENCE: 1347

Asp Tyr Ile Phe Gly Asn Tyr Ile Glu Arg
1               5                   10

<210> SEQ ID NO 1348
<211> LENGTH: 15
<212> TYPE: PRT
<213> ORGANISM: Homo sapiens

<400> SEQUENCE: 1348

Glu His Leu Val Gln Ala Thr Pro Glu Asn Leu Gln Glu Ala Arg
1               5                   10                  15

<210> SEQ ID NO 1349
<211> LENGTH: 27
<212> TYPE: PRT
<213> ORGANISM: Homo sapiens

<400> SEQUENCE: 1349

Glu Ser Pro Gly Asn Val Gln Ile Val Asn Gly Tyr Phe Val His Phe
1               5                   10                  15

Phe Ala Pro Gln Gly Leu Pro Val Val Pro Lys
            20                  25

<210> SEQ ID NO 1350
<211> LENGTH: 21
<212> TYPE: PRT
<213> ORGANISM: Homo sapiens

<400> SEQUENCE: 1350

Gly His Gly Ala Thr Asn Asp Leu Thr Phe Thr Glu Glu Val Asp Met
1               5                   10                  15

Lys Glu Met Glu Lys
            20

<210> SEQ ID NO 1351
<211> LENGTH: 13
<212> TYPE: PRT
<213> ORGANISM: Homo sapiens

<400> SEQUENCE: 1351

Gly His Val Ser Phe Lys Pro Ser Leu Asp Gln Gln Arg
1               5                   10

<210> SEQ ID NO 1352
<211> LENGTH: 7
<212> TYPE: PRT
<213> ORGANISM: Homo sapiens

<400> SEQUENCE: 1352

Gly Ile Ser Met Leu Asn Lys
1               5

<210> SEQ ID NO 1353
<211> LENGTH: 11
<212> TYPE: PRT
<213> ORGANISM: Homo sapiens

<400> SEQUENCE: 1353

Gly Met Thr Asn Ile Asn Asp Gly Leu Leu Arg
1               5                   10

<210> SEQ ID NO 1354
<211> LENGTH: 14
<212> TYPE: PRT
<213> ORGANISM: Homo sapiens

<400> SEQUENCE: 1354

Lys Gly His Val Ser Phe Lys Pro Ser Leu Asp Gln Gln Arg
1               5                   10

<210> SEQ ID NO 1355
<211> LENGTH: 10
<212> TYPE: PRT
<213> ORGANISM: Homo sapiens

<400> SEQUENCE: 1355

Leu Val Asp Glu Asp Met Asn Ser Phe Lys
1               5                   10

<210> SEQ ID NO 1356
<211> LENGTH: 14
<212> TYPE: PRT
<213> ORGANISM: Homo sapiens

<400> SEQUENCE: 1356

Leu Val Asp Glu Asp Met Asn Ser Phe Lys Ala Asp Val Lys
1               5                   10

<210> SEQ ID NO 1357
<211> LENGTH: 13
<212> TYPE: PRT
<213> ORGANISM: Homo sapiens

<400> SEQUENCE: 1357

Leu Trp Ala Tyr Leu Thr Ile Glu Gln Leu Leu Glu Lys
1               5                   10

<210> SEQ ID NO 1358
<211> LENGTH: 16
<212> TYPE: PRT
<213> ORGANISM: Homo sapiens

<400> SEQUENCE: 1358

Ser Leu Pro Glu Gly Val Ala Asn Gly Ile Glu Val Tyr Ser Thr Lys
1               5                   10                  15

<210> SEQ ID NO 1359

```
<211> LENGTH: 6
<212> TYPE: PRT
<213> ORGANISM: Homo sapiens

<400> SEQUENCE: 1359

Thr Ala Gly Leu Val Lys
1               5

<210> SEQ ID NO 1360
<211> LENGTH: 22
<212> TYPE: PRT
<213> ORGANISM: Homo sapiens

<400> SEQUENCE: 1360

Tyr His Phe Val Thr Pro Leu Thr Ser Met Val Val Thr Lys Pro Glu
1               5                   10                  15

Asp Asn Glu Asp Glu Arg
            20

<210> SEQ ID NO 1361
<211> LENGTH: 14
<212> TYPE: PRT
<213> ORGANISM: Homo sapiens

<400> SEQUENCE: 1361

Ala Gly Leu Leu Arg Pro Asp Tyr Ala Leu Leu Gly His Arg
1               5                   10

<210> SEQ ID NO 1362
<211> LENGTH: 32
<212> TYPE: PRT
<213> ORGANISM: Homo sapiens

<400> SEQUENCE: 1362

Glu Gly Lys Glu Tyr Gly Val Val Leu Ala Pro Asp Gly Ser Thr Val
1               5                   10                  15

Ala Val Glu Pro Leu Leu Ala Gly Leu Glu Ala Gly Leu Gln Gly Arg
            20                  25                  30

<210> SEQ ID NO 1363
<211> LENGTH: 23
<212> TYPE: PRT
<213> ORGANISM: Homo sapiens

<400> SEQUENCE: 1363

Gly Ser Gln Thr Gln Ser His Pro Asp Leu Gly Thr Glu Gly Cys Trp
1               5                   10                  15

Asp Gln Leu Ser Ala Pro Arg
            20

<210> SEQ ID NO 1364
<211> LENGTH: 15
<212> TYPE: PRT
<213> ORGANISM: Homo sapiens

<400> SEQUENCE: 1364

Gly Trp His Trp Val Gly Ala His Thr Leu Gly His Asn Ser Arg
1               5                   10                  15

<210> SEQ ID NO 1365
<211> LENGTH: 19
<212> TYPE: PRT
<213> ORGANISM: Homo sapiens

<400> SEQUENCE: 1365
```

Ser Leu Pro Leu Leu Met Asp Ser Val Ile Gln Ala Leu Ala Glu Leu
1               5                   10                  15

Glu Gln Lys

<210> SEQ ID NO 1366
<211> LENGTH: 24
<212> TYPE: PRT
<213> ORGANISM: Homo sapiens

<400> SEQUENCE: 1366

Ser Leu Pro Leu Leu Met Asp Ser Val Ile Gln Ala Leu Ala Glu Leu
1               5                   10                  15

Glu Gln Lys Val Pro Ala Ala Lys
            20

<210> SEQ ID NO 1367
<211> LENGTH: 13
<212> TYPE: PRT
<213> ORGANISM: Homo sapiens

<400> SEQUENCE: 1367

Thr Asp Cys Pro Gly Asp Ala Leu Phe Asp Leu Leu Arg
1               5                   10

<210> SEQ ID NO 1368
<211> LENGTH: 18
<212> TYPE: PRT
<213> ORGANISM: Homo sapiens

<400> SEQUENCE: 1368

Ala Phe Leu Asn Gly Ala Leu Asp Gly Val Ile Leu Gly Asp Tyr Leu
1               5                   10                  15

Ser Arg

<210> SEQ ID NO 1369
<211> LENGTH: 26
<212> TYPE: PRT
<213> ORGANISM: Homo sapiens

<400> SEQUENCE: 1369

Ala Lys Ser Pro Pro Thr Met Val Asp Ser Leu Leu Ala Val Thr Leu
1               5                   10                  15

Ala Gly Asn Leu Gly Leu Thr Phe Leu Arg
            20                  25

<210> SEQ ID NO 1370
<211> LENGTH: 15
<212> TYPE: PRT
<213> ORGANISM: Homo sapiens

<400> SEQUENCE: 1370

Glu Phe Thr Glu Ala Phe Leu Gly Cys Pro Ala Ile His Pro Arg
1               5                   10                  15

<210> SEQ ID NO 1371
<211> LENGTH: 13
<212> TYPE: PRT
<213> ORGANISM: Homo sapiens

<400> SEQUENCE: 1371

Gly Cys Pro Asp Val Gln Ala Ser Leu Pro Asp Ala Lys
1               5                   10

```
<210> SEQ ID NO 1372
<211> LENGTH: 18
<212> TYPE: PRT
<213> ORGANISM: Homo sapiens

<400> SEQUENCE: 1372

His Thr Ala Ser Ala Trp Leu Met Ser Ala Pro Asn Ser Gly Pro His
1               5                   10                  15

Asn Arg

<210> SEQ ID NO 1373
<211> LENGTH: 22
<212> TYPE: PRT
<213> ORGANISM: Homo sapiens

<400> SEQUENCE: 1373

Pro Leu Leu Met Asp Ser Val Ile Gln Ala Leu Ala Glu Leu Glu Gln
1               5                   10                  15

Lys Val Pro Ala Ala Lys
            20

<210> SEQ ID NO 1374
<211> LENGTH: 25
<212> TYPE: PRT
<213> ORGANISM: Homo sapiens

<400> SEQUENCE: 1374

Gln Asn Gly Ala Ala Leu Thr Ser Ala Ser Ile Leu Ala Gln Gln Val
1               5                   10                  15

Trp Gly Thr Leu Val Leu Leu Gln Arg
            20                  25

<210> SEQ ID NO 1375
<211> LENGTH: 26
<212> TYPE: PRT
<213> ORGANISM: Homo sapiens

<400> SEQUENCE: 1375

Arg Gln Asn Gly Ala Ala Leu Thr Ser Ala Ser Ile Leu Ala Gln Gln
1               5                   10                  15

Val Trp Gly Thr Leu Val Leu Leu Gln Arg
            20                  25

<210> SEQ ID NO 1376
<211> LENGTH: 31
<212> TYPE: PRT
<213> ORGANISM: Homo sapiens

<400> SEQUENCE: 1376

Arg Val Ile Asn Leu Pro Leu Asp Ser Met Ala Ala Pro Trp Glu Thr
1               5                   10                  15

Gly Asp Thr Phe Pro Asp Val Val Ala Ile Ala Pro Asp Val Arg
            20                  25                  30

<210> SEQ ID NO 1377
<211> LENGTH: 22
<212> TYPE: PRT
<213> ORGANISM: Homo sapiens

<400> SEQUENCE: 1377

Thr Pro Glu Pro Arg Pro Ser Leu Ser His Leu Leu Ser Gln Tyr Tyr
1               5                   10                  15
```

```
Gly Ala Gly Val Ala Arg
            20

<210> SEQ ID NO 1378
<211> LENGTH: 12
<212> TYPE: PRT
<213> ORGANISM: Homo sapiens

<400> SEQUENCE: 1378

Thr Val Arg Asp Thr Leu Pro Ser Cys Ala Val Arg
1               5                   10

<210> SEQ ID NO 1379
<211> LENGTH: 7
<212> TYPE: PRT
<213> ORGANISM: Homo sapiens

<400> SEQUENCE: 1379

Trp Gly Ala Ala Pro Tyr Arg
1               5

<210> SEQ ID NO 1380
<211> LENGTH: 8
<212> TYPE: PRT
<213> ORGANISM: Homo sapiens

<400> SEQUENCE: 1380

Phe Asn Ala Leu Gln Tyr Leu Arg
1               5

<210> SEQ ID NO 1381
<211> LENGTH: 9
<212> TYPE: PRT
<213> ORGANISM: Homo sapiens

<400> SEQUENCE: 1381

Ile Leu Gly Pro Leu Ser Tyr Ser Lys
1               5

<210> SEQ ID NO 1382
<211> LENGTH: 10
<212> TYPE: PRT
<213> ORGANISM: Homo sapiens

<400> SEQUENCE: 1382

Ile Ser Asn Ile Pro Asp Glu Tyr Phe Lys
1               5                   10

<210> SEQ ID NO 1383
<211> LENGTH: 10
<212> TYPE: PRT
<213> ORGANISM: Homo sapiens

<400> SEQUENCE: 1383

Lys Glu Asp Ala Val Ser Ala Ala Phe Lys
1               5                   10

<210> SEQ ID NO 1384
<211> LENGTH: 18
<212> TYPE: PRT
<213> ORGANISM: Homo sapiens

<400> SEQUENCE: 1384

Leu Pro Ser Gly Leu Pro Val Ser Leu Leu Thr Leu Tyr Leu Asp Asn
1               5                   10                  15
```

Asn Lys

<210> SEQ ID NO 1385
<211> LENGTH: 21
<212> TYPE: PRT
<213> ORGANISM: Homo sapiens

<400> SEQUENCE: 1385

Asn Ile Pro Thr Val Asn Glu Asn Leu Glu Asn Tyr Tyr Leu Glu Val
1               5                   10                  15

Asn Gln Leu Glu Lys
            20

<210> SEQ ID NO 1386
<211> LENGTH: 10
<212> TYPE: PRT
<213> ORGANISM: Homo sapiens

<400> SEQUENCE: 1386

Asn Asn Gln Ile Asp His Ile Asp Glu Lys
1               5                   10

<210> SEQ ID NO 1387
<211> LENGTH: 11
<212> TYPE: PRT
<213> ORGANISM: Homo sapiens

<400> SEQUENCE: 1387

Ser Leu Glu Asp Leu Gln Leu Thr His Asn Lys
1               5                   10

<210> SEQ ID NO 1388
<211> LENGTH: 14
<212> TYPE: PRT
<213> ORGANISM: Homo sapiens

<400> SEQUENCE: 1388

Ser Leu Glu Tyr Leu Asp Leu Ser Phe Asn Gln Ile Ala Arg
1               5                   10

<210> SEQ ID NO 1389
<211> LENGTH: 16
<212> TYPE: PRT
<213> ORGANISM: Homo sapiens

<400> SEQUENCE: 1389

Ala Ala Gly Asn Glu Cys Pro Glu Leu Gln Pro Pro Val His Gly Lys
1               5                   10                  15

<210> SEQ ID NO 1390
<211> LENGTH: 15
<212> TYPE: PRT
<213> ORGANISM: Homo sapiens

<400> SEQUENCE: 1390

Thr Gly Val Ile Thr Ser Pro Asp Phe Pro Asn Pro Tyr Pro Lys
1               5                   10                  15

<210> SEQ ID NO 1391
<211> LENGTH: 16
<212> TYPE: PRT
<213> ORGANISM: Homo sapiens

<400> SEQUENCE: 1391

Tyr Phe Phe Lys Asp Gln Val Leu Val Ser Cys Asp Thr Gly Tyr Lys

-continued

```
1               5                   10                  15
```

<210> SEQ ID NO 1392
<211> LENGTH: 16
<212> TYPE: PRT
<213> ORGANISM: Homo sapiens

<400> SEQUENCE: 1392

```
Ala Ala Gly Asn Glu Cys Pro Glu Leu Gln Pro Pro Val His Gly Lys
1               5                   10                  15
```

<210> SEQ ID NO 1393
<211> LENGTH: 15
<212> TYPE: PRT
<213> ORGANISM: Homo sapiens

<400> SEQUENCE: 1393

```
Thr Gly Val Ile Thr Ser Pro Asp Phe Pro Asn Pro Tyr Pro Lys
1               5                   10                  15
```

<210> SEQ ID NO 1394
<211> LENGTH: 16
<212> TYPE: PRT
<213> ORGANISM: Homo sapiens

<400> SEQUENCE: 1394

```
Tyr Phe Phe Lys Asp Gln Val Leu Val Ser Cys Asp Thr Gly Tyr Lys
1               5                   10                  15
```

<210> SEQ ID NO 1395
<211> LENGTH: 12
<212> TYPE: PRT
<213> ORGANISM: Homo sapiens

<400> SEQUENCE: 1395

```
Ala Ala Val Ser Asn Phe Gly Tyr Asp Leu Tyr Arg
1               5                   10
```

<210> SEQ ID NO 1396
<211> LENGTH: 40
<212> TYPE: PRT
<213> ORGANISM: Homo sapiens

<400> SEQUENCE: 1396

```
Ala Gly Phe Glu Trp Asn Glu Asp Gly Ala Gly Thr Thr Pro Ser Pro
1               5                   10                  15

Gly Leu Gln Pro Ala His Leu Thr Phe Pro Leu Asp Tyr His Leu Asn
            20                  25                  30

Gln Pro Phe Ile Phe Val Leu Arg
        35                  40
```

<210> SEQ ID NO 1397
<211> LENGTH: 17
<212> TYPE: PRT
<213> ORGANISM: Homo sapiens

<400> SEQUENCE: 1397

```
Ala Leu Tyr Tyr Asp Leu Ile Ser Ser Pro Asp Ile His Gly Thr Tyr
1               5                   10                  15

Lys
```

<210> SEQ ID NO 1398
<211> LENGTH: 12
<212> TYPE: PRT

<213> ORGANISM: Homo sapiens

<400> SEQUENCE: 1398

Asp Thr Asp Thr Gly Ala Leu Leu Phe Ile Gly Lys
1               5                   10

<210> SEQ ID NO 1399
<211> LENGTH: 17
<212> TYPE: PRT
<213> ORGANISM: Homo sapiens

<400> SEQUENCE: 1399

Glu Ile Pro Asp Glu Ile Ser Ile Leu Leu Leu Gly Val Ala His Phe
1               5                   10                  15

Lys

<210> SEQ ID NO 1400
<211> LENGTH: 11
<212> TYPE: PRT
<213> ORGANISM: Homo sapiens

<400> SEQUENCE: 1400

Glu Leu Leu Asp Thr Val Thr Ala Pro Gln Lys
1               5                   10

<210> SEQ ID NO 1401
<211> LENGTH: 19
<212> TYPE: PRT
<213> ORGANISM: Homo sapiens

<400> SEQUENCE: 1401

Ile Ala Gln Leu Pro Leu Thr Gly Ser Met Ser Ile Ile Phe Phe Leu
1               5                   10                  15

Pro Leu Lys

<210> SEQ ID NO 1402
<211> LENGTH: 11
<212> TYPE: PRT
<213> ORGANISM: Homo sapiens

<400> SEQUENCE: 1402

Ile Lys Ser Ser Phe Val Ala Pro Leu Glu Lys
1               5                   10

<210> SEQ ID NO 1403
<211> LENGTH: 7
<212> TYPE: PRT
<213> ORGANISM: Homo sapiens

<400> SEQUENCE: 1403

Ile Thr Gly Lys Pro Ile Lys
1               5

<210> SEQ ID NO 1404
<211> LENGTH: 14
<212> TYPE: PRT
<213> ORGANISM: Homo sapiens

<400> SEQUENCE: 1404

Ile Thr Gly Lys Pro Ile Lys Leu Thr Gln Val Glu His Arg
1               5                   10

<210> SEQ ID NO 1405
<211> LENGTH: 13

```
<212> TYPE: PRT
<213> ORGANISM: Homo sapiens

<400> SEQUENCE: 1405

Lys Thr Ser Leu Glu Asp Phe Tyr Leu Asp Glu Glu Arg
1               5                   10

<210> SEQ ID NO 1406
<211> LENGTH: 14
<212> TYPE: PRT
<213> ORGANISM: Homo sapiens

<400> SEQUENCE: 1406

Leu Ala Ala Ala Val Ser Asn Phe Gly Tyr Asp Leu Tyr Arg
1               5                   10

<210> SEQ ID NO 1407
<211> LENGTH: 15
<212> TYPE: PRT
<213> ORGANISM: Homo sapiens

<400> SEQUENCE: 1407

Leu Asp Leu Gln Glu Ile Asn Asn Trp Val Gln Ala Gln Met Lys
1               5                   10                  15

<210> SEQ ID NO 1408
<211> LENGTH: 11
<212> TYPE: PRT
<213> ORGANISM: Homo sapiens

<400> SEQUENCE: 1408

Leu Lys Leu Ser Tyr Glu Gly Glu Val Thr Lys
1               5                   10

<210> SEQ ID NO 1409
<211> LENGTH: 12
<212> TYPE: PRT
<213> ORGANISM: Homo sapiens

<400> SEQUENCE: 1409

Leu Gln Ser Leu Phe Asp Ser Pro Asp Phe Ser Lys
1               5                   10

<210> SEQ ID NO 1410
<211> LENGTH: 9
<212> TYPE: PRT
<213> ORGANISM: Homo sapiens

<400> SEQUENCE: 1410

Leu Ser Tyr Glu Gly Glu Val Thr Lys
1               5

<210> SEQ ID NO 1411
<211> LENGTH: 32
<212> TYPE: PRT
<213> ORGANISM: Homo sapiens

<400> SEQUENCE: 1411

Pro Ala Ser Pro Pro Glu Glu Gly Ser Pro Asp Pro Asp Ser Thr Gly
1               5                   10                  15

Ala Leu Val Glu Glu Asp Pro Phe Phe Lys Val Pro Val Asn Lys
                20                  25                  30

<210> SEQ ID NO 1412
<211> LENGTH: 15
```

```
<212> TYPE: PRT
<213> ORGANISM: Homo sapiens

<400> SEQUENCE: 1412

Pro Asp Glu Ile Ser Ile Leu Leu Gly Val Ala His Phe Lys
1               5                   10                  15

<210> SEQ ID NO 1413
<211> LENGTH: 30
<212> TYPE: PRT
<213> ORGANISM: Homo sapiens

<400> SEQUENCE: 1413

Ser Pro Pro Glu Glu Gly Ser Pro Asp Pro Asp Ser Thr Gly Ala Leu
1               5                   10                  15

Val Glu Glu Glu Asp Pro Phe Phe Lys Val Pro Val Asn Lys
            20                  25                  30

<210> SEQ ID NO 1414
<211> LENGTH: 9
<212> TYPE: PRT
<213> ORGANISM: Homo sapiens

<400> SEQUENCE: 1414

Ser Ser Phe Val Ala Pro Leu Glu Lys
1               5

<210> SEQ ID NO 1415
<211> LENGTH: 30
<212> TYPE: PRT
<213> ORGANISM: Homo sapiens

<400> SEQUENCE: 1415

Ser Ser Met Ser Pro Thr Thr Asn Val Leu Ser Pro Leu Ser Val
1               5                   10                  15

Ala Thr Ala Leu Ser Ala Leu Ser Leu Gly Ala Glu Gln Arg
            20                  25                  30

<210> SEQ ID NO 1416
<211> LENGTH: 7
<212> TYPE: PRT
<213> ORGANISM: Homo sapiens

<400> SEQUENCE: 1416

Thr Glu Ser Ile Ile His Arg
1               5

<210> SEQ ID NO 1417
<211> LENGTH: 10
<212> TYPE: PRT
<213> ORGANISM: Homo sapiens

<400> SEQUENCE: 1417

Thr Val Gln Ala Val Leu Thr Val Pro Lys
1               5                   10

<210> SEQ ID NO 1418
<211> LENGTH: 11
<212> TYPE: PRT
<213> ORGANISM: Homo sapiens

<400> SEQUENCE: 1418

Thr Val Arg Val Pro Met Met Ser Asp Pro Lys
1               5                   10
```

```
<210> SEQ ID NO 1419
<211> LENGTH: 10
<212> TYPE: PRT
<213> ORGANISM: Homo sapiens

<400> SEQUENCE: 1419

Tyr Gly Leu Asp Ser Asp Leu Ser Cys Lys
1               5                   10

<210> SEQ ID NO 1420
<211> LENGTH: 18
<212> TYPE: PRT
<213> ORGANISM: Homo sapiens

<400> SEQUENCE: 1420

Cys Leu Leu Phe Ser Phe Leu Pro Ala Ser Ser Ile Asn Asp Met Glu
1               5                   10                  15

Lys Arg

<210> SEQ ID NO 1421
<211> LENGTH: 9
<212> TYPE: PRT
<213> ORGANISM: Homo sapiens

<400> SEQUENCE: 1421

Leu Ser Met Asp Gly Ser Pro Thr Arg
1               5

<210> SEQ ID NO 1422
<211> LENGTH: 13
<212> TYPE: PRT
<213> ORGANISM: Homo sapiens

<400> SEQUENCE: 1422

Cys Gln Phe Phe Ser Tyr Ala Thr Gln Thr Phe His Lys
1               5                   10

<210> SEQ ID NO 1423
<211> LENGTH: 17
<212> TYPE: PRT
<213> ORGANISM: Homo sapiens

<400> SEQUENCE: 1423

Cys Gln Phe Phe Thr Tyr Ser Leu Leu Pro Glu Asp Cys Lys Glu Glu
1               5                   10                  15

Lys

<210> SEQ ID NO 1424
<211> LENGTH: 6
<212> TYPE: PRT
<213> ORGANISM: Homo sapiens

<400> SEQUENCE: 1424

Cys Thr Phe His Pro Arg
1               5

<210> SEQ ID NO 1425
<211> LENGTH: 14
<212> TYPE: PRT
<213> ORGANISM: Homo sapiens

<400> SEQUENCE: 1425

Asp Ala Cys Lys Gly Asp Ser Gly Gly Pro Leu Val Cys Lys
1               5                   10
```

```
<210> SEQ ID NO 1426
<211> LENGTH: 9
<212> TYPE: PRT
<213> ORGANISM: Homo sapiens

<400> SEQUENCE: 1426

Asp Ser Val Thr Gly Thr Leu Pro Lys
1               5

<210> SEQ ID NO 1427
<211> LENGTH: 8
<212> TYPE: PRT
<213> ORGANISM: Homo sapiens

<400> SEQUENCE: 1427

Asp Thr Pro Phe Ser Gln Ile Lys
1               5

<210> SEQ ID NO 1428
<211> LENGTH: 18
<212> TYPE: PRT
<213> ORGANISM: Homo sapiens

<400> SEQUENCE: 1428

Glu Gly Gly Lys Asp Ala Cys Lys Gly Asp Ser Gly Gly Pro Leu Val
1               5                   10                  15

Cys Lys

<210> SEQ ID NO 1429
<211> LENGTH: 11
<212> TYPE: PRT
<213> ORGANISM: Homo sapiens

<400> SEQUENCE: 1429

Glu Lys Gly Glu Ile Gln Asn Ile Leu Gln Lys
1               5                   10

<210> SEQ ID NO 1430
<211> LENGTH: 15
<212> TYPE: PRT
<213> ORGANISM: Homo sapiens

<400> SEQUENCE: 1430

Phe Gly Cys Phe Leu Lys Asp Ser Val Thr Gly Thr Leu Pro Lys
1               5                   10                  15

<210> SEQ ID NO 1431
<211> LENGTH: 13
<212> TYPE: PRT
<213> ORGANISM: Homo sapiens

<400> SEQUENCE: 1431

Gly Cys Leu Thr Gln Leu Tyr Glu Asn Ala Phe Phe Arg
1               5                   10

<210> SEQ ID NO 1432
<211> LENGTH: 18
<212> TYPE: PRT
<213> ORGANISM: Homo sapiens

<400> SEQUENCE: 1432

Gly Gly Asp Val Ala Ser Met Tyr Thr Pro Asn Ala Gln Tyr Cys Gln
1               5                   10                  15
```

Met Arg

<210> SEQ ID NO 1433
<211> LENGTH: 11
<212> TYPE: PRT
<213> ORGANISM: Homo sapiens

<400> SEQUENCE: 1433

Gly Val Asn Val Cys Gln Glu Thr Cys Thr Lys
1               5                   10

<210> SEQ ID NO 1434
<211> LENGTH: 14
<212> TYPE: PRT
<213> ORGANISM: Homo sapiens

<400> SEQUENCE: 1434

Ile Ala Tyr Gly Thr Gln Gly Ser Ser Gly Tyr Ser Leu Arg
1               5                   10

<210> SEQ ID NO 1435
<211> LENGTH: 13
<212> TYPE: PRT
<213> ORGANISM: Homo sapiens

<400> SEQUENCE: 1435

Leu Val Gly Ile Thr Ser Trp Gly Glu Gly Cys Ala Arg
1               5                   10

<210> SEQ ID NO 1436
<211> LENGTH: 7
<212> TYPE: PRT
<213> ORGANISM: Homo sapiens

<400> SEQUENCE: 1436

Met Val Cys Ala Gly Tyr Lys
1               5

<210> SEQ ID NO 1437
<211> LENGTH: 9
<212> TYPE: PRT
<213> ORGANISM: Homo sapiens

<400> SEQUENCE: 1437

Arg Glu Gln Pro Gly Val Tyr Thr Lys
1               5

<210> SEQ ID NO 1438
<211> LENGTH: 10
<212> TYPE: PRT
<213> ORGANISM: Homo sapiens

<400> SEQUENCE: 1438

Thr Gly Ala Val Ser Gly His Ser Leu Lys
1               5                   10

<210> SEQ ID NO 1439
<211> LENGTH: 26
<212> TYPE: PRT
<213> ORGANISM: Homo sapiens

<400> SEQUENCE: 1439

Thr Ser Glu Ser Gly Thr Pro Ser Ser Thr Pro Gln Glu Asn Thr
1               5                   10                  15

Ile Ser Gly Tyr Ser Leu Leu Thr Cys Lys 20                  25

<210> SEQ ID NO 1440
<211> LENGTH: 11
<212> TYPE: PRT
<213> ORGANISM: Homo sapiens

<400> SEQUENCE: 1440

Val Ala Glu Tyr Met Asp Trp Ile Leu Glu Lys
1               5                   10

<210> SEQ ID NO 1441
<211> LENGTH: 38
<212> TYPE: PRT
<213> ORGANISM: Homo sapiens

<400> SEQUENCE: 1441

Val Leu Ser Asn Val Glu Ser Gly Phe Ser Leu Lys Pro Cys Ala Leu
1               5                   10                  15

Ser Glu Ile Gly Cys His Met Asn Ile Phe Gln His Leu Ala Phe Ser
            20                  25                  30

Asp Val Asp Val Ala Arg
        35

<210> SEQ ID NO 1442
<211> LENGTH: 10
<212> TYPE: PRT
<213> ORGANISM: Homo sapiens

<400> SEQUENCE: 1442

Val Leu Thr Pro Asp Ala Phe Val Cys Arg
1               5                   10

<210> SEQ ID NO 1443
<211> LENGTH: 14
<212> TYPE: PRT
<213> ORGANISM: Homo sapiens

<400> SEQUENCE: 1443

Val Asn Ile Pro Leu Val Thr Asn Glu Glu Cys Gln Lys Arg
1               5                   10

<210> SEQ ID NO 1444
<211> LENGTH: 12
<212> TYPE: PRT
<213> ORGANISM: Homo sapiens

<400> SEQUENCE: 1444

Val Ser Glu Gly Asn His Asp Ile Ala Leu Ile Lys
1               5                   10

<210> SEQ ID NO 1445
<211> LENGTH: 10
<212> TYPE: PRT
<213> ORGANISM: Homo sapiens

<400> SEQUENCE: 1445

Val Ser Ser Val Glu Glu Cys Gln Lys Arg
1               5                   10

<210> SEQ ID NO 1446
<211> LENGTH: 11
<212> TYPE: PRT
<213> ORGANISM: Homo sapiens

```
<400> SEQUENCE: 1446

Tyr Ser Pro Gly Gly Thr Pro Thr Ala Ile Lys
1               5                   10

<210> SEQ ID NO 1447
<211> LENGTH: 10
<212> TYPE: PRT
<213> ORGANISM: Homo sapiens

<400> SEQUENCE: 1447

Ala Ile Met Glu Lys Leu Glu Met Ser Lys
1               5                   10

<210> SEQ ID NO 1448
<211> LENGTH: 10
<212> TYPE: PRT
<213> ORGANISM: Homo sapiens

<400> SEQUENCE: 1448

Asp Phe Thr Cys Val His Gln Ala Leu Lys
1               5                   10

<210> SEQ ID NO 1449
<211> LENGTH: 10
<212> TYPE: PRT
<213> ORGANISM: Homo sapiens

<400> SEQUENCE: 1449

Phe Gln Pro Thr Leu Leu Thr Leu Pro Arg
1               5                   10

<210> SEQ ID NO 1450
<211> LENGTH: 17
<212> TYPE: PRT
<213> ORGANISM: Homo sapiens

<400> SEQUENCE: 1450

Gly Val Thr Ser Val Ser Gln Ile Phe His Ser Pro Asp Leu Ala Ile
1               5                   10                  15

Arg

<210> SEQ ID NO 1451
<211> LENGTH: 16
<212> TYPE: PRT
<213> ORGANISM: Homo sapiens

<400> SEQUENCE: 1451

His Arg Leu Glu Asp Met Glu Gln Ala Leu Ser Pro Ser Val Phe Lys
1               5                   10                  15

<210> SEQ ID NO 1452
<211> LENGTH: 15
<212> TYPE: PRT
<213> ORGANISM: Homo sapiens

<400> SEQUENCE: 1452

Ile Lys Val Thr Thr Ser Gln Asp Met Leu Ser Ile Met Glu Lys
1               5                   10                  15

<210> SEQ ID NO 1453
<211> LENGTH: 29
<212> TYPE: PRT
<213> ORGANISM: Homo sapiens

<400> SEQUENCE: 1453
```

Lys Val Glu Thr Asn Met Ala Phe Ser Pro Phe Ser Ile Ala Ser Leu
1               5                   10                  15

Leu Thr Gln Val Leu Leu Gly Ala Gly Glu Asn Thr Lys
                20                  25

<210> SEQ ID NO 1454
<211> LENGTH: 13
<212> TYPE: PRT
<213> ORGANISM: Homo sapiens

<400> SEQUENCE: 1454

Lys Tyr Pro Val Ala His Phe Ile Asp Gln Thr Leu Lys
1               5                   10

<210> SEQ ID NO 1455
<211> LENGTH: 14
<212> TYPE: PRT
<213> ORGANISM: Homo sapiens

<400> SEQUENCE: 1455

Leu Glu Asp Met Glu Gln Ala Leu Ser Pro Ser Val Phe Lys
1               5                   10

<210> SEQ ID NO 1456
<211> LENGTH: 10
<212> TYPE: PRT
<213> ORGANISM: Homo sapiens

<400> SEQUENCE: 1456

Leu Leu Asp Ser Leu Pro Ser Asp Thr Arg
1               5                   10

<210> SEQ ID NO 1457
<211> LENGTH: 22
<212> TYPE: PRT
<213> ORGANISM: Homo sapiens

<400> SEQUENCE: 1457

Leu Leu Asp Ser Leu Pro Ser Asp Thr Arg Leu Val Leu Leu Asn Ala
1               5                   10                  15

Ile Tyr Leu Ser Ala Lys
                20

<210> SEQ ID NO 1458
<211> LENGTH: 12
<212> TYPE: PRT
<213> ORGANISM: Homo sapiens

<400> SEQUENCE: 1458

Leu Val Leu Leu Asn Ala Ile Tyr Leu Ser Ala Lys
1               5                   10

<210> SEQ ID NO 1459
<211> LENGTH: 9
<212> TYPE: PRT
<213> ORGANISM: Homo sapiens

<400> SEQUENCE: 1459

Leu Tyr His Ala Phe Ser Ala Met Lys
1               5

<210> SEQ ID NO 1460
<211> LENGTH: 10
<212> TYPE: PRT

<213> ORGANISM: Homo sapiens

<400> SEQUENCE: 1460

Leu Tyr His Ala Phe Ser Ala Met Lys Lys
1               5                   10

<210> SEQ ID NO 1461
<211> LENGTH: 18
<212> TYPE: PRT
<213> ORGANISM: Homo sapiens

<400> SEQUENCE: 1461

Ser Ile Ala Ser Leu Leu Thr Gln Val Leu Leu Gly Ala Gly Glu Asn
1               5                   10                  15

Thr Lys

<210> SEQ ID NO 1462
<211> LENGTH: 28
<212> TYPE: PRT
<213> ORGANISM: Homo sapiens

<400> SEQUENCE: 1462

Thr Leu Leu Val Phe Glu Val Gln Gln Pro Phe Leu Phe Val Leu Trp
1               5                   10                  15

Asp Gln Gln His Lys Phe Pro Val Phe Met Gly Arg
            20                  25

<210> SEQ ID NO 1463
<211> LENGTH: 8
<212> TYPE: PRT
<213> ORGANISM: Homo sapiens

<400> SEQUENCE: 1463

Thr Leu Tyr Ser Ser Ser Pro Arg
1               5

<210> SEQ ID NO 1464
<211> LENGTH: 21
<212> TYPE: PRT
<213> ORGANISM: Homo sapiens

<400> SEQUENCE: 1464

Thr Asn Leu Glu Ser Ile Leu Ser Tyr Pro Lys Asp Phe Thr Cys Val
1               5                   10                  15

His Gln Ala Leu Lys
            20

<210> SEQ ID NO 1465
<211> LENGTH: 8
<212> TYPE: PRT
<213> ORGANISM: Homo sapiens

<400> SEQUENCE: 1465

Val Ala Thr Thr Val Ile Ser Lys
1               5

<210> SEQ ID NO 1466
<211> LENGTH: 7
<212> TYPE: PRT
<213> ORGANISM: Homo sapiens

<400> SEQUENCE: 1466

Asp Val Val Leu Phe Glu Lys
1               5

<210> SEQ ID NO 1467
<211> LENGTH: 7
<212> TYPE: PRT
<213> ORGANISM: Homo sapiens

<400> SEQUENCE: 1467

Lys Ser Ser Ile Ile Ile Arg
1               5

<210> SEQ ID NO 1468
<211> LENGTH: 9
<212> TYPE: PRT
<213> ORGANISM: Homo sapiens

<400> SEQUENCE: 1468

Met Arg Asp Val Val Leu Phe Glu Lys
1               5

<210> SEQ ID NO 1469
<211> LENGTH: 15
<212> TYPE: PRT
<213> ORGANISM: Homo sapiens

<400> SEQUENCE: 1469

Gly Lys Glu Glu Ser Leu Asp Ser Asp Leu Tyr Ala Glu Leu Arg
1               5                   10                  15

<210> SEQ ID NO 1470
<211> LENGTH: 14
<212> TYPE: PRT
<213> ORGANISM: Homo sapiens

<400> SEQUENCE: 1470

Gly Thr His Cys Asn Gln Val Glu Val Ile Ala Thr Leu Lys
1               5                   10

<210> SEQ ID NO 1471
<211> LENGTH: 9
<212> TYPE: PRT
<213> ORGANISM: Homo sapiens

<400> SEQUENCE: 1471

Ile Cys Leu Asp Pro Asp Ala Pro Arg
1               5

<210> SEQ ID NO 1472
<211> LENGTH: 10
<212> TYPE: PRT
<213> ORGANISM: Homo sapiens

<400> SEQUENCE: 1472

Lys Ile Cys Leu Asp Pro Asp Ala Pro Arg
1               5                   10

<210> SEQ ID NO 1473
<211> LENGTH: 10
<212> TYPE: PRT
<213> ORGANISM: Homo sapiens

<400> SEQUENCE: 1473

Asn Ile Gln Ser Leu Glu Val Ile Gly Lys
1               5                   10

<210> SEQ ID NO 1474

```
<211> LENGTH: 24
<212> TYPE: PRT
<213> ORGANISM: Homo sapiens

<400> SEQUENCE: 1474

His Gln Met Asp Leu Val Ala Thr Leu Ser Gln Leu Gly Leu Gln Glu
1               5                   10                  15

Leu Phe Gln Ala Pro Asp Leu Arg
            20

<210> SEQ ID NO 1475
<211> LENGTH: 13
<212> TYPE: PRT
<213> ORGANISM: Homo sapiens

<400> SEQUENCE: 1475

Leu Gly Asn Gln Glu Pro Gly Gly Gln Thr Ala Leu Lys
1               5                   10

<210> SEQ ID NO 1476
<211> LENGTH: 10
<212> TYPE: PRT
<213> ORGANISM: Homo sapiens

<400> SEQUENCE: 1476

Asn Lys Phe Asp Pro Ser Leu Thr Gln Arg
1               5                   10

<210> SEQ ID NO 1477
<211> LENGTH: 19
<212> TYPE: PRT
<213> ORGANISM: Homo sapiens

<400> SEQUENCE: 1477

Asp Ser Phe His Leu Asp Glu Gln Phe Thr Val Pro Val Glu Met Met
1               5                   10                  15

Gln Ala Arg

<210> SEQ ID NO 1478
<211> LENGTH: 21
<212> TYPE: PRT
<213> ORGANISM: Homo sapiens

<400> SEQUENCE: 1478

Leu Gly Asn Gln Glu Pro Gly Gly Gln Thr Ala Leu Lys Ser Pro Pro
1               5                   10                  15

Gly Val Cys Ser Arg
            20

<210> SEQ ID NO 1479
<211> LENGTH: 17
<212> TYPE: PRT
<213> ORGANISM: Homo sapiens

<400> SEQUENCE: 1479

Ser Pro Pro Gly Val Cys Ser Arg Asp Pro Thr Pro Glu Gln Thr His
1               5                   10                  15

Arg

<210> SEQ ID NO 1480
<211> LENGTH: 17
<212> TYPE: PRT
<213> ORGANISM: Homo sapiens
```

<400> SEQUENCE: 1480

Trp Phe Leu Leu Glu Gln Pro Glu Ile Gln Val Ala His Phe Pro Phe
1               5                   10                  15

Lys

<210> SEQ ID NO 1481
<211> LENGTH: 28
<212> TYPE: PRT
<213> ORGANISM: Homo sapiens

<400> SEQUENCE: 1481

Gly Met Ala Asp Gln Asp Gly Leu Lys Pro Thr Ile Asp Lys Pro Ser
1               5                   10                  15

Glu Asp Ser Pro Pro Leu Glu Met Leu Gly Pro Arg
            20                  25

<210> SEQ ID NO 1482
<211> LENGTH: 25
<212> TYPE: PRT
<213> ORGANISM: Homo sapiens

<400> SEQUENCE: 1482

Ala Asp Val Gln Ala His Gly Glu Gly Gln Glu Phe Ser Ile Thr Cys
1               5                   10                  15

Leu Val Asp Glu Glu Glu Met Lys Lys
            20                  25

<210> SEQ ID NO 1483
<211> LENGTH: 12
<212> TYPE: PRT
<213> ORGANISM: Homo sapiens

<400> SEQUENCE: 1483

Glu Arg Gly His Met Leu Glu Asn His Val Glu Arg
1               5                   10

<210> SEQ ID NO 1484
<211> LENGTH: 17
<212> TYPE: PRT
<213> ORGANISM: Homo sapiens

<400> SEQUENCE: 1484

Met Ser Leu Asp Tyr Gly Phe Val Thr Pro Leu Thr Ser Met Ser Ile
1               5                   10                  15

Arg

<210> SEQ ID NO 1485
<211> LENGTH: 24
<212> TYPE: PRT
<213> ORGANISM: Homo sapiens

<400> SEQUENCE: 1485

Ala Asp Val Gln Ala His Gly Glu Gly Gln Glu Phe Ser Ile Thr Cys
1               5                   10                  15

Leu Val Asp Glu Glu Glu Met Lys
            20

<210> SEQ ID NO 1486
<211> LENGTH: 10
<212> TYPE: PRT
<213> ORGANISM: Homo sapiens

<400> SEQUENCE: 1486

```
Gly His Met Leu Glu Asn His Val Glu Arg
1               5                  10

<210> SEQ ID NO 1487
<211> LENGTH: 29
<212> TYPE: PRT
<213> ORGANISM: Homo sapiens

<400> SEQUENCE: 1487

Gly Arg Phe Pro Leu Tyr Asn Leu Gly Phe Gly His Asn Val Asp Phe
1               5                   10                  15

Asn Phe Leu Glu Val Met Ser Met Glu Asn Asn Gly Arg
            20                  25

<210> SEQ ID NO 1488
<211> LENGTH: 10
<212> TYPE: PRT
<213> ORGANISM: Homo sapiens

<400> SEQUENCE: 1488

Ile Ala Asp Asn Lys Gln Ser Ser Phe Lys
1               5                  10

<210> SEQ ID NO 1489
<211> LENGTH: 20
<212> TYPE: PRT
<213> ORGANISM: Homo sapiens

<400> SEQUENCE: 1489

Ile Tyr Glu Asp His Asp Ala Thr Gln Gln Leu Gln Gly Phe Tyr Ser
1               5                   10                  15

Gln Val Ala Lys
            20

<210> SEQ ID NO 1490
<211> LENGTH: 14
<212> TYPE: PRT
<213> ORGANISM: Homo sapiens

<400> SEQUENCE: 1490

Leu Trp Ala Tyr Leu Thr Ile Gln Glu Leu Leu Ala Lys Arg
1               5                  10

<210> SEQ ID NO 1491
<211> LENGTH: 8
<212> TYPE: PRT
<213> ORGANISM: Homo sapiens

<400> SEQUENCE: 1491

Met Lys Val Asp Arg Glu Glu Arg
1               5

<210> SEQ ID NO 1492
<211> LENGTH: 24
<212> TYPE: PRT
<213> ORGANISM: Homo sapiens

<400> SEQUENCE: 1492

Pro Leu Leu Val Asp Val Asp Leu Gln Tyr Pro Gln Asp Ala Val Leu
1               5                   10                  15

Ala Leu Thr Gln Asn His His Lys
            20
```

<210> SEQ ID NO 1493
<211> LENGTH: 23
<212> TYPE: PRT
<213> ORGANISM: Homo sapiens

<400> SEQUENCE: 1493

Cys Ser Ala Pro Glu Pro Ser Gln Lys Pro Pro Gly Lys Pro Cys Pro
1               5                   10                  15

Gly Leu Ala Tyr Glu Gln Arg
            20

<210> SEQ ID NO 1494
<211> LENGTH: 15
<212> TYPE: PRT
<213> ORGANISM: Homo sapiens

<400> SEQUENCE: 1494

Asp Pro Val Leu Cys Phe Thr Gln Tyr Glu Glu Ser Ser Gly Lys
1               5                   10                  15

<210> SEQ ID NO 1495
<211> LENGTH: 24
<212> TYPE: PRT
<213> ORGANISM: Homo sapiens

<400> SEQUENCE: 1495

Lys Cys Ser Ala Pro Glu Pro Ser Gln Lys Pro Gly Lys Pro Cys
1               5                   10                  15

Pro Gly Leu Ala Tyr Glu Gln Arg
            20

<210> SEQ ID NO 1496
<211> LENGTH: 17
<212> TYPE: PRT
<213> ORGANISM: Homo sapiens

<400> SEQUENCE: 1496

Arg Pro Cys Leu His Val Pro Ala Cys Lys Asp Pro Glu Glu Glu
1               5                   10                  15

Leu

<210> SEQ ID NO 1497
<211> LENGTH: 20
<212> TYPE: PRT
<213> ORGANISM: Homo sapiens

<400> SEQUENCE: 1497

Thr Cys Asn His Pro Val Pro Gln His Gly Gly Pro Phe Cys Ala Gly
1               5                   10                  15

Asp Ala Thr Arg
            20

<210> SEQ ID NO 1498
<211> LENGTH: 17
<212> TYPE: PRT
<213> ORGANISM: Homo sapiens

<400> SEQUENCE: 1498

Ile Thr Asp Asn Met Phe Cys Ala Gly Tyr Lys Pro Asp Glu Gly Lys
1               5                   10                  15

Arg

<210> SEQ ID NO 1499

```
<211> LENGTH: 21
<212> TYPE: PRT
<213> ORGANISM: Homo sapiens

<400> SEQUENCE: 1499

Arg Gln Glu Cys Ser Ile Pro Val Cys Gly Gln Asp Gln Val Thr Val
1               5                   10                  15

Ala Met Thr Pro Arg
            20

<210> SEQ ID NO 1500
<211> LENGTH: 20
<212> TYPE: PRT
<213> ORGANISM: Homo sapiens

<400> SEQUENCE: 1500

Asp Lys Leu Ala Ala Cys Leu Glu Gly Asn Cys Ala Glu Gly Leu Gly
1               5                   10                  15

Thr Asn Tyr Arg
            20

<210> SEQ ID NO 1501
<211> LENGTH: 11
<212> TYPE: PRT
<213> ORGANISM: Homo sapiens

<400> SEQUENCE: 1501

Glu Asn Leu Asp Arg Asp Ile Ala Leu Met Lys
1               5                   10

<210> SEQ ID NO 1502
<211> LENGTH: 15
<212> TYPE: PRT
<213> ORGANISM: Homo sapiens

<400> SEQUENCE: 1502

Gly Asp Ala Cys Glu Gly Asp Ser Gly Gly Pro Phe Val Met Lys
1               5                   10                  15

<210> SEQ ID NO 1503
<211> LENGTH: 20
<212> TYPE: PRT
<213> ORGANISM: Homo sapiens

<400> SEQUENCE: 1503

Gly Gln Pro Ser Val Leu Gln Val Val Asn Leu Pro Ile Val Glu Arg
1               5                   10                  15

Pro Val Cys Lys
            20

<210> SEQ ID NO 1504
<211> LENGTH: 16
<212> TYPE: PRT
<213> ORGANISM: Homo sapiens

<400> SEQUENCE: 1504

His Gln Asp Phe Asn Ser Ala Val Gln Leu Val Glu Asn Phe Cys Arg
1               5                   10                  15

<210> SEQ ID NO 1505
<211> LENGTH: 16
<212> TYPE: PRT
<213> ORGANISM: Homo sapiens

<400> SEQUENCE: 1505
```

Lys Ser Pro Gln Glu Leu Leu Cys Gly Ala Ser Leu Ile Ser Asp Arg
1               5                   10                  15

<210> SEQ ID NO 1506
<211> LENGTH: 18
<212> TYPE: PRT
<213> ORGANISM: Homo sapiens

<400> SEQUENCE: 1506

Leu Ala Ala Cys Leu Glu Gly Asn Cys Ala Glu Gly Leu Gly Thr Asn
1               5                   10                  15

Tyr Arg

<210> SEQ ID NO 1507
<211> LENGTH: 19
<212> TYPE: PRT
<213> ORGANISM: Homo sapiens

<400> SEQUENCE: 1507

Leu Ala Val Thr Thr His Gly Leu Pro Cys Leu Ala Trp Ala Ser Ala
1               5                   10                  15

Gln Ala Lys

<210> SEQ ID NO 1508
<211> LENGTH: 31
<212> TYPE: PRT
<213> ORGANISM: Homo sapiens

<400> SEQUENCE: 1508

Leu Lys Lys Pro Val Ala Phe Ser Asp Tyr Ile His Pro Val Cys Leu
1               5                   10                  15

Pro Asp Arg Glu Thr Ala Ala Ser Leu Leu Gln Ala Gly Tyr Lys
            20                  25                  30

<210> SEQ ID NO 1509
<211> LENGTH: 20
<212> TYPE: PRT
<213> ORGANISM: Homo sapiens

<400> SEQUENCE: 1509

Gln Glu Cys Ser Ile Pro Val Cys Gly Gln Asp Gln Val Thr Val Ala
1               5                   10                  15

Met Thr Pro Arg
            20

<210> SEQ ID NO 1510
<211> LENGTH: 19
<212> TYPE: PRT
<213> ORGANISM: Homo sapiens

<400> SEQUENCE: 1510

Ser Glu Gly Ser Ser Val Asn Leu Ser Pro Pro Leu Glu Gln Cys Val
1               5                   10                  15

Pro Asp Arg

<210> SEQ ID NO 1511
<211> LENGTH: 9
<212> TYPE: PRT
<213> ORGANISM: Homo sapiens

<400> SEQUENCE: 1511

Ser Gly Ile Glu Cys Gln Leu Trp Arg

```
1               5
```

<210> SEQ ID NO 1512
<211> LENGTH: 13
<212> TYPE: PRT
<213> ORGANISM: Homo sapiens

<400> SEQUENCE: 1512

```
Thr Ala Thr Ser Glu Tyr Gln Thr Phe Phe Asn Pro Arg
1               5                   10
```

<210> SEQ ID NO 1513
<211> LENGTH: 18
<212> TYPE: PRT
<213> ORGANISM: Homo sapiens

<400> SEQUENCE: 1513

```
Thr Phe Gly Ser Gly Glu Ala Asp Cys Gly Leu Arg Pro Leu Phe Glu
1               5                   10                  15

Lys Lys
```

<210> SEQ ID NO 1514
<211> LENGTH: 7
<212> TYPE: PRT
<213> ORGANISM: Homo sapiens

<400> SEQUENCE: 1514

```
Val Ile Asp Gln Phe Gly Glu
1               5
```

<210> SEQ ID NO 1515
<211> LENGTH: 9
<212> TYPE: PRT
<213> ORGANISM: Homo sapiens

<400> SEQUENCE: 1515

```
Tyr Gly Phe Tyr Thr His Val Phe Arg
1               5
```

<210> SEQ ID NO 1516
<211> LENGTH: 6
<212> TYPE: PRT
<213> ORGANISM: Homo sapiens

<400> SEQUENCE: 1516

```
Asp Ile Ala Leu Met Lys
1               5
```

<210> SEQ ID NO 1517
<211> LENGTH: 19
<212> TYPE: PRT
<213> ORGANISM: Homo sapiens

<400> SEQUENCE: 1517

```
Ile Arg Ile Thr Asp Asn Met Phe Cys Ala Gly Tyr Lys Pro Asp Glu
1               5                   10                  15

Gly Lys Arg
```

<210> SEQ ID NO 1518
<211> LENGTH: 16
<212> TYPE: PRT
<213> ORGANISM: Homo sapiens

<400> SEQUENCE: 1518

Ile Thr Asp Asn Met Phe Cys Ala Gly Tyr Lys Pro Asp Glu Gly Lys
1               5                   10                  15

<210> SEQ ID NO 1519
<211> LENGTH: 20
<212> TYPE: PRT
<213> ORGANISM: Homo sapiens

<400> SEQUENCE: 1519

Ile Val Glu Gly Ser Asp Ala Glu Ile Gly Met Ser Pro Trp Gln Val
1               5                   10                  15

Met Leu Phe Arg
            20

<210> SEQ ID NO 1520
<211> LENGTH: 29
<212> TYPE: PRT
<213> ORGANISM: Homo sapiens

<400> SEQUENCE: 1520

Lys Pro Val Ala Phe Ser Asp Tyr Ile His Pro Val Cys Leu Pro Asp
1               5                   10                  15

Arg Glu Thr Ala Ala Ser Leu Leu Gln Ala Gly Tyr Lys
            20                  25

<210> SEQ ID NO 1521
<211> LENGTH: 18
<212> TYPE: PRT
<213> ORGANISM: Homo sapiens

<400> SEQUENCE: 1521

Leu Ala Val Thr Thr His Gly Leu Pro Cys Leu Ala Trp Ala Ser Ala
1               5                   10                  15

Gln Ala

<210> SEQ ID NO 1522
<211> LENGTH: 19
<212> TYPE: PRT
<213> ORGANISM: Homo sapiens

<400> SEQUENCE: 1522

Leu Lys Lys Pro Val Ala Phe Ser Asp Tyr Ile His Pro Val Cys Leu
1               5                   10                  15

Pro Asp Arg

<210> SEQ ID NO 1523
<211> LENGTH: 18
<212> TYPE: PRT
<213> ORGANISM: Homo sapiens

<400> SEQUENCE: 1523

Pro Ser Val Leu Gln Val Val Asn Leu Pro Ile Val Glu Arg Pro Val
1               5                   10                  15

Cys Lys

<210> SEQ ID NO 1524
<211> LENGTH: 26
<212> TYPE: PRT
<213> ORGANISM: Homo sapiens

<400> SEQUENCE: 1524

Ser Glu Gly Ser Ser Val Asn Leu Ser Pro Pro Leu Glu Gln Cys Val
1               5                   10                  15

Pro Asp Arg Gly Gln Gln Tyr Gln Gly Arg
            20                  25

<210> SEQ ID NO 1525
<211> LENGTH: 18
<212> TYPE: PRT
<213> ORGANISM: Homo sapiens

<400> SEQUENCE: 1525

Ser Leu Glu Asp Lys Thr Glu Arg Glu Leu Glu Ser Tyr Ile Asp
1               5                   10                  15

Gly Arg

<210> SEQ ID NO 1526
<211> LENGTH: 15
<212> TYPE: PRT
<213> ORGANISM: Homo sapiens

<400> SEQUENCE: 1526

Ser Pro Gln Glu Leu Leu Cys Gly Ala Ser Leu Ile Ser Asp Arg
1               5                   10                  15

<210> SEQ ID NO 1527
<211> LENGTH: 17
<212> TYPE: PRT
<213> ORGANISM: Homo sapiens

<400> SEQUENCE: 1527

Thr Phe Gly Ser Gly Glu Ala Asp Cys Gly Leu Arg Pro Leu Phe Glu
1               5                   10                  15

Lys

<210> SEQ ID NO 1528
<211> LENGTH: 8
<212> TYPE: PRT
<213> ORGANISM: Homo sapiens

<400> SEQUENCE: 1528

Val Thr Gly Trp Gly Asn Leu Lys
1               5

<210> SEQ ID NO 1529
<211> LENGTH: 17
<212> TYPE: PRT
<213> ORGANISM: Homo sapiens

<400> SEQUENCE: 1529

Val Thr Gly Trp Gly Asn Leu Lys Glu Thr Trp Thr Ala Asn Val Gly
1               5                   10                  15

Lys

<210> SEQ ID NO 1530
<211> LENGTH: 15
<212> TYPE: PRT
<213> ORGANISM: Homo sapiens

<400> SEQUENCE: 1530

Tyr Asn Trp Arg Glu Asn Leu Asp Arg Asp Ile Ala Leu Met Lys
1               5                   10                  15

<210> SEQ ID NO 1531
<211> LENGTH: 16
<212> TYPE: PRT

```
<213> ORGANISM: Homo sapiens

<400> SEQUENCE: 1531

Ala Ala Gly Asn Glu Cys Pro Glu Leu Gln Pro Pro Val His Gly Lys
1               5                   10                  15

<210> SEQ ID NO 1532
<211> LENGTH: 15
<212> TYPE: PRT
<213> ORGANISM: Homo sapiens

<400> SEQUENCE: 1532

Thr Gly Val Ile Thr Ser Pro Asp Phe Pro Asn Pro Tyr Pro Lys
1               5                   10                  15

<210> SEQ ID NO 1533
<211> LENGTH: 16
<212> TYPE: PRT
<213> ORGANISM: Homo sapiens

<400> SEQUENCE: 1533

Tyr Phe Phe Lys Asp Gln Val Leu Val Ser Cys Asp Thr Gly Tyr Lys
1               5                   10                  15

<210> SEQ ID NO 1534
<211> LENGTH: 10
<212> TYPE: PRT
<213> ORGANISM: Homo sapiens

<400> SEQUENCE: 1534

Ala Ile Met Glu Lys Leu Glu Met Ser Lys
1               5                   10

<210> SEQ ID NO 1535
<211> LENGTH: 10
<212> TYPE: PRT
<213> ORGANISM: Homo sapiens

<400> SEQUENCE: 1535

Asp Phe Thr Cys Val His Gln Ala Leu Lys
1               5                   10

<210> SEQ ID NO 1536
<211> LENGTH: 10
<212> TYPE: PRT
<213> ORGANISM: Homo sapiens

<400> SEQUENCE: 1536

Phe Gln Pro Thr Leu Leu Thr Leu Pro Arg
1               5                   10

<210> SEQ ID NO 1537
<211> LENGTH: 17
<212> TYPE: PRT
<213> ORGANISM: Homo sapiens

<400> SEQUENCE: 1537

Gly Val Thr Ser Val Ser Gln Ile Phe His Ser Pro Asp Leu Ala Ile
1               5                   10                  15
Arg

<210> SEQ ID NO 1538
<211> LENGTH: 16
<212> TYPE: PRT
<213> ORGANISM: Homo sapiens
```

<400> SEQUENCE: 1538

His Arg Leu Glu Asp Met Glu Gln Ala Leu Ser Pro Ser Val Phe Lys
1               5                   10                  15

<210> SEQ ID NO 1539
<211> LENGTH: 15
<212> TYPE: PRT
<213> ORGANISM: Homo sapiens

<400> SEQUENCE: 1539

Ile Lys Val Thr Thr Ser Gln Asp Met Leu Ser Ile Met Glu Lys
1               5                   10                  15

<210> SEQ ID NO 1540
<211> LENGTH: 13
<212> TYPE: PRT
<213> ORGANISM: Homo sapiens

<400> SEQUENCE: 1540

Lys Tyr Pro Val Ala His Phe Ile Asp Gln Thr Leu Lys
1               5                   10

<210> SEQ ID NO 1541
<211> LENGTH: 14
<212> TYPE: PRT
<213> ORGANISM: Homo sapiens

<400> SEQUENCE: 1541

Leu Glu Asp Met Glu Gln Ala Leu Ser Pro Ser Val Phe Lys
1               5                   10

<210> SEQ ID NO 1542
<211> LENGTH: 10
<212> TYPE: PRT
<213> ORGANISM: Homo sapiens

<400> SEQUENCE: 1542

Leu Leu Asp Ser Leu Pro Ser Asp Thr Arg
1               5                   10

<210> SEQ ID NO 1543
<211> LENGTH: 22
<212> TYPE: PRT
<213> ORGANISM: Homo sapiens

<400> SEQUENCE: 1543

Leu Leu Asp Ser Leu Pro Ser Asp Thr Arg Leu Val Leu Leu Asn Ala
1               5                   10                  15
Ile Tyr Leu Ser Ala Lys
                20

<210> SEQ ID NO 1544
<211> LENGTH: 12
<212> TYPE: PRT
<213> ORGANISM: Homo sapiens

<400> SEQUENCE: 1544

Leu Val Leu Leu Asn Ala Ile Tyr Leu Ser Ala Lys
1               5                   10

<210> SEQ ID NO 1545
<211> LENGTH: 28
<212> TYPE: PRT
<213> ORGANISM: Homo sapiens

```
<400> SEQUENCE: 1545

Thr Leu Leu Val Phe Glu Val Gln Gln Pro Phe Leu Phe Val Leu Trp
1               5                   10                  15

Asp Gln Gln His Lys Phe Pro Val Phe Met Gly Arg
            20                  25

<210> SEQ ID NO 1546
<211> LENGTH: 8
<212> TYPE: PRT
<213> ORGANISM: Homo sapiens

<400> SEQUENCE: 1546

Thr Leu Tyr Ser Ser Ser Pro Arg
1               5

<210> SEQ ID NO 1547
<211> LENGTH: 21
<212> TYPE: PRT
<213> ORGANISM: Homo sapiens

<400> SEQUENCE: 1547

Thr Asn Leu Glu Ser Ile Leu Ser Tyr Pro Lys Asp Phe Thr Cys Val
1               5                   10                  15

His Gln Ala Leu Lys
            20

<210> SEQ ID NO 1548
<211> LENGTH: 22
<212> TYPE: PRT
<213> ORGANISM: Homo sapiens

<400> SEQUENCE: 1548

Lys Pro Val Asp Glu Tyr Lys Asp Cys His Leu Ala Gln Val Pro Ser
1               5                   10                  15

His Thr Val Val Ala Arg
            20

<210> SEQ ID NO 1549
<211> LENGTH: 22
<212> TYPE: PRT
<213> ORGANISM: Homo sapiens

<400> SEQUENCE: 1549

Ser Met Gly Gly Lys Glu Asp Leu Ile Trp Glu Leu Leu Asn Gln Ala
1               5                   10                  15

Gln Glu His Phe Gly Lys
            20

<210> SEQ ID NO 1550
<211> LENGTH: 15
<212> TYPE: PRT
<213> ORGANISM: Homo sapiens

<400> SEQUENCE: 1550

Ala Asp Arg Asp Gln Tyr Glu Leu Leu Cys Leu Asp Asn Thr Arg
1               5                   10                  15

<210> SEQ ID NO 1551
<211> LENGTH: 38
<212> TYPE: PRT
<213> ORGANISM: Homo sapiens

<400> SEQUENCE: 1551
```

-continued

Ala Ile Ala Ala Asn Glu Ala Asp Ala Val Thr Leu Asp Ala Gly Leu
1               5                   10                  15

Val Tyr Asp Ala Tyr Leu Ala Pro Asn Asn Leu Lys Pro Val Val Ala
            20                  25                  30

Glu Phe Tyr Gly Ser Lys
            35

<210> SEQ ID NO 1552
<211> LENGTH: 9
<212> TYPE: PRT
<213> ORGANISM: Homo sapiens

<400> SEQUENCE: 1552

Ala Pro Asn His Ala Val Val Thr Arg
1               5

<210> SEQ ID NO 1553
<211> LENGTH: 8
<212> TYPE: PRT
<213> ORGANISM: Homo sapiens

<400> SEQUENCE: 1553

Ala Ser Tyr Leu Asp Cys Ile Arg
1               5

<210> SEQ ID NO 1554
<211> LENGTH: 15
<212> TYPE: PRT
<213> ORGANISM: Homo sapiens

<400> SEQUENCE: 1554

Asp Cys His Leu Ala Gln Val Pro Ser His Thr Val Val Ala Arg
1               5                   10                  15

<210> SEQ ID NO 1555
<211> LENGTH: 10
<212> TYPE: PRT
<213> ORGANISM: Homo sapiens

<400> SEQUENCE: 1555

Asp Gly Ala Gly Asp Val Ala Phe Val Lys
1               5                   10

<210> SEQ ID NO 1556
<211> LENGTH: 8
<212> TYPE: PRT
<213> ORGANISM: Homo sapiens

<400> SEQUENCE: 1556

Asp Lys Glu Ala Cys Val His Lys
1               5

<210> SEQ ID NO 1557
<211> LENGTH: 8
<212> TYPE: PRT
<213> ORGANISM: Homo sapiens

<400> SEQUENCE: 1557

Asp Ser Ala His Gly Phe Leu Lys
1               5

<210> SEQ ID NO 1558
<211> LENGTH: 6
<212> TYPE: PRT

```
<213> ORGANISM: Homo sapiens

<400> SEQUENCE: 1558

Asp Ser Ser Leu Cys Lys
1               5

<210> SEQ ID NO 1559
<211> LENGTH: 17
<212> TYPE: PRT
<213> ORGANISM: Homo sapiens

<400> SEQUENCE: 1559

Glu Asp Leu Ile Trp Glu Leu Leu Asn Gln Ala Gln Glu His Phe Gly
1               5                   10                  15

Lys

<210> SEQ ID NO 1560
<211> LENGTH: 14
<212> TYPE: PRT
<213> ORGANISM: Homo sapiens

<400> SEQUENCE: 1560

Glu Asp Pro Gln Thr Phe Tyr Tyr Ala Val Ala Val Val Lys
1               5                   10

<210> SEQ ID NO 1561
<211> LENGTH: 11
<212> TYPE: PRT
<213> ORGANISM: Homo sapiens

<400> SEQUENCE: 1561

Glu Phe Gln Leu Phe Ser Ser Pro His Gly Lys
1               5                   10

<210> SEQ ID NO 1562
<211> LENGTH: 16
<212> TYPE: PRT
<213> ORGANISM: Homo sapiens

<400> SEQUENCE: 1562

Glu Gly Thr Cys Pro Glu Ala Pro Thr Asp Glu Cys Lys Pro Val Lys
1               5                   10                  15

<210> SEQ ID NO 1563
<211> LENGTH: 11
<212> TYPE: PRT
<213> ORGANISM: Homo sapiens

<400> SEQUENCE: 1563

Glu Gly Tyr Tyr Gly Tyr Thr Gly Ala Phe Arg
1               5                   10

<210> SEQ ID NO 1564
<211> LENGTH: 14
<212> TYPE: PRT
<213> ORGANISM: Homo sapiens

<400> SEQUENCE: 1564

Phe Asp Glu Phe Phe Ser Glu Gly Cys Ala Pro Gly Ser Lys
1               5                   10

<210> SEQ ID NO 1565
<211> LENGTH: 11
<212> TYPE: PRT
<213> ORGANISM: Homo sapiens
```

```
<400> SEQUENCE: 1565

His Gln Thr Val Pro Gln Asn Thr Gly Gly Lys
1               5                   10

<210> SEQ ID NO 1566
<211> LENGTH: 11
<212> TYPE: PRT
<213> ORGANISM: Homo sapiens

<400> SEQUENCE: 1566

His Ser Thr Ile Phe Glu Asn Leu Ala Asn Lys
1               5                   10

<210> SEQ ID NO 1567
<211> LENGTH: 15
<212> TYPE: PRT
<213> ORGANISM: Homo sapiens

<400> SEQUENCE: 1567

Leu Cys Met Gly Ser Gly Leu Asn Leu Cys Glu Pro Asn Asn Lys
1               5                   10                  15

<210> SEQ ID NO 1568
<211> LENGTH: 16
<212> TYPE: PRT
<213> ORGANISM: Homo sapiens

<400> SEQUENCE: 1568

Asn Leu Asn Glu Lys Asp Tyr Glu Leu Leu Cys Leu Asp Gly Thr Arg
1               5                   10                  15

<210> SEQ ID NO 1569
<211> LENGTH: 19
<212> TYPE: PRT
<213> ORGANISM: Homo sapiens

<400> SEQUENCE: 1569

Ser Ala Gly Trp Asn Ile Pro Ile Gly Leu Leu Tyr Cys Asp Leu Pro
1               5                   10                  15

Glu Pro Arg

<210> SEQ ID NO 1570
<211> LENGTH: 11
<212> TYPE: PRT
<213> ORGANISM: Homo sapiens

<400> SEQUENCE: 1570

Ser Ala Ser Asp Leu Thr Trp Asp Asn Leu Lys
1               5                   10

<210> SEQ ID NO 1571
<211> LENGTH: 8
<212> TYPE: PRT
<213> ORGANISM: Homo sapiens

<400> SEQUENCE: 1571

Ser Cys His Thr Gly Leu Gly Arg
1               5

<210> SEQ ID NO 1572
<211> LENGTH: 14
<212> TYPE: PRT
<213> ORGANISM: Homo sapiens
```

-continued

<400> SEQUENCE: 1572

Ser Val Ile Pro Ser Asp Gly Pro Ser Val Ala Cys Val Lys
1               5                   10

<210> SEQ ID NO 1573
<211> LENGTH: 14
<212> TYPE: PRT
<213> ORGANISM: Homo sapiens

<400> SEQUENCE: 1573

Thr Ala Gly Trp Asn Ile Pro Met Gly Leu Leu Tyr Asn Lys
1               5                   10

<210> SEQ ID NO 1574
<211> LENGTH: 11
<212> TYPE: PRT
<213> ORGANISM: Homo sapiens

<400> SEQUENCE: 1574

Trp Cys Ala Val Ser Glu His Glu Ala Thr Lys
1               5                   10

<210> SEQ ID NO 1575
<211> LENGTH: 8
<212> TYPE: PRT
<213> ORGANISM: Homo sapiens

<400> SEQUENCE: 1575

Tyr Leu Gly Glu Glu Tyr Val Lys
1               5

<210> SEQ ID NO 1576
<211> LENGTH: 15
<212> TYPE: PRT
<213> ORGANISM: Homo sapiens

<400> SEQUENCE: 1576

Phe Thr Val Asp Arg Pro Phe Leu Phe Leu Ile Tyr Glu His Arg
1               5                   10                  15

<210> SEQ ID NO 1577
<211> LENGTH: 18
<212> TYPE: PRT
<213> ORGANISM: Homo sapiens

<400> SEQUENCE: 1577

Gly Ser Trp Val Asn Lys Phe Pro Val Glu Met Thr His Asn His Asn
1               5                   10                  15

Phe Arg

<210> SEQ ID NO 1578
<211> LENGTH: 15
<212> TYPE: PRT
<213> ORGANISM: Homo sapiens

<400> SEQUENCE: 1578

Leu Phe Asp Lys Asn Gly Asn Met Ala Gly Ile Ser Asp Gln Arg
1               5                   10                  15

<210> SEQ ID NO 1579
<211> LENGTH: 7
<212> TYPE: PRT
<213> ORGANISM: Homo sapiens

<400> SEQUENCE: 1579

Asn Phe Gly Tyr Thr Leu Arg
1               5

<210> SEQ ID NO 1580
<211> LENGTH: 9
<212> TYPE: PRT
<213> ORGANISM: Homo sapiens

<400> SEQUENCE: 1580

Ser Val Asn Asp Leu Tyr Ile Gln Lys
1               5

<210> SEQ ID NO 1581
<211> LENGTH: 13
<212> TYPE: PRT
<213> ORGANISM: Homo sapiens

<400> SEQUENCE: 1581

Thr Arg Glu Val Leu Leu Pro Lys Phe Lys Leu Glu Lys
1               5                   10

<210> SEQ ID NO 1582
<211> LENGTH: 19
<212> TYPE: PRT
<213> ORGANISM: Homo sapiens

<400> SEQUENCE: 1582

Glu Leu Lys Glu Gln Gln Asp Ser Pro Gly Asn Lys Asp Phe Leu Gln
1               5                   10                  15

Ser Leu Lys

<210> SEQ ID NO 1583
<211> LENGTH: 24
<212> TYPE: PRT
<213> ORGANISM: Homo sapiens

<400> SEQUENCE: 1583

His Gln Met Asp Leu Val Ala Thr Leu Ser Gln Leu Gly Leu Gln Glu
1               5                   10                  15

Leu Phe Gln Ala Pro Asp Leu Arg
            20

<210> SEQ ID NO 1584
<211> LENGTH: 13
<212> TYPE: PRT
<213> ORGANISM: Homo sapiens

<400> SEQUENCE: 1584

Leu Gly Asn Gln Glu Pro Gly Gly Gln Thr Ala Leu Lys
1               5                   10

<210> SEQ ID NO 1585
<211> LENGTH: 19
<212> TYPE: PRT
<213> ORGANISM: Homo sapiens

<400> SEQUENCE: 1585

Leu Gln Gln Val Leu His Ala Gly Ser Gly Pro Cys Leu Pro His Leu
1               5                   10                  15

Leu Ser Arg

<210> SEQ ID NO 1586
<211> LENGTH: 16

-continued

```
<212> TYPE: PRT
<213> ORGANISM: Homo sapiens

<400> SEQUENCE: 1586

Leu Val Pro Pro Met Glu Glu Asp Tyr Pro Gln Phe Gly Ser Pro Lys
1               5                   10                  15

<210> SEQ ID NO 1587
<211> LENGTH: 10
<212> TYPE: PRT
<213> ORGANISM: Homo sapiens

<400> SEQUENCE: 1587

Asn Lys Phe Asp Pro Ser Leu Thr Gln Arg
1               5                   10

<210> SEQ ID NO 1588
<211> LENGTH: 19
<212> TYPE: PRT
<213> ORGANISM: Homo sapiens

<400> SEQUENCE: 1588

Asp Ser Phe His Leu Asp Glu Gln Phe Thr Val Pro Val Glu Met Met
1               5                   10                  15

Gln Ala Arg

<210> SEQ ID NO 1589
<211> LENGTH: 10
<212> TYPE: PRT
<213> ORGANISM: Homo sapiens

<400> SEQUENCE: 1589

Gly Asp Lys Leu Phe Gly Pro Asp Leu Lys
1               5                   10

<210> SEQ ID NO 1590
<211> LENGTH: 27
<212> TYPE: PRT
<213> ORGANISM: Homo sapiens

<400> SEQUENCE: 1590

Ile Gln Glu Phe Leu Ser Gly Leu Pro Glu Asp Thr Val Leu Leu Leu
1               5                   10                  15

Leu Asn Ala Ile His Phe Gln Gly Phe Trp Arg
            20                  25

<210> SEQ ID NO 1591
<211> LENGTH: 11
<212> TYPE: PRT
<213> ORGANISM: Homo sapiens

<400> SEQUENCE: 1591

Leu Cys Gln Asp Leu Gly Pro Gly Ala Phe Arg
1               5                   10

<210> SEQ ID NO 1592
<211> LENGTH: 7
<212> TYPE: PRT
<213> ORGANISM: Homo sapiens

<400> SEQUENCE: 1592

Leu Phe Gly Pro Asp Leu Lys
1               5
```

```
<210> SEQ ID NO 1593
<211> LENGTH: 21
<212> TYPE: PRT
<213> ORGANISM: Homo sapiens

<400> SEQUENCE: 1593

Leu Gly Asn Gln Glu Pro Gly Gly Gln Thr Ala Leu Lys Ser Pro Pro
1               5                   10                  15

Gly Val Cys Ser Arg
            20

<210> SEQ ID NO 1594
<211> LENGTH: 31
<212> TYPE: PRT
<213> ORGANISM: Homo sapiens

<400> SEQUENCE: 1594

Met Ser Leu Ser Ser Phe Ser Val Asn Arg Pro Phe Leu Phe Phe Ile
1               5                   10                  15

Phe Glu Asp Thr Thr Gly Leu Pro Leu Phe Val Gly Ser Val Arg
            20                  25                  30

<210> SEQ ID NO 1595
<211> LENGTH: 17
<212> TYPE: PRT
<213> ORGANISM: Homo sapiens

<400> SEQUENCE: 1595

Ser Pro Pro Gly Val Cys Ser Arg Asp Pro Thr Pro Glu Gln Thr His
1               5                   10                  15

Arg

<210> SEQ ID NO 1596
<211> LENGTH: 17
<212> TYPE: PRT
<213> ORGANISM: Homo sapiens

<400> SEQUENCE: 1596

Trp Phe Leu Leu Glu Gln Pro Glu Ile Gln Val Ala His Phe Pro Phe
1               5                   10                  15

Lys

<210> SEQ ID NO 1597
<211> LENGTH: 13
<212> TYPE: PRT
<213> ORGANISM: Homo sapiens

<400> SEQUENCE: 1597

Ala Ala Asp Asp Thr Trp Glu Pro Phe Ala Ser Gly Lys
1               5                   10

<210> SEQ ID NO 1598
<211> LENGTH: 12
<212> TYPE: PRT
<213> ORGANISM: Homo sapiens

<400> SEQUENCE: 1598

Ala Asp Asp Thr Trp Glu Pro Phe Ala Ser Gly Lys
1               5                   10

<210> SEQ ID NO 1599
<211> LENGTH: 23
<212> TYPE: PRT
<213> ORGANISM: Homo sapiens
```

```
<400> SEQUENCE: 1599

Ala Leu Gly Ile Ser Pro Phe His Glu His Ala Glu Val Val Phe Thr
1               5                   10                  15

Ala Asn Asp Ser Gly Pro Arg
            20

<210> SEQ ID NO 1600
<211> LENGTH: 6
<212> TYPE: PRT
<213> ORGANISM: Homo sapiens

<400> SEQUENCE: 1600

Cys Pro Leu Met Val Lys
1               5

<210> SEQ ID NO 1601
<211> LENGTH: 15
<212> TYPE: PRT
<213> ORGANISM: Homo sapiens

<400> SEQUENCE: 1601

Gly Pro Thr Gly Thr Gly Glu Ser Lys Cys Pro Leu Met Val Lys
1               5                   10                  15

<210> SEQ ID NO 1602
<211> LENGTH: 14
<212> TYPE: PRT
<213> ORGANISM: Homo sapiens

<400> SEQUENCE: 1602

Gly Ser Pro Ala Ile Asn Val Ala Val His Val Phe Arg Lys
1               5                   10

<210> SEQ ID NO 1603
<211> LENGTH: 24
<212> TYPE: PRT
<213> ORGANISM: Homo sapiens

<400> SEQUENCE: 1603

Arg Tyr Thr Ile Ala Ala Leu Leu Ser Pro Tyr Ser Tyr Ser Thr Thr
1               5                   10                  15

Ala Val Val Thr Asn Pro Lys Glu
            20

<210> SEQ ID NO 1604
<211> LENGTH: 22
<212> TYPE: PRT
<213> ORGANISM: Homo sapiens

<400> SEQUENCE: 1604

Thr Ser Glu Ser Gly Glu Leu His Gly Leu Thr Thr Glu Glu Glu Phe
1               5                   10                  15

Val Glu Gly Ile Tyr Lys
            20

<210> SEQ ID NO 1605
<211> LENGTH: 13
<212> TYPE: PRT
<213> ORGANISM: Homo sapiens

<400> SEQUENCE: 1605

Ala Ala Asp Asp Thr Trp Glu Pro Phe Ala Ser Gly Lys
1               5                   10
```

<210> SEQ ID NO 1606
<211> LENGTH: 12
<212> TYPE: PRT
<213> ORGANISM: Homo sapiens

<400> SEQUENCE: 1606

Ala Asp Asp Thr Trp Glu Pro Phe Ala Ser Gly Lys
1               5                   10

<210> SEQ ID NO 1607
<211> LENGTH: 23
<212> TYPE: PRT
<213> ORGANISM: Homo sapiens

<400> SEQUENCE: 1607

Ala Leu Gly Ile Ser Pro Phe His Glu His Ala Glu Val Val Phe Thr
1               5                   10                  15

Ala Asn Asp Ser Gly Pro Arg
            20

<210> SEQ ID NO 1608
<211> LENGTH: 6
<212> TYPE: PRT
<213> ORGANISM: Homo sapiens

<400> SEQUENCE: 1608

Cys Pro Leu Met Val Lys
1               5

<210> SEQ ID NO 1609
<211> LENGTH: 15
<212> TYPE: PRT
<213> ORGANISM: Homo sapiens

<400> SEQUENCE: 1609

Gly Pro Thr Gly Thr Gly Glu Ser Lys Cys Pro Leu Met Val Lys
1               5                   10                  15

<210> SEQ ID NO 1610
<211> LENGTH: 14
<212> TYPE: PRT
<213> ORGANISM: Homo sapiens

<400> SEQUENCE: 1610

Gly Ser Pro Ala Ile Asn Val Ala Val His Val Phe Arg Lys
1               5                   10

<210> SEQ ID NO 1611
<211> LENGTH: 24
<212> TYPE: PRT
<213> ORGANISM: Homo sapiens

<400> SEQUENCE: 1611

Arg Tyr Thr Ile Ala Ala Leu Leu Ser Pro Tyr Ser Tyr Ser Thr Thr
1               5                   10                  15

Ala Val Val Thr Asn Pro Lys Glu
            20

<210> SEQ ID NO 1612
<211> LENGTH: 22
<212> TYPE: PRT
<213> ORGANISM: Homo sapiens

<400> SEQUENCE: 1612

Thr Ser Glu Ser Gly Glu Leu His Gly Leu Thr Thr Glu Glu Phe
1               5                   10                  15

Val Glu Gly Ile Tyr Lys
            20

<210> SEQ ID NO 1613
<211> LENGTH: 10
<212> TYPE: PRT
<213> ORGANISM: Homo sapiens

<400> SEQUENCE: 1613

Ala Gly Glu Val Gln Glu Pro Glu Leu Arg
1               5                   10

<210> SEQ ID NO 1614
<211> LENGTH: 10
<212> TYPE: PRT
<213> ORGANISM: Homo sapiens

<400> SEQUENCE: 1614

Cys Leu Ala Tyr Asp Phe Tyr Pro Gly Lys
1               5                   10

<210> SEQ ID NO 1615
<211> LENGTH: 21
<212> TYPE: PRT
<213> ORGANISM: Homo sapiens

<400> SEQUENCE: 1615

His Val Glu Asp Val Pro Ala Phe Gln Ala Leu Gly Ser Leu Asn Asp
1               5                   10                  15

Leu Gln Phe Phe Arg
            20

<210> SEQ ID NO 1616
<211> LENGTH: 7
<212> TYPE: PRT
<213> ORGANISM: Homo sapiens

<400> SEQUENCE: 1616

Ile Asp Val His Trp Thr Arg
1               5

<210> SEQ ID NO 1617
<211> LENGTH: 16
<212> TYPE: PRT
<213> ORGANISM: Homo sapiens

<400> SEQUENCE: 1617

Gln Val Glu Gly Met Glu Asp Trp Lys Gln Asp Ser Gln Leu Gln Lys
1               5                   10                  15

<210> SEQ ID NO 1618
<211> LENGTH: 12
<212> TYPE: PRT
<213> ORGANISM: Homo sapiens

<400> SEQUENCE: 1618

Tyr Ser Leu Thr Tyr Ile Tyr Thr Gly Leu Ser Lys
1               5                   10

<210> SEQ ID NO 1619
<211> LENGTH: 17
<212> TYPE: PRT

<213> ORGANISM: Homo sapiens

<400> SEQUENCE: 1619

Ala Gln Thr Thr Val Thr Cys Met Glu Asn Gly Trp Ser Pro Thr Pro
1               5                   10                  15

Arg

<210> SEQ ID NO 1620
<211> LENGTH: 10
<212> TYPE: PRT
<213> ORGANISM: Homo sapiens

<400> SEQUENCE: 1620

Cys Asn Met Gly Tyr Glu Tyr Ser Glu Arg
1               5                   10

<210> SEQ ID NO 1621
<211> LENGTH: 10
<212> TYPE: PRT
<213> ORGANISM: Homo sapiens

<400> SEQUENCE: 1621

His Gly Gly Leu Tyr His Glu Asn Met Arg
1               5                   10

<210> SEQ ID NO 1622
<211> LENGTH: 18
<212> TYPE: PRT
<213> ORGANISM: Homo sapiens

<400> SEQUENCE: 1622

Ala Val Tyr Thr Cys Asn Glu Gly Tyr Gln Leu Leu Gly Glu Ile Asn
1               5                   10                  15

Tyr Arg

<210> SEQ ID NO 1623
<211> LENGTH: 29
<212> TYPE: PRT
<213> ORGANISM: Homo sapiens

<400> SEQUENCE: 1623

Cys Asn Met Gly Tyr Glu Tyr Ser Glu Arg Gly Asp Ala Val Cys Thr
1               5                   10                  15

Glu Ser Gly Trp Arg Pro Leu Pro Ser Cys Glu Glu Lys
                20                  25

<210> SEQ ID NO 1624
<211> LENGTH: 12
<212> TYPE: PRT
<213> ORGANISM: Homo sapiens

<400> SEQUENCE: 1624

Cys Thr Leu Lys Pro Cys Asp Tyr Pro Asp Ile Lys
1               5                   10

<210> SEQ ID NO 1625
<211> LENGTH: 11
<212> TYPE: PRT
<213> ORGANISM: Homo sapiens

<400> SEQUENCE: 1625

Cys Thr Ser Thr Gly Trp Ile Pro Ala Pro Arg
1               5                   10

<210> SEQ ID NO 1626
<211> LENGTH: 19
<212> TYPE: PRT
<213> ORGANISM: Homo sapiens

<400> SEQUENCE: 1626

Gly Asp Ala Val Cys Thr Glu Ser Gly Trp Arg Pro Leu Pro Ser Cys
1               5                   10                  15

Glu Glu Lys

<210> SEQ ID NO 1627
<211> LENGTH: 12
<212> TYPE: PRT
<213> ORGANISM: Homo sapiens

<400> SEQUENCE: 1627

His Arg Thr Gly Asp Glu Ile Thr Tyr Gln Cys Arg
1               5                   10

<210> SEQ ID NO 1628
<211> LENGTH: 8
<212> TYPE: PRT
<213> ORGANISM: Homo sapiens

<400> SEQUENCE: 1628

Ile Ile Tyr Lys Glu Asn Glu Arg
1               5

<210> SEQ ID NO 1629
<211> LENGTH: 12
<212> TYPE: PRT
<213> ORGANISM: Homo sapiens

<400> SEQUENCE: 1629

Lys Gly Glu Trp Val Ala Leu Asn Pro Leu Arg Lys
1               5                   10

<210> SEQ ID NO 1630
<211> LENGTH: 8
<212> TYPE: PRT
<213> ORGANISM: Homo sapiens

<400> SEQUENCE: 1630

Asn Gly Phe Tyr Pro Ala Thr Arg
1               5

<210> SEQ ID NO 1631
<211> LENGTH: 23
<212> TYPE: PRT
<213> ORGANISM: Homo sapiens

<400> SEQUENCE: 1631

Asn Thr Glu Ile Leu Thr Gly Ser Trp Ser Asp Gln Thr Tyr Pro Glu
1               5                   10                  15

Gly Thr Gln Ala Ile Tyr Lys
            20

<210> SEQ ID NO 1632
<211> LENGTH: 24
<212> TYPE: PRT
<213> ORGANISM: Homo sapiens

<400> SEQUENCE: 1632

Arg Asn Thr Glu Ile Leu Thr Gly Ser Trp Ser Asp Gln Thr Tyr Pro

```
                1               5                  10                 15
Glu Gly Thr Gln Ala Ile Tyr Lys
                20
```

<210> SEQ ID NO 1633
<211> LENGTH: 27
<212> TYPE: PRT
<213> ORGANISM: Homo sapiens

<400> SEQUENCE: 1633

```
Arg Pro Cys Gly His Pro Gly Asp Thr Pro Phe Gly Thr Phe Thr Leu
1               5                   10                  15
Thr Gly Gly Asn Val Phe Glu Tyr Gly Val Lys
                20                  25
```

<210> SEQ ID NO 1634
<211> LENGTH: 10
<212> TYPE: PRT
<213> ORGANISM: Homo sapiens

<400> SEQUENCE: 1634

```
Arg Pro Tyr Phe Pro Val Ala Val Gly Lys
1               5                   10
```

<210> SEQ ID NO 1635
<211> LENGTH: 16
<212> TYPE: PRT
<213> ORGANISM: Homo sapiens

<400> SEQUENCE: 1635

```
Ser Cys Asp Asn Pro Tyr Ile Pro Asn Gly Asp Tyr Ser Pro Leu Arg
1               5                   10                  15
```

<210> SEQ ID NO 1636
<211> LENGTH: 10
<212> TYPE: PRT
<213> ORGANISM: Homo sapiens

<400> SEQUENCE: 1636

```
Ser Leu Gly Asn Val Ile Met Val Cys Arg
1               5                   10
```

<210> SEQ ID NO 1637
<211> LENGTH: 13
<212> TYPE: PRT
<213> ORGANISM: Homo sapiens

<400> SEQUENCE: 1637

```
Ser Pro Asp Val Ile Asn Gly Ser Pro Ile Ser Gln Lys
1               5                   10
```

<210> SEQ ID NO 1638
<211> LENGTH: 36
<212> TYPE: PRT
<213> ORGANISM: Homo sapiens

<400> SEQUENCE: 1638

```
Tyr Tyr Ser Tyr Tyr Cys Asp Glu His Phe Glu Thr Pro Ser Gly Ser
1               5                   10                  15
Tyr Trp Asp His Ile His Cys Thr Gln Asp Gly Trp Ser Pro Ala Val
                20                  25                  30
Pro Cys Leu Arg
        35
```

```
<210> SEQ ID NO 1639
<211> LENGTH: 10
<212> TYPE: PRT
<213> ORGANISM: Homo sapiens

<400> SEQUENCE: 1639

Ala Gly Glu Val Gln Glu Pro Glu Leu Arg
1               5                   10

<210> SEQ ID NO 1640
<211> LENGTH: 10
<212> TYPE: PRT
<213> ORGANISM: Homo sapiens

<400> SEQUENCE: 1640

Cys Leu Ala Tyr Asp Phe Tyr Pro Gly Lys
1               5                   10

<210> SEQ ID NO 1641
<211> LENGTH: 7
<212> TYPE: PRT
<213> ORGANISM: Homo sapiens

<400> SEQUENCE: 1641

Ile Asp Val His Trp Thr Arg
1               5

<210> SEQ ID NO 1642
<211> LENGTH: 22
<212> TYPE: PRT
<213> ORGANISM: Homo sapiens

<400> SEQUENCE: 1642

Ser Thr Ser Ile Val Ile Met Leu Thr Asp Gly Asp Ala Asn Val Gly
1               5                   10                  15

Glu Ser Arg Pro Glu Lys
            20

<210> SEQ ID NO 1643
<211> LENGTH: 10
<212> TYPE: PRT
<213> ORGANISM: Homo sapiens

<400> SEQUENCE: 1643

Ala Arg Glu Glu His Arg Ile Pro Glu Arg
1               5                   10

<210> SEQ ID NO 1644
<211> LENGTH: 10
<212> TYPE: PRT
<213> ORGANISM: Homo sapiens

<400> SEQUENCE: 1644

Asp Tyr Ile Phe Gly Asn Tyr Ile Glu Arg
1               5                   10

<210> SEQ ID NO 1645
<211> LENGTH: 15
<212> TYPE: PRT
<213> ORGANISM: Homo sapiens

<400> SEQUENCE: 1645

Glu His Leu Val Gln Ala Thr Pro Glu Asn Leu Gln Glu Ala Arg
1               5                   10                  15
```

-continued

<210> SEQ ID NO 1646
<211> LENGTH: 27
<212> TYPE: PRT
<213> ORGANISM: Homo sapiens

<400> SEQUENCE: 1646

Glu Ser Pro Gly Asn Val Gln Ile Val Asn Gly Tyr Phe Val His Phe
1               5                   10                  15

Phe Ala Pro Gln Gly Leu Pro Val Val Pro Lys
            20                  25

<210> SEQ ID NO 1647
<211> LENGTH: 21
<212> TYPE: PRT
<213> ORGANISM: Homo sapiens

<400> SEQUENCE: 1647

Gly His Gly Ala Thr Asn Asp Leu Thr Phe Thr Glu Glu Val Asp Met
1               5                   10                  15

Lys Glu Met Glu Lys
            20

<210> SEQ ID NO 1648
<211> LENGTH: 13
<212> TYPE: PRT
<213> ORGANISM: Homo sapiens

<400> SEQUENCE: 1648

Gly His Val Ser Phe Lys Pro Ser Leu Asp Gln Gln Arg
1               5                   10

<210> SEQ ID NO 1649
<211> LENGTH: 7
<212> TYPE: PRT
<213> ORGANISM: Homo sapiens

<400> SEQUENCE: 1649

Gly Ile Ser Met Leu Asn Lys
1               5

<210> SEQ ID NO 1650
<211> LENGTH: 11
<212> TYPE: PRT
<213> ORGANISM: Homo sapiens

<400> SEQUENCE: 1650

Gly Met Thr Asn Ile Asn Asp Gly Leu Leu Arg
1               5                   10

<210> SEQ ID NO 1651
<211> LENGTH: 14
<212> TYPE: PRT
<213> ORGANISM: Homo sapiens

<400> SEQUENCE: 1651

Lys Gly His Val Ser Phe Lys Pro Ser Leu Asp Gln Gln Arg
1               5                   10

<210> SEQ ID NO 1652
<211> LENGTH: 10
<212> TYPE: PRT
<213> ORGANISM: Homo sapiens

<400> SEQUENCE: 1652

```
Leu Val Asp Glu Asp Met Asn Ser Phe Lys
1               5                   10
```

<210> SEQ ID NO 1653
<211> LENGTH: 14
<212> TYPE: PRT
<213> ORGANISM: Homo sapiens

<400> SEQUENCE: 1653

```
Leu Val Asp Glu Asp Met Asn Ser Phe Lys Ala Asp Val Lys
1               5                   10
```

<210> SEQ ID NO 1654
<211> LENGTH: 13
<212> TYPE: PRT
<213> ORGANISM: Homo sapiens

<400> SEQUENCE: 1654

```
Leu Trp Ala Tyr Leu Thr Ile Glu Gln Leu Leu Glu Lys
1               5                   10
```

<210> SEQ ID NO 1655
<211> LENGTH: 16
<212> TYPE: PRT
<213> ORGANISM: Homo sapiens

<400> SEQUENCE: 1655

```
Ser Leu Pro Glu Gly Val Ala Asn Gly Ile Glu Val Tyr Ser Thr Lys
1               5                   10                  15
```

<210> SEQ ID NO 1656
<211> LENGTH: 6
<212> TYPE: PRT
<213> ORGANISM: Homo sapiens

<400> SEQUENCE: 1656

```
Thr Ala Gly Leu Val Lys
1               5
```

<210> SEQ ID NO 1657
<211> LENGTH: 22
<212> TYPE: PRT
<213> ORGANISM: Homo sapiens

<400> SEQUENCE: 1657

```
Tyr His Phe Val Thr Pro Leu Thr Ser Met Val Val Thr Lys Pro Glu
1               5                   10                  15

Asp Asn Glu Asp Glu Arg
            20
```

<210> SEQ ID NO 1658
<211> LENGTH: 42
<212> TYPE: PRT
<213> ORGANISM: Homo sapiens

<400> SEQUENCE: 1658

```
Leu Arg Leu Glu Pro Gly Lys Glu Tyr Leu Ile Met Gly Leu Asp Gly
1               5                   10                  15

Ala Thr Tyr Asp Leu Glu Gly His Pro Gln Tyr Leu Leu Asp Ser Asn
            20                  25                  30

Ser Trp Ile Glu Glu Met Pro Ser Glu Arg
        35                  40
```

<210> SEQ ID NO 1659

```
<211> LENGTH: 20
<212> TYPE: PRT
<213> ORGANISM: Homo sapiens

<400> SEQUENCE: 1659

Ala Ala Cys Ala Gln Leu Asn Asp Phe Leu Gln Glu Tyr Gly Thr Gln
1               5                   10                  15

Gly Cys Gln Val
            20

<210> SEQ ID NO 1660
<211> LENGTH: 9
<212> TYPE: PRT
<213> ORGANISM: Homo sapiens

<400> SEQUENCE: 1660

Met Lys Phe Ala Cys Tyr Tyr Pro Arg
1               5

<210> SEQ ID NO 1661
<211> LENGTH: 8
<212> TYPE: PRT
<213> ORGANISM: Homo sapiens

<400> SEQUENCE: 1661

Val Glu Tyr Gly Phe Gln Val Lys
1               5
```

METHOD FOR IDENTIFYING TYPE I DIABETES MELLITUS IN HUMANS

CROSS REFERENCE TO RELATED APPLICATION

This application claims priority from Provisional application No. 60/985,333 filed 5 Nov. 2007, incorporated herein in its entirety.

STATEMENT AS TO RIGHTS TO INVENTIONS MADE UNDER FEDERALLY-SPONSORED RESEARCH AND DEVELOPMENT

This invention was made with Government support under Contract DE-AC0576RLO1830 awarded by the U.S. Department of Energy, as well as NIH grant DK070146. The Government has certain rights in the invention.

BACKGROUND OF THE INVENTION

1. Field of the Invention

The present invention generally relates to methods and systems for the screening and detection of disease and more particularly to methods and systems for the screening and detection of persons at risk for developing type I diabetes mellitus.

2. Background of the Invention

Diabetes mellitus is a life changing disease that affects millions of persons. While the disease may be clinically diagnosed and confirmed fairly easily in some cases, earlier detection may lead to the possibility of intervention(s) that would alter or lessen the onset of clinical symptoms or allow other forms of preventative care to be undertaken. Currently, one of the best approaches for predicting who may be at risk for developing diabetes before the onset of clinical symptoms is the measurement of autoantibodies to islet cell antigens. However, for the major autoantibodies predictive of type 1 diabetes, the sensitivities for these antibodies varies considerably. While progress has been made to improve the accuracy and reproducibility of the measurement of islet cell autoantibodies, surrogate biomarkers predictive of those at high risk for developing type 1 diabetes would benefit the clinical community, particularly if such surrogate biomarkers result in higher sensitivity and specificity.

Accordingly what is needed is a method and system of screening for persons with increased risk of developing diabetes mellitus that utilizes candidate biomarkers allowing for broad based, reliable screening of large population bases. In addition, effective strategies for characterizing, archiving, and contrasting data from multiple sample types under varying conditions (e.g. control versus disease) are also needed.

Additional advantages and novel features of the present invention will be set forth as follows and will be readily apparent from the descriptions and demonstrations set forth herein. Accordingly, the following descriptions of the present invention should be seen as illustrative of the invention and not as limiting in any way.

SUMMARY OF THE INVENTION

The present application describes novel methods and systems for classifying subject populations and discovering predictive and diagnostic biomarkers for diabetes mellitus. In preliminary studies a variety of markers including alpha-2-glycoprotein 1 (zinc), corticosteroid-binding globulin, and lumican demonstrated serum/plasma concentrations that were 2-fold up-regulated in type 1 diabetic samples relative to nondiabetic control samples, whereas clusterin and serotransferrin were 2-fold up-regulated in control samples relative to type 1 diabetic samples. The observed perturbations in the levels of all five proteins are consistent with the metabolic aberrations found in type 1 diabetes. A complete set of markers that also demonstrated promise in are attached hereto as Appendix 1.

The method and system described herein for identifying populations and individuals who may be predisposed to the later development of type I diabetes mellitus includes the steps of obtaining a sample of serum or blood plasma from an individual, this sample having a total mixture of serum or plasma constituents, analyzing the serum or blood plasma to determine the quantity of at least one serum constituent selected from the group described in appendix 1 and comparing the quantity of the at least one serum constituent to a standardized range of levels for this constituent to determine whether the level of the serum constituent when compared to the normal range is indicative of a predisposition for type I diabetes mellitus. A system for performing the method of the present invention is made up of the requisite pieces and parts that would allow such a method to be performed. A flow chart of the general method is shown in FIG. 1.

DETAILED DESCRIPTION

Figure 1:
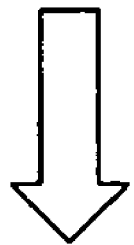
FIG. 1 shows a flow chart of the general method of the present invention

In one embodiment of the present invention, the method for determining whether a persons has an increased risk of developing diabetes mellitus involves the steps of obtaining plasma or serum from an individual and then testing this plasma or serum for the presence of at least of the following serum constituent biomarkers: alpha-2-glycoprotein 1 (zinc), corticosteroid-binding globulin, lumican, clusterin and serotransferrin present in said sample. The results of this test are then compared to a standardized range to determine whether the level of the particular serum constituent is within a preselected range indicative of type I diabetes mellitus.

The following description of one set of experiments related to one embodiment of the present invention provides a description related to particular experiments that demonstrate the application of the present invention, and the identification of the bio markers described above. While the following description is provided, it is to be distinctly understood that the invention is not limited thereto but may be variously embodied according to the needs and necessities of the user.

To identify candidate biomarkers, a label-free quantitation strategy based on LC-FTICR analyses of individual samples from control and patient subjects was utilized. Peptides, and later proteins, were identified by matching detected LC-FTICR features to the plasma AMT tag database using the AMT tag approach. In this study, 9116±710 (mean±standard deviation) features from 59 LC-FTICR datasets (one dataset for control individual 5 was excluded as an outlier, see below) were matched to 1517±199 AMT tags, representing ~16% of data identified. A total of 1930 unique peptides were identified during this quantitative study, corresponding to 120 unique proteins ($\geq 2$ unique peptides per protein), based on stringent filtering. The total number of unique peptide identifications across all 20 individuals was also quite consistent given the expected biological variations between samples. Following the application of statistical t-test at the protein level, 30 out of a total 120 proteins were shown to have significant abundance differences ($p<0.05$) between control and patient individuals. These proteins were further examined at the peptide level where we required the average peptide p-value to be $<0.1$. Nine proteins showing statistically significant abundance differences based on both the peptide- and protein-level t-tests were identified. Of these 9 proteins, only 5 were identified with $\geqq 2$ unique peptides in at least 8 of 10 control and patient individuals; therefore, emphasis will be placed on alpha-2-glycoprotein 1 (zinc), clusterin (apolipoprotein J), corticosteroid-binding globulin, lumican, and serotransferrin.

Alpha-2-glycoprotein 1 (zinc). Relative levels of alpha-2-glycoprotein 1 (zinc) were determined in all individuals using three unique peptides. This protein was consistently up-regulated in patient samples versus controls; however, control individuals 2 and 3 exhibited relatively higher levels compared to the other eight control individuals. Alpha-2-glycoprotein 1 (zinc) is a member of the immunoglobulin superfamily and displays lipid mobilization activity. The patient samples collected as part of the DASP study correspond to recently diagnosed individuals, several of whom may have been ketotic; therefore, increased levels of alpha-2-glycoprotein 1 (zinc) in patient relative to control samples may be an indication of a system-wide mobilization of fats for energy production. Indeed, the patient samples were suspected to be hyperlipidemic relative to control samples during sample preparation for proteomic analysis, based on observed opaqueness and increased viscosity (also possibly due to hyperglycemia) of the plasma and serum. In addition, several isoforms of alpha-2-glycoprotein 1 (zinc) have been shown to exist in human plasma and human serum, leaving open the possibility of genetic differences in the expression or isoforms of this protein in patients relative to controls.

Clusterin. Fourteen unique peptides were used to determine relative levels of clusterin in patient and control samples, although detection of peptides was variable among individuals. Clusterin, or apolipoprotein J, demonstrates a nearly ubiquitous tissue distribution and is produced in two immunologically distinct forms by alternative splicing. A glycosylated form is secreted and displays cytoprotective effects, whereas a non-glycosylated, cytoplasmic/nuclear form displays apoptotic properties. In this study, 7 control individuals exhibited relatively high levels of clusterin, whereas 5 patients exhibited relatively low levels of this protein. It is possible that low levels of clusterin in patient samples indicate poor cytoprotective capability, which may facilitate autoimmune destruction of pancreatic beta cells leading to development of type 1 diabetes mellitus.

Corticosteroid-binding globulin. Relative levels of corticosteroid-binding globulin were determined in control and patient individuals using up to three unique peptides (at least 2 unique peptides mapping to this protein were detected in all individuals). This protein was consistently up-regulated in patient samples versus controls; however, control individuals 2 and 9 exhibited relatively higher levels compared to the other eight control individuals. Insulin and insulin-like growth factor I have been reported to inhibit secretion of corticosteroid-binding globulin by a human hepatoma cell line, and plasma corticosteroid-binding globulin was recently shown to correlate positively with fasting glucose and hemoglobin A1c but negatively with insulin response to intravenous and oral glucose administration in obese individuals with glucose intolerance. In the current study, the observation of relatively high levels of corticosteroid-binding globulin in patients relative to controls likely reflects the absence or lower circulating levels of insulin in the plasma and serum of patients.

Lumican. Up to nine unique peptides were used to determine relative levels of lumican in patient and control samples, although detection of peptides was variable among individuals. This protein was consistently and strongly up-regulated in patient samples versus controls, with the exception of patients 1 (no up-regulation), 7, and 8 (moderate up-regulation). In addition, the LC-MS/MS data for this protein, while semi-quantitative, strongly support these results. Lumican is a member of the small leucine-rich proteoglycan family and is a component of the extracellular matrix (ECM) and binding partner of TGF-$\beta$, a key mediator of fibrotic diseases. This protein was reported to be expressed in the cornea, dermis, cartilage, heart, lung, and kidney of developing mouse embryos, thus it is difficult to speculate on the specific tissue source of plasma/serum lumican in patient samples. However, lumican has been shown to be up-regulated in the tubulointerstitium and glomeruli of diabetic patients with nephropathy. In addition, lumican (as well as other proteoglycans) has been reported to be up-regulated in kidneys of rats experiencing unilateral ureteral obstruction. These studies suggest that increased thickening of the ECM and possibly glomerulosclerosis may be accompanied by up-regulation of select proteoglycans, including lumican. Because the samples involved in the DASP study are from recently diagnosed patients, it is difficult to estimate the degree to which plasma hyperglycemia affects the morphology and function of the kidney. However, it is possible that increased plasma lumican in patient samples reflects an acute response of the kidney to high levels of plasma glucose.

Serotransferrin. Relative levels of serotransferrin were determined in control and patient individuals using up to twenty-nine unique peptides, although detection of these peptides was highly variable among individuals. This protein was strongly up-regulated in four control individuals and moderately up-regulated in six control individuals relative to patients. In addition, the LC-MS/MS data for this protein, while semi-quantitative, strongly support these results. Increased urinary transferrin excretion rates have been reported in type 1 diabetic patients with normal urinary albumin excretion rates, suggesting that transferrin might be released preferentially from the diabetic kidney leading to lower levels in plasma. Indeed, van Campenhout and colleagues found lower levels of transferrin and total iron-binding capacity in serum of type 1 diabetic subjects relative to controls.

Five candidate protein biomarkers for type 1 diabetes have been identified. It is believed that serum or plasma testing for any or all of these five proteins discussed may serve as a predictive or diagnostic screen or test for type 1 diabetes.

The purpose of the foregoing abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Various advantages and novel features of the present invention are described herein and will become further readily apparent to those skilled in this art. As will be realized, the invention is capable of modification in various respects without departing from the invention. While various preferred embodiments of the invention are shown and described, it is to be distinctly understood that this invention is not limited thereto but may be variously embodied to practice within the scope of the following claims. From the foregoing description, it will be apparent that various changes may be made without departing from the spirit and scope of the invention as defined by the following claims.

APPENDIX 1

| International Protein Index (IPI) | Protein Description | SEQ ID NOs: |
|---|---|---|
| IPI:IPI00879551.1 | 12 kDa protein | 1 |
| IPI:IPI00790473.1 | 12 kDa protein | 2-5 |
| IPI:IPI00879551.1 | 12 kDa protein | 6-10 |
| IPI:IPI00642045.1 | 14 kDa protein | 11-13 |
| IPI:IPI00879915.1 | 15 kDa protein | 14-17 |
| IPI:IPI00879984.1 | 16 kDa protein | 18-24 |
| IPI:IPI00879718.1 | 17 kDa protein | 25-32 |
| IPI:IPI00877698.1 | 18 kDa protein | 33-35 |
| IPI:IPI00879608.1 | 19 kDa protein | 36-37 |
| IPI:IPI00793626.1 | 22 kDa protein | 38-41 |
| IPI:IPI00796279.1 | 25 kDa protein | 42-53 |
| IPI:IPI00791901.1 | 26 kDa protein | 54-55 |
| IPI:IPI00879937.1 | 28 kDa protein | 56-62 |
| IPI:IPI00795830.1 | 29 kDa protein | 63-69 |
| IPI:IPI00795257.1 | 32 kDa protein | 70-71 |
| IPI:IPI00749466.1 | 35 kDa protein | 72-75 |
| IPI:IPI00788737.1 | 39 kDa protein | 76-77 |
| IPI:IPI00795153.2 | 43 kDa protein | 78-94 |
| IPI:IPI00793848.1 | 54 kDa protein | 95-109 |
| IPI:IPI00798006.1 | 7 kDa protein | 110-111 |
| IPI:IPI00871139.1 | 92 kDa protein | 112-114 |
| IPI:IPI00019943.1 | Afamin precursor | 115-127 |
| IPI:IPI00550991.3 | Alpha-1-antichymotrypsin precursor | 128-152 |
| IPI:IPI00879231.1 | Alpha-2-antiplasmin precursor | 153-167 |
| IPI:IPI00166729.4 | alpha-2-glycoprotein 1; zinc | 168-181 |
| IPI:IPI00022431.1 | Alpha-2-HS-glycoprotein precursor | 182-192 |
| IPI:IPI00022229.1 | Apolipoprotein B-100 precursor | 193-194 |
| IPI:IPI00797309.1 | BCHE protein | 195-196 |
| IPI:IPI00064667.4 | Beta-Ala-His dipeptidase precursor | 197-205 |
| IPI:IPI00639937.1 | B-factor; properdin | 206-259 |
| IPI:IPI00385045.1 | C1 inhibitor mutant (Fragment) | 260-262 |
| IPI:IPI00418163.3 | C4B1 | 263-365 |
| IPI:IPI00442286.1 | CDNA FLJ16195 fis; clone BRTHA3000296 | 366-367 |
| IPI:IPI00871960.2 | cDNA FLJ75203; highly similar to *Homo sapiens* mannan-binding lectin serine protease 1 (C4/C2activating component of Ra-reactive factor) (MASP1); transcriptvariant 2; mRNA | 368-370 |
| IPI:IPI00879931.1 | cDNA FLJ78023; highly similar to *Homo sapiens* serine (or cysteine) proteinase inhibitor; clade G (C1inhibitor); member 1; (angioedema; hereditary) (SERPING1); mRNA | 371-387 |
| IPI:IPI00794070.1 | CFI protein | 388-404 |
| IPI:IPI00025864.5 | Cholinesterase precursor | 405-418 |
| IPI:IPI00795633.1 | CLU | 419-437 |
| IPI:IPI00400826.1 | clusterin isoform 1 | 438-456 |
| IPI:IPI00291262.3 | Clusterin precursor | 457-481 |
| IPI:IPI00296176.2 | Coagulation factor IX precursor | 482-485 |
| IPI:IPI00296165.5 | Complement C1r subcomponent precursor | 486-498 |
| IPI:IPI00783987.2 | Complement C3 precursor (Fragment) | 499-542 |
| IPI:IPI00032258.4 | Complement C4-A precursor | 543-642 |
| IPI:IPI00654875.1 | Complement C4-B precursor | 643-742 |
| IPI:IPI00515098.1 | Complement component 2 (Fragment) | 743-747 |
| IPI:IPI00643525.1 | Complement component 4A | 748-850 |
| IPI:IPI00294395.1 | Complement component C8 beta chain precursor | 851-877 |
| IPI:IPI00165972.3 | Complement factor D preproprotein | 878-884 |
| IPI:IPI00299307.4 | Complement-activating component of Ra-reactive factor precursor | 885-887 |
| IPI:IPI00027482.1 | Corticosteroid-binding globulin precursor | 888-890 |
| IPI:IPI00642842.1 | C-reactive protein; pentraxin-related | 891-892 |
| IPI:IPI00333770.6 | dedicator of cytokinesis 10 | 893-894 |
| IPI:IPI00645849.1 | Extracellular matrix protein 1 | 895-907 |
| IPI:IPI00003351.2 | Extracellular matrix protein 1 precursor | 908-921 |
| IPI:IPI00743766.2 | Fetuin-B precursor | 922-933 |
| IPI:IPI00377087.4 | Gelsolin | 934-953 |
| IPI:IPI00789134.1 | Glyceraldehyde 3-phosphate dehydrogenase | 954-955 |
| IPI:IPI00219018.7 | Glyceraldehyde-3-pho | 956-957 |
| IPI:IPI00552199.3 | GUGU beta form | 958-967 |
| IPI:IPI00553061.1 | GUGU gamma form | 968-976 |

APPENDIX 1-continued

| International Protein Index (IPI) | Protein Description | SEQ ID NOs: |
|---|---|---|
| IPI:IPI00879573.1 | Heparin cofactor 2 precursor | 977-982 |
| IPI:IPI00029193.1 | Hepatocyte growth factor activator precursor | 983-986 |
| IPI:IPI00292218.4 | Hepatocyte growth factor-like protein precursor | 987-990 |
| IPI:IPI00022371.1 | Histidine-rich glycoprotein precursor | 991-1008 |
| IPI:IPI00385264.1 | Ig mu heavy chain disease protein | 1009-1012 |
| IPI:IPI00477090.6 | IGHM protein | 1013-1014 |
| IPI:IPI00479708.5 | IGHM protein | 1015-1016 |
| IPI:IPI00549291.4 | IGHM protein | 1017-1018 |
| IPI:IPI00828205.1 | IGHM protein | 1019-1020 |
| IPI:IPI00883614.1 | IGHM protein | 1021-1022 |
| IPI:IPI00884141.1 | IGHM protein | 1023-1024 |
| IPI:IPI00884180.1 | IGHM protein | 1025-1026 |
| IPI:IPI00884293.1 | IGHM protein | 1027-1028 |
| IPI:IPI00884452.1 | IGHM protein | 1029-1030 |
| IPI:IPI00292530.1 | Inter-alpha-trypsin inhibitor heavy chain H1 precursor | 1031-1061 |
| IPI:IPI00847635.1 | Isoform 1 of Alpha-1-antichymotrypsin precursor | 1062-1086 |
| IPI:IPI00329775.7 | Isoform 1 of Carboxypeptidase B2 precursor | 1087-1099 |
| IPI:IPI00019591.1 | Isoform 1 of Complement | 1100-1055 |
| IPI:IPI00029739.5 | Isoform 1 of Complement factor H precursor | 1156-1225 |
| IPI:IPI00022389.1 | Isoform 1 of C-reactive protein precursor | 1226-1227 |
| IPI:IPI00026314.1 | Isoform 1 of Gelsolin precursor | 1228-1246 |
| IPI:IPI00028413.8 | Isoform 1 of Inter-alpha-trypsin inhibitor heavy chain H3 precursor | 1247-1262 |
| IPI:IPI00163207.1 | Isoform 1 of N-acetylmuramoyl-L-alanine amidase precursor | 1263-1282 |
| IPI:IPI00293057.5 | Isoform 2 of Carboxypeptidase B2 precursor | 1283-1292 |
| IPI:IPI00218999.2 | Isoform 2 of Complement factor H precursor | 1293-1322 |
| IPI:IPI00218876.3 | Isoform 2 of C-reactive protein precursor | 1323-1324 |
| IPI:IPI00375113.2 | Isoform 2 of Dedicator of cytokinesis protein 10 | 1325-1326 |
| IPI:IPI00646773.2 | Isoform 2 of Gelsolin precursor | 1327-1344 |
| IPI:IPI00876950.1 | Isoform 2 of Inter-alpha-trypsin inhibitor heavy chain H3 precursor | 1345-1360 |
| IPI:IPI00394992.1 | Isoform 2 of N-acetylmuramoyl-L-alanine amidase precursor | 1361-1379 |
| IPI:IPI00020986.2 | Lumican precursor | 1380-1388 |
| IPI:IPI00290283.6 | mannan-binding lectin serine protease 1 isoform 2 precursor | 1389-1391 |
| IPI:IPI00216882.4 | mannan-binding lectin serine protease 1 isoform 3 | 1392-1394 |
| IPI:IPI00006114.4 | Pigment epithelium-derived factor precursor | 1395-1419 |
| IPI:IPI00654888.4 | Plasma kallikrein precursor | 1420-1446 |
| IPI:IPI00291866.5 | Plasma protease C1 inhibitor precursor | 1447-1465 |
| IPI:IPI00156243.1 | Plasminogen-related protein A precursor | 1466-1468 |
| IPI:IPI00022445.1 | Platelet basic protein precursor | 1469-1473 |
| IPI:IPI00877925.1 | Pre-alpha 2-plasmin inhibitor | 1474-1480 |
| IPI:IPI00383338.1 | PRO2769 | 1481-1492 |
| IPI:IPI00021364.1 | Properdin precursor | 1493-1497 |
| IPI:IPI00019568.1 | Prothrombin precursor (Fragment) | 1498-1530 |
| IPI:IPI00873401.1 | Putative uncharacterized protein DKFZp686I01199 | 1531-1533 |
| IPI:IPI00556459.1 | Serine/cysteine proteinase inhibitor clade G member 1 splice variant 2 (Fragment) | 1534-1547 |
| IPI:IPI00022463.1 | Serotransferrin precursor | 1548-1575 |
| IPI:IPI00292950.4 | Serpin peptidase inhibitor; clade D (Heparin cofactor); member 1 | 1576-1581 |
| IPI:IPI00029863.4 | SERPINF2 protein | 1582-1596 |
| IPI:IPI00855916.1 | Transthyretin | 1597-1604 |
| IPI:IPI00022432.1 | Transthyretin precursor | 1605-1612 |
| IPI:IPI00871596.1 | Uncharacterized protein AZGP1 (Fragment) | 1613-1618 |
| IPI:IPI00515041.5 | Uncharacterized protein CFH | 1619-1638 |
| IPI:IPI00871622.1 | Uncharacterized protein ENSP00000381161 | 1639-1641 |
| IPI:IPI00873416.1 | Uncharacterized protein ITIH3 | 1642-1657 |
| IPI:IPI00843913.2 | ZA protein | 1658-1661 |

What is claimed is:

1. A method of identifying individual humans predisposed for the development of type I diabetes mellitus said method comprising the steps of:
    analyzing a serum or blood plasma sample from a human to determine the quantity of at least three constituents selected from the group consisting of alpha-2-glycoprotein 1 (zinc), corticosteroid-binding globulin, lumican, and clusterin present in said sample; and
    comparing said quantity of said at least three constituents to a standardized range of values from healthy individuals to determine whether the level of said at least three constituents is elevated above said standardized range of values wherein a quantity of said at least three constituents that is elevated above said standardized range of values is indicative of type I diabetes mellitus in the human.

2. The method of claim 1 wherein said method comprises identifying and comparing at least 4 constituents from said group.

3. The method of claim 1 wherein said method comprises identifying and comparing the quantity of alpha-2-glycoprotein 1 (zinc) present in said sample.

4. The method of claim 1 wherein said method comprises identifying and comparing the quantity of corticosteroid-binding globulin present in said sample.

5. The method of claim 1 wherein said method comprises identifying and comparing the quantity of lumican present in said sample.

6. The method of claim 1 wherein said method comprises identifying and comparing the quantity of clusterin present in said sample.

* * * * *